US009845291B2

(12) United States Patent
Liang et al.

(10) Patent No.: US 9,845,291 B2
(45) Date of Patent: Dec. 19, 2017

(54) ESTROGEN RECEPTOR MODULATORS AND USES THEREOF

(71) Applicant: Genentech, Inc., South San Francisco, CA (US)

(72) Inventors: Jun Liang, Los Altos Hills, CA (US); Daniel Fred Ortwine, San Ramon, CA (US); Xiaojing Wang, Foster City, CA (US); Steven P. Govek, San Diego, CA (US); Mehmet Kahraman, La Jolla, CA (US); Johnny Y. Nagasawa, San Diego, CA (US); Nicholas D. Smith, San Diego, CA (US); Simon Charles Goodacre, Harlow Essex (GB); Nicholas Charles Ray, Harlow Essex (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/972,333

(22) Filed: Dec. 17, 2015

(65) Prior Publication Data
US 2016/0304450 A1 Oct. 20, 2016
US 2017/0197915 A9 Jul. 13, 2017

Related U.S. Application Data

(60) Provisional application No. 62/093,929, filed on Dec. 18, 2014, provisional application No. 62/110,998, filed on Feb. 2, 2015.

(51) Int. Cl.
| | | |
|---|---|---|
| *A61K 31/397* | (2006.01) | |
| *C07D 205/04* | (2006.01) | |
| *C07D 403/12* | (2006.01) | |
| *A61K 31/404* | (2006.01) | |
| *A61K 45/06* | (2006.01) | |
| *C07D 207/04* | (2006.01) | |
| *A61K 31/40* | (2006.01) | |
| *C07D 409/12* | (2006.01) | |
| *A61K 31/4025* | (2006.01) | |
| *C07D 413/12* | (2006.01) | |
| *A61K 31/422* | (2006.01) | |
| *C07D 417/12* | (2006.01) | |

(Continued)

(52) U.S. Cl.
CPC .......... *C07D 205/04* (2013.01); *A61K 31/397* (2013.01); *A61K 31/40* (2013.01); *A61K 31/404* (2013.01); *A61K 31/4025* (2013.01); *A61K 31/422* (2013.01); *A61K 31/427* (2013.01); *A61K 31/4439* (2013.01); *A61K 45/06* (2013.01); *C07D 207/04* (2013.01); *C07D 401/14* (2013.01); *C07D 403/12* (2013.01); *C07D 409/12* (2013.01); *C07D 413/12* (2013.01); *C07D 417/12* (2013.01)

(58) Field of Classification Search
CPC .. C07D 205/04; C07D 207/04; C07D 207/08; C07D 401/14; C07D 403/02; C07D 403/12; C07D 403/14; C07D 409/02; C07D 409/12; C07D 411/02; C07D 411/12; C07D 417/02; C07D 417/12; C07D 417/14; C07D 493/04; A61K 31/397; A61K 31/40; A61K 31/4025; A61K 31/404; A61K 31/422; A61K 31/427; A61K 31/4439
USPC ..... 548/247, 509, 525, 576, 950; 514/210.2, 514/210.19, 210.21, 415
See application file for complete search history.

(56) References Cited

U.S. PATENT DOCUMENTS

| | | |
|---|---|---|
| 8,703,810 B2 | 4/2014 | Kahraman et al. |
| 8,853,423 B2 | 10/2014 | Govek |

(Continued)

FOREIGN PATENT DOCUMENTS

| | | |
|---|---|---|
| EP | 0826680 A1 | 3/1998 |
| EP | 0835867 A1 | 4/1998 |

(Continued)

OTHER PUBLICATIONS

Gura et al., Systems for identifying new drugs are often faulty, Science, 278:1041-1042, 1997.*

(Continued)

*Primary Examiner* — Deepak Rao
(74) *Attorney, Agent, or Firm* — Kevin M. Clark

(57) ABSTRACT

Described herein are compounds that are estrogen receptor modulators of Formula (I):

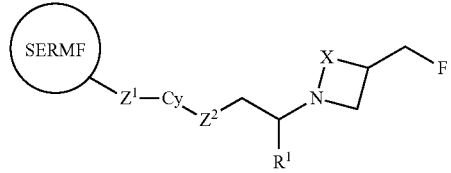

Formula (I)

and stereoisomers, tautomers, or pharmaceutically acceptable salts thereof, wherein SERMF is a selective estrogen receptor modulator fragment and with the substituents and structural features described herein. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

14 Claims, No Drawings

(51) Int. Cl.
    *A61K 31/427*  (2006.01)
    *C07D 401/14*  (2006.01)
    *A61K 31/4439* (2006.01)
    *C07D 411/12*  (2006.01)

(56) References Cited

U.S. PATENT DOCUMENTS

| | | | |
|---|---|---|---|
| 9,187,460 | B2 | 11/2015 | Smith et al. |
| 9,193,714 | B2 | 11/2015 | Smith |
| 2003/0130274 | A1 | 7/2003 | Miller |
| 2013/0116232 | A1 | 5/2013 | Kahraman |
| 2013/0137746 | A1 | 5/2013 | Govek |
| 2014/0364427 | A1 | 12/2014 | Smith |
| 2016/0090377 | A1 | 3/2016 | Govek |
| 2016/0090378 | A1 | 3/2016 | Kahraman |
| 2016/0175284 | A1 | 6/2016 | Labadie |
| 2016/0175289 | A1 | 6/2016 | Labadie |

FOREIGN PATENT DOCUMENTS

| | | |
|---|---|---|
| WO | 96/11677 A1 | 4/1996 |
| WO | 01/77093 A1 | 10/2001 |
| WO | 2005/073190 A1 | 8/2005 |
| WO | 2006/019833 A1 | 2/2006 |
| WO | 2015/082990 A1 | 6/2011 |
| WO | 2011/156518 A2 | 12/2011 |
| WO | 2011/159769 A2 | 12/2011 |
| WO | 2013/090829 A1 | 6/2013 |
| WO | 2013/090836 A1 | 6/2013 |
| WO | 2014/039412 A1 | 3/2014 |
| WO | 2014/205136 A1 | 12/2014 |
| WO | 2014/205138 A1 | 12/2014 |
| WO | 2015/102426 A1 | 7/2015 |
| WO | 2015/136016 A2 | 9/2015 |
| WO | 2015/136017 A1 | 9/2015 |
| WO | 2016/097072 A1 | 6/2016 |
| WO | 2016/097073 A1 | 6/2016 |

OTHER PUBLICATIONS

Johnson et al., Relationships between drug activity in NCI preclinical in vitro models and early clinical trials, British Journal of Cancer, 84(10):1424-1431,2001.*

Pearce et al., Failure models in anticancer drug discovery and development, Cancer Drug Design and Discovery Edited by Stephen Neidle, Chapter 18, pp. 424-435(2008).*

Simone, Oncology: Introduction, Cecil Textbook of Medicin, 20th Edition, vol. 1, pp. 1004-101 O, 1995.*

(ISR for PCT/EP2015/080118), dated 2015.

Gennari, "Lasofoxifene: A New Type of Selective Estrogen Receptor Modulator for the Treatment of Osteoporosis" Drug of Today 42(6):355-67 ( 2006).

* cited by examiner

ESTROGEN RECEPTOR MODULATORS AND USES THEREOF

CROSS REFERENCE TO RELATED APPLICATIONS

This non-provisional application filed under 37 CFR §1.53(b), claims the benefit under 35 USC §119(e) of U.S. Provisional Application Ser. No. 62/093,929 filed on 18 Dec. 2014, and U.S. Provisional Application Ser. No. 62/110,998 filed on 2 Feb. 2015, which are incorporated by reference in their entirety.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β.

Estrogens and estrogen receptors are implicated in a number of diseases or conditions, such as bone cancer, breast cancer, colorectal cancer, endometrial cancer, prostate cancer, ovarian cancer, uterine cancer, cervical cancer, lung cancer, as well as others diseases or conditions.

SUMMARY OF THE INVENTION

In one aspect, presented herein are compounds of Formulas (I), (II), (IIa), (IIb), (IIc), (III), (IIIa), (IIIb), (IIIc), (IV), (IVa), (IVb), (IVc), (IVd), (V), (VI), (VII), (VIII), (IX) and (X), or a pharmaceutically acceptable salt, solvate or prodrug thereof, that diminish the effects of estrogens with estrogen receptors and/or lower the concentrations of estrogen receptors, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are estrogen receptor degrader compounds.

In one aspect, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is useful for the treatment of ER-related diseases or conditions including, but not limited to, ER-α dysfunction associated with cancer (e.g. bone cancer, breast cancer, colorectal cancer, endometrial cancer, prostate cancer, ovarian cancer, uterine cancer, cervical cancer, lung cancer).

In one aspect, described herein are compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) and (X), pharmaceutically acceptable salts, solvates, metabolites and prodrugs thereof. Compounds described herein are estrogen receptor modulators. In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X) is an estrogen receptor antagonist. In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X) is an estrogen receptor degrader. In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X) is an estrogen receptor antagonist as well as an estrogen receptor degrader. In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X) displays minimal or no estrogen receptor agonist activity. In some embodiments, in the context of treating cancers, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X) may offer improved therapeutic activity characterized by complete or longer-lasting tumor regression, a lower incidence or rate of development of resistance to treatment, and/or a reduction in tumor invasiveness.

In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from active metabolites, tautomers, pharmaceutically acceptable solvates, pharmaceutically acceptable salts or prodrugs of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X).

In one aspect, described herein is a compound of Formula (I):

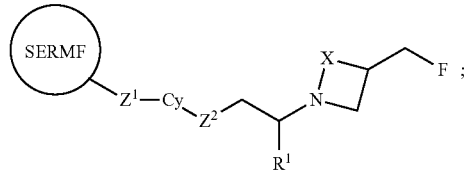

Formula (I)

and stereoisomers, tautomers, or pharmaceutically acceptable salts thereof, wherein:

is a selective estrogen receptor modulator fragment;

$Z^1$ and $Z^2$ are independently selected from —O—, —(CH$_2$)—, —C(O)—, or a bond;

Cy is C$_6$-C$_{20}$aryl, C$_3$-C$_{12}$carbocyclyl, C$_2$-C$_{20}$heterocyclyl, or C$_1$-C$_{20}$heteroaryl;

X is —(CH$_2$)— or —(CH$_2$CH$_2$)—; and $R^1$ is selected from H, F, Cl, —CN, —CH$_2$OH, —CH(CH$_3$)OH, —C(CH$_3$)$_2$OH, —CH(CF$_3$)OH, —CH$_2$F, —CHF$_2$, —CH$_2$CHF$_2$, —CF$_3$, —CH$_3$, —C(O)NH$_2$, —C(O)NHCH$_3$, and —C(O)N(CH$_3$)$_2$;

where carbocyclyl, heterocyclyl, aryl, and heteroaryl are optionally substituted with one or more groups independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OCF$_3$, —OCHF$_2$, —OP(O)(OH)$_2$, —S(O)$_2$N(CH$_3$)$_2$, —SCH$_3$, —S(O)$_2$CH$_3$, —S(O)$_3$H, cyclopropyl, oxetanyl, azetidinyl, 1-methylazetidin-3-yl)oxy, N-methyl-N-oxetan-3-ylamino, azetidin-1-ylmethyl, pyrrolidin-1-yl, and morpholino.

In some embodiments, the compound of Formula (I) has the structure of Formula (II):

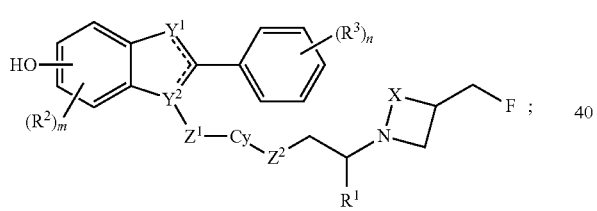

Formula (II)

wherein:

═══ indicates a single or double bond where one ═══ is a double bond and one ═══ is a single bond;

$Y^1$ is CR$^6$ and $Y^2$ is N; $Y^1$ is S and $Y^2$ is C; or $Y^1$ is NR$^7$ and $Y^2$ is C;

each $R^2$ and each $R^3$ are independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(═O)OR$^{12}$, —NHC(═O)R$^{11}$, —C(═O)NHR$^{12}$, —SO$_2$R$^{11}$, —NHSO$_2$R$^{11}$, and —SO$_2$NHR$^{12}$;

$R^6$ is selected from H, halogen, C$_1$-C$_6$alkyl, C$_1$-C$_6$fluoroalkyl, C$_3$-C$_{12}$carbocyclyl, —(C$_1$-C$_6$alkyl)-(C$_3$-C$_{12}$carbocyclyl), C$_2$-C$_{20}$heterocyclyl, —(C$_1$-C$_6$alkyl)-(C$_2$-C$_{20}$heterocyclyl), —SO$_2$R$^{11}$, —(C$_1$-C$_6$alkyl)-(C$_1$-C$_{20}$heteroaryl), C$_1$-C$_{20}$heteroaryl, and C$_6$-C$_{20}$aryl;

$R^7$ is selected from H and C$_1$-C$_4$alkyl;

each $R^{10}$ is independently selected from H, C$_1$-C$_4$alkyl, and C$_1$-C$_4$fluoroalkyl;

each $R^{11}$ is independently selected from C$_1$-C$_4$alkyl and C$_1$-C$_4$fluoroalkyl;

each $R^{12}$ is independently selected from H, C$_1$-C$_4$alkyl, and C$_1$-C$_4$fluoroalkyl;

each $R^{13}$ and each $R^{14}$ are independently selected from H and C$_1$-C$_4$alkyl;

m is 0, 1, 2 or 3; and n is 0, 1, 2 or 3.

In some embodiments, the compound of Formula (II) has the structure of Formula (IIa):

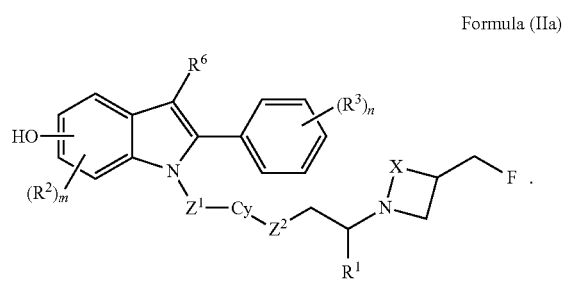

Formula (IIa)

In some embodiments is a compound of Formula (IIa), wherein $R^6$ is C$_1$-C$_6$alkyl. In some embodiments is a compound of Formula (IIa), wherein $R^6$ is —CH$_3$. In some embodiments is a compound of Formula (IIa), wherein $Z^1$ is —(CH$_2$)—.

In some embodiments, the compound of Formula (II) has the structure of Formula (IIb):

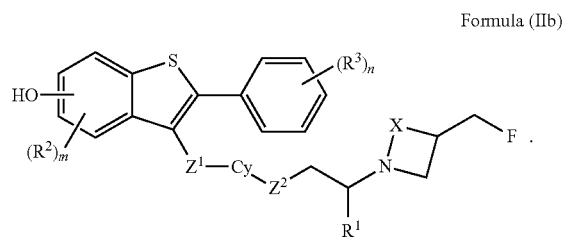

Formula (IIb)

In some embodiments is a compound of Formula (IIb), wherein $Z^1$ is —O—. In some embodiments is a compound of Formula (IIb), wherein $Z^1$ is —C(O)—.

In some embodiments, the compound of Formula (II) has the structure of Formula (IIc):

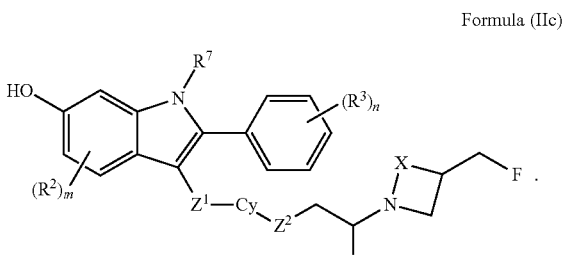

Formula (IIc)

In some embodiments is a compound of Formula (IIc), wherein $R^7$ is C$_1$-C$_4$alkyl. In some embodiments is a compound of Formula (IIc), wherein $R^7$ is —CH$_3$. In some embodiments is a compound of Formula (IIc), wherein $Z^1$ is —C(O)—.

In some embodiments, the compound of Formula (I) has the structure of Formula (III):

Formula (III)

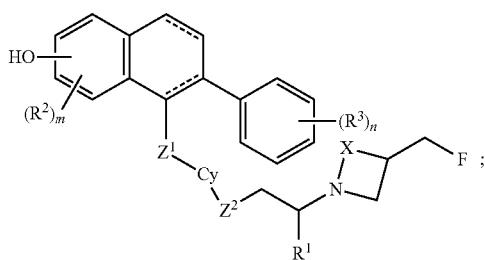

wherein:
═══ indicates a single or double bond;
each $R^2$ and each $R^3$ are independently selected from halogen, —CN, —OR$^{10}$, —NR$^{13}$R$^{14}$, $C_1$-$C_4$alkyl, —$C_1$-$C_4$alkyl-OH, —OC$_2$-$C_4$alkyl-OH, $C_1$-$C_4$fluoroalkyl, —C(═O)OR$^{12}$, —NHC(═O)R$^{11}$, —C(═O)NHR$^{12}$, —SO$_2$R$^{11}$, —NHSO$_2$R$^{11}$, and —SO$_2$NHR$^{12}$;
each $R^{10}$ is independently selected from H, $C_1$-$C_4$alkyl, and $C_1$-$C_4$fluoroalkyl;
each $R^{11}$ is independently selected from $C_1$-$C_4$alkyl and $C_1$-$C_4$fluoroalkyl;
each $R^{12}$ is independently selected from H, $C_1$-$C_4$alkyl, and $C_1$-$C_4$fluoroalkyl;
each $R^{13}$ and each $R^{14}$ are independently selected from H and $C_1$-$C_4$alkyl;
m is 0, 1, 2 or 3; and
n is 0, 1, 2 or 3.

In some embodiments, the compound of Formula (III) has the structure of Formula (IIIa):

Formula (IIIa)

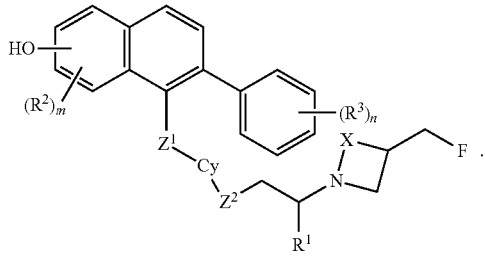

In some embodiments is a compound of Formula (IIIa), wherein $Z^1$ is —O—.

In some embodiments, the compound of Formula (III) has the structure of Formula (IIIb):

Formula (IIIb)

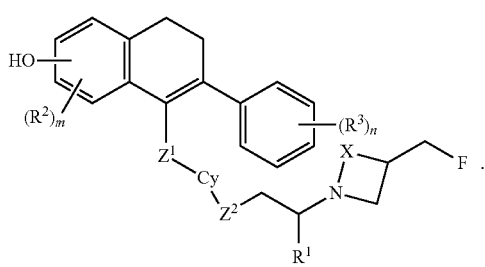

In some embodiments is a compound of Formula (IIb), wherein $Z^1$ is —O—. In some embodiments is a compound of Formula (IIIb), wherein $Z^1$ is —C(O)—.

In some embodiments, the compound of Formula (III) has the structure of Formula (IIIc):

Formula (IIIc)

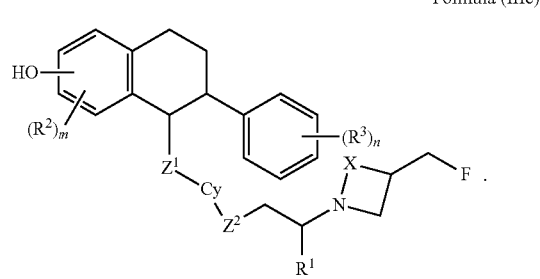

In some embodiments is a compound of Formula (IIIc), wherein $Z^1$ is a bond. In some embodiments is a compound of Formula (IIb), wherein $Z^1$ is —C(O)—.

In some embodiments, the compound of Formula (I) has the structure of Formula (IV):

Formula (IV)

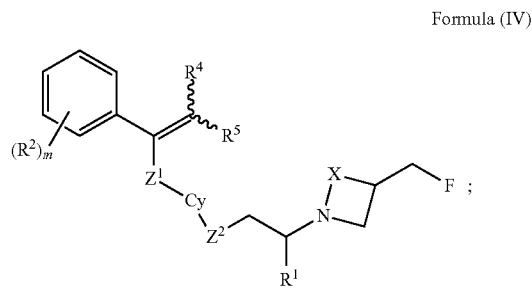

wherein:
each $R^2$ is independently selected from halogen, —CN, —OR$^{10}$, —NR$^{13}$R$^{14}$, $C_1$-$C_4$alkyl, —$C_1$-$C_4$alkyl-OH, —OC$_2$-$C_4$alkyl-OH, $C_1$-$C_4$fluoroalkyl, —C(═O)OR$^{12}$, —NHC(═O)R$^{11}$, —C(═O)NHR$^{12}$, —SO$_2$R$^{11}$, —NHSO$_2$R$^{11}$, and —SO$_2$NHR$^{12}$; or two $R^2$ together with the carbon atoms to which they are attached are combined to form a $C_2$-$C_9$heterocyclyl, or $C_1$-$C_{12}$heteroaryl;
$R^4$ is

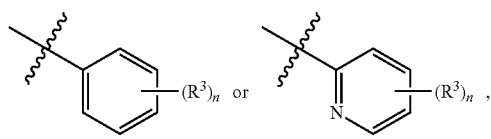

and $R^5$ is $C_1$-$C_4$alkyl or $C_3$-$C_8$carbocyclyl; or $R^4$ and $R^5$ together with the carbon atom to which they are attached are combined to form a $C_3$-$C_{12}$carbocyclyl;
each $R^{10}$ is independently selected from H, $C_1$-$C_4$alkyl, and $C_1$-$C_4$fluoroalkyl;
each $R^{11}$ is independently selected from $C_1$-$C_4$alkyl and $C_1$-$C_4$fluoroalkyl;
each $R^{12}$ is independently selected from H, $C_1$-$C_4$alkyl, and $C_1$-$C_4$fluoroalkyl;
each $R^{13}$ and each $R^{14}$ are independently selected from H and $C_1$-$C_4$alkyl;

m is 0, 1, 2 or 3; and n is 0, 1, 2 or 3.

In some embodiments, the compound of Formula (IV) has the structure of Formula (IVa):

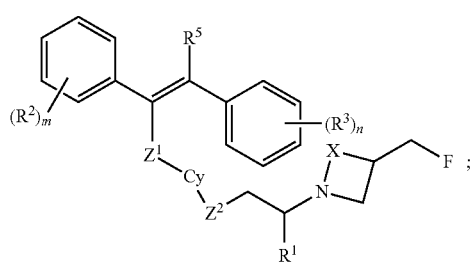

Formula (IVa)

wherein each $R^3$ is independently selected from halogen, —CN, —OR$^{10}$—NR$^{13}$R$^{14}$, $C_1$-$C_4$alkyl, —$C_1$-$C_4$alkyl-OH, —OC$_2$-$C_4$alkyl-OH, $C_1$-$C_4$fluoroalkyl, —C(=O)OR$^{12}$, —NHC(=O)R$^1$, —C(=O)NHR$^{12}$, —SO$_2$R$^{11}$, —NHSO$_2$R$^{11}$, and —SO$_2$NHR$^{12}$.

In some embodiments, the compound of Formula (IV) has the structure of Formula (IVb):

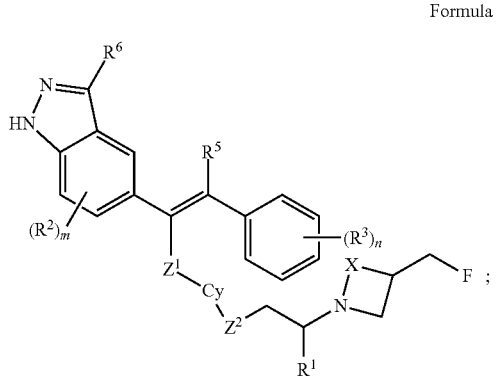

Formula (IVb)

wherein $R^6$ is H, halogen, CN, $C_1$-$C_4$alkyl or $C_3$-$C_8$carbocyclyl.

In some embodiments, the compound of Formula (IV) has the structure of Formula (IVc):

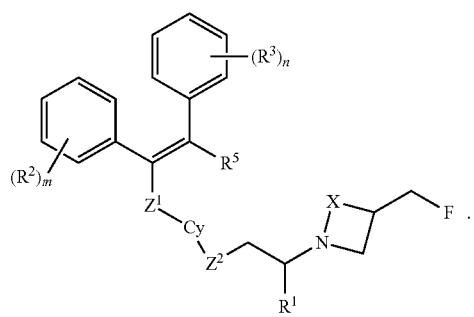

Formula (IVc)

In some embodiments, the compound of Formula (IV) has the structure of Formula (IVd):

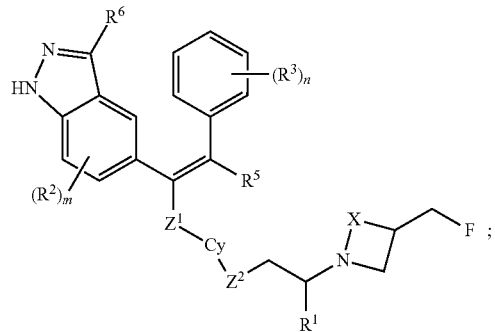

Formula (IVd)

wherein $R^6$ is H, halogen, CN, $C_1$-$C_4$alkyl or $C_3$-$C_8$carbocyclyl.

In some embodiments is a compound of Formula (IV), (IVa), (IVb), (IVc), or (IVd), wherein $Z^1$ is a bond. In some embodiments is a compound of Formula (IV), (IVa), (IVb), (IVc), or (IVd), wherein $R^5$ is —CH$_2$CH$_3$.

In some embodiments, the compound of Formula (I) has the structure of Formula (V):

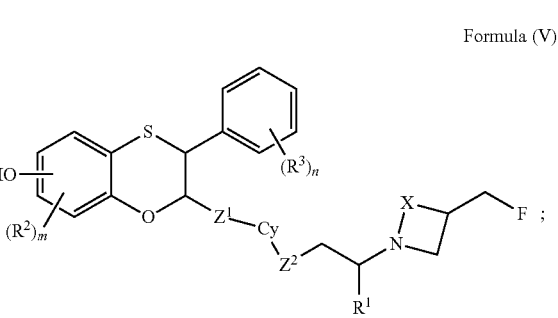

Formula (V)

wherein:

each $R^2$ and each $R^3$ are independently selected from halogen, —CN, —OR$^{10}$, —NR$^{13}$R$^{14}$, $C_1$-$C_4$alkyl, —$C_1$-$C_4$alkyl-OH, —OC$_2$-$C_4$alkyl-OH, $C_1$-$C_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;

each $R^{10}$ is independently selected from H, $C_1$-$C_4$alkyl, and $C_1$-$C_4$fluoroalkyl;

each $R^{11}$ is independently selected from $C_1$-$C_4$alkyl and $C_1$-$C_4$fluoroalkyl;

each $R^{12}$ is independently selected from H, $C_1$-$C_4$alkyl, and $C_1$-$C_4$fluoroalkyl;

each $R^{13}$ and each $R^{14}$ are independently selected from H and $C_1$-$C_4$alkyl;

m is 0, 1, 2 or 3; and n is 0, 1, 2 or 3.

In some embodiments is a compound of Formula (V), wherein $Z^1$ is a bond.

In some embodiments, the compound of Formula (I) has the structure of Formula (VI):

Formula (VI)

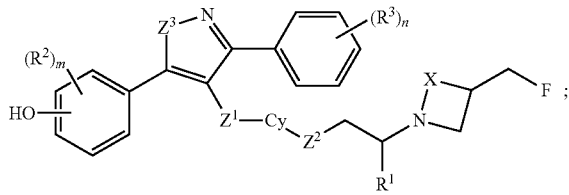

wherein:
$Z^3$ is —O—, —S—, or —N(R$^4$)—;
each R$^2$ and each R$^3$ are independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;
R$^4$ is H, C$_1$-C$_4$alkyl or C$_3$-C$_8$carbocyclyl;
each R$^{10}$ is independently selected from H, C$_1$-C$_4$alkyl, and C$_1$-C$_4$fluoroalkyl;
each R$^{11}$ is independently selected from C$_1$-C$_4$alkyl and C$_1$-C$_4$fluoroalkyl;
each R$^{12}$ is independently selected from H, C$_1$-C$_4$alkyl, and C$_1$-C$_4$fluoroalkyl;
each R$^{13}$ and each R$^{14}$ are independently selected from H and C$_1$-C$_4$alkyl;
m is 0, 1, 2 or 3; and
n is 0, 1, 2 or 3.

In some embodiments is a compound of Formula (VI), wherein $Z^1$ is a bond.

In some embodiments, the compound of Formula (I) has the structure of Formula (VII):

Formula (VII)

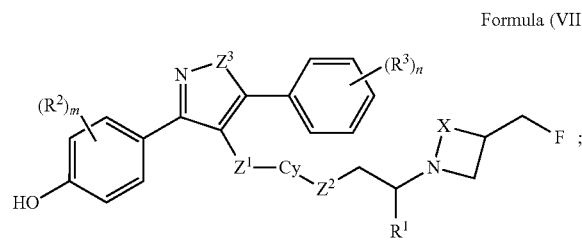

wherein:
$Z^3$ is —O—, —S—, or —N(R$^4$)—;
each R$^2$ and each R$^3$ are independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;
R$^4$ is H, C$_1$-C$_4$alkyl or C$_3$-C$_8$carbocyclyl;
each R$^{10}$ is independently selected from H, C$_1$-C$_4$alkyl, and C$_1$-C$_4$fluoroalkyl;
each R$^{11}$ is independently selected from C$_1$-C$_4$alkyl and C$_1$-C$_4$fluoroalkyl;
each R$^{12}$ is independently selected from H, C$_1$-C$_4$alkyl, and C$_1$-C$_4$fluoroalkyl;
each R$^{13}$ and each R$^{14}$ are independently selected from H and C$_1$-C$_4$alkyl;
m is 0, 1, 2 or 3; and
n is 0, 1, 2 or 3.

In some embodiments is a compound of Formula (VII), wherein $Z^1$ is —C(O)—.

In some embodiments, the compound of Formula (I) has the structure of Formula (VIII):

Formula (VIII)

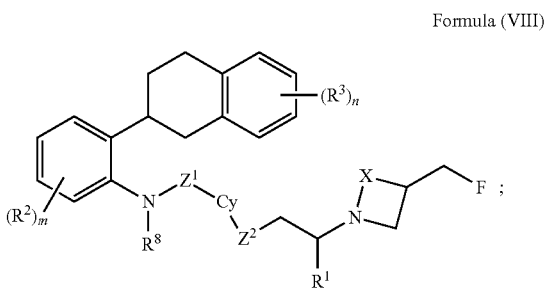

wherein:
$Z^1$ is —(CH$_2$)—;
$Z^2$ is selected from —O—, —(CH$_2$)—, —C(O)—, and a bond;
each R$^2$ and each R$^3$ are independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;
R$^8$ is selected from H and C$_1$-C$_4$alkyl;
each R$^{10}$ is independently selected from H, C$_1$-C$_4$alkyl, and C$_1$-C$_4$fluoroalkyl;
each R$^{11}$ is independently selected from C$_1$-C$_4$alkyl and C$_1$-C$_4$fluoroalkyl;
each R$^{12}$ is independently selected from H, C$_1$-C$_4$alkyl, and C$_1$-C$_4$fluoroalkyl;
each R$^{13}$ and each R$^{14}$ are independently selected from H and C$_1$-C$_4$alkyl;
m is 0, 1, 2 or 3; and
n is 0, 1, 2 or 3.

In some embodiments, the compound of Formula (I) has the structure of Formula (IX):

Formula (IX)

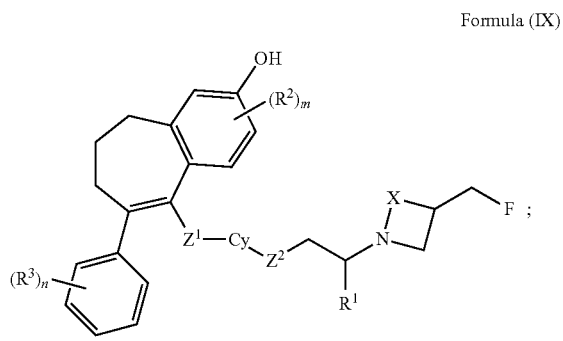

wherein:
each R$^2$ and each R$^3$ are independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;
each R$^{10}$ is independently selected from H, C$_1$-C$_4$alkyl, and C$_1$-C$_4$fluoroalkyl;
each R$^{11}$ is independently selected from C$_1$-C$_4$alkyl and C$_1$-C$_4$fluoroalkyl;
each R$^{12}$ is independently selected from H, C$_1$-C$_4$alkyl, and C$_1$-C$_4$fluoroalkyl;

each $R^{13}$ and each $R^{14}$ are independently selected from H and $C_1$-$C_4$alkyl;

m is 0, 1, 2 or 3; and n is 0, 1, 2 or 3.

In some embodiments is a compound of Formula (IX), wherein $Z^1$ is a bond.

In some embodiments, the compound of Formula (I) has the structure of Formula (X):

Formula (X)

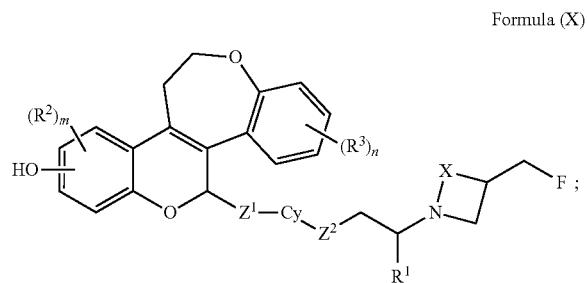

wherein:

each $R^2$ and each $R^3$ are independently selected from halogen, —CN, —$OR^{10}$, —$NR^{13}R^{14}$, $C_1$-$C_4$ alkyl, —$C_1$-$C_4$ alkyl-OH, —$OC_2$-$C_4$ alkyl-OH, $C_1$-$C_4$ fluoroalkyl, —C(=O)$OR^{12}$, —NHC(=O)$R^{11}$, —C(=O)$NHR^{12}$, —$SO_2R^{11}$, —$NHSO_2R^{11}$, and —$SO_2NHR^{12}$;

each $R^{10}$ is independently selected from H, $C_1$-$C_4$ alkyl, and $C_1$-$C_4$ fluoroalkyl;

each $R^{11}$ is independently selected from $C_1$-$C_4$ alkyl and $C_1$-$C_4$ fluoroalkyl;

each $R^{12}$ is independently selected from H, $C_1$-$C_4$ alkyl, and $C_1$-$C_4$ fluoroalkyl;

each $R^{13}$ and each $R^{14}$ are independently selected from H and $C_1$-$C_4$ alkyl;

m is 0, 1, 2 or 3; and n is 0, 1, 2 or 3.

In some embodiments is a compound of Formula (X), wherein $Z^1$ is a bond.

In some embodiments is a compound of Formula (II), (IIa), (IIb), (IIc), (III), (IIIa), (IIIb), (IIIc), (IV), (IVa), (IVb), (IVc), (IVd), (V), (VI), (VII), (VIII), (IX), or (X), wherein each $R^3$ is independently selected from halogen, —OH, —$OCH_3$, and $C_1$-$C_4$alkyl. In some embodiments is a compound of Formula (II), (IIa), (IIb), (IIc), (III), (IIIa), (IIIb), (IIIc), (IV), (IVa), (IVb), (IVc), (IVd), (V), (VI), (VII), (VIII), (IX), or (X), wherein n is 1. In some embodiments is a compound of Formula (II), (IIa), (IIb), (IIc), (III), (IIIa), (IIIb), (IIIc), (IV), (IVa), (IVb), (IVc), (IVd), (V), (VI), (VII), (VIII), (IX), or (X), wherein n is 2.

In some embodiments is a compound of Formula (II), (IIa), (IIb), (IIc), (III), (IIIa), (IIIb), (IIIc), (IV), (IVa), (IVb), (IVc), (IVd), (V), (VI), (VII), (VIII), (IX) or (X), wherein m is 0. In some embodiments is a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), wherein Cy is $C_2$-$C_9$heteroaryl. In some embodiments is a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), wherein $Z^2$ is —O—. In some embodiments is a compound of Formula (I), (IIa), (IIb), (IIc), (III), (IIIa), (IIIb), (IIIc), (IV), (IVa), (IVb), (IVc), (IVd), (V), (VI), (VII), (VIII), (IX) or (X), wherein X is —($CH_2$)—. In some embodiments is a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), wherein X is —($CH_2CH_2$)—. In some embodiments is a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), wherein $R^1$ is H. In some embodiments is a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), wherein $R^1$ is —$CH_3$.

In another aspect, described herein is a pharmaceutically acceptable salt of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X). In some embodiments, the pharmaceutically acceptable salt of the compound is an acid addition salt. In some embodiments, the pharmaceutically acceptable salt of the compound is a hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt. In some embodiments, the pharmaceutically acceptable salt of the compound is a hydrochloric acid salt. In some embodiments, the pharmaceutically acceptable salt of the compound is formed by reacting the compound with an inorganic acid. In some embodiments, the pharmaceutically acceptable salt of the compound is formed by reacting the compound with an inorganic acid, wherein the inorganic acid is hydrochloric acid, hydrobromic acid, sulfuric acid, phosphoric acid, or metaphosphoric acid. In some embodiments, the pharmaceutically acceptable salt of the compound is formed by reacting the compound with an organic acid. In some embodiments, the pharmaceutically acceptable salt of the compound is formed by reacting the compound with an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid. In some embodiments, described herein is a hydrochloride salt of a compound that has the structure of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X).

In another aspect, described herein is a prodrug of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X). In yet another aspect, described herein is a pharmaceutically acceptable salt of a prodrug of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X). In some embodiments, the pharmaceutically acceptable salt of a prodrug of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X) is a hydrochloride salt.

In yet another aspect, described herein is a pharmaceutical composition comprising a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt or prodrug thereof. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion.

Also described herein is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, in the treatment of cancer in a mammal. In some embodiments is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, in the treatment of cancer in a mammal wherein the cancer is amenable to treatment with an estrogen receptor modulator. In some embodiments is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, in the treatment of cancer in a mammal wherein the cancer is bone cancer, breast cancer, colorectal cancer, endometrial cancer, prostate cancer, ovarian cancer, uterine cancer, cervical cancer, or lung cancer.

In some embodiments, the pharmaceutical composition described herein further comprises, in addition to the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, poly ADP-ribose polymerase (PARP) inhibitors, and aromatase inhibitors.

In some embodiments, provided herein is a method comprising administering a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt or prodrug thereof, to a human with a diseases or condition that is estrogen sensitive, estrogen receptor meditated or estrogen receptor dependent. In some embodiments, the human is already being administered one or more additional therapeutically active agents other than a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt or prodrug thereof. In some embodiments, the method further comprises administering one or more additional therapeutically active agents other than a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt or prodrug thereof.

In some embodiments, the one or more additional therapeutically active agents other than a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt or prodrug thereof, are selected from: corticosteroids, anti-emetic agents, analgesics, anti-cancer agents, anti-inflammatories, kinase inhibitors, antibodies, HSP90 inhibitors, histone deacetylase (HDAC) inhibitors, and aromatase inhibitors.

Pharmaceutical formulations described herein are administered to a mammal in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is administered orally.

In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is administered systemically.

In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is administered intravenously.

In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is administered subcutaneously.

In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is administered topically. In such embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, is administered topically to the skin of mammal.

In another aspect is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, for treating a disease, disorder or conditions in which the activity of estrogen receptors contributes to the pathology and/or symptoms of the disease or condition. In one aspect, the disease or condition is any of the diseases or conditions specified herein.

In another aspect is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, in the manufacture of a medicament for treating a disease, disorder or conditions in which the activity of estrogen receptors contributes to the pathology and/or symptoms of the disease or condition. In one aspect, the disease or condition is any of the diseases or conditions specified herein.

In any of the aforementioned aspects are further embodiments in which the effective amount of the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, solvate or prodrug thereof is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of reducing ER activation in a mammal comprising administering to the mammal at least one compound having the structure of Formula (I), (II), (IIa), (IIb), (IIc), (III), (IIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof. In some embodiments, the method comprises reducing ER activation in breast cells, lung cells, ovarian cells, colon cells, prostate cells, endometrial cells, or uterine cells in the mammal. In some embodiments, the method comprises reducing ER activation in breast cells, ovarian cells, colon cells, prostate cells, endometrial cells, or uterine cells in the mammal. In some embodiments, the method of reducing ER activation in the mammal comprises reducing the binding of estrogens to estrogen receptors in the mammal. In some embodiments, the method of reducing ER activation in the mammal comprises reducing ER concentrations in the mammal.

In one aspect is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In one aspect is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, in the manufacture of a medicament for the treatment of diseases or conditions that are estrogen sensitive, estrogen receptor dependent or estrogen receptor mediated. In some embodiments, the disease or condition is bone cancer, breast cancer, colorectal cancer, endometrial cancer, prostate cancer, ovarian cancer, uterine cancer, cervical cancer, or lung cancer. In some embodiments, the disease or condition is described herein.

In some cases disclosed herein is the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, in the treatment or prevention of diseases or conditions that are estrogen sensitive, estrogen receptor dependent or estrogen receptor mediated. In some embodiments, the disease or condition is described herein.

In any of the embodiments disclosed herein, the mammal is a human.

In some embodiments, compounds provided herein are used to diminish, reduce, or eliminate the activity of estrogen receptors.

Articles of manufacture, which include: packaging material; a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineral corticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, Biofactors 35: 528-536, 2009). One of the involved phosphorylation sites (S118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for disease or conditions that estrogen-sensitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (FASLODEX®), a steroid-based ER antagonist, is used to treat breast cancer in women which have progressed despite therapy with tamoxifen. Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplication of the ERB-B/HER2 tyrosine kinase receptor are treated with the monoclonal antibody trastuzumab (Herceptin™) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance. In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies.

Given the central role of ER-α in breast cancer development and progression, compounds disclosed herein are useful in the treatment of breast cancer, either alone or in combination with other agent agents that can modulate other critical pathways in breast cancer, including but not limited to those that target IGF 1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agent used to treat breast cancer, including but not limited to aromatase inhibitors, anthracylines, platins, nitrogen mustard alkylating agents, taxanes. Illustrative agent used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

ER-related diseases or conditions include ER-α dysfunction is associated with cancer (e.g. bone cancer, breast cancer, colorectal cancer, endometrial cancer, prostate cancer, ovarian cancer, uterine cancer, cervical cancer, and lung cancer).

In some embodiments, compounds disclosed herein are used in the treatment of an estrogen receptor dependent or estrogen receptor mediated disease or condition in mammal.

In some embodiments, the estrogen receptor dependent or estrogen receptor mediated disease or condition is cancer.

In some embodiments, the estrogen receptor dependent or estrogen receptor mediated disease or condition is selected from bone cancer, breast cancer, colorectal cancer, endometrial cancer, prostate cancer, ovarian cancer, uterine cancer, cervical cancer, and lung cancer.

In some embodiments, compounds disclosed herein are used to treat cancer in a mammal. In some embodiments, the cancer is bone cancer, breast cancer, colorectal cancer, endometrial cancer, prostate cancer, ovarian cancer, uterine cancer, cervical cancer, or lung cancer. In some embodiments, the cancer is breast cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, the compound used in any of the methods described herein is an estrogen receptor degrader; is an estrogen receptor antagonist; has minimal or negligible estrogen receptor agonist activity; or combinations thereof.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-naïve.

In some embodiments, compounds disclosed herein are used in the treatment of cancer in a mammal. In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In some embodiments, compounds disclosed herein are used in the treatment of endometriosis in a mammal.

In some embodiments, compounds disclosed herein are used in the treatment of leiomyoma in a mammal. In some embodiments, the leiomyoma is a uterine leiomyoma, esophageal leiomyoma, cutaneous leiomyoma, or small bowel leiomyoma. In some embodiments, compounds disclosed herein are used in the treatment of fibroids in a mammal.

In some embodiments, compounds disclosed herein are used in the treatment of uterine fibroids in a mammal.

Compounds

The compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX), and (X), including pharmaceutically acceptable salts, prodrugs, active metabolites and pharmaceutically acceptable solvates thereof, are estrogen receptor modulators. In specific embodiments, the compound is estrogen receptor degrader. In specific embodiments, the compound is an estrogen receptor antagonist. In specific embodiments, the compound is an estrogen receptor degrader and estrogen receptor antagonist with minimal or no estrogen receptor agonist activity.

In some embodiments, compounds disclosed herein are estrogen receptor degraders and estrogen receptor antagonists that exhibit: no estrogen receptor agonism; and/or anti-proliferative activity against breast cancer, ovarian cancer, endometrial cancer, cervical cancer cell lines; and/or maximal anti-proliferative efficacy against breast cancer, ovarian cancer, endometrial cancer, cervical cell lines in-vitro; and/or minimal agonism in the human endometrial (Ishikawa) cell line; and/or no agonism in the human endometrial (Ishikawa) cell line; and/or no agonism in the immature rat uterine assay in-vivo; and/or inverse agonism in the immature rat uterine assay in-vivo; and/or anti-tumor activity in breast cancer, ovarian cancer, endometrial cancer, cervical cancer cell lines in xenograft assays in-vivo or other rodent models of these cancers.

In some embodiments, compounds described herein have reduced or minimal interaction with the hERG (the human Ether-á-go-go-Related Gene) channel and/or show a reduced potential for QT prolongation and/or a reduced risk of ventricular tachyarrhythmias like torsades de pointes.

In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), has reduced or minimal potential to access the hypothalamus and/or have reduced or minimal potential to modulate the Hypothalamic-Pituitary-Ovarian (HPO) axis and/or show a reduced potential to cause hyper-stimulation of the ovaries and/or show a reduced potential for ovary toxicity.

In some embodiments, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), for use in the treatment of a disease or condition in a pre-menopausal woman have reduced or minimal potential to access the hypothalamus and/or have reduced or minimal potential to modulate the Hypothalamic-Pituitary-Ovarian (HPO) axis and/or show a reduced potential to cause hyper-stimulation of the ovaries and/or show a reduced potential for ovary toxicity. In some embodiments, the disease or condition in the pre-menopausal woman is endometriosis. In some embodiments, the disease or condition in the pre-menopausal woman is an uterine disease or condition.

In one aspect, described herein is a compound of Formula (I), or a pharmaceutically acceptable salt, solvate or prodrug thereof:

Formula (I)

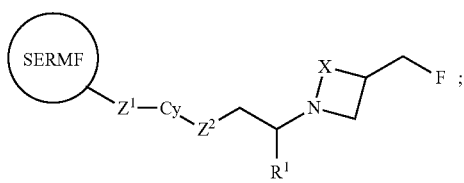

wherein:

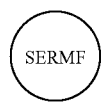

is a selective estrogen receptor modulator fragment;

$Z^1$ and $Z^2$ are independently selected from —O—, —(CH$_2$)—, —C(O)—, or a bond;

Cy is $C_6$-$C_{20}$aryl, $C_3$-$C_{12}$carbocyclyl, $C_2$-$C_{20}$heterocyclyl, or $C_1$-$C_{20}$heteroaryl;

X is —(CH$_2$)— or —(CH$_2$CH$_2$)—; and $R^1$ is selected from H, F, Cl, —CN, —CH$_2$OH, —CH(CH$_3$)OH, —C(CH$_3$)$_2$OH, —CH(CF$_3$)OH, —CH$_2$F, —CHF$_2$, —CH$_2$CHF$_2$, —CF$_3$, —CH$_3$, —C(O)NH$_2$, —C(O)NHCH$_3$, and —C(O)N(CH$_3$)$_2$;

where carbocyclyl, heterocyclyl, aryl, and heteroaryl are optionally substituted with one or more groups independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OCF$_3$, —OCHF$_2$, —OP(O)(OH)$_2$, —S(O)$_2$N(CH$_3$)$_2$, —SCH$_3$, —S(O)$_2$CH$_3$, —S(O)$_3$H, cyclopropyl, oxetanyl, azetidinyl, 1-methylazetidin-3-yl)oxy, N-methyl-N-oxetan-3-ylamino, azetidin-1-ylmethyl, pyrrolidin-1-yl, and morpholino;

or a pharmaceutically acceptable salt, solvate or prodrug thereof.

In some embodiments, the compound of Formula (I) has one of the following structures:

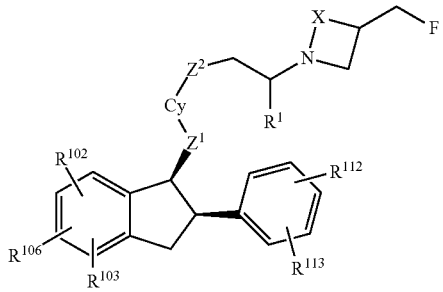

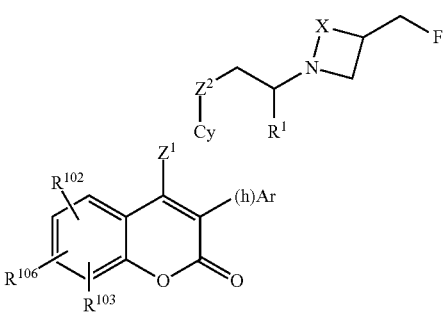

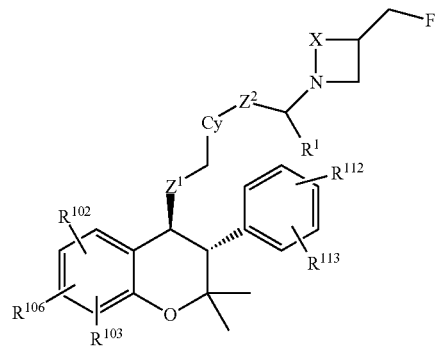

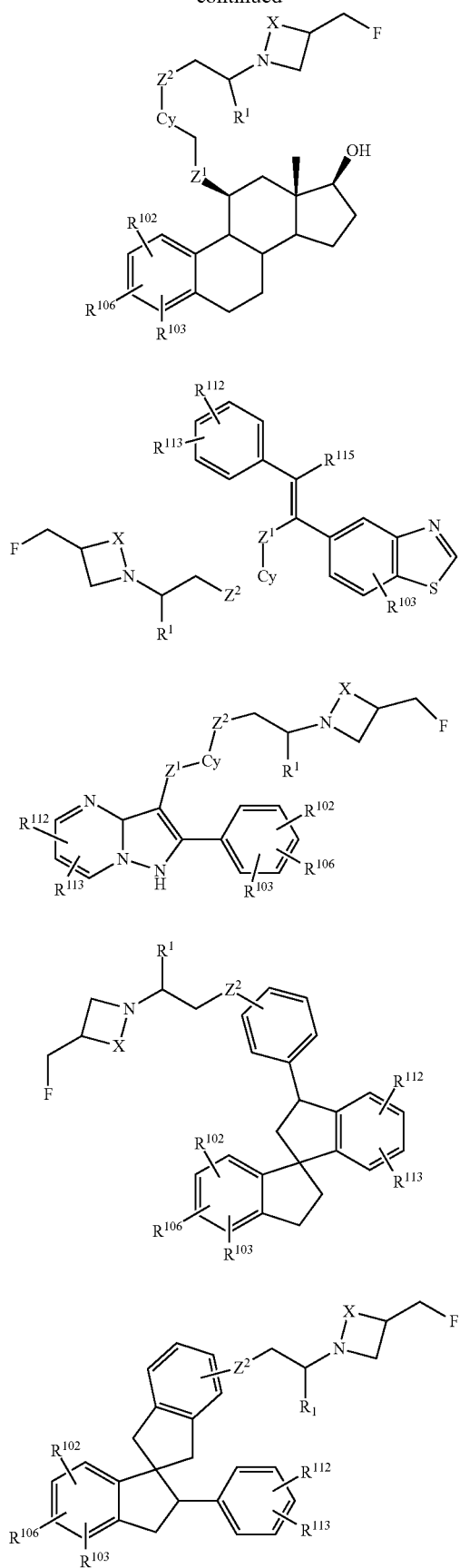
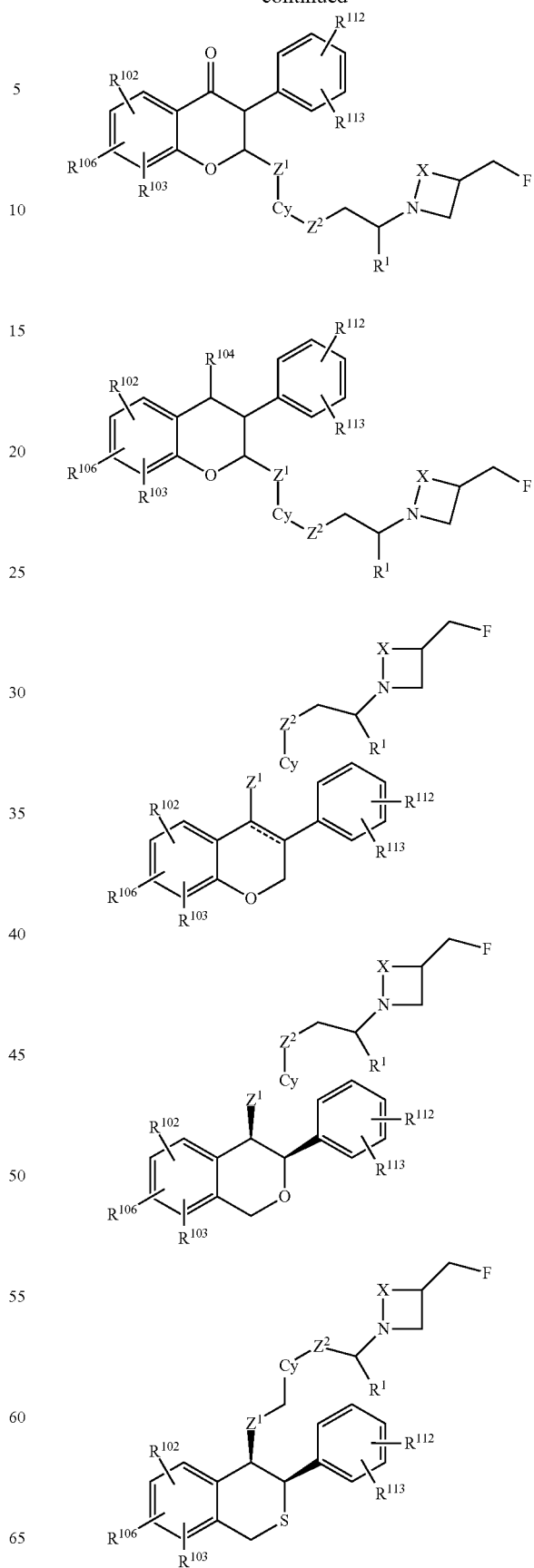

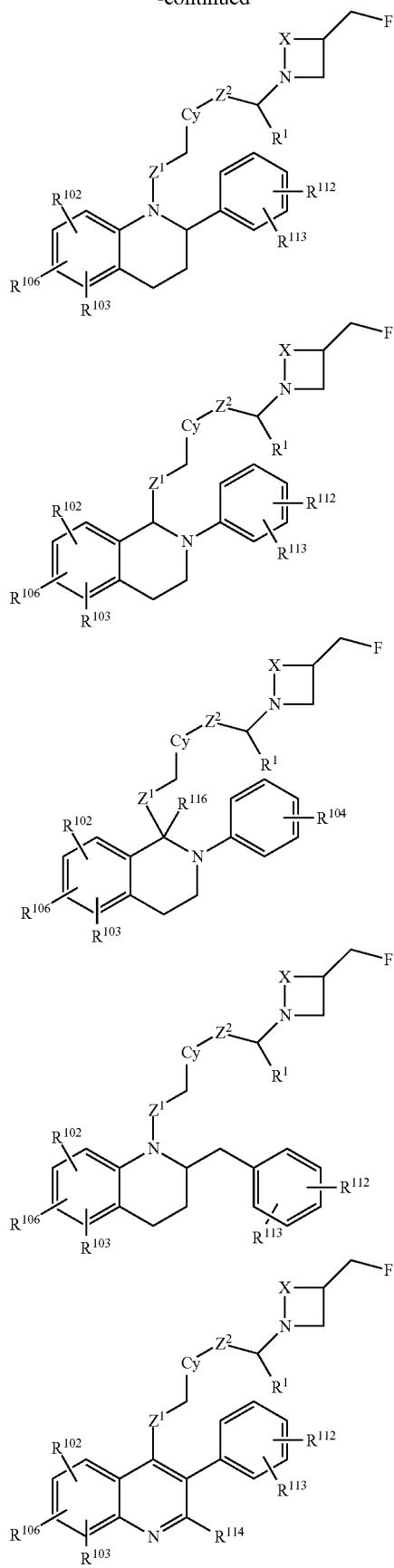
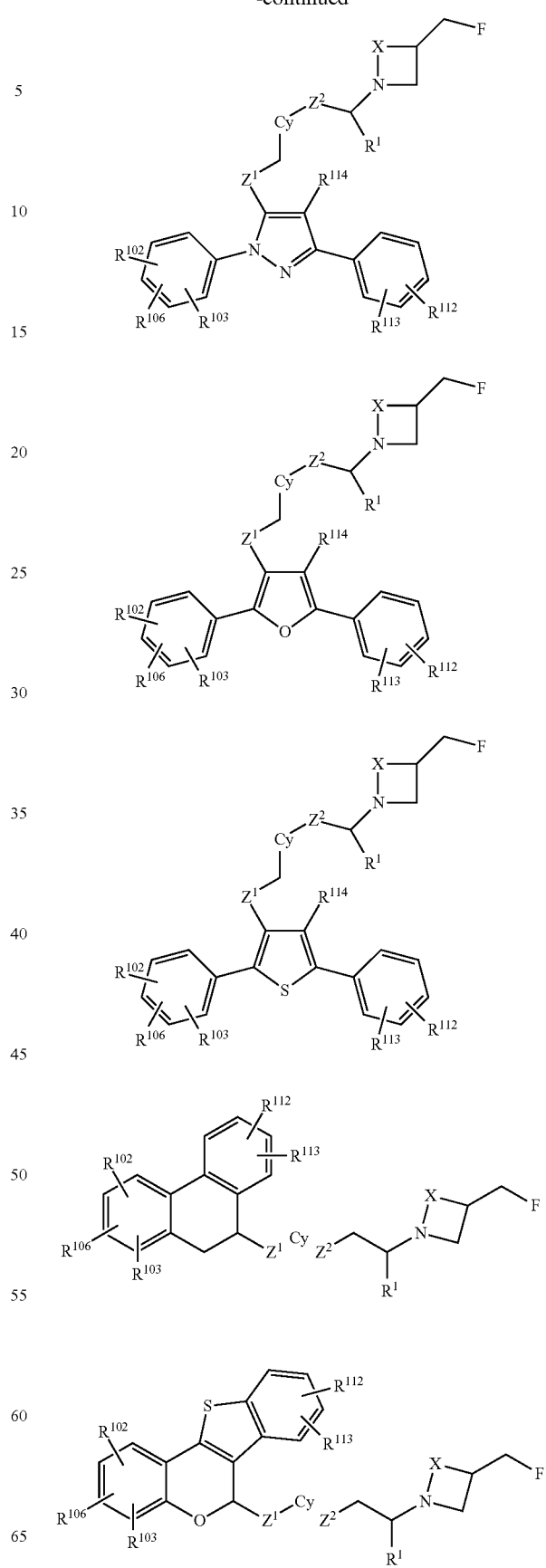

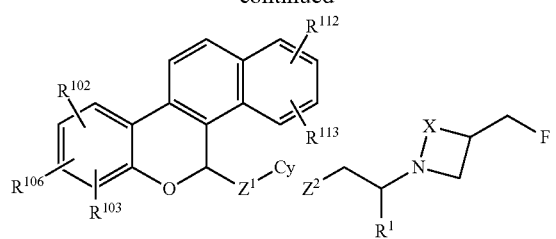
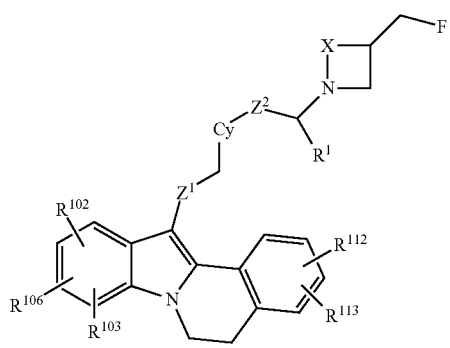
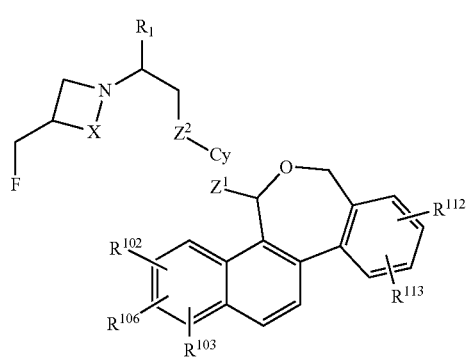
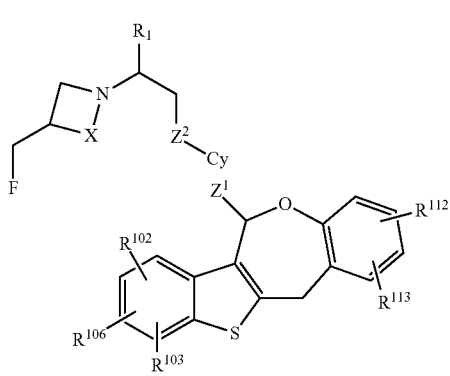
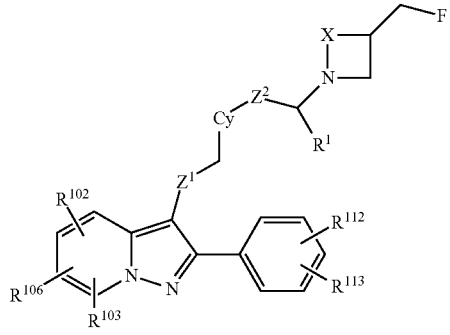
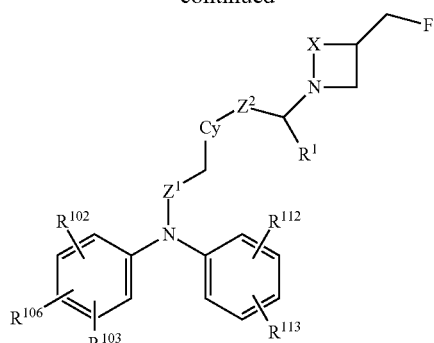
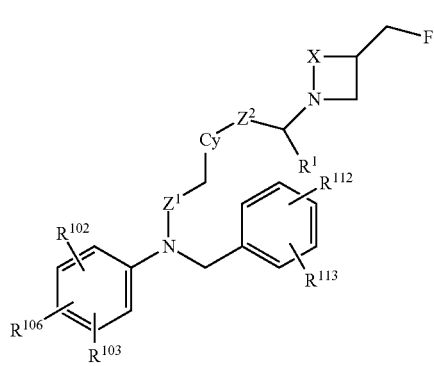
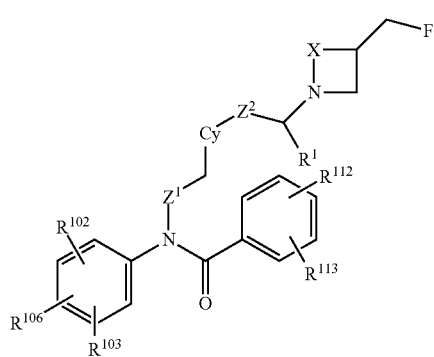
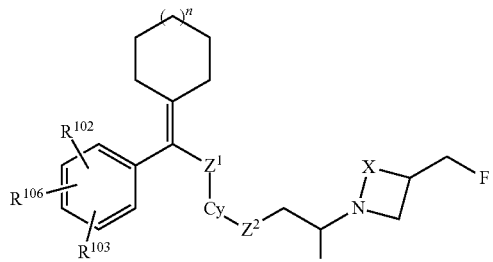
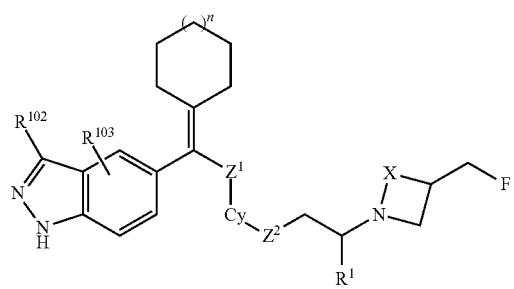

-continued

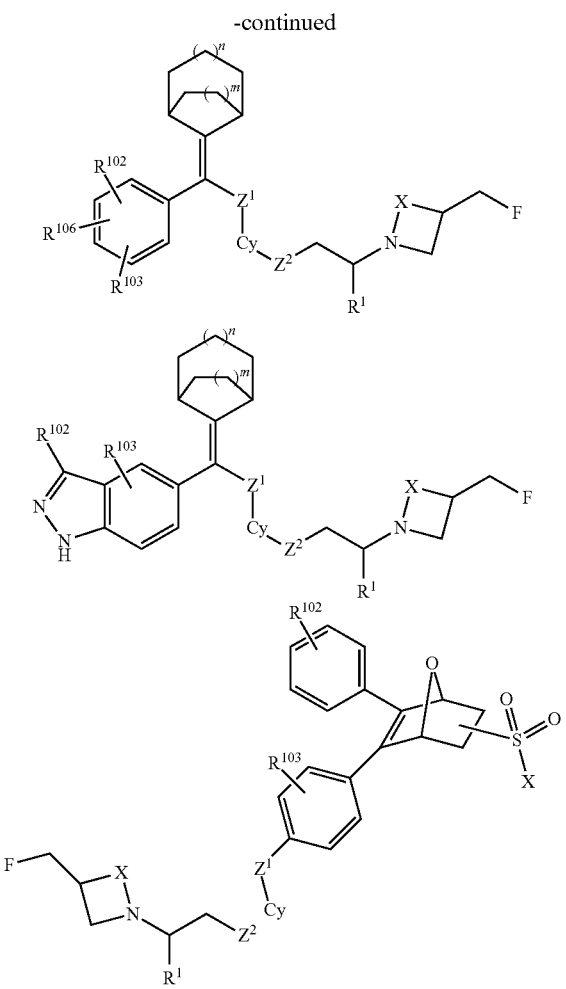

wherein:
R$^1$ is H, F, Cl, —CN, —CH$_2$OH, —CH(CH$_3$)OH, —C(CH$_3$)$_2$OH, —CH(CF$_3$)OH, —CH$_2$F, —CHF$_2$, —CH$_2$CHF$_2$, —CF$_3$, —CH$_3$, —C(O)NH$_2$, —C(O)NHCH$_3$, and —C(O)N(CH$_3$)$_2$;

(h)Ar is a (hetero)aromatic ring, optionally substituted with R$^{112}$ and R$^{113}$;

Z$^1$ and Z$^2$ are independently selected from —O—, —(CH$_2$)—, —C(O)—, or a bond;

Cy is C$_6$-C$_{20}$aryl, C$_3$-C$_{12}$carbocyclyl, C$_2$-C$_{20}$heterocyclyl, or C$_1$-C$_{20}$heteroaryl;

X is —(CH$_2$)— or —(CH$_2$CH$_2$)—;

R$^{102}$ and R$^{103}$ are independently selected from H, F, Cl, C$_1$-C$_3$alkyl, C$_1$-C$_3$alkoxy, C$_1$-C$_3$alkylthio, —CF$_3$ or —CN;

R$^{104}$ and R$^{107}$ are independently selected from H, fluorine, chlorine, C$_1$-C$_2$alkyl, —CF$_3$, or —CN;

R$^{112}$ is H, fluorine, chlorine, C$_1$-C$_2$alkyl, C$_1$-C$_2$alkoxy, —CN or hydroxyl;

R$^{113}$ is H, fluorine, chlorine, C$_1$-C$_3$alkyl, C$_1$-C$_3$alkoxy, C$_1$-C$_3$alkylthio, —CF$_3$ or —CN;

R$^{106}$ is H, hydroxyl, amine or C$_1$-C$_6$alkoxy;

R$^{106}$ and R$^{102}$ may be linked to form a (hetero)aromatic ring which is optionally substituted with fluorine, chlorine or C$_1$-C$_3$alkyl;

R$^{114}$ is H, halogen, nitro, nitrile or C$_1$-C$_6$alkyl, C$_1$-C$_6$cycloalkyl, optionally substituted with one or more halogen;

R$^{116}$ is H, C$_1$-C$_4$alkyl, C$_1$-C$_4$alkenyl, optionally substituted with one or more halogen;

m is 0, 1, 2 or 3; and n is 0, 1, 2 or 3;

or a pharmaceutically acceptable salt thereof.

In some embodiments is a compound of Formula (I) wherein Z$^1$ is a bond. In some embodiments is a compound of Formula (I) wherein Z$^1$ is —O—. In some embodiments is a compound of Formula (I) wherein Z$^1$ is —(CH$_2$)—. In some embodiments is a compound of Formula (I) wherein Z$^1$ is —C(O)—. In some embodiments is a compound of Formula (I) wherein Z$^2$ is a bond. In some embodiments is a compound of Formula (I) wherein Z$^2$ is —O—. In some embodiments is a compound of Formula (I) wherein Z$^2$ is —(CH$_2$)—. In some embodiments is a compound of Formula (I) wherein Z$^2$ is —C(O)—. In some embodiments is a compound of Formula (I) wherein Cy is C$_6$-C$_{20}$aryl. In some embodiments is a compound of Formula (I) wherein Cy is phenyl. In some embodiments is a compound of Formula (I) wherein Cy is C$_3$-C$_{12}$carbocyclyl. In some embodiments is a compound of Formula (I) wherein Cy is cyclohexyl. In some embodiments is a compound of Formula (I) wherein Cy is C$_2$-C$_{20}$heterocyclyl. In some embodiments is a compound of Formula (I) wherein Cy is pyrazinyl. In some embodiments is a compound of Formula (I) wherein Cy is piperidinyl. In some embodiments is a compound of Formula (I) wherein Cy is C$_1$-C$_{20}$heteroaryl. In some embodiments is a compound of Formula (I) wherein Cy is thiazolyl. In some embodiments is a compound of Formula (I) wherein Cy is oxazolyl. In some embodiments is a compound of Formula (I) wherein Cy is pyridyl. In some embodiments is a compound of Formula (I) wherein R$^1$ is H. In some embodiments is a compound of Formula (I) wherein R$^1$ is —CH$_3$. In some embodiments is a compound of Formula (I) wherein X is —(CH$_2$)—. In some embodiments is a compound of Formula (I) wherein X is —(CH$_2$)— and R$^1$ is H. In some embodiments is a compound of Formula (I) wherein X is —(CH$_2$CH$_2$)—. In some embodiments is a compound of Formula (I) wherein X is —(CH$_2$CH$_2$)— and R$^1$ is H. In some embodiments is a compound of Formula (I) wherein X is —(CH$_2$CH$_2$)— and R$^1$ is —CH$_3$.

In some embodiments is a compound of Formula (I) wherein Z$^1$ is a bond, Z$^2$ is —O—, Cy is phenyl, X is —(CH$_2$)—, and R$^1$ is H. In some embodiments is a compound of Formula (I) wherein Z$^1$ is a bond, Z$^2$ is —O—, Cy is phenyl, X is —(CH$_2$CH$_2$)—, and R$^1$ is H. In some embodiments is a compound of Formula (I) wherein Z$^1$ is a bond, Z$^2$ is —O—, Cy is phenyl, X is —(CH$_2$CH$_2$)—, and R$^1$ is —CH$_3$.

In some embodiments, the compound of Formula (I) has the following structure of Formula (II):

Formula (II)

wherein:
===== indicates a single or double bond where one ===== is a double bond and one ===== is a single bond;

$Y^1$ is $CR^6$ and $Y^2$ is N; $Y^1$ is S and $Y^2$ is C; or $Y^1$ is $NR^7$ and $Y^2$ is C;

each $R^2$ and each $R^3$ are independently selected from halogen, —CN, —$OR^{10}$, —$NR^{13}R^{14}$, $C_1$-$C_4$alkyl, —$C_1$-$C_4$alkyl-OH, —$OC_2$-$C_4$alkyl-OH, $C_1$-$C_4$fluoroalkyl, —C(=O)$OR^{12}$, —NHC(=O)$R^{11}$, —C(=O)$NHR^{12}$, —$SO_2R^{11}$, —$NHSO_2R^{11}$, and —$SO_2NHR^{12}$;

$R^6$ is selected from H, halogen, $C_1$-$C_6$alkyl, $C_1$-$C_6$fluoroalkyl, $C_3$-$C_{12}$carbocyclyl, —($C_1$-$C_6$alkyl)-($C_3$-$C_{12}$carbocyclyl), $C_2$-$C_{20}$heterocyclyl, —($C_1$-$C_6$alkyl)-($C_2$-$C_{20}$heterocyclyl), —$SO_2R^{11}$, —($C_1$-$C_6$alkyl)-($C_1$-$C_{20}$heteroaryl), $C_1$-$C_{20}$heteroaryl, and $C_6$-$C_{20}$aryl;

$R^7$ is selected from H and $C_1$-$C_4$alkyl;

each $R^{10}$ is independently selected from H, $C_1$-$C_4$alkyl, and $C_1$-$C_4$fluoroalkyl;

each $R^{11}$ is independently selected from $C_1$-$C_4$alkyl and $C_1$-$C_4$fluoroalkyl;

each $R^{12}$ is independently selected from H, $C_1$-$C_4$alkyl, and $C_1$-$C_4$fluoroalkyl;

each $R^{13}$ and each $R^{14}$ are independently selected from H and $C_1$-$C_4$alkyl;

m is 0, 1, 2 or 3; and n is 0, 1, 2 or 3;

or a pharmaceutically acceptable salt, solvate or prodrug thereof.

In some embodiments, the compound of Formula (II) has the following structure of Formula (IIa):

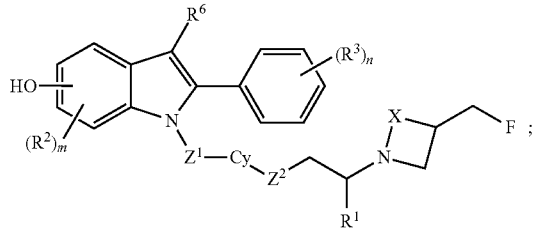

Formula (IIa)

or a pharmaceutically acceptable salt, solvate or prodrug thereof.

In some embodiments is a compound of Formula (IIa) wherein n is 1.

In some embodiments is a compound of Formula (IIa) wherein n is 1 having one of the following structures:

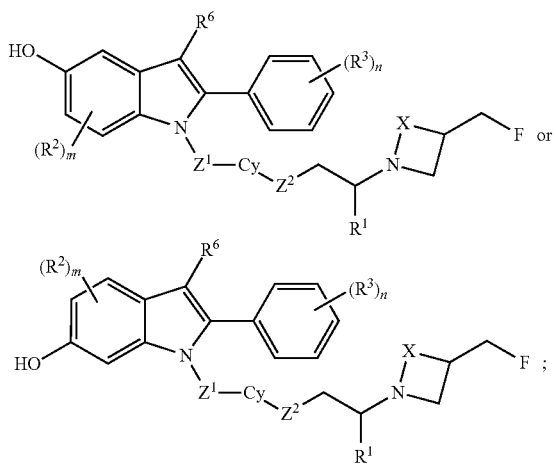

or a pharmaceutically acceptable salt, solvate or prodrug thereof.

In some embodiments is a compound of Formula (IIa) wherein n is 1 and $R^3$ is selected from the group consisting of F, Cl, —CN, —$CH_2OH$, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (IIa) wherein n is 1 and $R^3$ is selected from the group consisting of F, Cl, —CN, —OH, —$CH_3$, and —$SO_2CH_3$. In some embodiments is a compound of Formula (IIa) wherein n is 1 and $R^3$ is F. In some embodiments is a compound of Formula (IIa) wherein n is 1 and $R^3$ is —OH. In some embodiments is a compound of Formula (IIa) wherein n is 1 and $R^3$ is Cl. In some embodiments is a compound of Formula (IIa) wherein n is 1 and $R^3$ is —CN. In some embodiments is a compound of Formula (IIa) wherein n is 1 and $R^3$ is —$CH_3$. In some embodiments is a compound of Formula (IIa) wherein n is 1 and $R^3$ is —$SO_2CH_3$.

In some embodiments is a compound of Formula (IIa) wherein n is 2. In some embodiments is a compound of Formula (IIa) wherein n is 2 and each $R^3$ is independently selected from the group consisting of F, Cl, —CN, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (IIa) wherein n is 2 and each $R^3$ is independently selected from the group consisting of F, Cl, —CN, —OH, —$CH_3$, and —$SO_2CH_3$. In some embodiments is a compound of Formula (IIa) wherein n is 2 and each $R^3$ is independently selected from the group consisting of F and Cl. In some embodiments is a compound of Formula (IIa) wherein n is 2 and each $R^3$ is independently selected from the group consisting of F and —CN. In some embodiments is a compound of Formula (IIa) wherein n is 2 and each $R^3$ is F.

In some embodiments is a compound of Formula (IIa) wherein n is 3. In some embodiments is a compound of Formula (IIa) wherein n is 3 and each $R^3$ is independently selected from the group consisting of F, Cl, —CN, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (IIa) wherein n is 3 and each $R^3$ is independently selected from the group consisting of F, Cl, —CN, —OH, —$CH_3$, and —$SO_2CH_3$. In some embodiments is a compound of Formula (IIa) wherein n is 3 and each $R^3$ is independently selected from the group consisting of F and Cl. In some embodiments is a compound of Formula (IIa) wherein n is 3 and each $R^3$ is independently selected from the group consisting of F and —CN. In some embodiments is a compound of Formula (IIa) wherein n is 3 and each $R^3$ is F.

In some of the aforementioned embodiments is a compound of Formula (IIa) wherein $R^6$ is H. In some of the aforementioned embodiments is a compound of Formula (IIa) wherein $R^6$ is halogen. In some of the aforementioned embodiments is a compound of Formula (IIa) wherein $R^6$ is Cl. In some of the aforementioned embodiments is a compound of Formula (IIa) wherein $R^6$ is $C_1$-$C_4$alkyl. In some of the aforementioned embodiments is a compound of Formula (IIa) wherein $R^6$ is —$CH_3$. In some of the aforementioned embodiments is a compound of Formula (IIa) wherein $R^6$ is —$CH_2CH_3$. In some of the aforementioned embodiments is a compound of Formula (IIa) wherein m is 0. In some of the aforementioned embodiments is a compound of Formula (IIa) wherein m is 1. In some of the aforementioned embodiments is a compound of Formula (IIa) wherein m is 1 and $R^2$ is halogen. In some of the aforementioned embodiments is a compound of Formula (IIa) wherein m is 1 and $R^2$ is F. In some of the aforementioned embodiments is a compound of Formula (IIa) wherein m is 1 and $R^2$ is Cl. In some of the aforementioned embodiments is a compound of Formula (IIa) wherein m is 1 and $R^2$ is $C_1$-$C_4$alkyl. In some of the aforementioned embodiments is a compound of Formula (IIa) wherein m is 1 and $R^2$ is —$CH_3$.

In some of the aforementioned embodiments is a compound of Formula (IIa) wherein $Z^1$ is a bond. In some of the aforementioned embodiments is a compound of Formula (IIa) wherein $Z^1$ is —O—. In some of the aforementioned embodiments is a compound of Formula (IIa) wherein $Z^1$ is —($CH_2$)—. In some embodiments is a compound of Formula (IIa) wherein $Z^1$ is —C(O)—. In some of the aforementioned embodiments is a compound of Formula (IIa) wherein $Z^2$ is a bond. In some of the aforementioned embodiments is a compound of Formula (IIa) wherein $Z^2$ is —O—. In some of the aforementioned embodiments is a compound of Formula (IIa) wherein $Z^2$ is —($CH_2$)—. In some of the aforementioned embodiments is a compound of Formula (IIa) wherein $Z^2$ is —C(O)—. In some of the aforementioned embodiments is a compound of Formula (IIa) wherein Cy is $C_6$-$C_{20}$aryl. In some of the aforementioned embodiments is a compound of Formula (IIa) wherein Cy is phenyl. In some of the aforementioned embodiments is a compound of Formula (IIa) wherein Cy is $C_3$-$C_{12}$-carbocyclyl. In some of the aforementioned embodiments is a compound of Formula (IIa) wherein Cy is cyclohexyl. In some of the aforementioned embodiments is a compound of Formula (IIa) wherein Cy is $C_2$-$C_{20}$heterocyclyl. In some of the aforementioned embodiments is a compound of Formula (IIa) wherein Cy is pyrazinyl. In some of the aforementioned embodiments is a compound of Formula (IIa) wherein Cy is piperidinyl. In some of the aforementioned embodiments is a compound of Formula (IIa) wherein Cy is $C_1$-$C_{20}$heteroaryl. In some of the aforementioned embodiments is a compound of Formula (IIa) wherein Cy is thiazolyl. In some of the aforementioned embodiments is a compound of Formula (IIa) wherein Cy is oxazolyl. In some of the aforementioned embodiments is a compound of Formula (IIa) wherein Cy is pyridyl. In some of the aforementioned embodiments is a compound of Formula (IIa) wherein $R^1$ is H. In some of the aforementioned embodiments is a compound of Formula (IIa) wherein $R^1$ is —$CH_3$. In some of the aforementioned embodiments is a compound of Formula (IIa) wherein X is —($CH_2$)—. In some of the aforementioned embodiments is a compound of Formula (IIa) wherein X is —($CH_2$)— and $R^1$ is H. In some of the aforementioned embodiments is a compound of Formula (IIa) wherein X is —($CH_2CH_2$)—. In some of the aforementioned embodiments is a compound of Formula (IIa) wherein X is —($CH_2CH_2$)— and $R^1$ is H. In some of the aforementioned embodiments is a compound of Formula (IIa) wherein X is —($CH_2CH_2$)— and $R^1$ is —$CH_3$.

In some of the aforementioned embodiments is a compound of Formula (IIa) wherein $Z^1$ is a bond, $Z^2$ is —O—, Cy is phenyl, X is —($CH_2$)—, and $R^1$ is H. In some of the aforementioned embodiments is a compound of Formula (IIa) wherein $Z^1$ is a bond, $Z^2$ is —O—, Cy is phenyl, X is —($CH_2CH_2$)—, and $R^1$ is H. In some of the aforementioned embodiments is a compound of Formula (IIa) wherein $Z^1$ is a bond, $Z^2$ is —O—, Cy is phenyl, X is —($CH_2CH_2$)—, and $R^1$ is —$CH_3$.

In some embodiments, the compound of Formula (II) has the following structure of Formula (IIb):

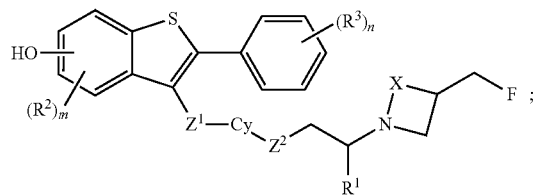

Formula (IIb)

or a pharmaceutically acceptable salt, solvate or prodrug thereof.

In some embodiments is a compound of Formula (IIb) wherein n is 1.

In some embodiments is a compound of Formula (IIb) wherein n is 1 having one of the following structures:

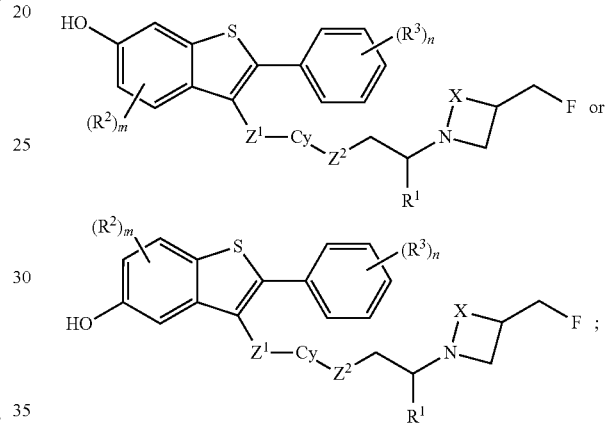

or a pharmaceutically acceptable salt, solvate or prodrug thereof.

In some embodiments is a compound of Formula (IIb) wherein n is 1 and $R^3$ is selected from the group consisting of F, Cl, —CN, —$CH_2OH$, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (IIb) wherein n is 1 and $R^3$ is selected from the group consisting of F, Cl, —CN, —OH, —$CH_3$, and —$SO_2CH_3$. In some embodiments is a compound of Formula (IIb) wherein n is 1 and $R^3$ is F. In some embodiments is a compound of Formula (IIb) wherein n is 1 and $R^3$ is —OH. In some embodiments is a compound of Formula (IIb) wherein n is 1 and $R^3$ is Cl. In some embodiments is a compound of Formula (IIb) wherein n is 1 and $R^3$ is —CN. In some embodiments is a compound of Formula (IIb) wherein n is 1 and $R^3$ is —$CH_3$. In some embodiments is a compound of Formula (IIb) wherein n is 1 and $R^3$ is —$SO_2CH_3$.

In some embodiments is a compound of Formula (IIb) wherein n is 2. In some embodiments is a compound of Formula (IIb) wherein n is 2 and each $R^3$ is independently selected from the group consisting of F, Cl, —CN, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (IIb) wherein n is 2 and each $R^3$ is independently selected from the group consisting of F, Cl, —CN, —OH, —$CH_3$, and —$SO_2CH_3$. In some embodiments is a compound of Formula (IIb) wherein n is 2 and each $R^3$ is independently selected from the group consisting of F and Cl. In some embodiments is a compound of Formula (IIb) wherein n is 2 and each $R^3$ is independently selected from the group consisting of F and —CN. In some embodiments is a compound of Formula (IIb) wherein n is 2 and each $R^3$ is F.

In some embodiments is a compound of Formula (IIb) wherein n is 3. In some embodiments is a compound of Formula (IIb) wherein n is 3 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIb) wherein n is 3 and each $R^3$ is independently selected from the group consisting of F, Cl, —CN, —OH, —CH$_3$, and —SO$_2$CH$_3$. In some embodiments is a compound of Formula (IIb) wherein n is 3 and each $R^3$ is independently selected from the group consisting of F and Cl. In some embodiments is a compound of Formula (IIb) wherein n is 3 and each $R^3$ is independently selected from the group consisting of F and —CN. In some embodiments is a compound of Formula (IIb) wherein n is 3 and each $R^3$ is F.

In some of the aforementioned embodiments is a compound of Formula (IIb) wherein m is 0. In some of the aforementioned embodiments is a compound of Formula (IIb) wherein m is 1. In some of the aforementioned embodiments is a compound of Formula (IIb) wherein m is 1 and $R^2$ is halogen. In some of the aforementioned embodiments is a compound of Formula (IIb) wherein m is 1 and $R^2$ is F. In some of the aforementioned embodiments is a compound of Formula (IIb) wherein m is 1 and $R^2$ is Cl. In some of the aforementioned embodiments is a compound of Formula (IIb) wherein m is 1 and $R^2$ is $C_1$-$C_4$alkyl. In some of the aforementioned embodiments is a compound of Formula (IIb) wherein m is 1 and $R^2$ is —CH$_3$.

In some of the aforementioned embodiments is a compound of Formula (IIb) wherein $Z^1$ is a bond. In some of the aforementioned embodiments is a compound of Formula (IIb) wherein $Z^1$ is —O—. In some of the aforementioned embodiments is a compound of Formula (IIb) wherein $Z^1$ is —(CH$_2$)—. In some embodiments is a compound of Formula (IIb) wherein $Z^1$ is —C(O)—. In some of the aforementioned embodiments is a compound of Formula (IIb) wherein $Z^2$ is a bond. In some of the aforementioned embodiments is a compound of Formula (IIb) wherein $Z^2$ is —O—. In some of the aforementioned embodiments is a compound of Formula (IIb) wherein $Z^2$ is —(CH$_2$)—. In some of the aforementioned embodiments is a compound of Formula (IIb) wherein $Z^2$ is —C(O)—. In some of the aforementioned embodiments is a compound of Formula (IIb) wherein Cy is $C_6$-$C_{20}$aryl. In some of the aforementioned embodiments is a compound of Formula (IIb) wherein Cy is phenyl. In some of the aforementioned embodiments is a compound of Formula (IIb) wherein Cy is $C_3$-$C_{12}$carbocyclyl. In some of the aforementioned embodiments is a compound of Formula (IIb) wherein Cy is cyclohexyl. In some of the aforementioned embodiments is a compound of Formula (IIb) wherein Cy is $C_2$-$C_{20}$heterocyclyl. In some of the aforementioned embodiments is a compound of Formula (IIb) wherein Cy is pyrazinyl. In some of the aforementioned embodiments is a compound of Formula (IIb) wherein Cy is piperidinyl. In some of the aforementioned embodiments is a compound of Formula (IIb) wherein Cy is $C_1$-$C_{20}$heteroaryl. In some of the aforementioned embodiments is a compound of Formula (IIb) wherein Cy is thiazolyl. In some of the aforementioned embodiments is a compound of Formula (IIb) wherein Cy is oxazolyl. In some of the aforementioned embodiments is a compound of Formula (IIb) wherein Cy is pyridyl. In some of the aforementioned embodiments is a compound of Formula (IIb) wherein $R^1$ is H. In some of the aforementioned embodiments is a compound of Formula (IIb) wherein $R^1$ is —CH$_3$. In some of the aforementioned embodiments is a compound of Formula (IIb) wherein X is —(CH$_2$)—. In some of the aforementioned embodiments is a compound of Formula (IIb) wherein X is —(CH$_2$)— and $R^1$ is H. In some of the aforementioned embodiments is a compound of Formula (IIb) wherein X is —(CH$_2$CH$_2$)—. In some of the aforementioned embodiments is a compound of Formula (IIb) wherein X is —(CH$_2$CH$_2$)— and $R^1$ is H. In some of the aforementioned embodiments is a compound of Formula (IIb) wherein X is —(CH$_2$CH$_2$)— and $R^1$ is —CH$_3$.

In some of the aforementioned embodiments is a compound of Formula (IIb) wherein $Z^1$ is a bond, $Z^2$ is —O—, Cy is phenyl, X is —(CH$_2$)—, and $R^1$ is H. In some of the aforementioned embodiments is a compound of Formula (IIb) wherein $Z^1$ is a bond, $Z^2$ is —O—, Cy is phenyl, X is —(CH$_2$CH$_2$)—, and $R^1$ is H. In some of the aforementioned embodiments is a compound of Formula (IIb) wherein $Z^1$ is a bond, $Z^2$ is —O—, Cy is phenyl, X is —(CH$_2$CH$_2$)—, and $R^1$ is —CH$_3$.

In some embodiments, the compound of Formula (II) has the following structure of Formula (IIc):

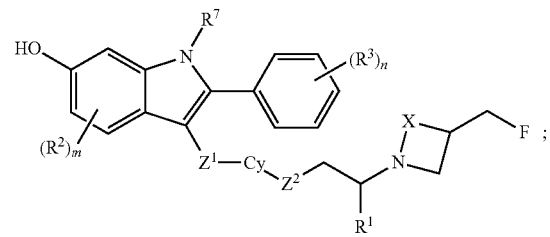

Formula (IIc)

or a pharmaceutically acceptable salt, solvate or prodrug thereof.

In some embodiments is a compound of Formula (IIc) wherein n is 1.

In some embodiments is a compound of Formula (IIc) wherein n is 1 having one of the following structures:

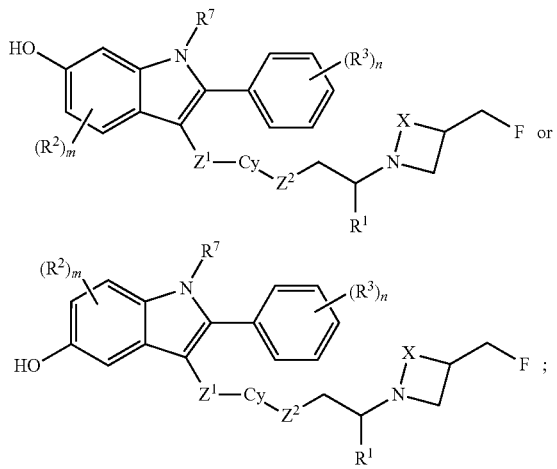

or a pharmaceutically acceptable salt, solvate or prodrug thereof.

In some embodiments is a compound of Formula (IIc) wherein n is 1 and $R^3$ is selected from the group consisting of F, Cl, —CN, —CH$_2$OH, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIc) wherein n is 1 and $R^3$ is selected from the group consisting of F, Cl, —CN, —OH, —CH$_3$, and —SO$_2$CH$_3$. In some embodiments is a compound of Formula (IIc) wherein n is 1 and $R^3$ is F. In some embodiments is a compound of Formula (IIc) wherein n is 1 and $R^3$ is —OH. In some embodiments is a compound of Formula (IIc) wherein n is 1 and $R^3$ is Cl. In some embodiments is a compound of Formula (IIc) wherein n is 1 and $R^3$ is —CN. In some embodiments is a compound of Formula (IIc) wherein n is 1 and $R^3$ is —CH$_3$. In some embodiments is a compound of Formula (IIc) wherein n is 1 and $R^3$ is —SO$_2$CH$_3$.

In some embodiments is a compound of Formula (IIc) wherein n is 2. In some embodiments is a compound of Formula (IIc) wherein n is 2 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIc) wherein n is 2 and each $R^3$ is independently selected from the group consisting of F, Cl, —CN, —OH, —CH$_3$, and —SO$_2$CH$_3$. In some embodiments is a compound of Formula (IIc) wherein n is 2 and each $R^3$ is independently selected from the group consisting of F and Cl. In some embodiments is a compound of Formula (IIc) wherein n is 2 and each $R^3$ is independently selected from the group consisting of F and —CN. In some embodiments is a compound of Formula (IIc) wherein n is 2 and each $R^3$ is F.

In some embodiments is a compound of Formula (IIc) wherein n is 3. In some embodiments is a compound of Formula (IIc) wherein n is 3 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIc) wherein n is 3 and each $R^3$ is independently selected from the group consisting of F, Cl, —CN, —OH, —CH$_3$, and —SO$_2$CH$_3$. In some embodiments is a compound of Formula (IIc) wherein n is 3 and each $R^3$ is independently selected from the group consisting of F and Cl. In some embodiments is a compound of Formula (IIc) wherein n is 3 and each $R^3$ is independently selected from the group consisting of F and —CN. In some embodiments is a compound of Formula (IIc) wherein n is 3 and each $R^3$ is F.

In some of the aforementioned embodiments is a compound of Formula (IIc) wherein $R^7$ is H. In some of the aforementioned embodiments is a compound of Formula (IIc) wherein $R^7$ is $C_1$-$C_4$alkyl. In some of the aforementioned embodiments is a compound of Formula (IIc) wherein $R^7$ is —CH$_3$. In some of the aforementioned embodiments is a compound of Formula (IIc) wherein $R^7$ is —CH$_2$CH$_3$. In some of the aforementioned embodiments is a compound of Formula (IIc) wherein m is 0. In some of the aforementioned embodiments is a compound of Formula (IIc) wherein m is 1. In some of the aforementioned embodiments is a compound of Formula (IIc) wherein m is 1 and $R^2$ is halogen. In some of the aforementioned embodiments is a compound of Formula (IIc) wherein m is 1 and $R^2$ is F. In some of the aforementioned embodiments is a compound of Formula (IIc) wherein m is 1 and $R^2$ is Cl. In some of the aforementioned embodiments is a compound of Formula (IIc) wherein m is 1 and $R^2$ is $C_1$-$C_4$alkyl. In some of the aforementioned embodiments is a compound of Formula (IIc) wherein m is 1 and $R^2$ is —CH$_3$.

In some of the aforementioned embodiments is a compound of Formula (IIc) wherein $Z^1$ is a bond. In some of the aforementioned embodiments is a compound of Formula (IIc) wherein $Z^1$ is —O—. In some of the aforementioned embodiments is a compound of Formula (IIc) wherein $Z^1$ is —(CH$_2$)—. In some embodiments is a compound of Formula (IIc) wherein $Z^1$ is —C(O)—. In some of the aforementioned embodiments is a compound of Formula (IIc) wherein $Z^2$ is a bond. In some of the aforementioned embodiments is a compound of Formula (IIc) wherein $Z^2$ is —O—. In some of the aforementioned embodiments is a compound of Formula (IIc) wherein $Z^2$ is —(CH$_2$)—. In some of the aforementioned embodiments is a compound of Formula (IIc) wherein $Z^2$ is —C(O)—. In some of the aforementioned embodiments is a compound of Formula (IIc) wherein Cy is $C_6$-$C_{20}$aryl. In some of the aforementioned embodiments is a compound of Formula (IIc) wherein Cy is phenyl. In some of the aforementioned embodiments is a compound of Formula (IIc) wherein Cy is $C_3$-$C_{12}$carbocyclyl. In some of the aforementioned embodiments is a compound of Formula (IIc) wherein Cy is cyclohexyl. In some of the aforementioned embodiments is a compound of Formula (IIc) wherein Cy is $C_2$-$C_{20}$heterocyclyl. In some of the aforementioned embodiments is a compound of Formula (IIc) wherein Cy is pyrazinyl. In some of the aforementioned embodiments is a compound of Formula (IIc) wherein Cy is piperidinyl. In some of the aforementioned embodiments is a compound of Formula (IIc) wherein Cy is $C_1$-$C_{20}$heteroaryl. In some of the aforementioned embodiments is a compound of Formula (IIc) wherein Cy is thiazolyl. In some of the aforementioned embodiments is a compound of Formula (IIc) wherein Cy is oxazolyl. In some of the aforementioned embodiments is a compound of Formula (IIc) wherein Cy is pyridyl. In some of the aforementioned embodiments is a compound of Formula (IIc) wherein $R^1$ is H. In some of the aforementioned embodiments is a compound of Formula (IIc) wherein $R^1$ is —CH$_3$. In some of the aforementioned embodiments is a compound of Formula (IIc) wherein X is —(CH$_2$)—. In some of the aforementioned embodiments is a compound of Formula (IIc) wherein X is —(CH$_2$)— and $R^1$ is H. In some of the aforementioned embodiments is a compound of Formula (IIc) wherein X is —(CH$_2$CH$_2$)—. In some of the aforementioned embodiments is a compound of Formula (IIc) wherein X is —(CH$_2$CH$_2$)— and $R^1$ is H. In some of the aforementioned embodiments is a compound of Formula (IIc) wherein X is —(CH$_2$CH$_2$)— and $R^1$ is —CH$_3$.

In some of the aforementioned embodiments is a compound of Formula (IIc) wherein $Z^1$ is a bond, $Z^2$ is —O—, Cy is phenyl, X is —(CH$_2$)—, and $R^1$ is H. In some of the aforementioned embodiments is a compound of Formula (IIc) wherein $Z^1$ is a bond, $Z^2$ is —O—, Cy is phenyl, X is —(CH$_2$CH$_2$)—, and $R^1$ is H. In some of the aforementioned embodiments is a compound of Formula (IIc) wherein $Z^1$ is a bond, $Z^2$ is —O—, Cy is phenyl, X is —(CH$_2$CH$_2$)—, and $R^1$ is —CH$_3$.

In some embodiments, the compound of Formula (I) has the following structure of Formula (III):

Formula (III)

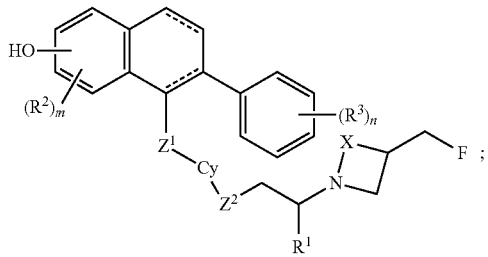

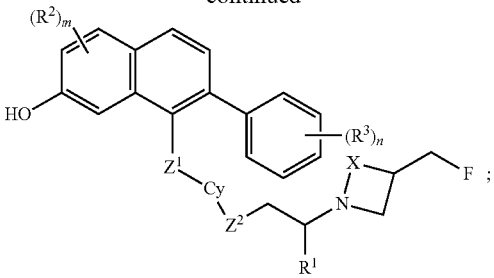

wherein:
≡≡≡ indicates a single or double bond;
each $R^2$ and each $R^3$ are independently selected from halogen, —CN, —OR$^{10}$, —NR$^{13}$R$^{14}$, $C_1$-$C_4$alkyl, $C_1$-$C_4$alkyl-OH, —OC$_2$-$C_4$alkyl-OH, $C_1$-$C_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;
each $R^{10}$ is independently selected from H, $C_1$-$C_4$alkyl, and $C_1$-$C_4$fluoroalkyl;
each $R^{11}$ is independently selected from $C_1$-$C_4$alkyl and $C_1$-$C_4$fluoroalkyl;
each $R^{12}$ is independently selected from H, $C_1$-$C_4$alkyl, and $C_1$-$C_4$fluoroalkyl;
each $R^{13}$ and each $R^{14}$ are independently selected from H and $C_1$-$C_4$alkyl;
m is 0, 1, 2 or 3; and
n is 0, 1, 2 or 3;
or a pharmaceutically acceptable salt, solvate or prodrug thereof.

In some embodiments, the compound of Formula (III) has the following structure of Formula (IIIa):

Formula (IIIa)

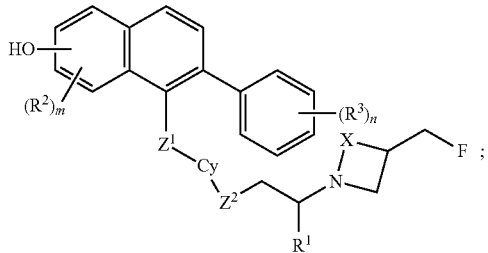

or a pharmaceutically acceptable salt, solvate or prodrug thereof.

In some embodiments is a compound of Formula (IIIa) wherein n is 1.

In some embodiments is a compound of Formula (IIIa) wherein n is 1 having one of the following structures:

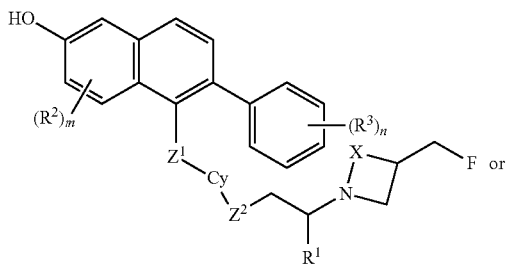

or a pharmaceutically acceptable salt, solvate or prodrug thereof.

In some embodiments is a compound of Formula (IIIa) wherein n is 1 and $R^3$ is selected from the group consisting of F, Cl, —CN, —CH$_2$OH, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIa) wherein n is 1 and $R^3$ is selected from the group consisting of F, Cl, —CN, —OH, —CH$_3$, and —SO$_2$CH$_3$. In some embodiments is a compound of Formula (IIIa) wherein n is 1 and $R^3$ is F. In some embodiments is a compound of Formula (IIIa) wherein n is 1 and $R^3$ is —OH. In some embodiments is a compound of Formula (IIIa) wherein n is 1 and $R^3$ is Cl. In some embodiments is a compound of Formula (IIIa) wherein n is 1 and $R^3$ is —CN. In some embodiments is a compound of Formula (IIIa) wherein n is 1 and $R^3$ is —CH$_3$. In some embodiments is a compound of Formula (IIIa) wherein n is 1 and $R^3$ is —SO$_2$CH$_3$.

In some embodiments is a compound of Formula (IIIa) wherein n is 2. In some embodiments is a compound of Formula (IIIa) wherein n is 2 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIa) wherein n is 2 and each $R^3$ is independently selected from the group consisting of F, Cl, —CN, —OH, —CH$_3$, and —SO$_2$CH$_3$. In some embodiments is a compound of Formula (IIIa) wherein n is 2 and each $R^3$ is independently selected from the group consisting of F and Cl. In some embodiments is a compound of Formula (IIIa) wherein n is 2 and each $R^3$ is independently selected from the group consisting of F and —CN. In some embodiments is a compound of Formula (IIIa) wherein n is 2 and each $R^3$ is F.

In some embodiments is a compound of Formula (IIIa) wherein n is 3. In some embodiments is a compound of Formula (IIIa) wherein n is 3 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIa) wherein n is 3 and each $R^3$ is independently selected from the group consisting of F, Cl, —CN, —OH, —CH$_3$, and —SO$_2$CH$_3$. In some embodiments is a compound of Formula (IIIa) wherein n is 3 and each $R^3$ is independently selected from the group consisting of F and Cl. In some embodiments is a compound of Formula (IIIa) wherein n is 3 and each $R^3$ is independently selected from the group consisting of F and —CN. In some embodiments is a compound of Formula (IIIa) wherein n is 3 and each $R^3$ is F.

In some of the aforementioned embodiments is a compound of Formula (IIIa) wherein m is 0. In some of the aforementioned embodiments is a compound of Formula (IIIa) wherein m is 1. In some of the aforementioned embodiments is a compound of Formula (IIIa) wherein m is 1 and $R^2$ is halogen. In some of the aforementioned embodiments is a compound of Formula (IIIa) wherein m is 1 and $R^2$ is F. In some of the aforementioned embodiments is a compound of Formula (IIIa) wherein m is 1 and $R^2$ is Cl. In some of the aforementioned embodiments is a compound of Formula (IIIa) wherein m is 1 and $R^2$ is $C_1$-$C_4$alkyl. In some of the aforementioned embodiments is a compound of Formula (IIIa) wherein m is 1 and $R^2$ is —$CH_3$.

In some of the aforementioned embodiments is a compound of Formula (IIIa) wherein $Z^1$ is a bond. In some of the aforementioned embodiments is a compound of Formula (IIIa) wherein $Z^1$ is —O—. In some of the aforementioned embodiments is a compound of Formula (IIIa) wherein $Z^1$ is —($CH_2$)—. In some embodiments is a compound of Formula (IIIa) wherein $Z^1$ is —C(O)—. In some of the aforementioned embodiments is a compound of Formula (IIIa) wherein $Z^2$ is a bond. In some of the aforementioned embodiments is a compound of Formula (IIIa) wherein $Z^2$ is —O—. In some of the aforementioned embodiments is a compound of Formula (IIIa) wherein $Z^2$ is —($CH_2$)—. In some of the aforementioned embodiments is a compound of Formula (IIIa) wherein $Z^2$ is —C(O)—. In some of the aforementioned embodiments is a compound of Formula (IIIa) wherein Cy is $C_6$-$C_{20}$aryl. In some of the aforementioned embodiments is a compound of Formula (IIIa) wherein Cy is phenyl. In some of the aforementioned embodiments is a compound of Formula (IIIa) wherein Cy is $C_3$-$C_{12}$carbocyclyl. In some of the aforementioned embodiments is a compound of Formula (IIIa) wherein Cy is cyclohexyl. In some of the aforementioned embodiments is a compound of Formula (IIIa) wherein Cy is $C_2$-$C_{20}$heterocyclyl. In some of the aforementioned embodiments is a compound of Formula (IIIa) wherein Cy is pyrazinyl. In some of the aforementioned embodiments is a compound of Formula (IIIa) wherein Cy is piperidinyl. In some of the aforementioned embodiments is a compound of Formula (IIIa) wherein Cy is $C_1$-$C_{20}$heteroaryl. In some of the aforementioned embodiments is a compound of Formula (IIIa) wherein Cy is thiazolyl. In some of the aforementioned embodiments is a compound of Formula (IIIa) wherein Cy is oxazolyl. In some of the aforementioned embodiments is a compound of Formula (IIIa) wherein Cy is pyridyl. In some of the aforementioned embodiments is a compound of Formula (IIIa) wherein $R^1$ is H. In some of the aforementioned embodiments is a compound of Formula (IIIa) wherein $R^1$ is —$CH_3$. In some of the aforementioned embodiments is a compound of Formula (IIIa) wherein X is —($CH_2$)—. In some of the aforementioned embodiments is a compound of Formula (IIIa) wherein X is —($CH_2$)— and $R^1$ is H. In some of the aforementioned embodiments is a compound of Formula (IIIa) wherein X is —($CH_2CH_2$)—. In some of the aforementioned embodiments is a compound of Formula (IIIa) wherein X is —($CH_2CH_2$)— and $R^1$ is H. In some of the aforementioned embodiments is a compound of Formula (IIIa) wherein X is —($CH_2CH_2$)— and $R^1$ is —$CH_3$.

In some of the aforementioned embodiments is a compound of Formula (IIIa) wherein $Z^1$ is a bond, $Z^2$ is —O—, Cy is phenyl, X is —($CH_2$)—, and $R^1$ is H. In some of the aforementioned embodiments is a compound of Formula (IIIa) wherein $Z^1$ is a bond, $Z^2$ is —O—, Cy is phenyl, X is —($CH_2CH_2$)—, and $R^1$ is H. In some of the aforementioned embodiments is a compound of Formula (IIIa) wherein $Z^1$ is a bond, $Z^2$ is —O—, Cy is phenyl, X is —($CH_2CH_2$)—, and $R^1$ is —$CH_3$.

In some embodiments, the compound of Formula (III) has the following structure of Formula (IIIb):

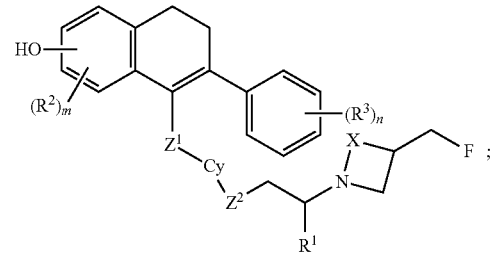

Formula (IIIb)

or a pharmaceutically acceptable salt, solvate or prodrug thereof.

In some embodiments is a compound of Formula (IIIb) wherein n is 1.

In some embodiments is a compound of Formula (IIIb) wherein n is 1 having one of the following structures:

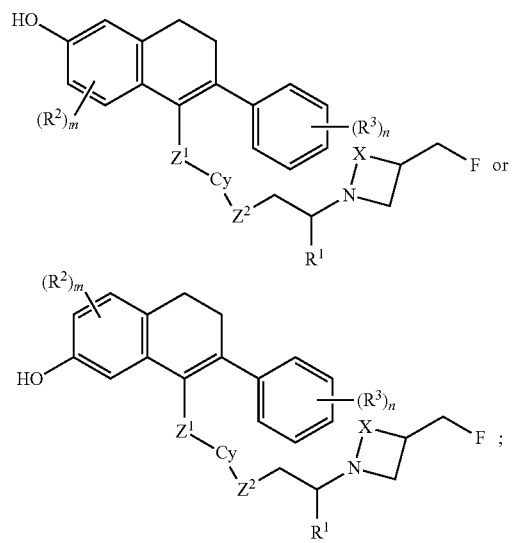

or a pharmaceutically acceptable salt, solvate or prodrug thereof.

In some embodiments is a compound of Formula (IIIb) wherein n is 1 and $R^3$ is selected from the group consisting of F, Cl, —CN, —$CH_2OH$, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (IIIb) wherein n is 1 and $R^3$ is selected from the group consisting of F, Cl, —CN, —OH, —$CH_3$, and —$SO_2CH_3$. In some embodiments is a compound of Formula (IIIb) wherein n is 1 and $R^3$ is F. In some embodiments is a compound of Formula (IIIb) wherein n is 1 and $R^3$ is —OH. In some embodiments is a compound of Formula (IIIb) wherein n is 1 and $R^3$ is Cl. In some embodiments is a compound of Formula (IIIb) wherein n is 1 and $R^3$ is —CN. In some embodiments is a compound of Formula (IIIb) wherein n is 1 and $R^3$ is —$CH_3$. In some embodiments is a compound of Formula (IIIb) wherein n is 1 and $R^3$ is —$SO_2CH_3$.

In some embodiments is a compound of Formula (IIIb) wherein n is 2. In some embodiments is a compound of Formula (IIIb) wherein n is 2 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIb) wherein n is 2 and each $R^3$ is independently selected from the group consisting of F, Cl, —CN, —OH, —CH$_3$, and —SO$_2$CH$_3$. In some embodiments is a compound of Formula (IIIb) wherein n is 2 and each $R^3$ is independently selected from the group consisting of F and Cl. In some embodiments is a compound of Formula (IIIb) wherein n is 2 and each $R^3$ is independently selected from the group consisting of F and —CN. In some embodiments is a compound of Formula (IIIb) wherein n is 2 and each $R^3$ is F.

In some embodiments is a compound of Formula (IIIb) wherein n is 3. In some embodiments is a compound of Formula (IIIb) wherein n is 3 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIb) wherein n is 3 and each $R^3$ is independently selected from the group consisting of F, Cl, —CN, —OH, —CH$_3$, and —SO$_2$CH$_3$. In some embodiments is a compound of Formula (IIIb) wherein n is 3 and each $R^3$ is independently selected from the group consisting of F and Cl. In some embodiments is a compound of Formula (IIIb) wherein n is 3 and each $R^3$ is independently selected from the group consisting of F and —CN. In some embodiments is a compound of Formula (IIIb) wherein n is 3 and each $R^3$ is F.

In some of the aforementioned embodiments is a compound of Formula (IIIb) wherein m is 0. In some of the aforementioned embodiments is a compound of Formula (IIIb) wherein m is 1. In some of the aforementioned embodiments is a compound of Formula (IIIb) wherein m is 1 and $R^2$ is halogen. In some of the aforementioned embodiments is a compound of Formula (IIIb) wherein m is 1 and $R^2$ is F. In some of the aforementioned embodiments is a compound of Formula (IIIb) wherein m is 1 and $R^2$ is Cl. In some of the aforementioned embodiments is a compound of Formula (IIIb) wherein m is 1 and $R^2$ is $C_1$-$C_4$alkyl. In some of the aforementioned embodiments is a compound of Formula (IIIb) wherein m is 1 and $R^2$ is —CH$_3$.

In some of the aforementioned embodiments is a compound of Formula (IIIb) wherein $Z^1$ is a bond. In some of the aforementioned embodiments is a compound of Formula (IIIb) wherein $Z^1$ is —O—. In some of the aforementioned embodiments is a compound of Formula (IIIb) wherein $Z^1$ is —(CH$_2$)—. In some embodiments is a compound of Formula (IIIb) wherein $Z^1$ is —C(O)—. In some of the aforementioned embodiments is a compound of Formula (IIIb) wherein $Z^2$ is a bond. In some of the aforementioned embodiments is a compound of Formula (IIIb) wherein $Z^2$ is —O—. In some of the aforementioned embodiments is a compound of Formula (IIIb) wherein $Z^2$ is —(CH$_2$)—. In some of the aforementioned embodiments is a compound of Formula (IIIb) wherein $Z^2$ is —C(O)—. In some of the aforementioned embodiments is a compound of Formula (IIIb) wherein Cy is $C_6$-$C_{20}$aryl. In some of the aforementioned embodiments is a compound of Formula (IIIb) wherein Cy is phenyl. In some of the aforementioned embodiments is a compound of Formula (IIIb) wherein Cy is $C_3$-$C_{12}$carbocyclyl. In some of the aforementioned embodiments is a compound of Formula (IIIb) wherein Cy is cyclohexyl. In some of the aforementioned embodiments is a compound of Formula (IIIb) wherein Cy is $C_2$-$C_{20}$heterocyclyl. In some of the aforementioned embodiments is a compound of Formula (IIIb) wherein Cy is pyrazinyl. In some of the aforementioned embodiments is a compound of Formula (IIIb) wherein Cy is piperidinyl. In some of the aforementioned embodiments is a compound of Formula (IIIb) wherein Cy is $C_1$-$C_{20}$heteroaryl. In some of the aforementioned embodiments is a compound of Formula (IIIb) wherein Cy is thiazolyl. In some of the aforementioned embodiments is a compound of Formula (IIIb) wherein Cy is oxazolyl. In some of the aforementioned embodiments is a compound of Formula (IIIb) wherein Cy is pyridyl. In some of the aforementioned embodiments is a compound of Formula (IIIb) wherein $R^1$ is H. In some of the aforementioned embodiments is a compound of Formula (IIIb) wherein $R^1$ is —CH$_3$. In some of the aforementioned embodiments is a compound of Formula (IIIb) wherein X is —(CH$_2$)—. In some of the aforementioned embodiments is a compound of Formula (IIIb) wherein X is —(CH$_2$)— and $R^1$ is H. In some of the aforementioned embodiments is a compound of Formula (IIIb) wherein X is —(CH$_2$CH$_2$)—. In some of the aforementioned embodiments is a compound of Formula (IIIb) wherein X is —(CH$_2$CH$_2$)— and $R^1$ is H. In some of the aforementioned embodiments is a compound of Formula (IIIb) wherein X is —(CH$_2$CH$_2$)— and $R^1$ is —CH$_3$.

In some of the aforementioned embodiments is a compound of Formula (IIIb) wherein $Z^1$ is a bond, $Z^2$ is —O—, Cy is phenyl, X is —(CH$_2$)—, and $R^1$ is H. In some of the aforementioned embodiments is a compound of Formula (IIIb) wherein $Z^1$ is a bond, $Z^2$ is —O—, Cy is phenyl, X is —(CH$_2$CH$_2$)—, and $R^1$ is H. In some of the aforementioned embodiments is a compound of Formula (IIIb) wherein $Z^1$ is a bond, $Z^2$ is —O—, Cy is phenyl, X is —(CH$_2$CH$_2$)—, and $R^1$ is —CH$_3$.

In some embodiments, the compound of Formula (III) has the following structure of Formula (IIIc):

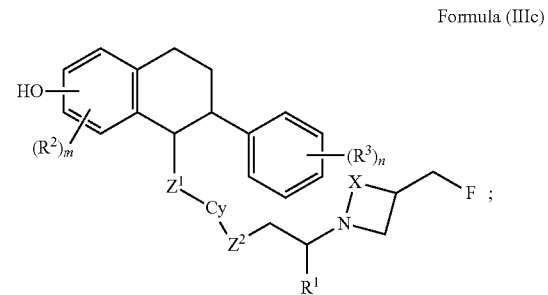

Formula (IIIc)

or a pharmaceutically acceptable salt, solvate or prodrug thereof.

In some embodiments is a compound of Formula (IIIc) wherein n is 1.

In some embodiments is a compound of Formula (IIIc) wherein n is 1 having one of the following structures:

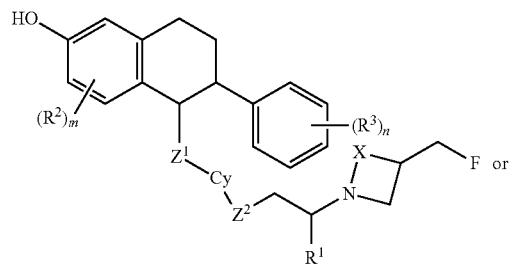

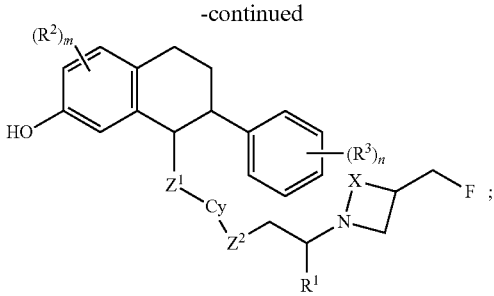

or a pharmaceutically acceptable salt, solvate or prodrug thereof.

In some embodiments is a compound of Formula (IIIc) wherein n is 1 and $R^3$ is selected from the group consisting of F, Cl, —CN, —CH$_2$OH, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIc) wherein n is 1 and $R^3$ is selected from the group consisting of F, Cl, —CN, —OH, —CH$_3$, and —SO$_2$CH$_3$. In some embodiments is a compound of Formula (IIIc) wherein n is 1 and $R^3$ is F. In some embodiments is a compound of Formula (IIIc) wherein n is 1 and $R^3$ is —OH. In some embodiments is a compound of Formula (IIIc) wherein n is 1 and $R^3$ is Cl. In some embodiments is a compound of Formula (IIIc) wherein n is 1 and $R^3$ is —CN. In some embodiments is a compound of Formula (IIIc) wherein n is 1 and $R^3$ is —CH$_3$. In some embodiments is a compound of Formula (IIIc) wherein n is 1 and $R^3$ is —SO$_2$CH$_3$.

In some embodiments is a compound of Formula (IIIc) wherein n is 2. In some embodiments is a compound of Formula (IIIc) wherein n is 2 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIc) wherein n is 2 and each $R^3$ is independently selected from the group consisting of F, Cl, —CN, —OH, —CH$_3$, and —SO$_2$CH$_3$. In some embodiments is a compound of Formula (IIIc) wherein n is 2 and each $R^3$ is independently selected from the group consisting of F and Cl. In some embodiments is a compound of Formula (IIIc) wherein n is 2 and each $R^3$ is independently selected from the group consisting of F and —CN. In some embodiments is a compound of Formula (IIIc) wherein n is 2 and each $R^3$ is F.

In some embodiments is a compound of Formula (IIIc) wherein n is 3. In some embodiments is a compound of Formula (IIIc) wherein n is 3 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (IIIc) wherein n is 3 and each $R^3$ is independently selected from the group consisting of F, Cl, —CN, —OH, —CH$_3$, and —SO$_2$CH$_3$. In some embodiments is a compound of Formula (IIIc) wherein n is 3 and each $R^3$ is independently selected from the group consisting of F and Cl. In some embodiments is a compound of Formula (IIIc) wherein n is 3 and each $R^3$ is independently selected from the group consisting of F and —CN. In some embodiments is a compound of Formula (IIIc) wherein n is 3 and each $R^3$ is F.

In some of the aforementioned embodiments is a compound of Formula (IIIc) wherein $R^7$ is H. In some of the aforementioned embodiments is a compound of Formula (IIIc) wherein $R^7$ is $C_1$-$C_4$alkyl. In some of the aforementioned embodiments is a compound of Formula (IIIc) wherein $R^7$ is —CH$_3$. In some of the aforementioned embodiments is a compound of Formula (IIIc) wherein $R^7$ is —CH$_2$CH$_3$. In some of the aforementioned embodiments is a compound of Formula (IIIc) wherein m is 0. In some of the aforementioned embodiments is a compound of Formula (IIIc) wherein m is 1. In some of the aforementioned embodiments is a compound of Formula (IIIc) wherein m is 1 and $R^2$ is halogen. In some of the aforementioned embodiments is a compound of Formula (IIIc) wherein m is 1 and $R^2$ is F. In some of the aforementioned embodiments is a compound of Formula (IIIc) wherein m is 1 and $R^2$ is Cl. In some of the aforementioned embodiments is a compound of Formula (IIIc) wherein m is 1 and $R^2$ is $C_1$-$C_4$alkyl. In some of the aforementioned embodiments is a compound of Formula (IIIc) wherein m is 1 and $R^2$ is —CH$_3$.

In some of the aforementioned embodiments is a compound of Formula (IIIc) wherein $Z^1$ is a bond. In some of the aforementioned embodiments is a compound of Formula (IIIc) wherein $Z^1$ is —O—. In some of the aforementioned embodiments is a compound of Formula (IIIc) wherein $Z^1$ is —(CH$_2$)—. In some embodiments is a compound of Formula (IIIc) wherein $Z^1$ is —C(O)—. In some of the aforementioned embodiments is a compound of Formula (IIIc) wherein $Z^2$ is a bond. In some of the aforementioned embodiments is a compound of Formula (IIIc) wherein $Z^2$ is —O—. In some of the aforementioned embodiments is a compound of Formula (IIIc) wherein $Z^2$ is —(CH$_2$)—. In some of the aforementioned embodiments is a compound of Formula (IIIc) wherein $Z^2$ is —C(O)—. In some of the aforementioned embodiments is a compound of Formula (IIIc) wherein Cy is $C_6$-$C_{20}$aryl. In some of the aforementioned embodiments is a compound of Formula (IIIc) wherein Cy is phenyl. In some of the aforementioned embodiments is a compound of Formula (IIIc) wherein Cy is $C_3$-$C_{12}$carbocyclyl. In some of the aforementioned embodiments is a compound of Formula (IIIc) wherein Cy is cyclohexyl. In some of the aforementioned embodiments is a compound of Formula (IIIc) wherein Cy is $C_2$-$C_{20}$heterocyclyl. In some of the aforementioned embodiments is a compound of Formula (IIIc) wherein Cy is pyrazinyl. In some of the aforementioned embodiments is a compound of Formula (IIIc) wherein Cy is piperidinyl. In some of the aforementioned embodiments is a compound of Formula (IIIc) wherein Cy is $C_1$-$C_{20}$heteroaryl. In some of the aforementioned embodiments is a compound of Formula (IIIc) wherein Cy is thiazolyl. In some of the aforementioned embodiments is a compound of Formula (IIIc) wherein Cy is oxazolyl. In some of the aforementioned embodiments is a compound of Formula (IIIc) wherein Cy is pyridyl. In some of the aforementioned embodiments is a compound of Formula (IIIc) wherein $R^1$ is H. In some of the aforementioned embodiments is a compound of Formula (IIIc) wherein $R^1$ is —CH$_3$. In some of the aforementioned embodiments is a compound of Formula (IIIc) wherein X is —(CH$_2$)—. In some of the aforementioned embodiments is a compound of Formula (IIIc) wherein X is —(CH$_2$)— and $R^1$ is H. In some of the aforementioned embodiments is a compound of Formula (IIIc) wherein X is —(CH$_2$CH$_2$)—. In some of the aforementioned embodiments is a compound of Formula (IIIc) wherein X is —(CH$_2$CH$_2$)— and $R^1$ is H. In some of the aforementioned embodiments is a compound of Formula (IIIc) wherein X is —(CH$_2$CH$_2$)— and $R^1$ is —CH$_3$.

In some of the aforementioned embodiments is a compound of Formula (IIIc) wherein $Z^1$ is a bond, $Z^2$ is —O—, Cy is phenyl, X is —(CH$_2$)—, and $R^1$ is H. In some of the aforementioned embodiments is a compound of Formula (IIIc) wherein $Z^1$ is a bond, $Z^2$ is —O—, Cy is phenyl, X is —(CH$_2$CH$_2$)—, and $R^1$ is H. In some of the aforementioned embodiments is a compound of Formula (IIIc) wherein $Z^1$ is a bond, $Z^2$ is —O—, Cy is phenyl, X is —(CH$_2$CH$_2$)—, and $R^1$ is —CH$_3$.

In some embodiments, the compound of Formula (I) has the following structure of Formula (IV):

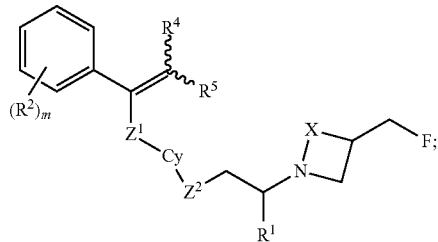

Formula (IV)

wherein:

each $R^2$ is independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$; or two $R^2$ together with the carbon atoms to which they are attached are combined to form a C$_2$-C$_9$heterocyclyl, or C$_1$-C$_{12}$heteroaryl, wherein heterocyclyl or heteroaryl are optionally substituted with halogen, CN, C$_1$-C$_4$alkyl or C$_3$-C$_8$carbocyclyl;

$R^4$ is

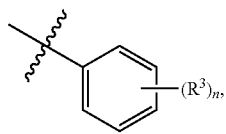

and $R^5$ is C$_1$-C$_4$alkyl; or $R^4$ and $R^5$ together with the carbon atom to which they are attached are combined to form a C$_3$-C$_{12}$carbocyclyl;

each $R^{10}$ is independently selected from H, C$_1$-C$_4$alkyl, and C$_1$-C$_4$fluoroalkyl;

each $R^{11}$ is independently selected from C$_1$-C$_4$alkyl and C$_1$-C$_4$fluoroalkyl;

each $R^{12}$ is independently selected from H, C$_1$-C$_4$alkyl, and C$_1$-C$_4$fluoroalkyl;

each $R^{13}$ and each $R^{14}$ are independently selected from H and C$_1$-C$_4$alkyl;

m is 0, 1, 2 or 3; and n is 0, 1, 2 or 3;

or a pharmaceutically acceptable salt, solvate or prodrug thereof.

In some embodiments, the compound of Formula (IV) has the following structure of Formula (IVa):

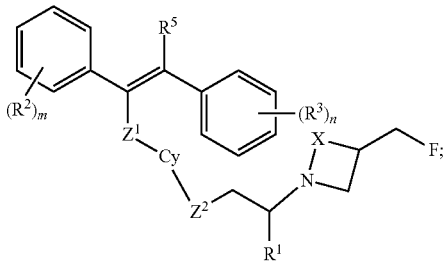

Formula (IVa)

wherein each $R^3$ is independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;

or a pharmaceutically acceptable salt, solvate or prodrug thereof.

In some embodiments is a compound of Formula (IVa) wherein n is 0. In some embodiments is a compound of Formula (IVa) wherein m is 0. In some embodiments is a compound of Formula (IVa) wherein m is 0 and n is 0. In some embodiments is a compound of Formula (IVa) wherein m is 1. In some embodiments is a compound of Formula (IVa) wherein m is 1 and n is 0.

In some embodiments is a compound of Formula (IVa) having one of the following structures:

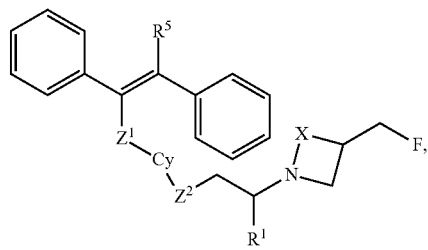

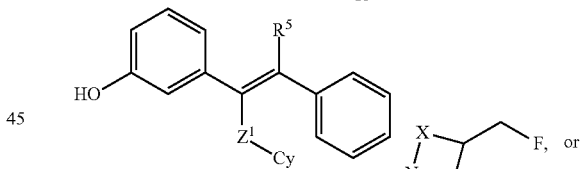

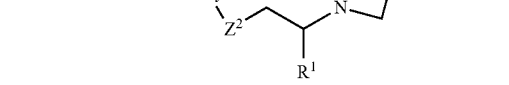

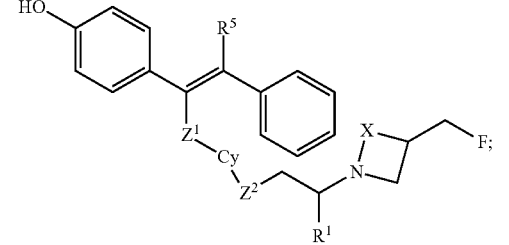

or a pharmaceutically acceptable salt, solvate or prodrug thereof.

In some embodiments is a compound of Formula (IVa) wherein $R^5$ is C$_1$-C$_4$alkyl. In some embodiments is a compound of Formula (IVa) wherein $R^5$ is —CH$_3$. In some embodiments is a compound of Formula (IVa) wherein $R^5$ is —CH$_2$CH$_3$.

In some embodiments is a compound of Formula (IVa) wherein $Z^1$ is a bond. In some embodiments is a compound of Formula (IVa) wherein $Z^1$ is —O—. In some embodiments is a compound of Formula (IVa) wherein $Z^1$ is —(CH$_2$)—. In some embodiments is a compound of Formula (IVa) wherein $Z^1$ is —C(O)—. In some embodiments is a compound of Formula (IVa) wherein $Z^2$ is a bond. In some embodiments is a compound of Formula (IVa) wherein $Z^2$ is —O—. In some embodiments is a compound of Formula (IVa) wherein $Z^2$ is —(CH$_2$)—. In some embodiments is a compound of Formula (IVa) wherein $Z^2$ is —C(O)—. In some embodiments is a compound of Formula (IVa) wherein Cy is $C_6$-$C_{20}$aryl. In some embodiments is a compound of Formula (IVa) wherein Cy is phenyl. In some embodiments is a compound of Formula (IVa) wherein Cy is $C_3$-$C_{12}$carbocyclyl. In some embodiments is a compound of Formula (IVa) wherein Cy is cyclohexyl. In some embodiments is a compound of Formula (IVa) wherein Cy is $C_2$-$C_{20}$heterocyclyl. In some embodiments is a compound of Formula (IVa) wherein Cy is pyrazinyl. In some embodiments is a compound of Formula (IVa) wherein Cy is piperidinyl. In some embodiments is a compound of Formula (IVa) wherein Cy is $C_1$-$C_{20}$heteroaryl. In some embodiments is a compound of Formula (IVa) wherein Cy is thiazolyl. In some embodiments is a compound of Formula (IVa) wherein Cy is oxazolyl. In some embodiments is a compound of Formula (IVa) wherein Cy is pyridyl. In some embodiments is a compound of Formula (IVa) wherein $R^1$ is H. In some embodiments is a compound of Formula (IVa) wherein $R^1$ is —CH$_3$. In some embodiments is a compound of Formula (IVa) wherein X is —(CH$_2$)—. In some embodiments is a compound of Formula (IVa) wherein X is —(CH$_2$)— and $R^1$ is H. In some embodiments is a compound of Formula (IVa) wherein X is —(CH$_2$CH$_2$)—. In some embodiments is a compound of Formula (IVa) wherein X is —(CH$_2$CH$_2$)— and $R^1$ is H. In some embodiments is a compound of Formula (IVa) wherein X is —(CH$_2$CH$_2$)— and $R^1$ is —CH$_3$.

In some embodiments is a compound of Formula (IVa) wherein $Z^1$ is a bond, $Z^2$ is —O—, Cy is phenyl, X is —(CH$_2$)—, and $R^1$ is H. In some embodiments is a compound of Formula (IVa) wherein $Z^1$ is a bond, $Z^2$ is —O—, Cy is phenyl, X is —(CH$_2$CH$_2$)—, and $R^1$ is H. In some embodiments is a compound of Formula (IVa) wherein $Z^1$ is a bond, $Z^2$ is —O—, Cy is phenyl, X is —(CH$_2$CH$_2$)—, and $R^1$ is —CH$_3$.

In some embodiments, the compound of Formula (IV) has the following structure of Formula (IVb):

Formula (IVb)

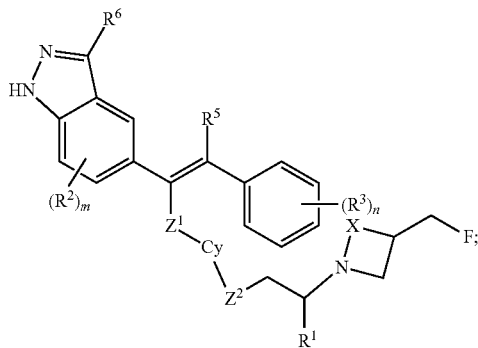

wherein $R^6$ is H, halogen, CN, $C_1$-$C_4$alkyl or $C_3$-$C_8$carbocyclyl; or a pharmaceutically acceptable salt, solvate or prodrug thereof.

In some embodiments is a compound of Formula (IVb) wherein n is 0. In some embodiments is a compound of Formula (IVb) wherein m is 0. In some embodiments is a compound of Formula (IVb) wherein m is 0 and n is 0. In some embodiments is a compound of Formula (IVb) wherein m is 1. In some embodiments is a compound of Formula (IVb) wherein m is 1 and n is 0. In some embodiments is a compound of Formula (IVb) wherein $R^6$ is H. In some embodiments is a compound of Formula (IVb) wherein $R^6$ is halogen. In some embodiments is a compound of Formula (IVb) wherein $R^6$ is $C_1$-$C_4$alkyl. In some embodiments is a compound of Formula (IVb) wherein $R^6$ is —CH$_3$.

In some embodiments is a compound of Formula (IVb) having the structure:

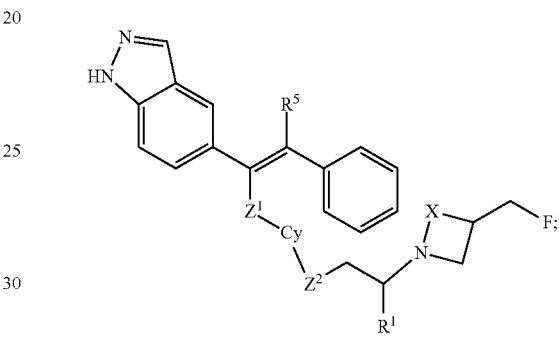

or a pharmaceutically acceptable salt, solvate or prodrug thereof.

In some embodiments is a compound of Formula (IVb) wherein $R^5$ is $C_1$-$C_4$alkyl. In some embodiments is a compound of Formula (IVb) wherein $R^5$ is —CH$_3$. In some embodiments is a compound of Formula (IVb) wherein $R^5$ is —CH$_2$CH$_3$.

In some embodiments is a compound of Formula (IVb) wherein $Z^1$ is a bond. In some embodiments is a compound of Formula (IVb) wherein $Z^1$ is —O—. In some embodiments is a compound of Formula (IVb) wherein $Z^1$ is —(CH$_2$)—. In some embodiments is a compound of Formula (IVb) wherein $Z^1$ is —C(O)—. In some embodiments is a compound of Formula (IVb) wherein $Z^2$ is a bond. In some embodiments is a compound of Formula (IVb) wherein $Z^2$ is —O—. In some embodiments is a compound of Formula (IVb) wherein $Z^2$ is —(CH$_2$)—. In some embodiments is a compound of Formula (IVb) wherein $Z^2$ is —C(O)—. In some embodiments is a compound of Formula (IVb) wherein Cy is $C_6$-$C_{20}$aryl. In some embodiments is a compound of Formula (IVb) wherein Cy is phenyl. In some embodiments is a compound of Formula (IVb) wherein Cy is $C_3$-$C_{12}$carbocyclyl. In some embodiments is a compound of Formula (IVb) wherein Cy is cyclohexyl. In some embodiments is a compound of Formula (IVb) wherein Cy is $C_2$-$C_{20}$heterocyclyl. In some embodiments is a compound of Formula (IVb) wherein Cy is pyrazinyl. In some embodiments is a compound of Formula (IVb) wherein Cy is piperidinyl. In some embodiments is a compound of Formula (IVb) wherein Cy is $C_1$-$C_{20}$heteroaryl. In some embodiments is a compound of Formula (IVb) wherein Cy is thiazolyl. In some embodiments is a compound of Formula (IVb) wherein Cy is oxazolyl. In some embodiments is a compound of Formula (IVb) wherein Cy is pyridyl. In some embodiments is a compound of Formula (IVb) wherein $R^1$ is H. In some embodiments is a compound of Formula (IVb) wherein $R^1$ is —$CH_3$. In some embodiments is a compound of Formula (IVb) wherein X is —($CH_2$)—. In some embodiments is a compound of Formula (IVb) wherein X is —($CH_2$)— and $R^1$ is H. In some embodiments is a compound of Formula (IVb) wherein X is —($CH_2CH_2$)—. In some embodiments is a compound of Formula (IVb) wherein X is —($CH_2CH_2$)— and $R^1$ is H. In some embodiments is a compound of Formula (IVb) wherein X is —($CH_2CH_2$)— and $R^1$ is —$CH_3$.

In some embodiments is a compound of Formula (IVb) wherein $Z^1$ is a bond, $Z^2$ is —O—, Cy is phenyl, X is —($CH_2$)—, and $R^1$ is H. In some embodiments is a compound of Formula (IVb) wherein $Z^1$ is a bond, $Z^2$ is —O—, Cy is phenyl, X is —($CH_2CH_2$)—, and $R^1$ is H. In some embodiments is a compound of Formula (IVb) wherein $Z^1$ is a bond, $Z^2$ is —O—, Cy is phenyl, X is —($CH_2CH_2$)—, and $R^1$ is —$CH_3$.

In some embodiments, the compound of Formula (IV) has the following structure of Formula (IVc):

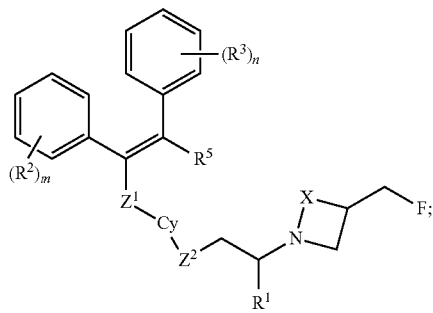

Formula (Ivc)

or a pharmaceutically acceptable salt, solvate or prodrug thereof.

In some embodiments is a compound of Formula (IVc) wherein n is 0. In some embodiments is a compound of Formula (IVc) wherein m is 0. In some embodiments is a compound of Formula (IVc) wherein m is 0 and n is 0. In some embodiments is a compound of Formula (IVc) wherein m is 1. In some embodiments is a compound of Formula (IVc) wherein m is 1 and n is 0.

In some embodiments is a compound of Formula (IVc) having one of the following structures:

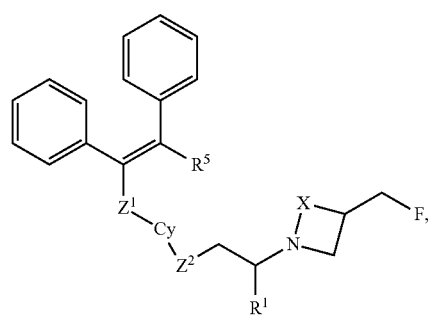

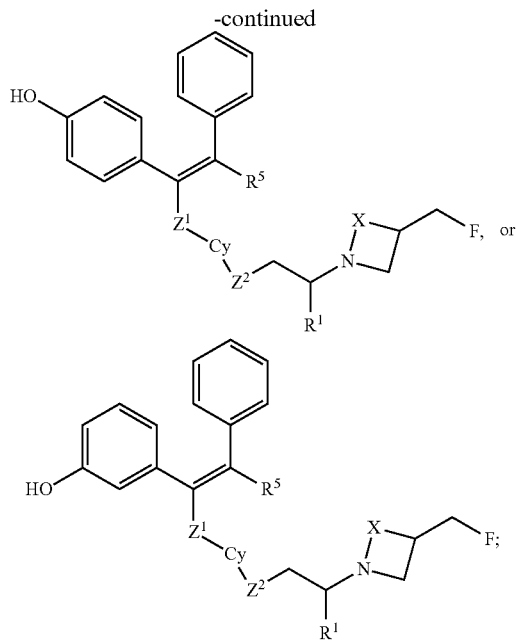

or a pharmaceutically acceptable salt, solvate or prodrug thereof.

In some embodiments is a compound of Formula (IVc) wherein $R^5$ is $C_1$-$C_4$alkyl. In some embodiments is a compound of Formula (IVc) wherein $R^5$ is —$CH_3$. In some embodiments is a compound of Formula (IVc) wherein $R^5$ is —$CH_2CH_3$.

In some embodiments is a compound of Formula (IVc) wherein $Z^1$ is a bond. In some embodiments is a compound of Formula (IVc) wherein $Z^1$ is —O—. In some embodiments is a compound of Formula (IVc) wherein $Z^1$ is —($CH_2$)—. In some embodiments is a compound of Formula (IVc) wherein $Z^1$ is —C(O)—. In some embodiments is a compound of Formula (IVc) wherein $Z^2$ is a bond. In some embodiments is a compound of Formula (IVc) wherein $Z^2$ is —O—. In some embodiments is a compound of Formula (IVc) wherein $Z^2$ is —($CH_2$)—. In some embodiments is a compound of Formula (IVc) wherein $Z^2$ is —C(O)—. In some embodiments is a compound of Formula (IVc) wherein Cy is $C_6$-$C_{20}$aryl. In some embodiments is a compound of Formula (IVc) wherein Cy is phenyl. In some embodiments is a compound of Formula (IVc) wherein Cy is $C_3$-$C_{12}$carbocyclyl. In some embodiments is a compound of Formula (IVc) wherein Cy is cyclohexyl. In some embodiments is a compound of Formula (IVc) wherein Cy is $C_2$-$C_{20}$heterocyclyl. In some embodiments is a compound of Formula (IVc) wherein Cy is pyrazinyl. In some embodiments is a compound of Formula (IVc) wherein Cy is piperidinyl. In some embodiments is a compound of Formula (IVc) wherein Cy is $C_1$-$C_{20}$heteroaryl. In some embodiments is a compound of Formula (IVc) wherein Cy is thiazolyl. In some embodiments is a compound of Formula (IVc) wherein Cy is oxazolyl. In some embodiments is a compound of Formula (IVc) wherein Cy is pyridyl. In some embodiments is a compound of Formula (IVc) wherein $R^1$ is H. In some embodiments is a compound of Formula (IVc) wherein $R^1$ is —$CH_3$. In some embodiments is a compound of Formula (IVc) wherein X is —($CH_2$)—. In some embodiments is a compound of Formula (IVc) wherein X is —($CH_2$)— and $R^1$ is H. In some embodiments is a compound of Formula (IVc) wherein X is —(CH$_2$CH$_2$)—. In some embodiments is a compound of Formula (IVc) wherein X is —(CH$_2$CH$_2$)— and R$^1$ is H. In some embodiments is a compound of Formula (IVc) wherein X is —(CH$_2$CH$_2$)— and R$^1$ is —CH$_3$.

In some embodiments is a compound of Formula (IVc) wherein Z$^1$ is a bond, Z$^2$ is —O—, Cy is phenyl, X is —(CH$_2$)—, and R$^1$ is H. In some embodiments is a compound of Formula (IVc) wherein Z$^1$ is a bond, Z$^2$ is —O—, Cy is phenyl, X is —(CH$_2$CH$_2$)—, and R$^1$ is H. In some embodiments is a compound of Formula (IVc) wherein Z$^1$ is a bond, Z$^2$ is —O—, Cy is phenyl, X is —(CH$_2$CH$_2$)—, and R$^1$ is —CH$_3$.

In some embodiments, the compound of Formula (IV) has the following structure of Formula (IVd):

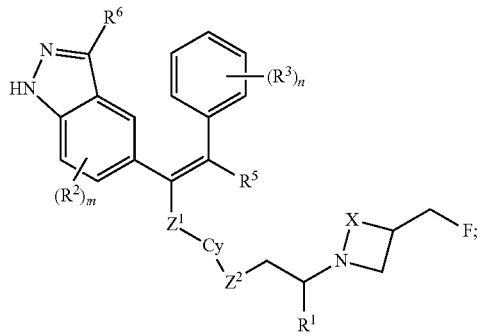

Formula (IVd)

wherein R$^6$ is H, halogen, CN, C$_1$-C$_4$alkyl or C$_3$-C$_8$carbocyclyl; or a pharmaceutically acceptable salt, solvate or prodrug thereof.

In some embodiments is a compound of Formula (IVd) wherein n is 0. In some embodiments is a compound of Formula (IVd) wherein m is 0. In some embodiments is a compound of Formula (IVd) wherein m is 0 and n is 0. In some embodiments is a compound of Formula (IVd) wherein m is 1. In some embodiments is a compound of Formula (IVd) wherein m is 1 and n is 0. In some embodiments is a compound of Formula (IVd) wherein R$^6$ is H. In some embodiments is a compound of Formula (IVd) wherein R$^6$ is halogen. In some embodiments is a compound of Formula (IVd) wherein R$^6$ is C$_1$-C$_4$alkyl. In some embodiments is a compound of Formula (IVd) wherein R$^6$ is —CH$_3$.

In some embodiments is a compound of Formula (IVd) having the structure:

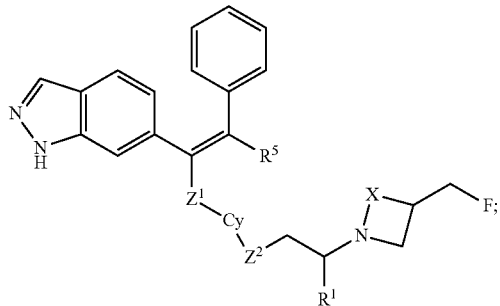

or a pharmaceutically acceptable salt, solvate or prodrug thereof.

In some embodiments is a compound of Formula (IVd) wherein R$^5$ is C$_1$-C$_4$alkyl. In some embodiments is a compound of Formula (IVd) wherein R$^5$ is —CH$_3$. In some embodiments is a compound of Formula (IVd) wherein R$^5$ is —CH$_2$CH$_3$.

In some embodiments is a compound of Formula (IVd) wherein Z$^1$ is a bond. In some embodiments is a compound of Formula (IVd) wherein Z$^1$ is —O—. In some embodiments is a compound of Formula (IVd) wherein Z$^1$ is —(CH$_2$)—. In some embodiments is a compound of Formula (IVd) wherein Z$^1$ is —C(O)—. In some embodiments is a compound of Formula (IVd) wherein Z$^2$ is a bond. In some embodiments is a compound of Formula (IVd) wherein Z$^2$ is —O—. In some embodiments is a compound of Formula (IVd) wherein Z$^2$ is —(CH$_2$)—. In some embodiments is a compound of Formula (IVd) wherein Z$^2$ is —C(O)—. In some embodiments is a compound of Formula (IVd) wherein Cy is C$_6$-C$_{20}$aryl. In some embodiments is a compound of Formula (IVd) wherein Cy is phenyl. In some embodiments is a compound of Formula (IVd) wherein Cy is C$_3$-C$_{12}$carbocyclyl. In some embodiments is a compound of Formula (IVd) wherein Cy is cyclohexyl. In some embodiments is a compound of Formula (IVd) wherein Cy is C$_2$-C$_{20}$heterocyclyl. In some embodiments is a compound of Formula (IVd) wherein Cy is pyrazinyl. In some embodiments is a compound of Formula (IVd) wherein Cy is piperidinyl. In some embodiments is a compound of Formula (IVd) wherein Cy is C$_1$-C$_{20}$heteroaryl. In some embodiments is a compound of Formula (IVd) wherein Cy is thiazolyl. In some embodiments is a compound of Formula (IVd) wherein Cy is oxazolyl. In some embodiments is a compound of Formula (IVd) wherein Cy is pyridyl. In some embodiments is a compound of Formula (IVd) wherein R$^1$ is H. In some embodiments is a compound of Formula (IVd) wherein R$^1$ is —CH$_3$. In some embodiments is a compound of Formula (IVd) wherein X is —(CH$_2$)—. In some embodiments is a compound of Formula (IVd) wherein X is —(CH$_2$)— and R$^1$ is H. In some embodiments is a compound of Formula (IVd) wherein X is —(CH$_2$CH$_2$)—. In some embodiments is a compound of Formula (IVd) wherein X is —(CH$_2$CH$_2$)— and R$^1$ is H. In some embodiments is a compound of Formula (IVd) wherein X is —(CH$_2$CH$_2$)— and R$^1$ is —CH$_3$.

In some embodiments is a compound of Formula (IVd) wherein Z$^1$ is a bond, Z$^2$ is —O—, Cy is phenyl, X is —(CH$_2$)—, and R$^1$ is H. In some embodiments is a compound of Formula (IVd) wherein Z$^1$ is a bond, Z$^2$ is —O—, Cy is phenyl, X is —(CH$_2$CH$_2$)—, and R$^1$ is H. In some embodiments is a compound of Formula (IVd) wherein Z$^1$ is a bond, Z$^2$ is —O—, Cy is phenyl, X is —(CH$_2$CH$_2$)—, and R$^1$ is —CH$_3$.

In some embodiments, the compound of Formula (I) has the following structure of Formula (V):

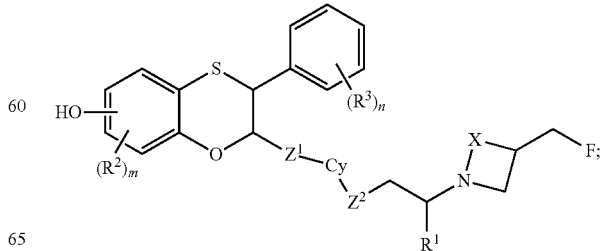

Formula (V)

wherein:

each $R^2$ and each $R^3$ are independently selected from halogen, —CN, —$OR^{10}$, —$NR^{13}R^{14}$, $C_1$-$C_4$alkyl, —$C_1$-$C_4$alkyl-OH, —$OC_2$-$C_4$alkyl-OH, $C_1$-$C_4$fluoroalkyl, —C(=O)$OR^{12}$, —NHC(=O)$R^{11}$, —C(=O)$NHR^{12}$, —$SO_2R^{11}$, —$NHSO_2R^{11}$, and —$SO_2NHR^{12}$;

each $R^{10}$ is independently selected from H, $C_1$-$C_4$alkyl, and $C_1$-$C_4$fluoroalkyl;

each $R^{11}$ is independently selected from $C_1$-$C_4$alkyl and $C_1$-$C_4$fluoroalkyl;

each $R^{12}$ is independently selected from H, $C_1$-$C_4$alkyl, and $C_1$-$C_4$fluoroalkyl;

each $R^{13}$ and each $R^{14}$ are independently selected from H and $C_1$-$C_4$alkyl;

m is 0, 1, 2 or 3; and n is 0, 1, 2 or 3;

or a pharmaceutically acceptable salt, solvate or prodrug thereof.

In some embodiments is a compound of Formula (V) wherein n is 1.

In some embodiments is a compound of Formula (V) wherein n is 1 having one of the following structures:

or a pharmaceutically acceptable salt, solvate or prodrug thereof.

In some embodiments is a compound of Formula (V) wherein n is 1 and $R^3$ is selected from the group consisting of F, Cl, —CN, —$CH_2OH$, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (V) wherein n is 1 and $R^3$ is selected from the group consisting of F, Cl, —CN, —OH, —$CH_3$, and —$SO_2CH_3$. In some embodiments is a compound of Formula (V) wherein n is 1 and $R^3$ is F. In some embodiments is a compound of Formula (V) wherein n is 1 and $R^3$ is —OH. In some embodiments is a compound of Formula (V) wherein n is 1 and $R^3$ is Cl. In some embodiments is a compound of Formula (V) wherein n is 1 and $R^3$ is —CN. In some embodiments is a compound of Formula (V) wherein n is 1 and $R^3$ is —$CH_3$. In some embodiments is a compound of Formula (V) wherein n is 1 and $R^3$ is —$SO_2CH_3$.

In some embodiments is a compound of Formula (V) wherein n is 2. In some embodiments is a compound of Formula (V) wherein n is 2 and each $R^3$ is independently selected from the group consisting of F, Cl, —CN, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (V) wherein n is 2 and each $R^3$ is independently selected from the group consisting of F, Cl, —CN, —OH, —$CH_3$, and —$SO_2CH_3$. In some embodiments is a compound of Formula (V) wherein n is 2 and each $R^3$ is independently selected from the group consisting of F and Cl. In some embodiments is a compound of Formula (V) wherein n is 2 and each $R^3$ is independently selected from the group consisting of F and —CN. In some embodiments is a compound of Formula (V) wherein n is 2 and each $R^3$ is F.

In some embodiments is a compound of Formula (V) wherein n is 3. In some embodiments is a compound of Formula (V) wherein n is 3 and each $R^3$ is independently selected from the group consisting of F, Cl, —CN, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (V) wherein n is 3 and each $R^3$ is independently selected from the group consisting of F, Cl, —CN, —OH, —$CH_3$, and —$SO_2CH_3$. In some embodiments is a compound of Formula (V) wherein n is 3 and each $R^3$ is independently selected from the group consisting of F and Cl. In some embodiments is a compound of Formula (V) wherein n is 3 and each $R^3$ is independently selected from the group consisting of F and —CN. In some embodiments is a compound of Formula (V) wherein n is 3 and each $R^3$ is F.

In some of the aforementioned embodiments is a compound of Formula (V) wherein m is 0. In some of the aforementioned embodiments is a compound of Formula (V) wherein m is 1. In some of the aforementioned embodiments is a compound of Formula (V) wherein m is 1 and $R^2$ is halogen. In some of the aforementioned embodiments is a compound of Formula (V) wherein m is 1 and $R^2$ is F. In some of the aforementioned embodiments is a compound of Formula (V) wherein m is 1 and $R^2$ is Cl. In some of the aforementioned embodiments is a compound of Formula (V) wherein m is 1 and $R^2$ is $C_1$-$C_4$alkyl. In some of the aforementioned embodiments is a compound of Formula (V) wherein m is 1 and $R^2$ is —$CH_3$.

In some of the aforementioned embodiments is a compound of Formula (V) wherein $Z^1$ is a bond. In some of the aforementioned embodiments is a compound of Formula (V) wherein $Z^1$ is —O—. In some of the aforementioned embodiments is a compound of Formula (V) wherein $Z^1$ is —($CH_2$)—. In some embodiments is a compound of Formula (V) wherein $Z^1$ is —C(O)—. In some of the aforementioned embodiments is a compound of Formula (V) wherein $Z^2$ is a bond. In some of the aforementioned embodiments is a compound of Formula (V) wherein $Z^2$ is —O—. In some of the aforementioned embodiments is a compound of Formula (V) wherein $Z^2$ is —($CH_2$)—. In some of the aforementioned embodiments is a compound of Formula (V) wherein $Z^2$ is —C(O)—. In some of the aforementioned embodiments is a compound of Formula (V) wherein Cy is $C_6$-$C_{20}$aryl. In some of the aforementioned embodiments is a compound of Formula (V) wherein Cy is phenyl. In some of the aforementioned embodiments is a compound of Formula (V) wherein Cy is $C_3$-$C_{12}$carbocyclyl. In some of the aforementioned embodiments is a compound of Formula (V) wherein Cy is cyclohexyl. In some of the aforementioned embodiments is a compound of Formula (V) wherein Cy is $C_2$-$C_{20}$heterocyclyl. In some of the aforementioned embodiments is a compound of Formula (V) wherein Cy is pyrazinyl. In some of the aforementioned embodiments is a compound of Formula (V) wherein Cy is piperidinyl. In some of the aforementioned embodiments is a compound of Formula (V) wherein Cy is $C_1$-$C_{20}$heteroaryl. In some of the aforementioned embodiments is a compound of Formula (V) wherein Cy is thiazolyl. In some of the aforementioned embodiments is a compound of Formula (V) wherein Cy is oxazolyl. In some of the aforementioned embodiments is a compound of Formula (V) wherein Cy is pyridyl. In some of the aforementioned embodiments is a compound of Formula (V) wherein $R^1$ is H. In some of the aforementioned embodiments is a compound of Formula (V) wherein $R^1$ is —$CH_3$. In some of the aforementioned embodiments is a compound of Formula (V) wherein X is —($CH_2$)—. In some of the aforementioned embodiments is a compound of Formula (V) wherein X is —($CH_2$)— and $R^1$ is H. In some of the aforementioned embodiments is a compound of Formula (V) wherein X is —($CH_2CH_2$)—. In some of the aforementioned embodiments is a compound of Formula (V) wherein X is —($CH_2CH_2$)— and $R^1$ is H. In some of the aforementioned embodiments is a compound of Formula (V) wherein X is —($CH_2CH_2$)— and $R^1$ is —$CH_3$.

In some of the aforementioned embodiments is a compound of Formula (V) wherein $Z^1$ is a bond, $Z^2$ is —O—, Cy is phenyl, X is —($CH_2$)—, and $R^1$ is H. In some of the aforementioned embodiments is a compound of Formula (V) wherein $Z^1$ is a bond, $Z^2$ is —O—, Cy is phenyl, X is —($CH_2CH_2$)—, and $R^1$ is H. In some of the aforementioned embodiments is a compound of Formula (V) wherein $Z^1$ is a bond, $Z^2$ is —O—, Cy is phenyl, X is —($CH_2CH_2$)—, and $R^1$ is —$CH_3$.

In some embodiments, the compound of Formula (I) has the following structure of Formula (VI):

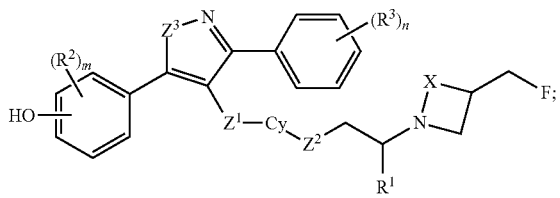

Formula (VI)

wherein:

$Z^3$ is —O—, —S—, or —N($R^4$)—;

each $R^2$ and each $R^3$ are independently selected from halogen, —CN, —$OR^{10}$, —$NR^{13}R^{14}$, $C_1$-$C_4$alkyl, —$C_1$-$C_4$alkyl-OH, —$OC_2$-$C_4$alkyl-OH, $C_1$-$C_4$fluoroalkyl, —C(=O)$OR^{12}$, —NHC(=O)$R^{11}$, —C(=O)$NHR^{12}$, —$SO_2R^{11}$, —$NHSO_2R^{11}$, and —$SO_2NHR^{12}$;

$R^4$ is H, $C_1$-$C_4$alkyl or $C_3$-$C_8$carbocyclyl;

each $R^{10}$ is independently selected from H, $C_1$-$C_4$alkyl, and $C_1$-$C_4$fluoroalkyl;

each $R^{11}$ is independently selected from $C_1$-$C_4$alkyl and $C_1$-$C_4$fluoroalkyl;

each $R^{12}$ is independently selected from H, $C_1$-$C_4$alkyl, and $C_1$-$C_4$fluoroalkyl;

each $R^{13}$ and each $R^{14}$ are independently selected from H and $C_1$-$C_4$alkyl;

m is 0, 1, 2 or 3; and n is 0, 1, 2 or 3;

or a pharmaceutically acceptable salt, solvate or prodrug thereof.

In some embodiments is a compound of Formula (VI) wherein n is 1.

In some embodiments is a compound of Formula (VI) wherein n is 1 having one of the following structures:

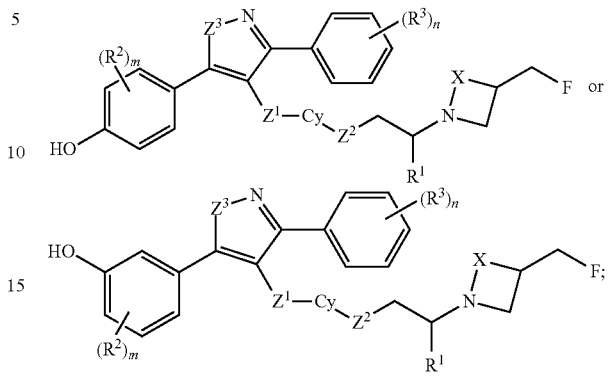

or a pharmaceutically acceptable salt, solvate or prodrug thereof.

In some embodiments is a compound of Formula (VI) wherein n is 1 and $R^3$ is selected from the group consisting of F, Cl, —CN, —$CH_2OH$, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (VI) wherein n is 1 and $R^3$ is selected from the group consisting of F, Cl, —CN, —OH, —$CH_3$, and —$SO_2CH_3$. In some embodiments is a compound of Formula (VI) wherein n is 1 and $R^3$ is F. In some embodiments is a compound of Formula (VI) wherein n is 1 and $R^3$ is —OH. In some embodiments is a compound of Formula (VI) wherein n is 1 and $R^3$ is Cl. In some embodiments is a compound of Formula (VI) wherein n is 1 and $R^3$ is —CN. In some embodiments is a compound of Formula (VI) wherein n is 1 and $R^3$ is —$CH_3$. In some embodiments is a compound of Formula (VI) wherein n is 1 and $R^3$ is —$SO_2CH_3$.

In some embodiments is a compound of Formula (VI) wherein n is 2. In some embodiments is a compound of Formula (VI) wherein n is 2 and each $R^3$ is independently selected from the group consisting of F, Cl, —CN, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (VI) wherein n is 2 and each $R^3$ is independently selected from the group consisting of F, Cl, —CN, —OH, —$CH_3$, and —$SO_2CH_3$. In some embodiments is a compound of Formula (VI) wherein n is 2 and each $R^3$ is independently selected from the group consisting of F and Cl. In some embodiments is a compound of Formula (VI) wherein n is 2 and each $R^3$ is independently selected from the group consisting of F and —CN. In some embodiments is a compound of Formula (VI) wherein n is 2 and each $R^3$ is F.

In some embodiments is a compound of Formula (VI) wherein n is 3. In some embodiments is a compound of Formula (VI) wherein n is 3 and each $R^3$ is independently selected from the group consisting of F, Cl, —CN, —OH, —$OCH_3$, —$CH_3$, —NHC(=O)$CH_3$, —C(=O)$NH_2$, $NHSO_2CH_3$, and —$SO_2CH_3$. In some embodiments is a compound of Formula (VI) wherein n is 3 and each $R^3$ is independently selected from the group consisting of F, Cl, —CN, —OH, —$CH_3$, and —$SO_2CH_3$. In some embodiments is a compound of Formula (VI) wherein n is 3 and each $R^3$ is independently selected from the group consisting of F and Cl. In some embodiments is a compound of Formula (VI) wherein n is 3 and each $R^3$ is independently selected from the group consisting of F and —CN. In some embodiments is a compound of Formula (VI) wherein n is 3 and each $R^3$ is F.

In some of the aforementioned embodiments is a compound of Formula (VI) wherein m is 0. In some of the aforementioned embodiments is a compound of Formula (VI) wherein m is 1. In some of the aforementioned embodiments is a compound of Formula (VI) wherein m is 1 and $R^2$ is halogen. In some of the aforementioned embodiments is a compound of Formula (VI) wherein m is 1 and $R^2$ is F. In some of the aforementioned embodiments is a compound of Formula (VI) wherein m is 1 and $R^2$ is Cl. In some of the aforementioned embodiments is a compound of Formula (VI) wherein m is 1 and $R^2$ is $C_1$-$C_4$alkyl. In some of the aforementioned embodiments is a compound of Formula (VI) wherein m is 1 and $R^2$ is —$CH_3$.

In some of the aforementioned embodiments is a compound of Formula (VI) wherein $Z^1$ is a bond. In some of the aforementioned embodiments is a compound of Formula (VI) wherein $Z^1$ is —O—. In some of the aforementioned embodiments is a compound of Formula (VI) wherein $Z^1$ is —($CH_2$)—. In some embodiments is a compound of Formula (VI) wherein $Z^1$ is —C(O)—. In some of the aforementioned embodiments is a compound of Formula (VI) wherein $Z^2$ is a bond. In some of the aforementioned embodiments is a compound of Formula (VI) wherein $Z^2$ is —O—. In some of the aforementioned embodiments is a compound of Formula (VI) wherein $Z^2$ is —($CH_2$)—. In some of the aforementioned embodiments is a compound of Formula (VI) wherein $Z^2$ is —C(O)—. In some of the aforementioned embodiments is a compound of Formula (VI) wherein Cy is $C_6$-$C_{20}$aryl. In some of the aforementioned embodiments is a compound of Formula (VI) wherein Cy is phenyl. In some of the aforementioned embodiments is a compound of Formula (VI) wherein Cy is $C_3$-$C_{12}$carbocyclyl. In some of the aforementioned embodiments is a compound of Formula (VI) wherein Cy is cyclohexyl. In some of the aforementioned embodiments is a compound of Formula (VI) wherein Cy is $C_2$-$C_{20}$heterocyclyl. In some of the aforementioned embodiments is a compound of Formula (VI) wherein Cy is pyrazinyl. In some of the aforementioned embodiments is a compound of Formula (VI) wherein Cy is piperidinyl. In some of the aforementioned embodiments is a compound of Formula (VI) wherein Cy is $C_1$-$C_{20}$heteroaryl. In some of the aforementioned embodiments is a compound of Formula (VI) wherein Cy is thiazolyl. In some of the aforementioned embodiments is a compound of Formula (VI) wherein Cy is oxazolyl. In some of the aforementioned embodiments is a compound of Formula (VI) wherein Cy is pyridyl. In some of the aforementioned embodiments is a compound of Formula (VI) wherein $R^1$ is H. In some of the aforementioned embodiments is a compound of Formula (VI) wherein $R^1$ is —$CH_3$. In some of the aforementioned embodiments is a compound of Formula (VI) wherein X is —($CH_2$)—. In some of the aforementioned embodiments is a compound of Formula (VI) wherein X is —($CH_2$)— and $R^1$ is H. In some of the aforementioned embodiments is a compound of Formula (VI) wherein X is —($CH_2CH_2$)—. In some of the aforementioned embodiments is a compound of Formula (VI) wherein X is —($CH_2CH_2$)— and $R^1$ is H. In some of the aforementioned embodiments is a compound of Formula (VI) wherein X is —($CH_2CH_2$)— and $R^1$ is —$CH_3$. In some of the aforementioned embodiments is a compound of Formula (VI) wherein $Z^3$ is —O—. In some of the aforementioned embodiments is a compound of Formula (VI) wherein $Z^3$ is —S—. In some of the aforementioned embodiments is a compound of Formula (VI) wherein $Z^3$ is —N($R^4$)—. In some of the aforementioned embodiments is a compound of Formula (VI) wherein $Z^3$ is —N(H)—. In some of the aforementioned embodiments is a compound of Formula (VI) wherein $Z^3$ is —N($CH_3$)—.

In some of the aforementioned embodiments is a compound of Formula (VI) wherein $Z^1$ is a bond, $Z^2$ is —O—, $Z^3$ is —O—, Cy is phenyl, X is —($CH_2$)—, and $R^1$ is H. In some of the aforementioned embodiments is a compound of Formula (VI) wherein $Z^1$ is a bond, $Z^2$ is —O—, $Z^3$ is —O—, Cy is phenyl, X is —($CH_2CH_2$)—, and $R^1$ is H. In some of the aforementioned embodiments is a compound of Formula (VI) wherein $Z^1$ is a bond, $Z^2$ is —O—, $Z^3$ is —O—, Cy is phenyl, X is —($CH_2CH_2$)—, and $R^1$ is —$CH_3$.

In some of the aforementioned embodiments is a compound of Formula (VI) wherein $Z^1$ is a bond, $Z^2$ is —O—, $Z^3$ is —S—, Cy is phenyl, X is —($CH_2$)—, and $R^1$ is H. In some of the aforementioned embodiments is a compound of Formula (VI) wherein $Z^1$ is a bond, $Z^2$ is —O—, $Z^3$ is —S—, Cy is phenyl, X is —($CH_2CH_2$)—, and $R^1$ is H. In some of the aforementioned embodiments is a compound of Formula (VI) wherein $Z^1$ is a bond, $Z^2$ is —O—, $Z^3$ is —S—, Cy is phenyl, X is —($CH_2CH_2$)—, and $R^1$ is —$CH_3$.

In some of the aforementioned embodiments is a compound of Formula (VI) wherein $Z^1$ is a bond, $Z^2$ is —O—, $Z^3$ is —N(H)—, Cy is phenyl, X is —($CH_2$)—, and $R^1$ is H. In some of the aforementioned embodiments is a compound of Formula (VI) wherein $Z^1$ is a bond, $Z^2$ is —O—, $Z^3$ is —N(H)—, Cy is phenyl, X is —($CH_2CH_2$)—, and $R^1$ is H. In some of the aforementioned embodiments is a compound of Formula (VI) wherein $Z^1$ is a bond, $Z^2$ is —O—, $Z^3$ is —N(H)—, Cy is phenyl, X is —($CH_2CH_2$)—, and $R^1$ is —$CH_3$.

In some embodiments, the compound of Formula (I) has the following structure of Formula (VII):

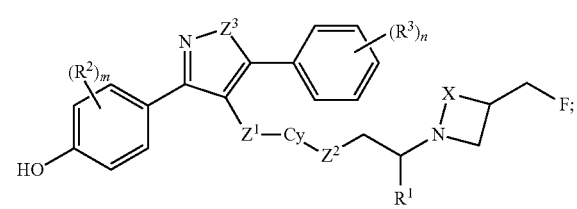

Formula (VII)

wherein:
$Z^3$ is —O—, —S—, or —N($R^4$)—;
each $R^2$ and each $R^3$ are independently selected from halogen, —CN, —$OR^{10}$, —$NR^{13}R^{14}$, $C_1$-$C_4$alkyl, $C_1$-$C_4$alkyl-OH, —$OC_2$-$C_4$alkyl-OH, $C_1$-$C_4$fluoroalkyl, —C(=O)$OR^{12}$, —NHC(=O)$R^{11}$, —C(=O)$NHR^{12}$, —$SO_2R^{11}$, —$NHSO_2R^{11}$, and —$SO_2NHR^{12}$;
$R^4$ is H, $C_1$-$C_4$alkyl or $C_3$-$C_8$carbocyclyl;
each $R^{10}$ is independently selected from H, $C_1$-$C_4$alkyl, and $C_1$-$C_4$fluoroalkyl;
each $R^{11}$ is independently selected from $C_1$-$C_4$alkyl and $C_1$-$C_4$fluoroalkyl;
each $R^{12}$ is independently selected from H, $C_1$-$C_4$alkyl, and $C_1$-$C_4$fluoroalkyl;
each $R^{13}$ and each $R^{14}$ are independently selected from H and $C_1$-$C_4$alkyl;
m is 0, 1, 2 or 3; and
n is 0, 1, 2 or 3;

or a pharmaceutically acceptable salt, solvate or prodrug thereof.

In some embodiments is a compound of Formula (VII) wherein n is 1.

In some embodiments is a compound of Formula (VII) wherein n is 1 having one of the following structures:

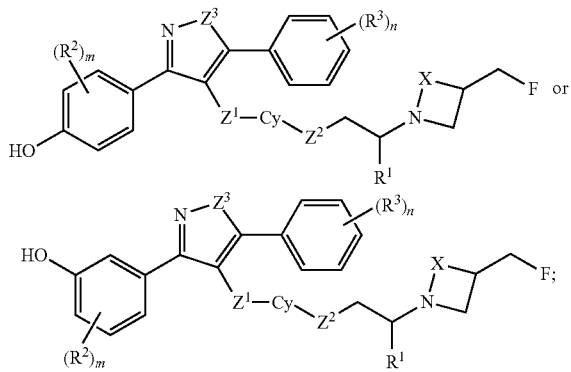

or a pharmaceutically acceptable salt, solvate or prodrug thereof.

In some embodiments is a compound of Formula (VII) wherein n is 1 and $R^3$ is selected from the group consisting of F, Cl, —CN, —CH$_2$OH, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (VII) wherein n is 1 and $R^3$ is selected from the group consisting of F, Cl, —CN, —OH, —CH$_3$, and —SO$_2$CH$_3$. In some embodiments is a compound of Formula (VII) wherein n is 1 and $R^3$ is F. In some embodiments is a compound of Formula (VII) wherein n is 1 and $R^3$ is —OH. In some embodiments is a compound of Formula (VII) wherein n is 1 and $R^3$ is Cl. In some embodiments is a compound of Formula (VII) wherein n is 1 and $R^3$ is —CN. In some embodiments is a compound of Formula (VII) wherein n is 1 and $R^3$ is —CH$_3$. In some embodiments is a compound of Formula (VII) wherein n is 1 and $R^3$ is —SO$_2$CH$_3$. In some embodiments is a compound of Formula (VII) wherein n is 2. In some embodiments is a compound of Formula (VII) wherein n is 2 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (VII) wherein n is 2 and each $R^3$ is independently selected from the group consisting of F, Cl, —CN, —OH, —CH$_3$, and —SO$_2$CH$_3$. In some embodiments is a compound of Formula (VII) wherein n is 2 and each $R^3$ is independently selected from the group consisting of F and Cl. In some embodiments is a compound of Formula (VII) wherein n is 2 and each $R^3$ is independently selected from the group consisting of F and —CN. In some embodiments is a compound of Formula (VII) wherein n is 2 and each $R^3$ is F.

In some embodiments is a compound of Formula (VII) wherein n is 3. In some embodiments is a compound of Formula (VII) wherein n is 3 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (VII) wherein n is 3 and each $R^3$ is independently selected from the group consisting of F, Cl, —CN, —OH, —CH$_3$, and —SO$_2$CH$_3$. In some embodiments is a compound of Formula (VII) wherein n is 3 and each $R^3$ is independently selected from the group consisting of F and Cl. In some embodiments is a compound of Formula (VII) wherein n is 3 and each $R^3$ is independently selected from the group consisting of F and —CN. In some embodiments is a compound of Formula (VII) wherein n is 3 and each $R^3$ is F.

In some of the aforementioned embodiments is a compound of Formula (VII) wherein m is 0. In some of the aforementioned embodiments is a compound of Formula (VII) wherein m is 1. In some of the aforementioned embodiments is a compound of Formula (VII) wherein m is 1 and $R^2$ is halogen. In some of the aforementioned embodiments is a compound of Formula (VII) wherein m is 1 and $R^2$ is F. In some of the aforementioned embodiments is a compound of Formula (VII) wherein m is 1 and $R^2$ is Cl. In some of the aforementioned embodiments is a compound of Formula (VII) wherein m is 1 and $R^2$ is $C_1$-$C_4$alkyl. In some of the aforementioned embodiments is a compound of Formula (VII) wherein m is 1 and $R^2$ is —CH$_3$.

In some of the aforementioned embodiments is a compound of Formula (VII) wherein $Z^1$ is a bond. In some of the aforementioned embodiments is a compound of Formula (VII) wherein $Z^1$ is —O—. In some of the aforementioned embodiments is a compound of Formula (VII) wherein $Z^1$ is —(CH$_2$)—. In some embodiments is a compound of Formula (VII) wherein $Z^1$ is —C(O)—. In some of the aforementioned embodiments is a compound of Formula (VII) wherein $Z^2$ is a bond. In some of the aforementioned embodiments is a compound of Formula (VII) wherein $Z^2$ is —O—. In some of the aforementioned embodiments is a compound of Formula (VII) wherein $Z^2$ is —(CH$_2$)—. In some of the aforementioned embodiments is a compound of Formula (VII) wherein $Z^2$ is —C(O)—. In some of the aforementioned embodiments is a compound of Formula (VII) wherein Cy is $C_6$-$C_{20}$aryl. In some of the aforementioned embodiments is a compound of Formula (VII) wherein Cy is phenyl. In some of the aforementioned embodiments is a compound of Formula (VII) wherein Cy is $C_3$-$C_{12}$carbocyclyl. In some of the aforementioned embodiments is a compound of Formula (VII) wherein Cy is cyclohexyl. In some of the aforementioned embodiments is a compound of Formula (VII) wherein Cy is $C_2$-$C_{20}$heterocyclyl. In some of the aforementioned embodiments is a compound of Formula (VII) wherein Cy is pyrazinyl. In some of the aforementioned embodiments is a compound of Formula (VII) wherein Cy is piperidinyl. In some of the aforementioned embodiments is a compound of Formula (VII) wherein Cy is $C_1$-$C_{20}$heteroaryl. In some of the aforementioned embodiments is a compound of Formula (VII) wherein Cy is thiazolyl. In some of the aforementioned embodiments is a compound of Formula (VII) wherein Cy is oxazolyl. In some of the aforementioned embodiments is a compound of Formula (VII) wherein Cy is pyridyl. In some of the aforementioned embodiments is a compound of Formula (VII) wherein $R^1$ is H. In some of the aforementioned embodiments is a compound of Formula (VII) wherein $R^1$ is —CH$_3$. In some of the aforementioned embodiments is a compound of Formula (VII) wherein X is —(CH$_2$)—. In some of the aforementioned embodiments is a compound of Formula (VII) wherein X is —(CH$_2$)— and $R^1$ is H. In some of the aforementioned embodiments is a compound of Formula (VII) wherein X is —(CH$_2$CH$_2$)—. In some of the aforementioned embodiments is a compound of Formula (VII) wherein X is —(CH$_2$CH$_2$)— and $R^1$ is H. In some of the aforementioned embodiments is a compound of Formula (VII) wherein X is —(CH$_2$CH$_2$)— and $R^1$ is —CH₃. In some of the aforementioned embodiments is a compound of Formula (VII) wherein Z³ is —O—. In some of the aforementioned embodiments is a compound of Formula (VII) wherein Z³ is —S—. In some of the aforementioned embodiments is a compound of Formula (VII) wherein Z³ is —N(R⁴)—. In some of the aforementioned embodiments is a compound of Formula (VII) wherein Z³ is —N(H)—. In some of the aforementioned embodiments is a compound of Formula (VII) wherein Z³ is —N(CH₃)—.

In some of the aforementioned embodiments is a compound of Formula (VII) wherein Z¹ is a bond, Z² is —O—, Z³ is —O—, Cy is phenyl, X is —(CH₂)—, and R¹ is H. In some of the aforementioned embodiments is a compound of Formula (VII) wherein Z¹ is a bond, Z² is —O—, Z³ is —O—, Cy is phenyl, X is —(CH₂CH₂)—, and R¹ is H. In some of the aforementioned embodiments is a compound of Formula (VII) wherein Z¹ is a bond, Z² is —O—, Z³ is —O—, Cy is phenyl, X is —(CH₂CH₂)—, and R¹ is —CH₃.

In some of the aforementioned embodiments is a compound of Formula (VII) wherein Z¹ is a bond, Z² is —O—, Z³ is —S—, Cy is phenyl, X is —(CH₂)—, and R¹ is H. In some of the aforementioned embodiments is a compound of Formula (VII) wherein Z¹ is a bond, Z² is —O—, Z³ is —S—, Cy is phenyl, X is —(CH₂CH₂)—, and R¹ is H. In some of the aforementioned embodiments is a compound of Formula (VII) wherein Z¹ is a bond, Z² is —S—, Z³ is —O—, Cy is phenyl, X is —(CH₂CH₂)—, and R¹ is —CH₃.

In some of the aforementioned embodiments is a compound of Formula (VII) wherein Z¹ is a bond, Z² is —O—, Z³ is —N(H)—, Cy is phenyl, X is —(CH₂)—, and R¹ is H. In some of the aforementioned embodiments is a compound of Formula (VII) wherein Z¹ is a bond, Z² is —O—, Z³ is —N(H)—, Cy is phenyl, X is —(CH₂CH₂)—, and R¹ is H. In some of the aforementioned embodiments is a compound of Formula (VII) wherein Z¹ is a bond, Z² is —O—, Z³ is —N(H)—, Cy is phenyl, X is —(CH₂CH₂)—, and R¹ is —CH₃.

In some embodiments, the compound of Formula (I) has the following structure of Formula (VIII):

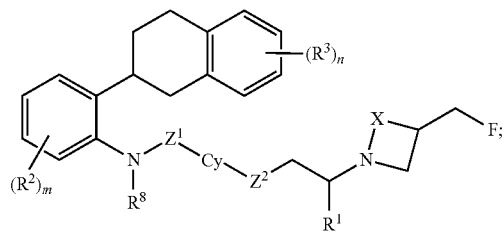

Formula (VIII)

wherein:
Z¹ is —(CH₂)—;
Z² is selected from —O—, —(CH₂)—, —C(O)—, and a bond;
each R² and each R³ are independently selected from halogen, —CN, —OR¹⁰, —NR¹³R¹⁴, C₁-C₄alkyl, —C₁-C₄alkyl-OH, —OC₂-C₄alkyl-OH, C₁-C₄fluoroalkyl, —C(=O)OR¹², —NHC(=O)R¹¹, —C(=O)NHR¹², —SO₂R¹¹, —NHSO₂R¹¹, and —SO₂NHR¹²;
R⁸ is selected from H and C₁-C₄alkyl;
each R¹⁰ is independently selected from H, C₁-C₄alkyl, and C₁-C₄fluoroalkyl;
each R¹¹ is independently selected from C₁-C₄alkyl and C₁-C₄fluoroalkyl;
each R¹² is independently selected from H, C₁-C₄alkyl, and C₁-C₄fluoroalkyl;
each R¹³ and each R¹⁴ are independently selected from H and C₁-C₄alkyl;
m is 0, 1, 2 or 3; and
n is 0, 1, 2 or 3 or a pharmaceutically acceptable salt, solvate or prodrug thereof.

In some embodiments is a compound of Formula (VIII) wherein n is 0. In some embodiments is a compound of Formula (VIII) wherein n is 1.

In some embodiments is a compound of Formula (VIII) wherein n is 1 and R³ is selected from the group consisting of F, Cl, —CN, —CH₂OH, —OH, —OCH₃, —CH₃, —NHC(=O)CH₃, —C(=O)NH₂, NHSO₂CH₃, and —SO₂CH₃. In some embodiments is a compound of Formula (VIII) wherein n is 1 and R³ is selected from the group consisting of F, Cl, —CN, —OH, —CH₃, and —SO₂CH₃. In some embodiments is a compound of Formula (VIII) wherein n is 1 and R³ is F. In some embodiments is a compound of Formula (VIII) wherein n is 1 and R³ is —OH. In some embodiments is a compound of Formula (VIII) wherein n is 1 and R³ is Cl. In some embodiments is a compound of Formula (VIII) wherein n is 1 and R³ is —CN. In some embodiments is a compound of Formula (VIII) wherein n is 1 and R³ is —CH₃. In some embodiments is a compound of Formula (VIII) wherein n is 1 and R³ is —SO₂CH₃.

In some embodiments is a compound of Formula (VIII) wherein n is 2. In some embodiments is a compound of Formula (VIII) wherein n is 2 and each R³ is independently selected from the group consisting of F, Cl, —CN, —OH, —OCH₃, —CH₃, —NHC(=O)CH₃, —C(=O)NH₂, NHSO₂CH₃, and —SO₂CH₃. In some embodiments is a compound of Formula (VIII) wherein n is 2 and each R³ is independently selected from the group consisting of F, Cl, —CN, —OH, —CH₃, and —SO₂CH₃. In some embodiments is a compound of Formula (VIII) wherein n is 2 and each R³ is independently selected from the group consisting of F and Cl. In some embodiments is a compound of Formula (VIII) wherein n is 2 and each R³ is independently selected from the group consisting of F and —CN. In some embodiments is a compound of Formula (VIII) wherein n is 2 and each R³ is F.

In some embodiments is a compound of Formula (VIII) wherein n is 3. In some embodiments is a compound of Formula (VIII) wherein n is 3 and each R³ is independently selected from the group consisting of F, Cl, —CN, —OH, —OCH₃, —CH₃, —NHC(=O)CH₃, —C(=O)NH₂, NHSO₂CH₃, and —SO₂CH₃. In some embodiments is a compound of Formula (VIII) wherein n is 3 and each R³ is independently selected from the group consisting of F, Cl, —CN, —OH, —CH₃, and —SO₂CH₃. In some embodiments is a compound of Formula (VIII) wherein n is 3 and each R³ is independently selected from the group consisting of F and Cl. In some embodiments is a compound of Formula (VIII) wherein n is 3 and each R³ is independently selected from the group consisting of F and —CN. In some embodiments is a compound of Formula (VIII) wherein n is 3 and each R³ is F.

In some of the aforementioned embodiments is a compound of Formula (VIII) wherein R⁸ is H. In some of the aforementioned embodiments is a compound of Formula (VIII) wherein R⁸ is C₁-C₄alkyl. In some of the aforementioned embodiments is a compound of Formula (VIII) wherein R⁸ is —CH₃. In some of the aforementioned embodiments is a compound of Formula (VIII) wherein R⁸ is —CH$_2$CH$_3$. In some of the aforementioned embodiments is a compound of Formula (VIII) wherein m is 0. In some of the aforementioned embodiments is a compound of Formula (VIII) wherein m is 1. In some of the aforementioned embodiments is a compound of Formula (VIII) wherein m is 1 and R$^2$ is —OH. In some of the aforementioned embodiments is a compound of Formula (VIII) wherein m is 1 and R$^2$ is —OC$_1$-C$_4$alkyl. In some of the aforementioned embodiments is a compound of Formula (VIII) wherein m is 1 and R$^2$ is —OCH$_3$. In some of the aforementioned embodiments is a compound of Formula (VIII) wherein m is 1 and R$^2$ is halogen. In some of the aforementioned embodiments is a compound of Formula (VIII) wherein m is 1 and R$^2$ is F. In some of the aforementioned embodiments is a compound of Formula (VIII) wherein m is 1 and R$^2$ is Cl. In some of the aforementioned embodiments is a compound of Formula (VIII) wherein m is 1 and R$^2$ is C$_1$-C$_4$alkyl. In some of the aforementioned embodiments is a compound of Formula (VIII) wherein m is 1 and R$^2$ is —CH$_3$.

In some of the aforementioned embodiments is a compound of Formula (VIII) wherein Z$^2$ is a bond. In some of the aforementioned embodiments is a compound of Formula (VIII) wherein Z$^2$ is —O—. In some of the aforementioned embodiments is a compound of Formula (VIII) wherein Z$^2$ is —(CH$_2$)—. In some of the aforementioned embodiments is a compound of Formula (VIII) wherein Z$^2$ is —C(O)—. In some of the aforementioned embodiments is a compound of Formula (VIII) wherein Cy is C$_6$-C$_{20}$aryl. In some of the aforementioned embodiments is a compound of Formula (VIII) wherein Cy is phenyl. In some of the aforementioned embodiments is a compound of Formula (VIII) wherein Cy is C$_3$-C$_{12}$carbocyclyl. In some of the aforementioned embodiments is a compound of Formula (VIII) wherein Cy is cyclohexyl. In some of the aforementioned embodiments is a compound of Formula (VIII) wherein Cy is C$_2$-C$_{20}$heterocyclyl. In some of the aforementioned embodiments is a compound of Formula (VIII) wherein Cy is pyrazinyl. In some of the aforementioned embodiments is a compound of Formula (VIII) wherein Cy is piperidinyl. In some of the aforementioned embodiments is a compound of Formula (VIII) wherein Cy is C$_1$-C$_{20}$heteroaryl. In some of the aforementioned embodiments is a compound of Formula (VIII) wherein Cy is thiazolyl. In some of the aforementioned embodiments is a compound of Formula (VIII) wherein Cy is oxazolyl. In some of the aforementioned embodiments is a compound of Formula (VIII) wherein Cy is pyridyl. In some of the aforementioned embodiments is a compound of Formula (VIII) wherein R$^1$ is H. In some of the aforementioned embodiments is a compound of Formula (VIII) wherein R$^1$ is —CH$_3$. In some of the aforementioned embodiments is a compound of Formula (VIII) wherein X is —(CH$_2$)—. In some of the aforementioned embodiments is a compound of Formula (VIII) wherein X is —(CH$_2$)— and R$^1$ is H. In some of the aforementioned embodiments is a compound of Formula (VIII) wherein X is —(CH$_2$CH$_2$)—. In some of the aforementioned embodiments is a compound of Formula (VIII) wherein X is —(CH$_2$CH$_2$)— and R$^1$ is H. In some of the aforementioned embodiments is a compound of Formula (VIII) wherein X is —(CH$_2$CH$_2$)— and R$^1$ is —CH$_3$.

In some of the aforementioned embodiments is a compound of Formula (VIII) wherein Z$^2$ is —O—, Cy is phenyl, X is —(CH$_2$)—, and R$^1$ is H. In some of the aforementioned embodiments is a compound of Formula (VIII) wherein Z$^2$ is —O—, Cy is phenyl, X is —(CH$_2$CH$_2$)—, and R$^1$ is H. In some of the aforementioned embodiments is a compound of Formula (VIII) wherein Z$^2$ is —O—, Cy is phenyl, X is —(CH$_2$CH$_2$)—, and R$^1$ is —CH$_3$.

In some embodiments, the compound of Formula (I) has the following structure of Formula (IX):

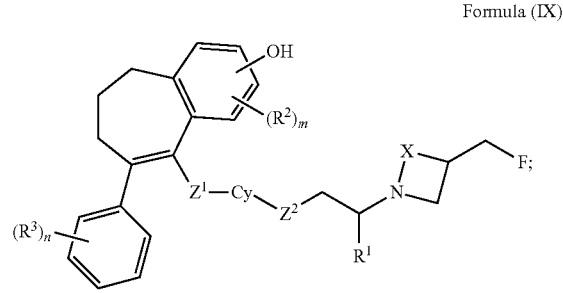

Formula (IX)

wherein:
each R$^2$ and each R$^3$ are independently selected from halogen, —CN, —OR$^{10}$, —NR$^{13}$R$^{14}$, C$_1$-C$_4$alkyl, —C$_1$-C$_4$alkyl-OH, —OC$_2$-C$_4$alkyl-OH, C$_1$-C$_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;
each R$^{10}$ is independently selected from H, C$_1$-C$_4$alkyl, and C$_1$-C$_4$fluoroalkyl;
each R$^{11}$ is independently selected from C$_1$-C$_4$alkyl and C$_1$-C$_4$fluoroalkyl;
each R$^{12}$ is independently selected from H, C$_1$-C$_4$alkyl, and C$_1$-C$_4$fluoroalkyl;
each R$^{13}$ and each R$^{14}$ are independently selected from H and C$_1$-C$_4$alkyl;
m is 0, 1, 2 or 3; and
n is 0, 1, 2 or 3;
or a pharmaceutically acceptable salt, solvate or prodrug thereof.

In some embodiments is a compound of Formula (IX) wherein n is 1.

In some embodiments is a compound of Formula (IX) wherein n is 1 having one of the following structures:

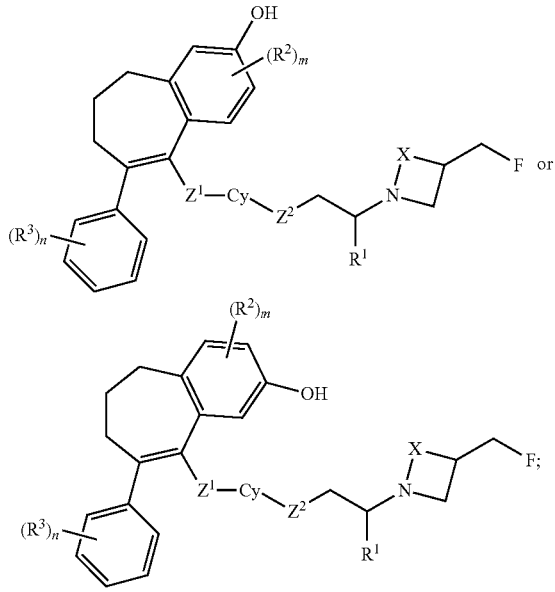

or a pharmaceutically acceptable salt, solvate or prodrug thereof.

In some embodiments is a compound of Formula (IX) wherein n is 1 and $R^3$ is selected from the group consisting of F, Cl, —CN, —$CH_2OH$, —OH, —$OCH_3$, —$CH_3$, —NHC(=O)$CH_3$, —C(=O)$NH_2$, NHS$O_2CH_3$, and —S$O_2CH_3$. In some embodiments is a compound of Formula (IX) wherein n is 1 and $R^3$ is selected from the group consisting of F, Cl, —CN, —OH, —$CH_3$, and —S$O_2CH_3$. In some embodiments is a compound of Formula (IX) wherein n is 1 and $R^3$ is F. In some embodiments is a compound of Formula (IX) wherein n is 1 and $R^3$ is —OH. In some embodiments is a compound of Formula (IX) wherein n is 1 and $R^3$ is Cl. In some embodiments is a compound of Formula (IX) wherein n is 1 and $R^3$ is —CN. In some embodiments is a compound of Formula (IX) wherein n is 1 and $R^3$ is —$CH_3$. In some embodiments is a compound of Formula (IX) wherein n is 1 and $R^3$ is —S$O_2CH_3$.

In some embodiments is a compound of Formula (IX) wherein n is 2. In some embodiments is a compound of Formula (IX) wherein n is 2 and each $R^3$ is independently selected from the group consisting of F, Cl, —CN, —OH, —$OCH_3$, —$CH_3$, —NHC(=O)$CH_3$, —C(=O)$NH_2$, NHS$O_2CH_3$, and —S$O_2CH_3$. In some embodiments is a compound of Formula (IX) wherein n is 2 and each $R^3$ is independently selected from the group consisting of F, Cl, —CN, —OH, —$CH_3$, and —S$O_2CH_3$. In some embodiments is a compound of Formula (IX) wherein n is 2 and each $R^3$ is independently selected from the group consisting of F and Cl. In some embodiments is a compound of Formula (IX) wherein n is 2 and each $R^3$ is independently selected from the group consisting of F and —CN. In some embodiments is a compound of Formula (IX) wherein n is 2 and each $R^3$ is F.

In some embodiments is a compound of Formula (IX) wherein n is 3. In some embodiments is a compound of Formula (IX) wherein n is 3 and each $R^3$ is independently selected from the group consisting of F, Cl, —CN, —OH, —$OCH_3$, —$CH_3$, —NHC(=O)$CH_3$, —C(=O)$NH_2$, NHS$O_2CH_3$, and —S$O_2CH_3$. In some embodiments is a compound of Formula (IX) wherein n is 3 and each $R^3$ is independently selected from the group consisting of F, Cl, —CN, —OH, —$CH_3$, and —S$O_2CH_3$. In some embodiments is a compound of Formula (IX) wherein n is 3 and each $R^3$ is independently selected from the group consisting of F and Cl. In some embodiments is a compound of Formula (IX) wherein n is 3 and each $R^3$ is independently selected from the group consisting of F and —CN. In some embodiments is a compound of Formula (IX) wherein n is 3 and each $R^3$ is F.

In some of the aforementioned embodiments is a compound of Formula (IX) wherein m is 0. In some of the aforementioned embodiments is a compound of Formula (IX) wherein m is 1. In some of the aforementioned embodiments is a compound of Formula (IX) wherein m is 1 and $R^2$ is halogen. In some of the aforementioned embodiments is a compound of Formula (IX) wherein m is 1 and $R^2$ is F. In some of the aforementioned embodiments is a compound of Formula (IX) wherein m is 1 and $R^2$ is Cl. In some of the aforementioned embodiments is a compound of Formula (IX) wherein m is 1 and $R^2$ is $C_1$-$C_4$alkyl. In some of the aforementioned embodiments is a compound of Formula (IX) wherein m is 1 and $R^2$ is —$CH_3$.

In some of the aforementioned embodiments is a compound of Formula (IX) wherein $Z^1$ is a bond. In some of the aforementioned embodiments is a compound of Formula (IX) wherein $Z^1$ is —O—. In some of the aforementioned embodiments is a compound of Formula (IX) wherein $Z^1$ is —($CH_2$)—. In some embodiments is a compound of Formula (IX) wherein $Z^1$ is —C(O)—. In some of the aforementioned embodiments is a compound of Formula (IX) wherein $Z^2$ is a bond. In some of the aforementioned embodiments is a compound of Formula (IX) wherein $Z^2$ is —O—. In some of the aforementioned embodiments is a compound of Formula (IX) wherein $Z^2$ is —($CH_2$)—. In some of the aforementioned embodiments is a compound of Formula (IX) wherein $Z^2$ is —C(O)—. In some of the aforementioned embodiments is a compound of Formula (IX) wherein Cy is $C_6$-$C_{20}$aryl. In some of the aforementioned embodiments is a compound of Formula (IX) wherein Cy is phenyl. In some of the aforementioned embodiments is a compound of Formula (IX) wherein Cy is $C_3$-$C_{12}$carbocyclyl. In some of the aforementioned embodiments is a compound of Formula (IX) wherein Cy is cyclohexyl. In some of the aforementioned embodiments is a compound of Formula (IX) wherein Cy is $C_2$-$C_{20}$heterocyclyl. In some of the aforementioned embodiments is a compound of Formula (IX) wherein Cy is pyrazinyl. In some of the aforementioned embodiments is a compound of Formula (IX) wherein Cy is piperidinyl. In some of the aforementioned embodiments is a compound of Formula (IX) wherein Cy is $C_1$-$C_{20}$heteroaryl. In some of the aforementioned embodiments is a compound of Formula (IX) wherein Cy is thiazolyl. In some of the aforementioned embodiments is a compound of Formula (IX) wherein Cy is oxazolyl. In some of the aforementioned embodiments is a compound of Formula (IX) wherein Cy is pyridyl. In some of the aforementioned embodiments is a compound of Formula (IX) wherein $R^1$ is H. In some of the aforementioned embodiments is a compound of Formula (IX) wherein $R^1$ is —$CH_3$. In some of the aforementioned embodiments is a compound of Formula (IX) wherein X is —($CH_2$)—. In some of the aforementioned embodiments is a compound of Formula (IX) wherein X is —($CH_2$)— and $R^1$ is H. In some of the aforementioned embodiments is a compound of Formula (IX) wherein X is —($CH_2CH_2$)—. In some of the aforementioned embodiments is a compound of Formula (IX) wherein X is —($CH_2CH_2$)— and $R^1$ is H. In some of the aforementioned embodiments is a compound of Formula (IX) wherein X is —($CH_2CH_2$)— and $R^1$ is —$CH_3$.

In some of the aforementioned embodiments is a compound of Formula (IX) wherein $Z^1$ is a bond, $Z^2$ is —O—, Cy is phenyl, X is —($CH_2$)—, and $R^1$ is H. In some of the aforementioned embodiments is a compound of Formula (IX) wherein $Z^1$ is a bond, $Z^2$ is —O—, Cy is phenyl, X is —($CH_2CH_2$)—, and $R^1$ is H. In some of the aforementioned embodiments is a compound of Formula (IX) wherein $Z^1$ is a bond, $Z^2$ is —O—, Cy is phenyl, X is —($CH_2CH_2$)—, and $R^1$ is —$CH_3$.

In some embodiments, the compound of Formula (I) has the following structure of Formula (X):

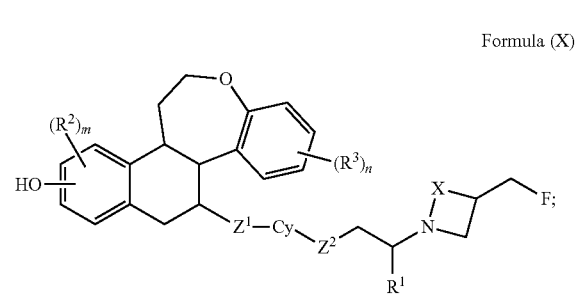

Formula (X)

wherein:

each $R^2$ and each $R^3$ are independently selected from halogen, —CN, —OR$^{10}$, —NR$^{13}$R$^{14}$, $C_1$-$C_4$alkyl, —$C_1$-$C_4$alkyl-OH, —OC$_2$-$C_4$alkyl-OH, $C_1$-$C_4$fluoroalkyl, —C(=O)OR$^{12}$, —NHC(=O)R$^{11}$, —C(=O)NHR$^{12}$, —SO$_2$R$^{11}$, —NHSO$_2$R$^{11}$, and —SO$_2$NHR$^{12}$;

each $R^{10}$ is independently selected from H, $C_1$-$C_4$alkyl, and $C_1$-$C_4$fluoroalkyl;

each $R^{11}$ is independently selected from $C_1$-$C_4$alkyl and $C_1$-$C_4$fluoroalkyl;

each $R^{12}$ is independently selected from H, $C_1$-$C_4$alkyl, and $C_1$-$C_4$fluoroalkyl;

each $R^{13}$ and each $R^{14}$ are independently selected from H and $C_1$-$C_4$alkyl;

m is 0, 1, 2 or 3; and n is 0, 1, 2 or 3;

or a pharmaceutically acceptable salt, solvate or prodrug thereof.

In some embodiments is a compound of Formula (X) wherein n is 1.

In some embodiments is a compound of Formula (X) wherein n is 1 having one of the following structures:

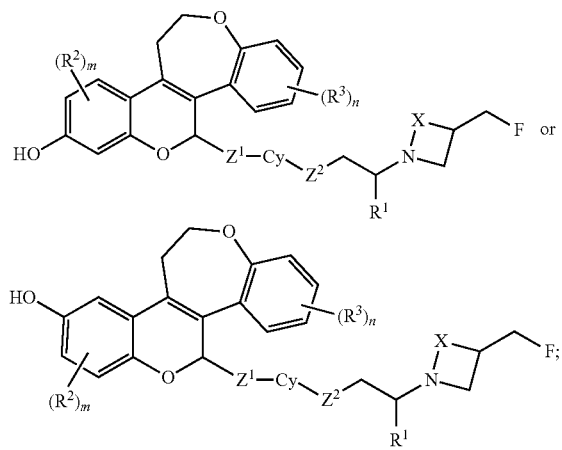

or a pharmaceutically acceptable salt, solvate or prodrug thereof.

In some embodiments is a compound of Formula (X) wherein n is 1 and $R^3$ is selected from the group consisting of F, C, —CN, —CH$_2$OH, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (X) wherein n is 1 and $R^3$ is selected from the group consisting of F, Cl, —CN, —OH, —CH$_3$, and —SO$_2$CH$_3$. In some embodiments is a compound of Formula (X) wherein n is 1 and $R^3$ is F. In some embodiments is a compound of Formula (X) wherein n is 1 and $R^3$ is —OH. In some embodiments is a compound of Formula (X) wherein n is 1 and $R^3$ is Cl. In some embodiments is a compound of Formula (X) wherein n is 1 and $R^3$ is —CN. In some embodiments is a compound of Formula (X) wherein n is 1 and $R^3$ is —CH$_3$. In some embodiments is a compound of Formula (X) wherein n is 1 and $R^3$ is —SO$_2$CH$_3$.

In some embodiments is a compound of Formula (X) wherein n is 2. In some embodiments is a compound of Formula (X) wherein n is 2 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (X) wherein n is 2 and each $R^3$ is independently selected from the group consisting of F, Cl, —CN, —OH, —CH$_3$, and —SO$_2$CH$_3$. In some embodiments is a compound of Formula (X) wherein n is 2 and each $R^3$ is independently selected from the group consisting of F and Cl. In some embodiments is a compound of Formula (X) wherein n is 2 and each $R^3$ is independently selected from the group consisting of F and —CN. In some embodiments is a compound of Formula (X) wherein n is 2 and each $R^3$ is F.

In some embodiments is a compound of Formula (X) wherein n is 3. In some embodiments is a compound of Formula (X) wherein n is 3 and each $R^3$ is independently selected from the group consisting of F, Cl, —CN, —OH, —OCH$_3$, —CH$_3$, —NHC(=O)CH$_3$, —C(=O)NH$_2$, NHSO$_2$CH$_3$, and —SO$_2$CH$_3$. In some embodiments is a compound of Formula (X) wherein n is 3 and each $R^3$ is independently selected from the group consisting of F, Cl, —CN, —OH, —CH$_3$, and —SO$_2$CH$_3$. In some embodiments is a compound of Formula (X) wherein n is 3 and each $R^3$ is independently selected from the group consisting of F and Cl. In some embodiments is a compound of Formula (X) wherein n is 3 and each $R^3$ is independently selected from the group consisting of F and —CN. In some embodiments is a compound of Formula (X) wherein n is 3 and each $R^3$ is F.

In some of the aforementioned embodiments is a compound of Formula (X) wherein m is 0. In some of the aforementioned embodiments is a compound of Formula (X) wherein m is 1. In some of the aforementioned embodiments is a compound of Formula (X) wherein m is 1 and $R^2$ is halogen. In some of the aforementioned embodiments is a compound of Formula (X) wherein m is 1 and $R^2$ is F. In some of the aforementioned embodiments is a compound of Formula (X) wherein m is 1 and $R^2$ is Cl. In some of the aforementioned embodiments is a compound of Formula (X) wherein m is 1 and $R^2$ is $C_1$-$C_4$alkyl. In some of the aforementioned embodiments is a compound of Formula (X) wherein m is 1 and $R^2$ is —CH$_3$.

In some of the aforementioned embodiments is a compound of Formula (X) wherein $Z^1$ is a bond. In some of the aforementioned embodiments is a compound of Formula (X) wherein $Z^1$ is —O—. In some of the aforementioned embodiments is a compound of Formula (X) wherein $Z^1$ is —(CH$_2$)—. In some embodiments is a compound of Formula (X) wherein $Z^1$ is —C(O)—. In some of the aforementioned embodiments is a compound of Formula (X) wherein $Z^2$ is a bond. In some of the aforementioned embodiments is a compound of Formula (X) wherein $Z^2$ is —O—. In some of the aforementioned embodiments is a compound of Formula (X) wherein $Z^2$ is —(CH$_2$)—. In some of the aforementioned embodiments is a compound of Formula (X) wherein $Z^2$ is —C(O)—. In some of the aforementioned embodiments is a compound of Formula (X) wherein Cy is $C_6$-$C_{20}$aryl. In some of the aforementioned embodiments is a compound of Formula (X) wherein Cy is phenyl. In some of the aforementioned embodiments is a compound of Formula (X) wherein Cy is $C_3$-$C_{12}$carbocyclyl. In some of the aforementioned embodiments is a compound of Formula (X) wherein Cy is cyclohexyl. In some of the aforementioned embodiments is a compound of Formula (X) wherein Cy is $C_2$-$C_{20}$heterocyclyl. In some of the aforementioned embodiments is a compound of Formula (X) wherein Cy is pyrazinyl. In some of the aforementioned embodiments is a compound of Formula (X) wherein Cy is piperidinyl. In some of the aforementioned embodiments is a compound of Formula (X) wherein Cy is $C_1$-$C_{20}$heteroaryl. In some of the aforementioned embodiments is a compound of Formula (X) wherein Cy is thiazolyl. In some of the aforementioned embodiments is a compound of Formula (X) wherein Cy is oxazolyl. In some of the aforementioned embodiments is a compound of Formula (X) wherein Cy is pyridyl. In some of the aforementioned embodiments is a compound of Formula (X) wherein $R^1$ is H. In some of the aforementioned embodiments is a compound of Formula (X) wherein $R^1$ is —$CH_3$. In some of the aforementioned embodiments is a compound of Formula (X) wherein X is —($CH_2$)—. In some of the aforementioned embodiments is a compound of Formula (X) wherein X is —($CH_2$)— and $R^1$ is H. In some of the aforementioned embodiments is a compound of Formula (X) wherein X is —($CH_2CH_2$)—. In some of the aforementioned embodiments is a compound of Formula (X) wherein X is —($CH_2CH_2$)— and $R^1$ is H. In some of the aforementioned embodiments is a compound of Formula (X) wherein X is —($CH_2CH_2$)— and $R^1$ is —$CH_3$.

In some of the aforementioned embodiments is a compound of Formula (X) wherein $Z^1$ is a bond, $Z^2$ is —O—, Cy is phenyl, X is —($CH_2$)—, and $R^1$ is H. In some of the aforementioned embodiments is a compound of Formula (X) wherein $Z^1$ is a bond, $Z^2$ is —O—, Cy is phenyl, X is —($CH_2CH_2$)—, and $R^1$ is H. In some of the aforementioned embodiments is a compound of Formula (X) wherein $Z^1$ is a bond, $Z^2$ is —O—, Cy is phenyl, X is —($CH_2CH_2$)—, and $R^1$ is —$CH_3$.

In some embodiments is a compound having the structure:

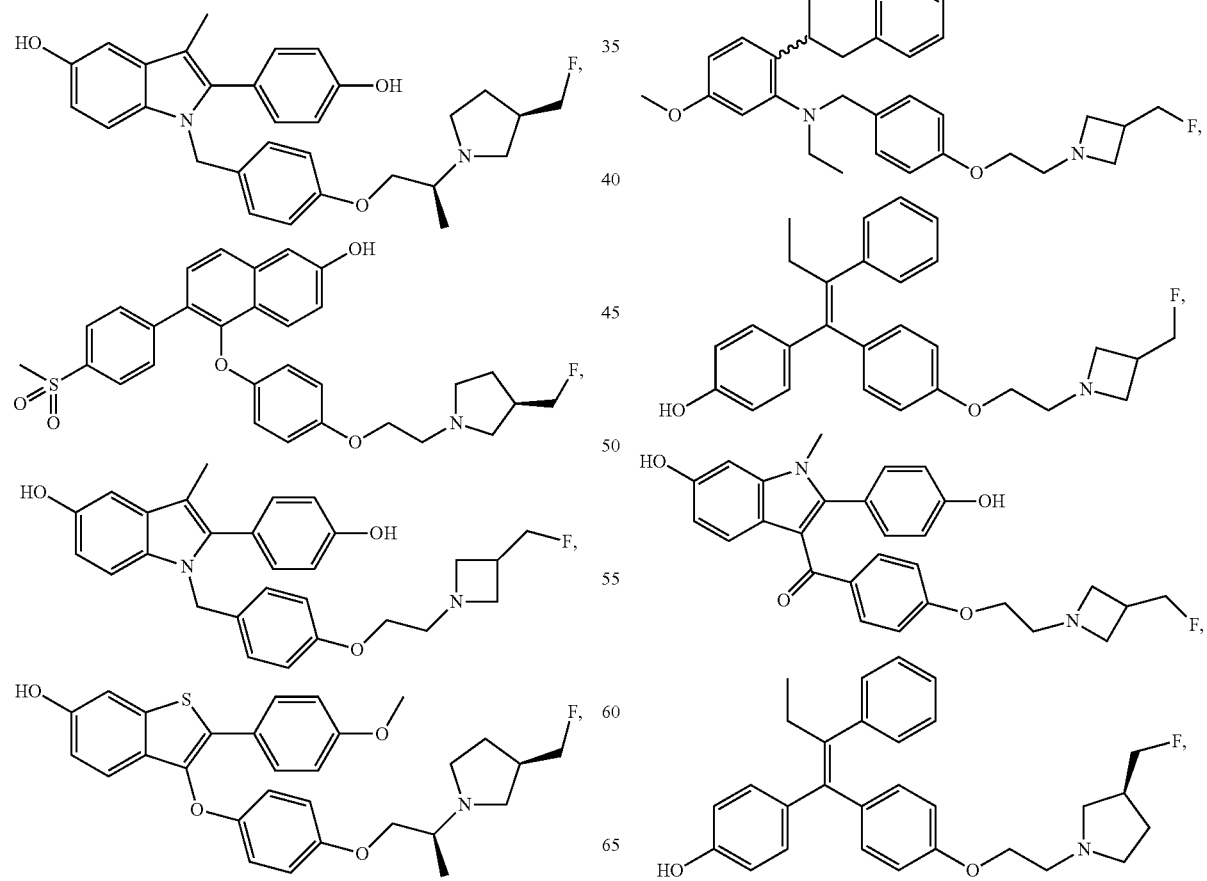

-continued

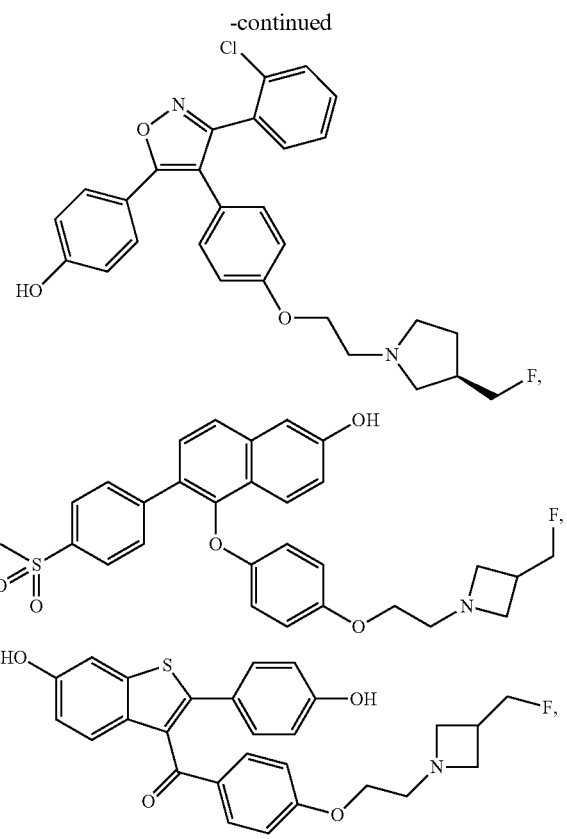

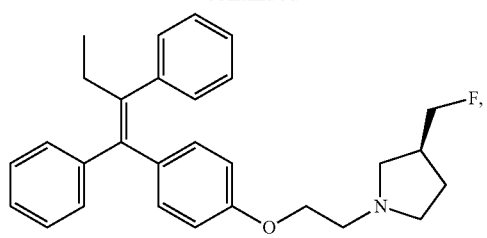
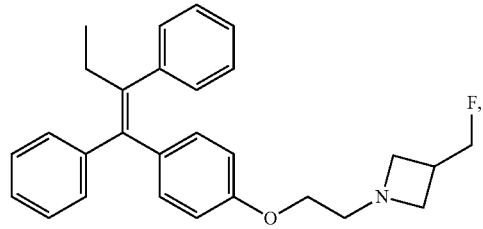
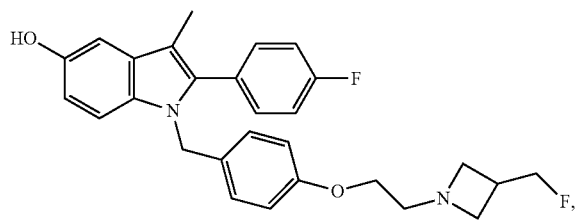
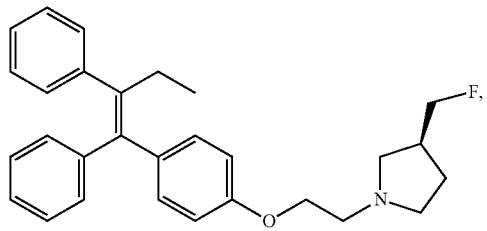
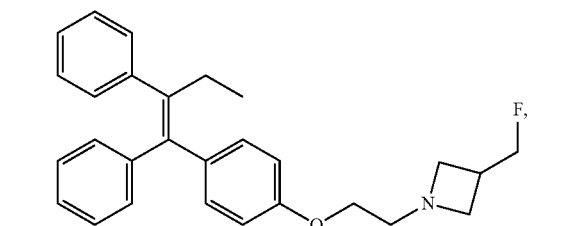
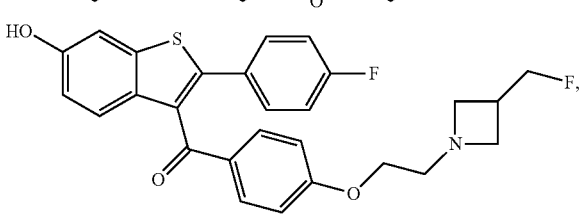
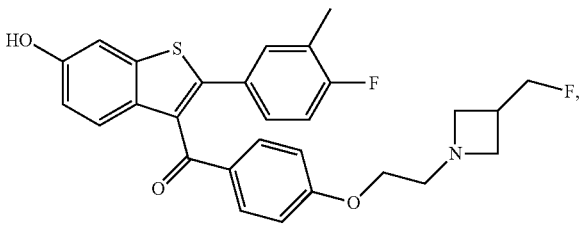
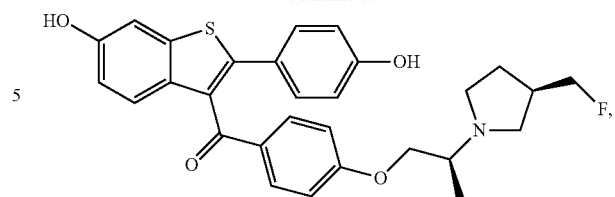
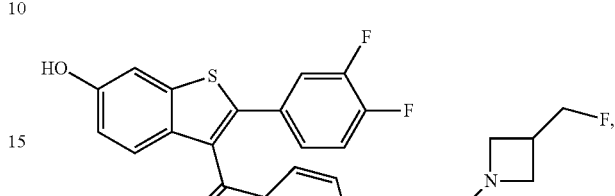
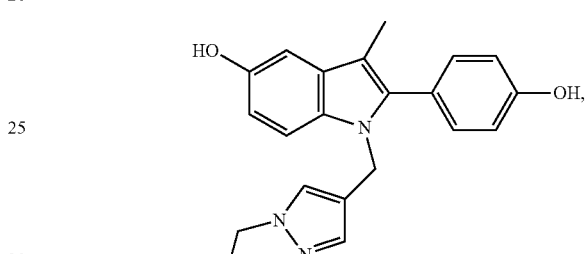
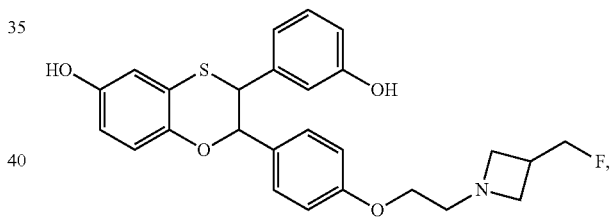
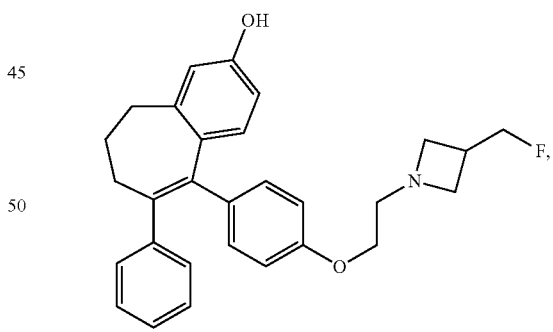
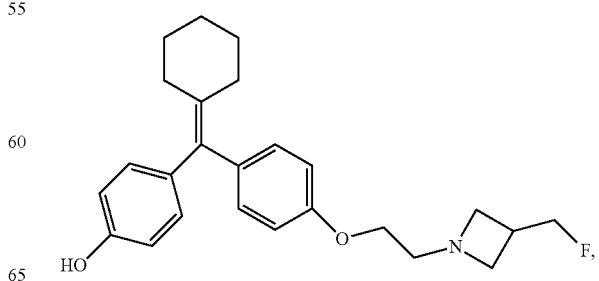

75
-continued
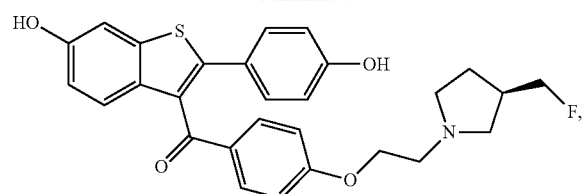
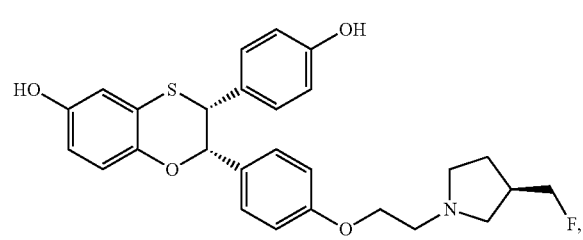
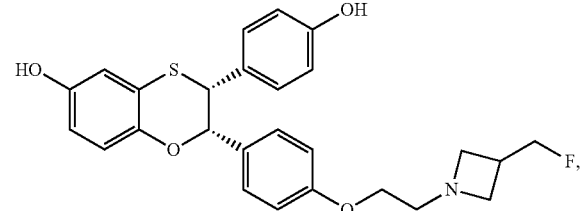
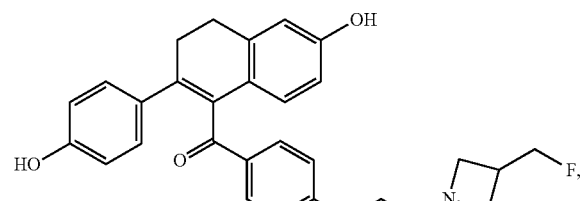
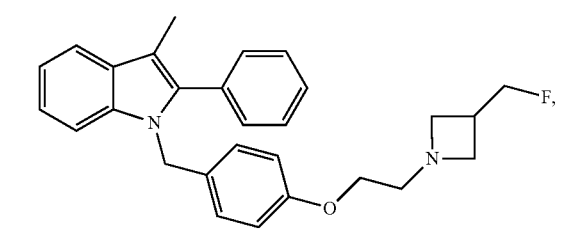
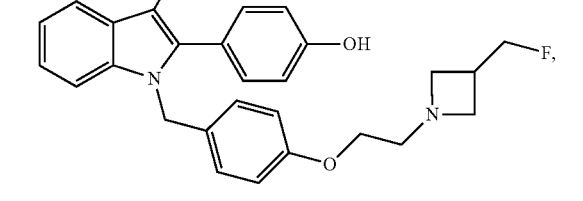
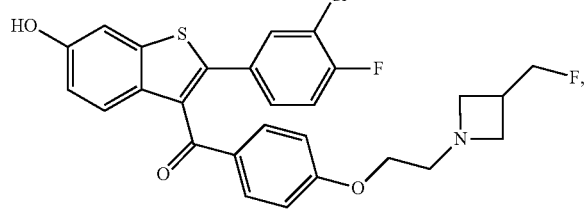
76
-continued
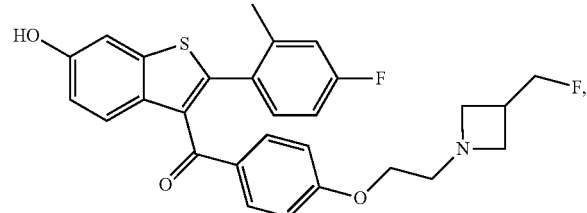
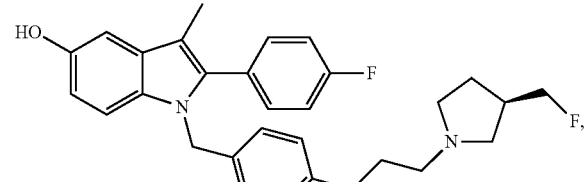
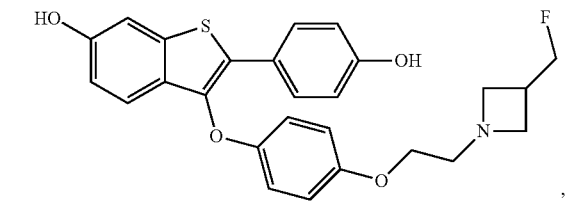
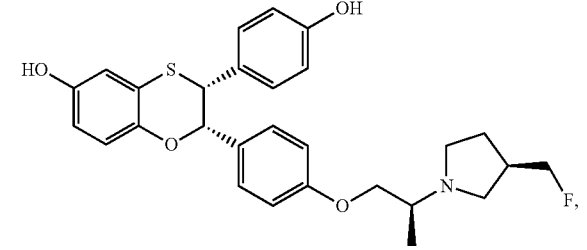
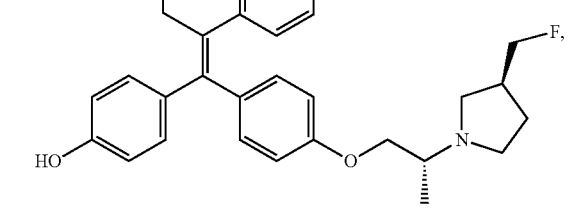
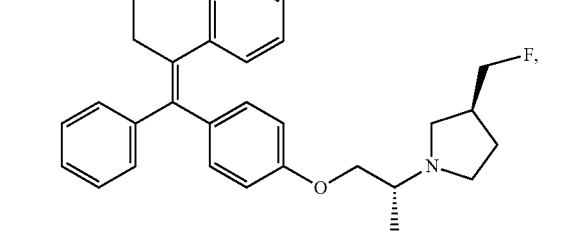
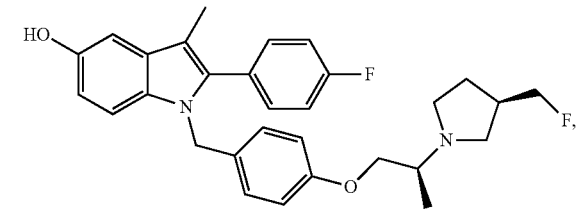

77
-continued
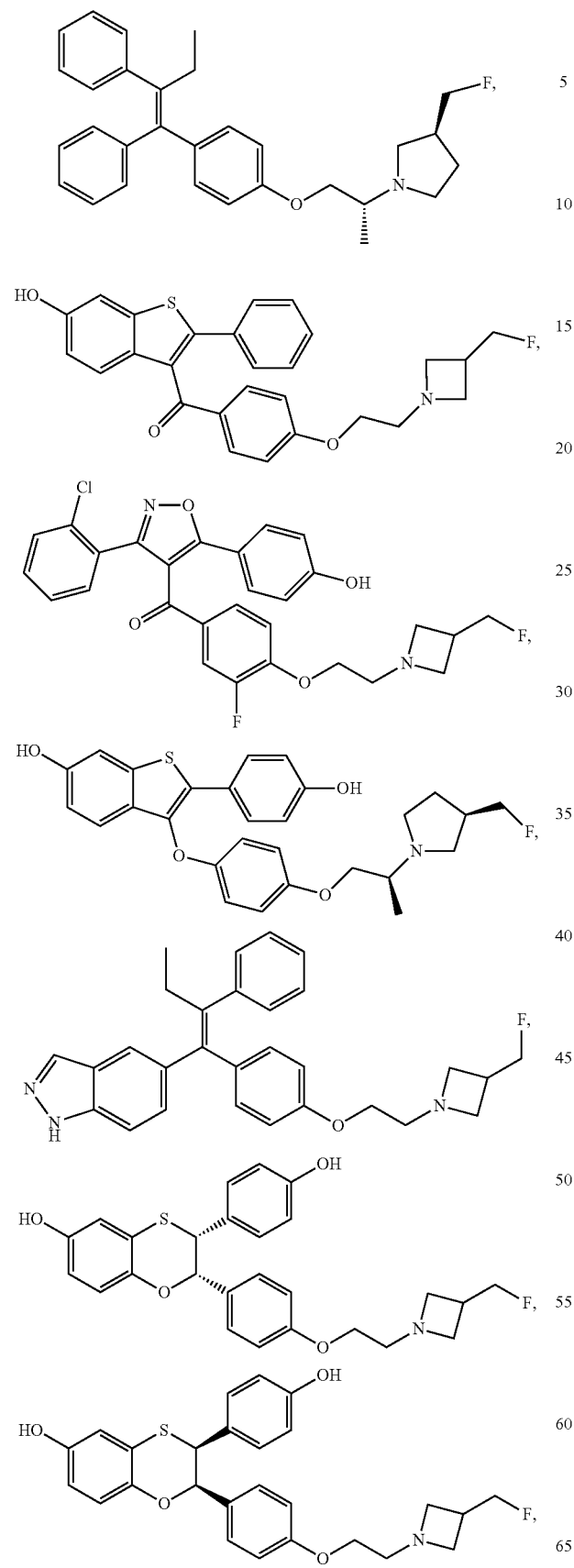
78
-continued
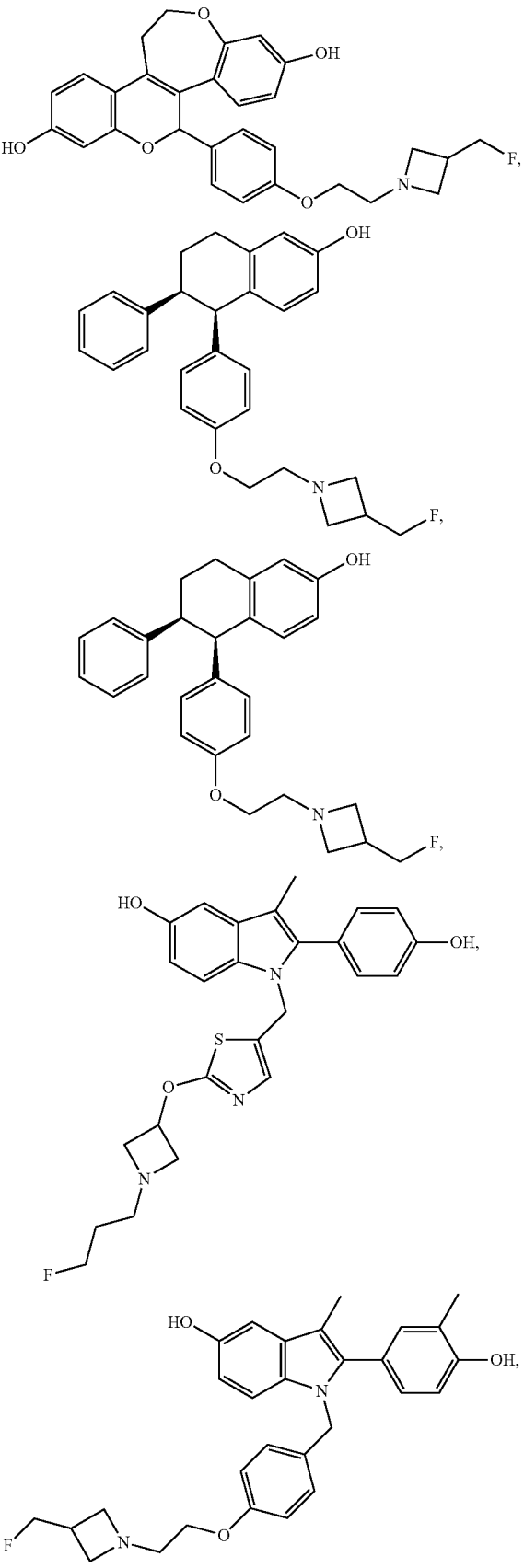

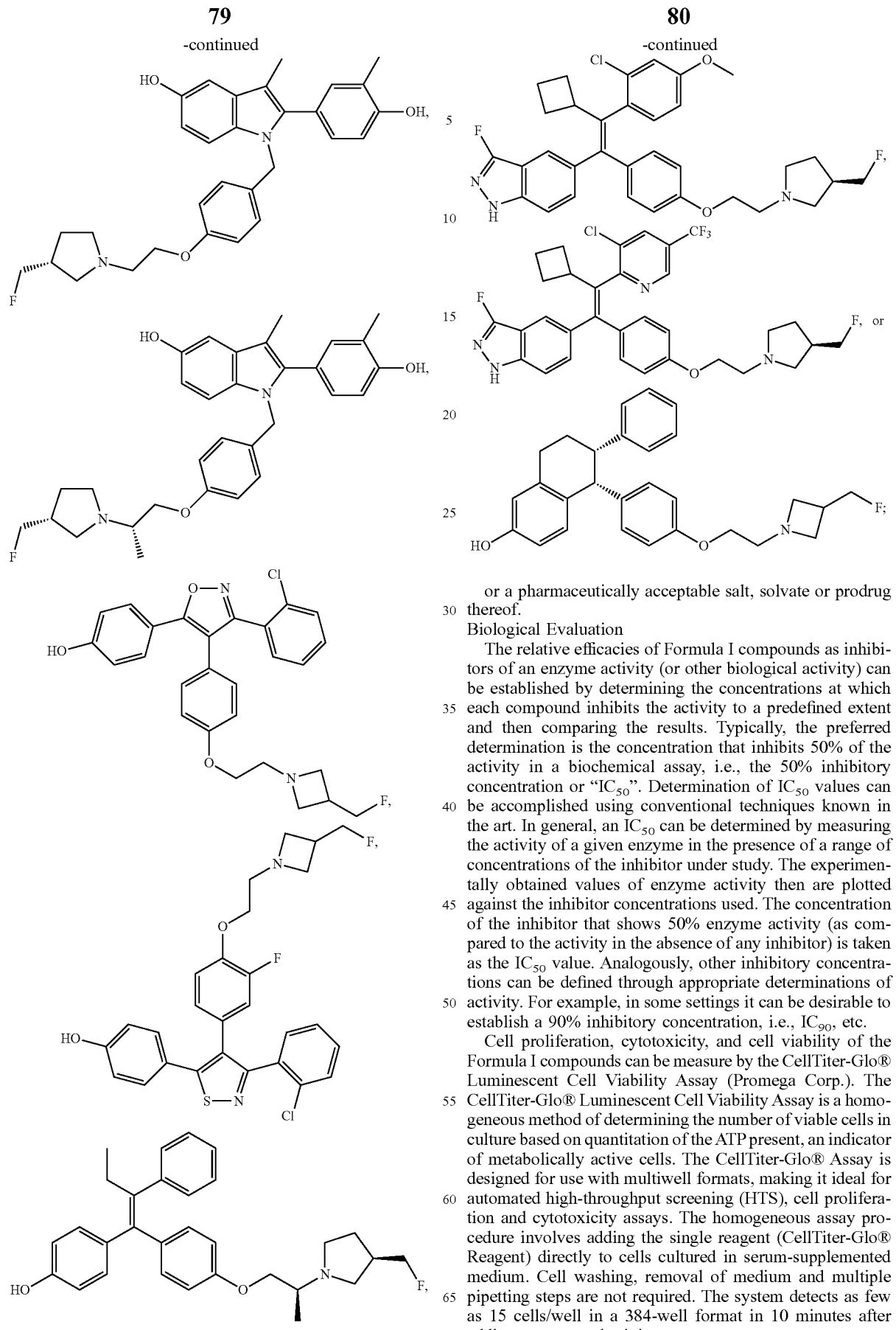

or a pharmaceutically acceptable salt, solvate or prodrug thereof.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Cell proliferation, cytotoxicity, and cell viability of the Formula I compounds can be measure by the CellTiter-Glo® Luminescent Cell Viability Assay (Promega Corp.). The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

Exemplary Formula I compounds in Tables 1a and 1b were made, characterized, and tested for binding to ERa (Estrogen Receptor alpha) and biological activity according to the assays, protocols, and procedures of Examples 901-914. ER-alpha MCF7 HCS $S_{inf}$ (%) values in Table 2 were measured by the Breast Cancer Cell ERa High Content Fluorescence Imaging Degradation Assay of Example 901. ER-alpha MCF7 HCS $EC_{50}$ (μM) values in Tables 2a and 2b were measured by the in vitro cell proliferation assays described in Example 901. The rat uterine wet weight assays of Examples 913 and 914 allow rapid determination of compound antagonist activity in an ER responsive tissue (immature rat uterus) while competing against the native ER ligand estradiol, i.e. antagonist mode (Ashby, J.; et al (1997) Regulatory toxicology and pharmacology: RTP, 25 (3):226-31). Exemplary Formula I compounds in Tables 1a and 1b have the following structures, corresponding names (Chem-BioDraw, Version 12.0.2, CambridgeSoft Corp., Cambridge Mass.), and biological activity. Where more than one name is associated with a Formula I compound or intermediate, the chemical structure shall define the compound.

TABLE 1a

| Example | Structure | Name | LCMS [M + H]+ or [M − H]+ |
|---|---|---|---|
| 1 | 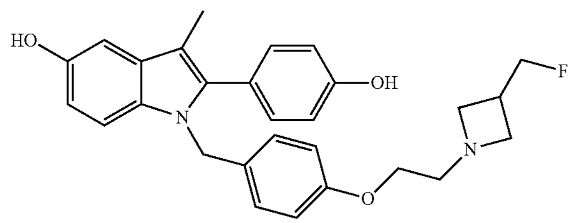 [SMILES: Cc1c(-c2ccc(O)cc2)n(Cc2ccc(OCCN3CC(CF)C3)cc2)c2ccc(O)cc12] | 1-(4-(2-(3-(Fluoromethyl)azetidin-1-yl)ethoxy)benzyl)-2-(4-hydroxyphenyl)-3-methyl-1H-indol-5-ol | 461.2 |
| 2 | 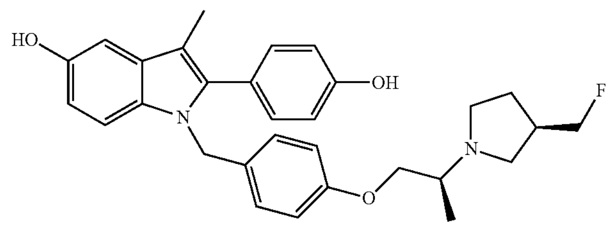 [SMILES: Cc1c(-c2ccc(O)cc2)n(Cc2ccc(OC[C@H](C)N3CC[C@@H](CF)C3)cc2)c2ccc(O)cc12] | 1-(4-((S)-2-((R)-3-(Fluoromethyl)pyrrolidin-1-yl)propoxy)benzyl)-2-(4-hydroxyphenyl)-3-methyl-1H-indol-5-ol | 489.3 |
| 3 | 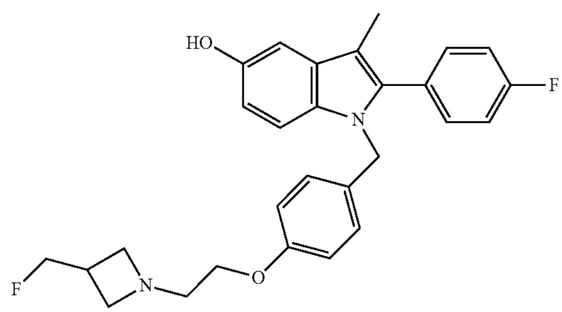 [SMILES: Cc1c(-c2ccc(F)cc2)n(Cc2ccc(OCCN3CC(CF)C3)cc2)c2ccc(O)cc12] | 1-(4-(2-(3-(Fluoromethyl)azetidin-1-yl)ethoxy)benzyl)-2-(4-fluorophenyl)-3-methyl-1H-indol-5-ol | 463.2 |
| 4 | 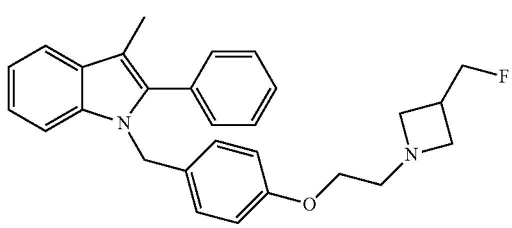 [SMILES: Cc1c(-c2ccccc2)n(Cc2ccc(OCCN3CC(CF)C3)cc2)c2ccccc12] | 1-(4-(2-(3-(Fluoromethyl)azetidin-1-yl)ethoxy)benzyl)-3-methyl-2-phenyl-1H-indole | 429.2 |
| 5 | 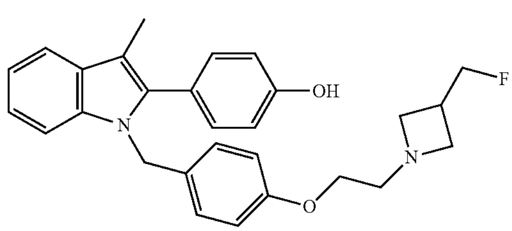 [SMILES: Cc1c(-c2ccc(O)cc2)n(Cc2ccc(OCCN3CC(CF)C3)cc2)c2ccccc12] | 4-(1-(4-(2-(3-(Fluoromethyl)azetidin-1-yl)ethoxy)benzyl)-3-methyl-1H-indol-2-yl)phenol | 445.2 |

TABLE 1a-continued

| Example | Structure | Name | LCMS [M + H]+ or [M − H]+ |
|---|---|---|---|
| 6 | 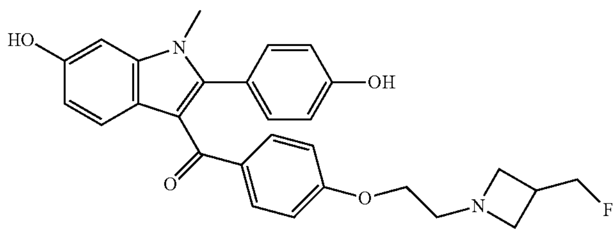 [SMILES: Cn1c(-c2ccc(O)cc2)c(C(=O)c2ccc(OCCN3CC(CF)C3)cc2)c2ccc(O)cc21] | (4-(2-(3-(Fluoromethyl)azetidin-1-yl)ethoxy)phenyl)(6-hydroxy-2-(4-hydroxyphenyl)-1-methyl-1H-indol-3-yl)methanone | 475.2 |
| 7 | 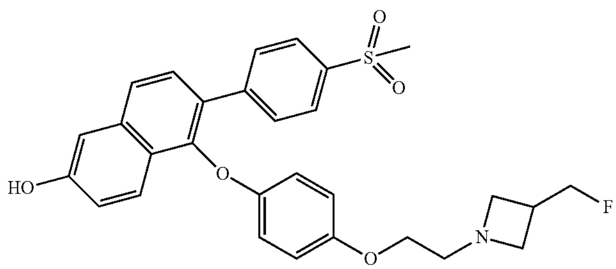 [SMILES: CS(=O)(=O)c1ccc(-c2ccc3cc(O)ccc3c2Oc2ccc(OCCN3CC(CF)C3)cc2)cc1] | 5-(4-(2-(3-(Fluoromethyl)azetidin-1-yl)ethoxy)phenoxy)-6-(4-(methylsulfonyl)phenyl)naphthalen-2-ol | 522.2 |
| 8 | 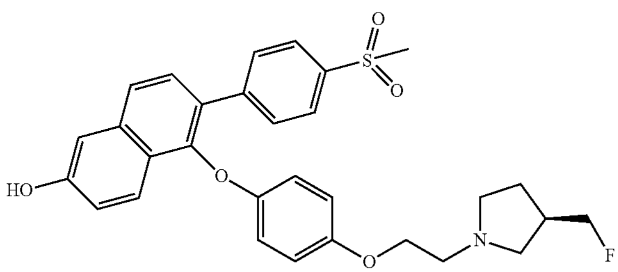 [SMILES: CS(=O)(=O)c1ccc(-c2ccc3cc(O)ccc3c2Oc2ccc(OCCN3CC[C@@H](CF)C3)cc2)cc1] | (R)-5-(4-(2-(3-(Fluoromethyl)pyrrolidin-1-yl)ethoxy)phenoxy)-6-(4-(methylsulfonyl)phenyl)naphthalen-2-ol | 536.0 |
| 9 | 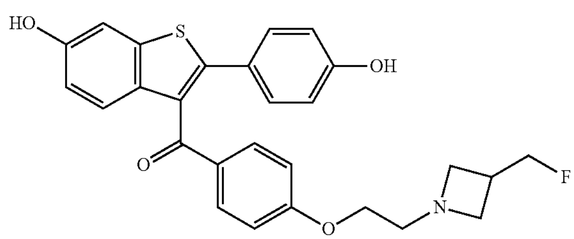 [SMILES: O=C(c1ccc(OCCN2CC(CF)C2)cc1)c1c(-c2ccc(O)cc2)sc2cc(O)ccc12] | (4-(2-(3-(fluoromethyl)azetidin-1-yl)ethoxy)phenyl)(6-hydroxy-2-(4-hydroxyphenyl)benzo[b]thiophen-3-yl)methanone | 478.2 |
| 10 | 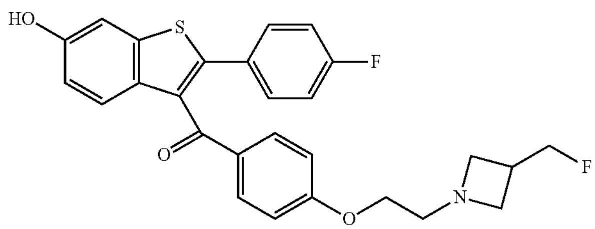 [SMILES: O=C(c1ccc(OCCN2CC(CF)C2)cc1)c1c(-c2ccc(F)cc2)sc2cc(O)ccc12] | (4-(2-(3-(fluoromethyl)azetidin-1-yl)ethoxy)phenyl)(2-(4-fluorophenyl)-6-hydroxybenzo[b]thiophen-3-yl)methanone | 480.2 |
| 11 | 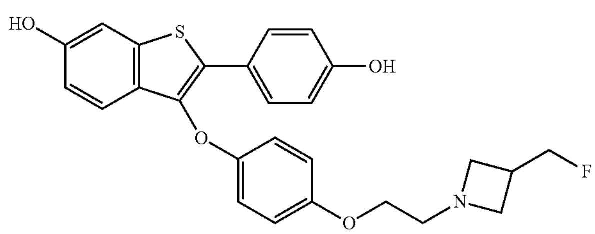 [SMILES: Oc1ccc(-c2sc3cc(O)ccc3c2Oc2ccc(OCCN3CC(CF)C3)cc2)cc1] | 3-(4-(2-(3-(Fluoromethyl)azetidin-1-yl)ethoxy)phenoxy)-2-(4-hydroxyphenyl)benzo[b]thiophen-6-ol | 466.1 |

TABLE 1a-continued

| Example | Structure | Name | LCMS [M + H]+ or [M − H]+ |
|---|---|---|---|
| 12 | 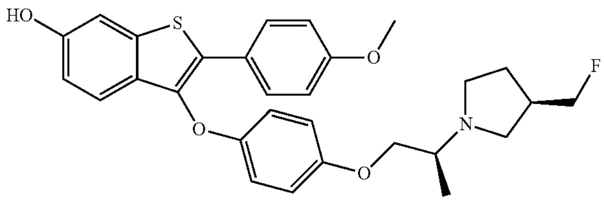 [SMILES: COc1ccc(-c2sc3cc(O)ccc3c2Oc2ccc(OC[C@H](C)N3CC[C@@H](CF)C3)cc2)cc1] | 3-(4-((S)-2-((R)-3-(Fluoromethyl)pyrrolidin-1-yl)propoxy)phenoxy)-2-(4-methoxyphenyl)benzo[6]thiophen-6-ol | 508.2 |
| 13 | 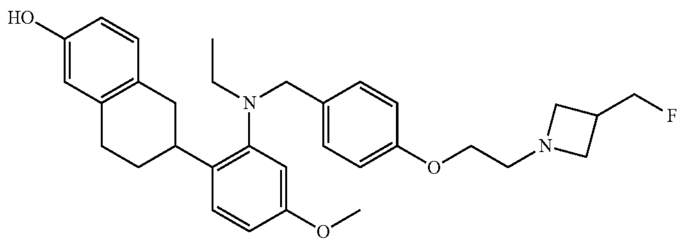 [SMILES: CCN(Cc1ccc(OCCN2CC(CF)C2)cc1)c1cc(OC)ccc1C1CCc2cc(O)ccc2C1] | 6-(2-(Ethyl(4-(2-(3-(fluoromethyl)azetidin-1-yl)ethoxy)benzyl)amino)-4-methoxyphenyl)-5,6,7,8-tetrahydronaphthalen-2-ol | 519.3 |
| 14 | 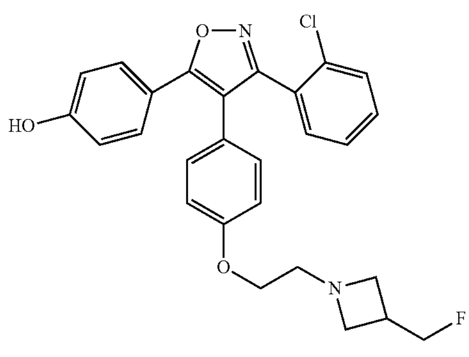 [SMILES: Oc1ccc(-c2onc(-c3ccccc3Cl)c2-c2ccc(OCCN3CC(CF)C3)cc2)cc1] | 4-(3-(2-Chlorophenyl)-4-(4-(2-(3-(fluoromethyl)azetidin-1-yl)ethoxy)phenyl)isoxazol-5-yl)phenol | 479.0 |
| 15 | 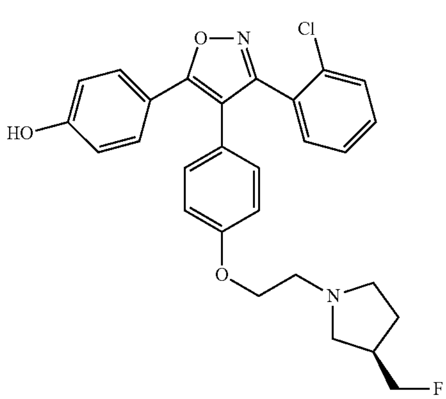 [SMILES: Oc1ccc(-c2onc(-c3ccccc3Cl)c2-c2ccc(OCCN3CC[C@@H](CF)C3)cc2)cc1] | (R)-4-(3-(2-Chlorophenyl)-4-(4-(2-(3-(fluoromethyl)pyrrolidin-1-yl)ethoxy)phenyl)isoxazol-5-yl)phenol | 493.0 |

TABLE 1a-continued

| Example | Structure | Name | LCMS [M + H]+ or [M − H]+ |
|---|---|---|---|
| 16 | 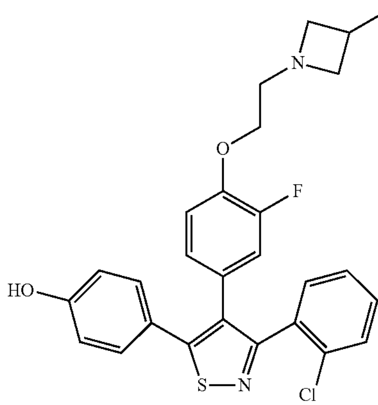 | 4-(3-(2-Chloro-phenyl)-4-{3-fluoro-4-[2-(3-fluoromethyl-azetidin-1-yl)-ethoxy]-phenyl}-isothiazol-5-yl)-phenol | 513.2 |
| 17 | 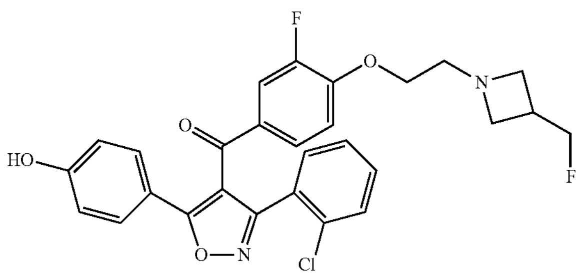 [SMILES: O=C(c1ccc(OCCN2CC(CF)C2)c(F)c1)c1c(-c2ccccc2Cl)noc1-c1ccc(O)cc1] | [3-(2-Chloro-phenyl)-5-(4-hydroxy-phenyl)-isoxazol-4-yl]-{3-fluoro-4-[2-(3-fluoromethyl-azetidin-1-yl)-ethoxy]-phenyl}-methanone | 525.1 |
| 18 | 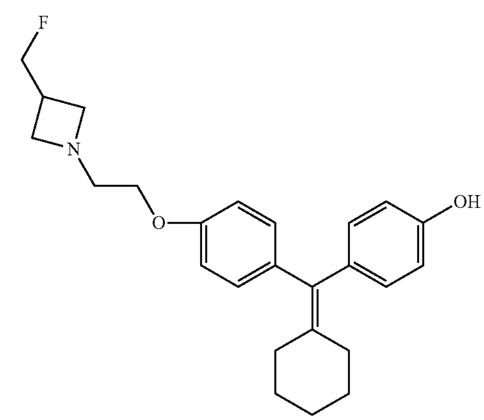 [SMILES: Oc1ccc(C(=C2CCCCC2)c2ccc(OCCN3CC(CF)C3)cc2)cc1] | 4-(Cyclohexylidene-{4-[2-(3-fluoromethyl-azetidin-1-yl)-ethoxy]-phenyl}-methyl)-phenol | 396.2 |
| 19 | 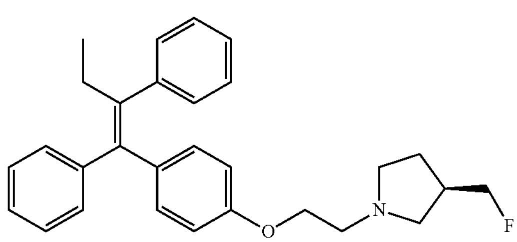 [SMILES: CC/C(=C(\c1ccccc1)c1ccc(OCCN2CC[C@@H](CF)C2)cc1)c1ccccc1] | (R,Z)-1-(2-(4-(1,2-Diphenylbut-1-en-yl)phenoxy)ethyl)-3-(fluoromethyl)pyrrolidine | 430.2 |

TABLE 1a-continued

| Example | Structure | Name | LCMS [M + H]+ or [M − H]+ |
|---|---|---|---|
| 20 | 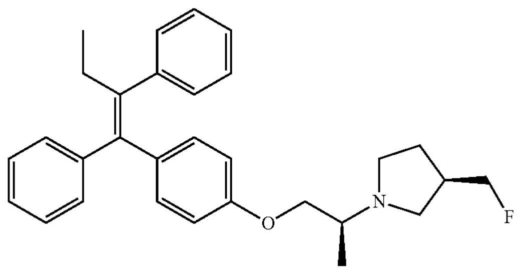 [SMILES: CC/C(=C(\c1ccccc1)c1ccc(OC[C@H](C)N2CC[C@@H](CF)C2)cc1)c1ccccc1] | (R)-1-((S)-1-(4-((Z)-1,2-Diphenylbut-1-en-1-yl)phenoxy)propan-2-yl)-3-(fluoromethyl)pyrrolidine | 444.2 |
| 21 | 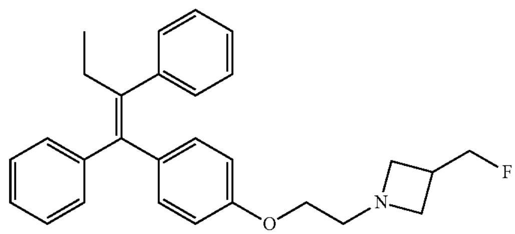 [SMILES: CC/C(=C(\c1ccccc1)c1ccc(OCCN2CC(CF)C2)cc1)c1ccccc1] | (Z)-1-(2-(4-(1,2-Diphenylbut-1-en-1-yl)phenoxy)ethyl)-3-(fluoromethyl)azetidine | 416.2 |
| 22 | 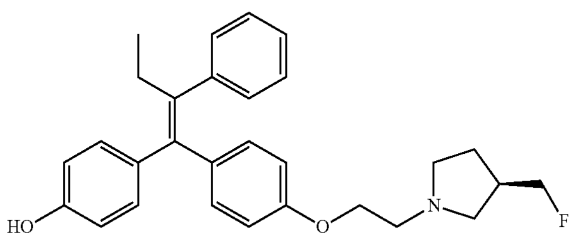 [SMILES: CC/C(=C(\c1ccc(O)cc1)c1ccc(OCCN2CC[C@@H](CF)C2)cc1)c1ccccc1] | (R,Z)-4-(1-(4-(2-(3-(Fluoromethyl)pyrrolidin-1-yl)ethoxy)phenyl)-2-phenylbut-1-en-yl)phenol | 446.2 |
| 23 | 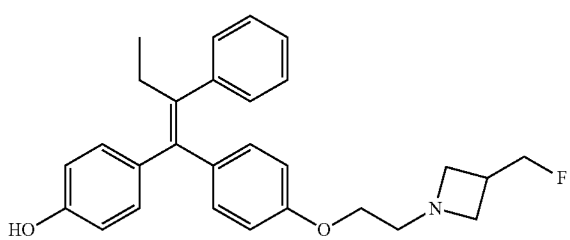 [SMILES: CC/C(=C(\c1ccc(O)cc1)c1ccc(OCCN2CC(CF)C2)cc1)c1ccccc1] | ((Z)-4-(1-(4-(2-(3-(Fluoromethyl)azetidin-1-yl)ethoxy)phenyl)-2-phenylbut-1-en-1-yl)phenol | 432.2 |
| 24 | 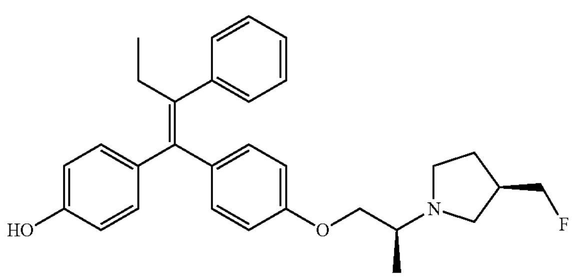 [SMILES: CC/C(=C(\c1ccc(O)cc1)c1ccc(OC[C@H](C)N2CC[C@@H](CF)C2)cc1)c1ccccc1] | 4-((Z)-1-(4-((S)-2-((R)-3-(Fluoromethyl)pyrrolidin-1-yl)propoxy)phenyl)-2-phenylbut-1-en-1-yl)phenol | 460.3 |
| 25 | 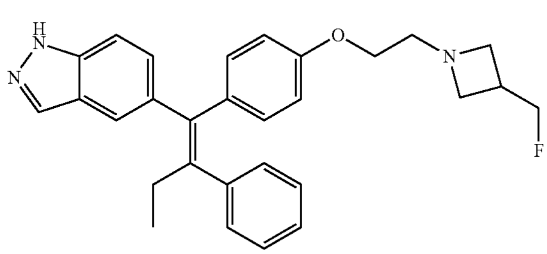 [SMILES: CC/C(=C(/c1ccc(OCCN2CC(CF)C2)cc1)c1ccc2[nH]ncc2c1)c1ccccc1] | (E)-5-(1-(4-(2-(3-(Fluoromethyl)azetidin-1-yl)ethoxy)phenyl)-2-phenylbut-1-en-1-yl)-1H-indazole | 456.2 |

TABLE 1a-continued

| Example | Structure | Name | LCMS [M + H]+ or [M − H]+ |
|---|---|---|---|
| 26 | 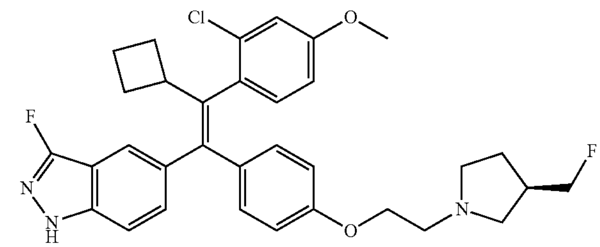 [SMILES: COc1ccc(/C(=C(\c2ccc(OCCN3CC[C@@H](CF)C3)cc2)c2ccc3[nH]nc(F)c3c2)C2CCC2)c(Cl)c1] | (R,E)-5-(2-(2-Chloro-4-methoxyphenyl)-2-cyclobutyl-1-(4-(2-(3-(fluoromethyl)pyrrolidin-1-yl)ethoxy)phenyl)vinyl)-3-fluoro-1H-indazole | 578.0 |
| 27 | 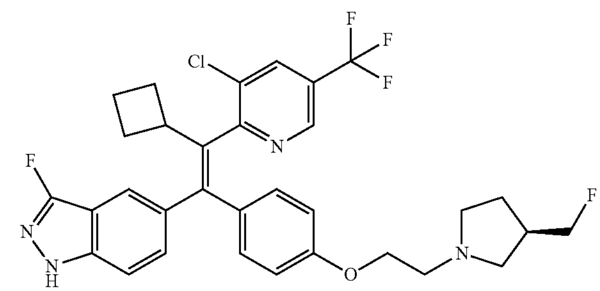 [SMILES: FC[C@@H]1CCN(CCOc2ccc(/C(=C(\c3ncc(C(F)(F)F)cc3Cl)C3CCC3)c3ccc4[nH]nc(F)c4c3)cc2)C1] | (R,E)-5-(2-(3-Chloro-5-(trifluoromethyl)pyridin-2-yl)-2-cyclobutyl-1-(4-(2-(3-(fluoromethyl)pyrrolidin-1-yl)ethoxy)phenyl)vinyl)-3-fluoro-1H-indazole | 616.9 |
| 28 | 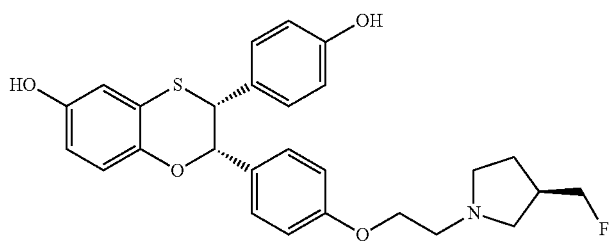 [SMILES: Oc1ccc([C@H]2Sc3cc(O)ccc3O[C@H]2c2ccc(OCCN3CC[C@@H](CF)C3)cc2)cc1] | 2-(4-(2-((R)-3-(Fluoromethyl)pyrrolidin-1-yl)ethoxy)phenyl)-3-(4-hydroxyphenyl)-2,3-dihydrobenzo[b][1,4]oxathiin-6-ol | 482.2 |
| 29 | 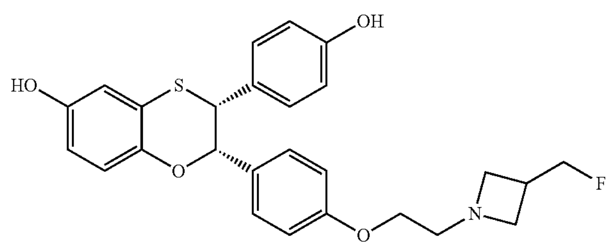 [SMILES: Oc1ccc([C@H]2Sc3cc(O)ccc3O[C@H]2c2ccc(OCCN3CC(CF)C3)cc2)cc1] | 2-(4-(2-(3-(Fluoromethyl)azetidin-1-yl)ethoxy)phenyl)-3-(4-hydroxyphenyl)-2,3-dihydrobenzo[b][1,4]oxathiin-6-ol | 468.1 |
| 30 | 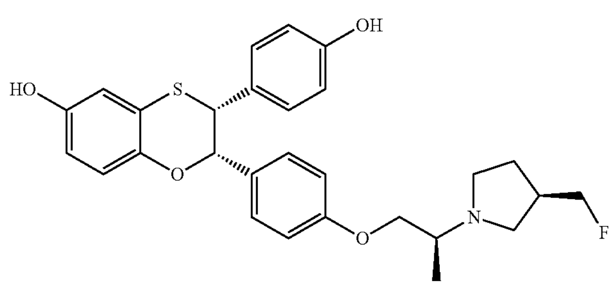 [SMILES: C[C@@H](COc1ccc([C@@H]2Oc3ccc(O)cc3S[C@@H]2c2ccc(O)cc2)cc1)N1CC[C@@H](CF)C1] | 2-(4-((S)-2-((R)-3-(Fluoromethyl)pyrrolidin-1-yl)propoxy)phenyl)-3-(4-hydroxyphenyl)-2,3-dihydrobenzo[b][1,4]oxathiin-6-ol | 496.2 |
| 31 | 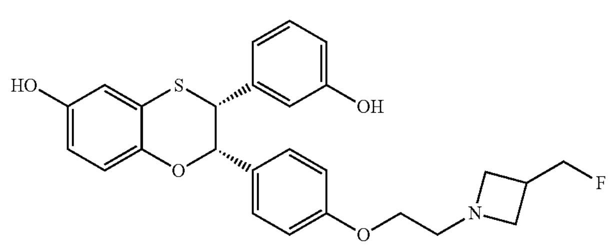 [SMILES: Oc1cccc([C@H]2Sc3cc(O)ccc3O[C@H]2c2ccc(OCCN3CC(CF)C3)cc2)c1] | 2-(4-(2-(3-(Fluoromethyl)azetidin-1-yl)ethoxy)phenyl)-3-(3-hydroxyphenyl)-2,3-dihydrobenzo[b][1,4]oxathiin-6-ol | 468.1 |

TABLE 1a-continued

| Example | Structure | Name | LCMS [M + H]+ or [M − H]+ |
|---|---|---|---|
| 32 | 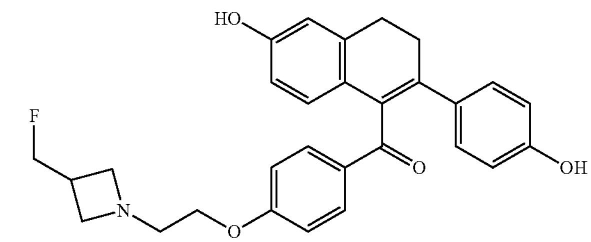 [SMILES: O=C(C1=C(c2ccc(O)cc2)CCc2cc(O)ccc21)c1ccc(OCCN2CC(CF)C2)cc1] | (4-(2-(3-(Fluoromethyl)azetidin-1-yl)ethoxy)phenyl)(6-hydroxy-2-(4-hydroxyphenyl)-3,4-dihydronaphthalen-1-yl)methanone | 474.2 |
| 33 | 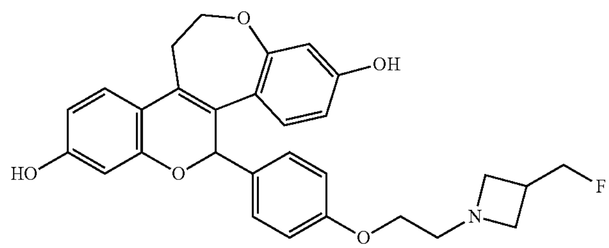 [SMILES: Oc1ccc2c(c1)OC(c1ccc(OCCN3CC(CF)C3)cc1)C1=C2CCOc2cc(O)ccc21] | 8-(4-(2-(3-(Fluoromethyl)azetidin-1-yl)ethoxy)phenyl)-2,8-dihydro-1H-benzo[2,3]oxepino[4,5-c]chromene-5,11-diol | 490.2 |
| 34 | 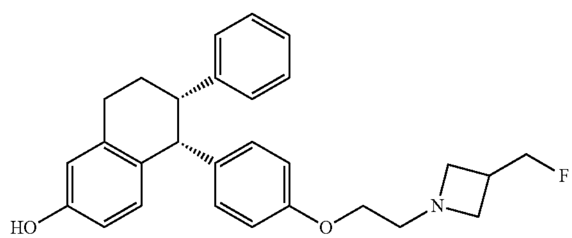 [SMILES: Oc1ccc2c(c1)CC[C@H](c1ccccc1)[C@@H]2c1ccc(OCCN2CC(CF)C2)cc1] | cis-5-(4-(2-(3-(Fluoromethyl)azetidin-1-yl)ethoxy)phenyl)-6-phenyl-5,6,7,8-tetrahydronaphthalen-2-ol | 431.9 |
| 35 | 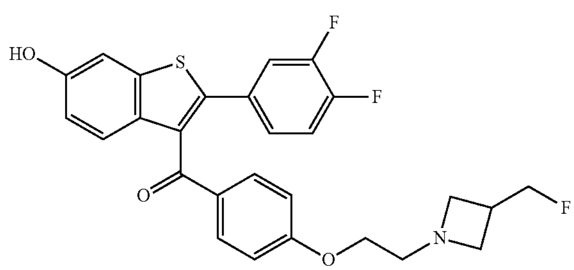 | (2-(3,4-difluorophenyl)-6-hydroxybenzo[b]thiophen-3-yl)(4-(2-(3-(fluoromethyl)azetidin-1-yl)ethoxy)phenyl)methanone | 498.2 |
| 36 | 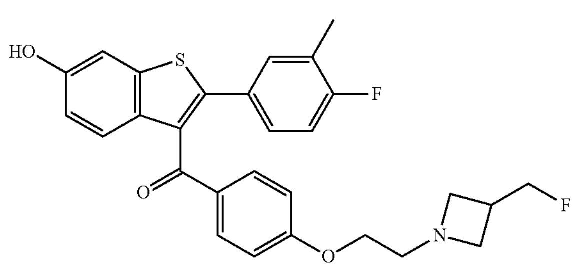 | (2-(4-fluoro-3-methylphenyl)-6-hydroxybenzo[b]thiophen-3-yl)(4-(2-(3-(fluoromethyl)azetidin-1-yl)ethoxy)phenyl)methanone | 494.2 |
| 37 | 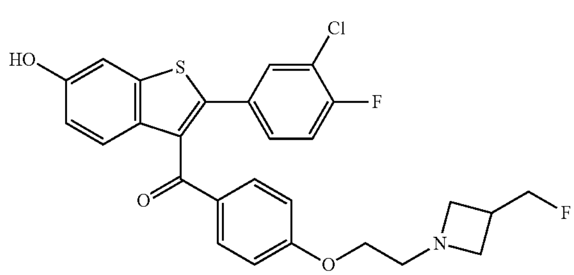 [SMILES: O=C(c1ccc(OCCN2CC(CF)C2)cc1)c1c(-c2ccc(F)c(F)c2)sc2cc(O)ccc12] | (2-(3-chloro-4-fluorophenyl)-6-hydroxybenzo[b]thiophen-3-yl)(4-(2-(3-(fluoromethyl)azetidin-1-yl)ethoxy)phenyl)methanone | 514.2 |

TABLE 1a-continued

| Example | Structure | Name | LCMS [M + H]+ or [M − H]+ |
|---|---|---|---|
| 38 | 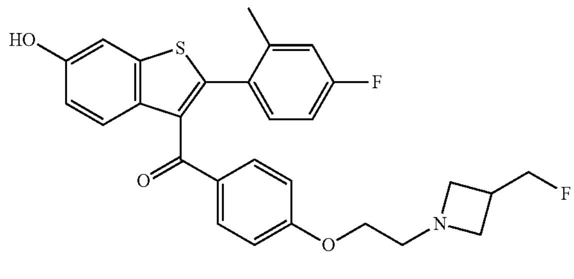 [SMILES: Cc1cc(F)ccc1-c1sc2cc(O)ccc2c1C(=O)c1ccc(OCCN2CC(CF)C2)cc1] | (2-(4-fluoro-2-methylphenyl)-6-hydroxybenzo[b]thiophen-3-yl)(4-(2-(3-(fluoromethyl)azetidin-1-yl)ethoxy)phenyl)methanone | 494.2 |
| 39 | 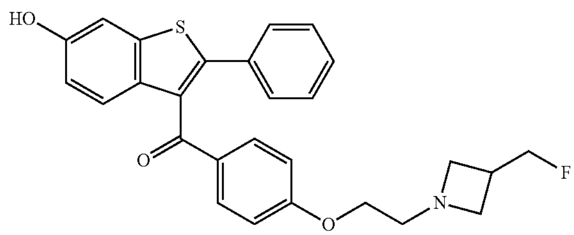 [SMILES: O=C(c1ccc(OCCN2CC(CF)C2)cc1)c1c(-c2ccccc2)sc2cc(O)ccc12] | (4-(2-(3-(fluoromethyl)azetidin-1-yl)ethoxy)phenyl)(6-hydroxy-2-phenylbenzo[b]thiophen-3-yl)methanone | 462.2 |
| 40 | 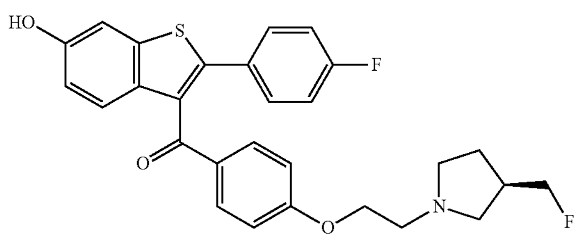 [SMILES: O=C(c1ccc(OCCN2CC[C@@H](CF)C2)cc1)c1c(-c2ccc(F)cc2)sc2cc(O)ccc12] | (R)-(4-(2-(3-(fluoromethyl)pyrrolidin-1-yl)ethoxy)phenyl)(6-hydroxy-2-(4-hydroxyphenyl)benzo[b]thiophen-3-yl)methanone | 492.2 |

TABLE 1b

| Example | Structure | Name | LCMS [M + H]+ or [M − H]− |
|---|---|---|---|
| 41 | 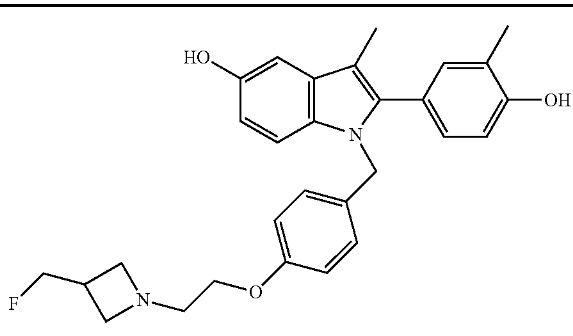 | 1-[[4-[2-[3-(fluoromethyl)azetidin-1-yl]ethoxy]phenyl]methyl]-2-(4-hydroxy-3-methyl-phenyl)-3-methyl-indol-5-ol | 475.1 |

TABLE 1b-continued

| Example | Structure | Name | LCMS [M + H]+ or [M − H]− |
|---|---|---|---|
| 42 | 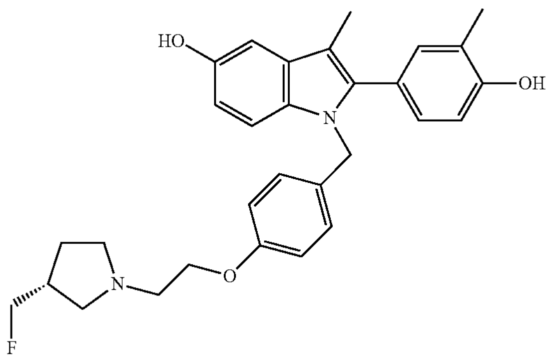 [SMILES: Cc1cc(-c2c(C)c3cc(O)ccc3n2Cc2ccc(OCCN3CC[C@@H](CF)C3)cc2)ccc1O] | (R)-1-(4-(2-(3-(fluoromethyl)pyrrolidin-1-yl)ethoxy)benzyl)-2-(4-hydroxy-3-methylphenyl)-3-methyl-1H-indol-5-ol | 489.1 |
| 43 | 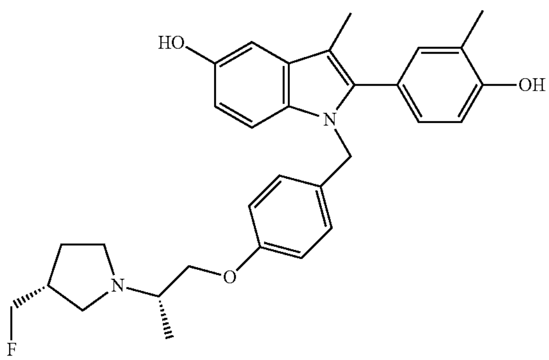 [SMILES: Cc1cc(-c2c(C)c3cc(O)ccc3n2Cc2ccc(OC[C@H](C)N3CC[C@@H](CF)C3)cc2)ccc1O] | 1-[[4-[(2S)-2-[(3R)-3-(fluoromethyl)pyrrolidin-1-yl]propoxy]phenyl]methyl]-2-(4-hydroxy-3-methyl-phenyl)-3-methyl-indol-5-ol | 503.2 |
| 44 | 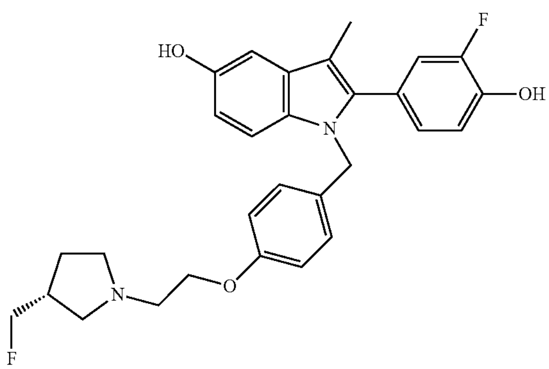 [SMILES: Cc1c(-c2ccc(O)c(F)c2)n(Cc2ccc(OCCN3CC[C@@H](CF)C3)cc2)c2ccc(O)cc12] | 2-(3-fluoro-4-hydroxy-phenyl)-1-[[4-[2-[(3R)-3-(fluoromethyl)pyrrolidin-1-yl]ethoxy]phenyl]methyl]-3-methyl-indol-5-ol | 493.0 |
| 45 | 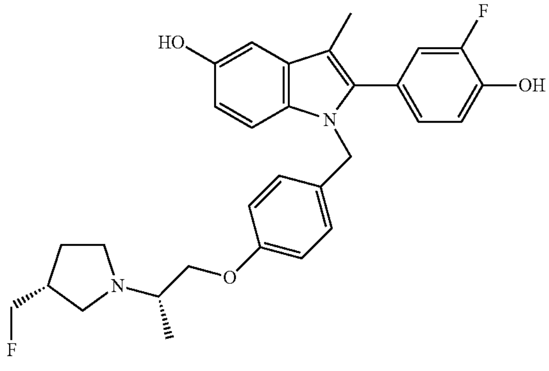 [SMILES: Cc1c(-c2ccc(O)c(F)c2)n(Cc2ccc(OC[C@H](C)N3CC[C@@H](CF)C3)cc2)c2ccc(O)cc12] | 2-(3-fluoro-4-hydroxy-phenyl)-1-[[4-[(2S)-2-[(3R)-3-(fluoromethyl)pyrrolidin-1-yl]propoxy]phenyl]methyl]-3-methyl-indol-5-ol | 507.0 |

TABLE 1b-continued

| Example | Structure | Name | LCMS [M + H]+ or [M − H]− |
|---|---|---|---|
| 46 | 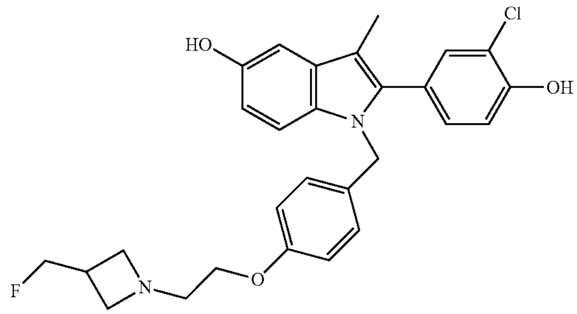 [SMILES: Cc1c(-c2ccc(O)c(Cl)c2)n(Cc2ccc(OCCN3CC(CF)C3)cc2)c2ccc(O)cc12] | 2-(3-chloro-4-hydroxy-phenyl)-1-[[4-[2-[3-(fluoromethyl)azetidin-1-yl]ethoxy]phenyl]methyl]-3-methyl-indol-5-ol | 495.2 |
| 47 | 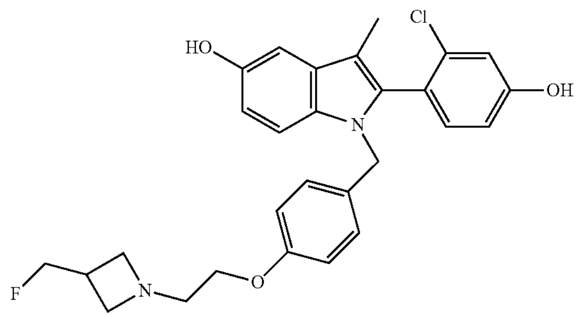 [SMILES: Cc1c(-c2ccc(O)cc2Cl)n(Cc2ccc(OCCN3CC(CF)C3)cc2)c2ccc(O)cc12] | 2-(2-chloro-4-hydroxy-phenyl)-1-[[4-[2-[3-(fluoromethyl)azetidin-1-yl]ethoxy]phenyl]methyl]-3-methyl-indol-5-ol | 495.1 |
| 48 | 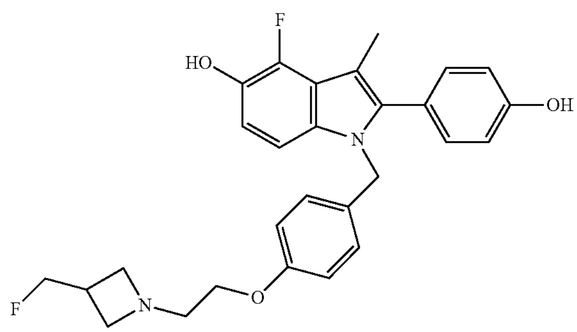 [SMILES: Cc1c(-c2ccc(O)cc2)n(Cc2ccc(OCCN3CC(CF)C3)cc2)c2ccc(O)c(F)c12] | 4-fluoro-1-[[4-[2-[3-(fluoromethyl)azetidin-1-yl]ethoxy]phenyl]methyl]-2-(4-hydroxyphenyl)-3-methyl-indol-5-ol | 479.3 |
| 49 | 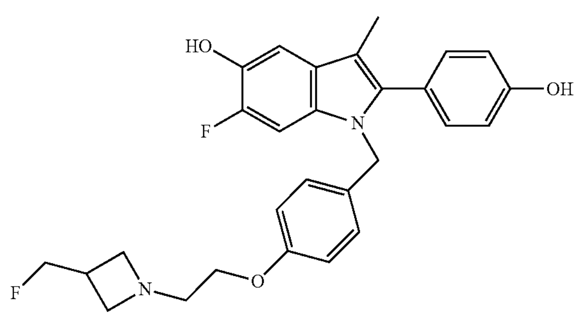 [SMILES: Cc1c(-c2ccc(O)cc2)n(Cc2ccc(OCCN3CC(CF)C3)cc2)c2cc(F)c(O)cc12] | 6-fluoro-1-(4-(2-(3-(fluoromethyl)azetidin-1-yl)ethoxy)benzyl)-2-(4-hydroxyphenyl)-3-methyl-1H-indol-5-ol | 479.3 |
| 50 | 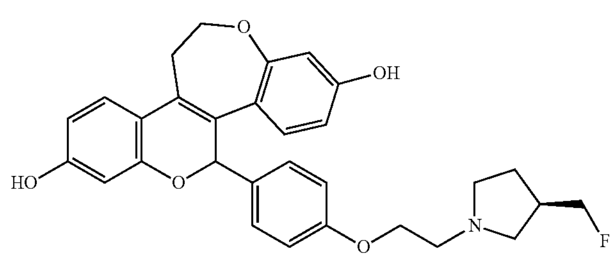 | 8-(4-(2-((R)-3-(fluoromethyl)pyrrolidin-1-yl)ethoxy)phenyl)-2,8-dihydro-1H-benzo[2,3]oxepino[4,5-c]chromene-5,11-diol | 504.4 |

TABLE 1b-continued

| Example | Structure | Name | LCMS [M + H]+ or [M − H]− |
|---|---|---|---|
| 51 | 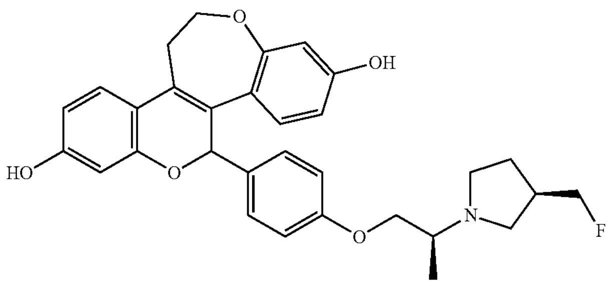 [SMILES: C[C@@H](COc1ccc(C2Oc3cc(O)ccc3C3=C2c2ccc(O)cc2OCC3)cc1)N1CC[C@@H](CF)C1] | 8-(4-((S)-2-((R)-3-(fluoromethyl)pyrrolidin-1-yl)propoxy)phenyl)-2,8-dihydro-1H-benzo[2,3]oxepino[4,5-c]chromene-5,11-diol | 518.3 |
| 52 | 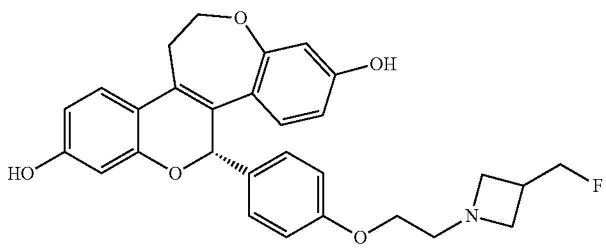 [SMILES: Oc1ccc2c(c1)O[C@@H](c1ccc(OCCN3CC(CF)C3)cc1)C1=C2CCOc2cc(O)ccc21] | (S)-8-(4-(2-(3-(fluoromethyl)azetidin-1-yl)ethoxy)phenyl)-2,8-dihydro-1H-benzo[2,3]oxepino[4,5-c]chromene-5,11-diol | 490.3 |
| 53 | 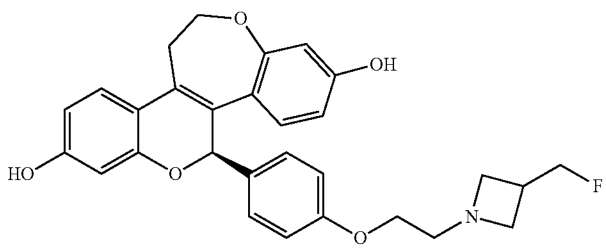 [SMILES: Oc1ccc2c(c1)O[C@H](c1ccc(OCCN3CC(CF)C3)cc1)C1=C2CCOc2cc(O)ccc21] | (R)-8-(4-(2-(3-(fluoromethyl)azetidin-1-yl)ethoxy)phenyl)-2,8-dihydro-1H-benzo[2,3]oxepino[4,5-c]chromene-5,11-diol | 490.3 |
| 54 | 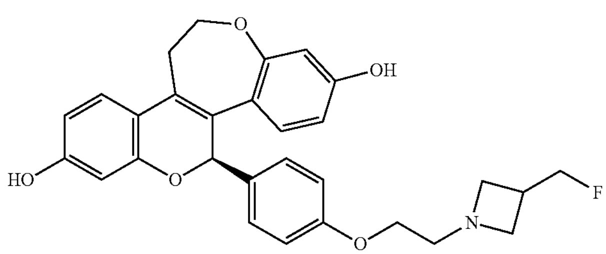 [SMILES: Oc1ccc2c(c1)O[C@H](c1ccc(OCCN3CC(CF)C3)cc1)C1=C2CCOc2cc(O)ccc21] | (R)-8-(4-(2-(3-(fluoromethyl)azetidin-1-yl)ethoxy)phenyl)-1,8-dihydro-2H-benzo[2,3]oxepino[4,5-c]chromene-5,11-diol | 490.2 |
| 55 | 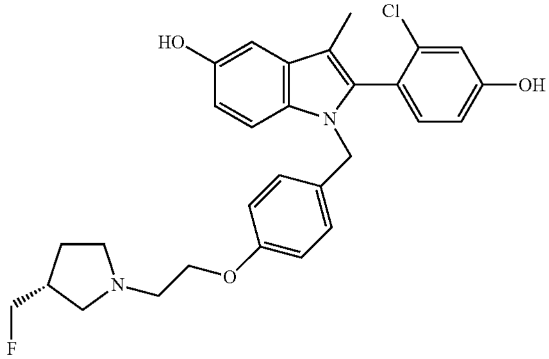 [SMILES: Cc1c(-c2ccc(O)cc2Cl)n(Cc2ccc(OCCN3CC[C@@H](CF)C3)cc2)c2ccc(O)cc12] | 2-(2-chloro-4-hydroxyphenyl)-1-(4-(2-((R)-3-(fluoromethyl)pyrrolidin-1-yl)ethoxy)benzyl)-3-methyl-1H-indol-5-ol | 509.2 |

TABLE 1b-continued

| Example | Structure | Name | LCMS [M + H]+ or [M − H]− |
|---|---|---|---|
| 56 | 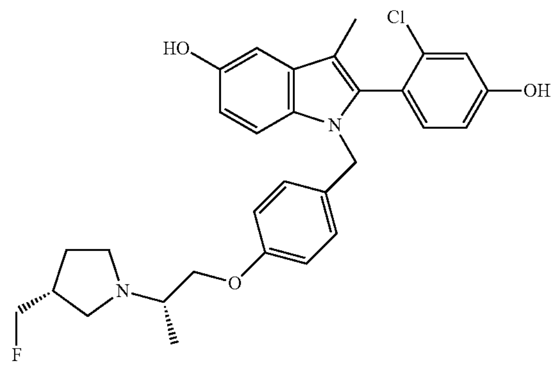 [SMILES: Cc1c(-c2ccc(O)cc2Cl)n(Cc2ccc(OC[C@H](C)N3CC[C@@H](CF)C3)cc2)c2ccc(O)cc12] | 2-(2-chloro-4-hydroxyphenyl)-1-(4-((S)-2-((R)-3-(fluoromethyl)pyrrolidin-1-yl)propoxy)benzyl)-3-methyl-1H-indol-5-ol | 523.1 |
| 57 | 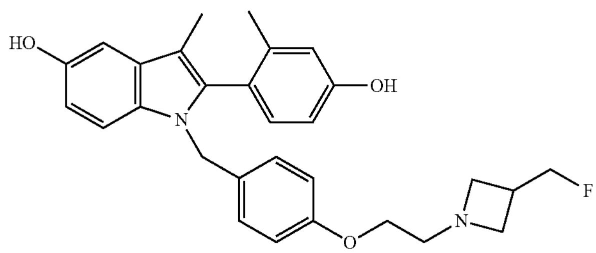 [SMILES: Cc1cc(O)ccc1-c1c(C)c2cc(O)ccc2n1Cc1ccc(OCCN2CC(CF)C2)cc1] | 1-[[4-[2-[3-(fluoromethyl)azetidin-1-yl]ethoxy]phenyl]methyl]-2-(4-hydroxy-2-methyl-phenyl)-3-methyl-indol-5-ol | 475.3 |
| 58 | 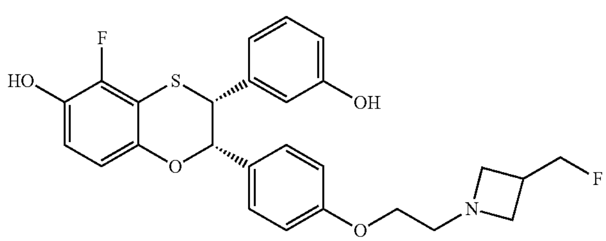 [SMILES: Oc1cccc([C@H]2Sc3c(ccc(O)c3F)O[C@H]2c2ccc(OCCN3CC(CF)C3)cc2)c1] | (2S,3R)-5-fluoro-2-(4-(2-(3-(fluoromethyl)azetidin-1-yl)ethoxy)phenyl)-3-(3-hydroxyphenyl)-2,3-dihydrobenzo[b][1,4]oxathiin-6-ol | 486.1 |
| 59 | 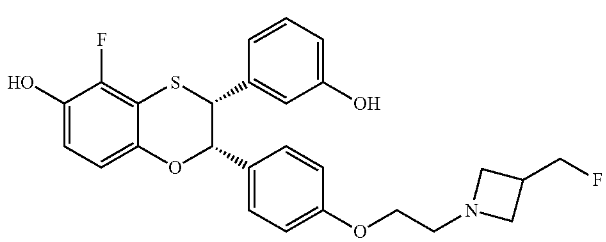 [SMILES: Oc1cccc([C@H]2Sc3c(ccc(O)c3F)O[C@H]2c2ccc(OCCN3CC(CF)C3)cc2)c1] | (2S,3R)-5-fluoro-2-(4-(2-(3-(fluoromethyl)azetidin-1-yl)ethoxy)phenyl)-3-(3-hydroxyphenyl)-2,3-dihydrobenzo[b][1,4]oxathiin-6-ol | 486.1 |
| 60 | 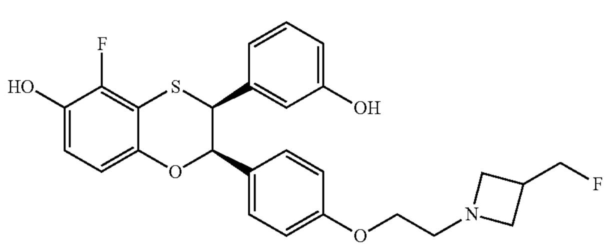 [SMILES: Oc1cccc([C@@H]2Sc3c(ccc(O)c3F)O[C@@H]2c2ccc(OCCN3CC(CF)C3)cc2)c1] | (2R,3S)-5-fluoro-2-(4-(2-(3-(fluoromethyl)azetidin-1-yl)ethoxy)phenyl)-3-(3-hydroxyphenyl)-2,3-dihydrobenzo[b][1,4]oxathiin-6-ol | 486.1 |

TABLE 1b-continued

| Example | Structure | Name | LCMS [M + H]+ or [M − H]− |
|---|---|---|---|
| 61 | 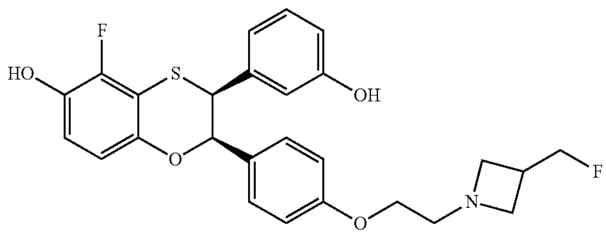 [SMILES: Oc1cccc([C@@H]2Sc3c(ccc(O)c3F)O[C@@H]2c2ccc(OCCN3CC(CF)C3)cc2)c1] | (2R,3S)-5-fluoro-2-(4-(2-(3-(fluoromethyl)azetidin-1-yl)ethoxy)phenyl)-3-(3-hydroxyphenyl)-2,3-dihydrobenzo[b][1,4]oxathiin-6-ol | 486.1 |
| 62 | 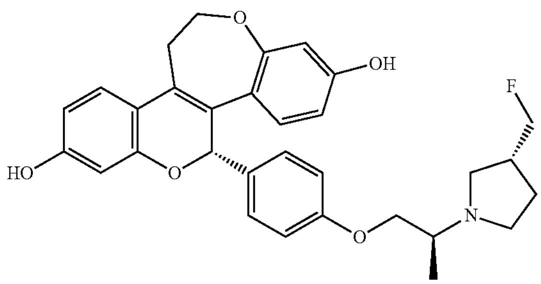 [SMILES: C[C@@H](COc1ccc([C@@H]2Oc3cc(O)ccc3C3=C2c2ccc(O)cc2OCC3)cc1)N1CC[C@@H](CF)C1] | (S)-8-(4-((S)-2-((R)-3-(fluoromethyl)pyrrolidin-1-yl)propoxy)phenyl)-2,8-dihydro-1H-benzo[2,3]oxepino[4,5-c]chromene-5,11-diol | 518.3 |
| 63 | 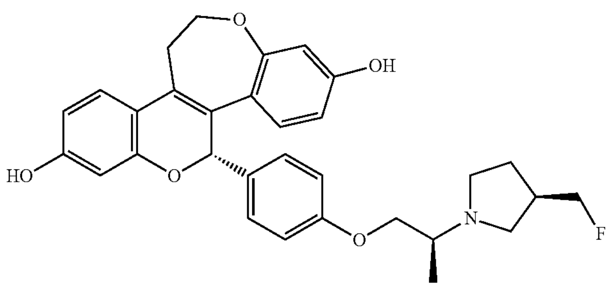 | (S)-8-(4-((S)-2-((R)-3-(fluoromethyl)pyrrolidin-1-yl)propoxy)phenyl)-1,8-dihydro-2H-benzo[2,3]oxepino[4,5-c]chromene-5,11-diol | 518.2 |
| 64 | 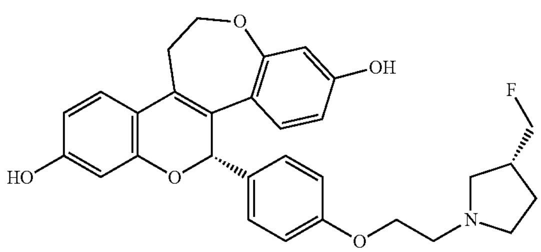 [SMILES: Oc1ccc2c(c1)O[C@@H](c1ccc(OCCN3CC[C@@H](CF)C3)cc1)C1=C2CCOc2cc(O)ccc21] | (S)-8-(4-(2-((R)-3-(fluoromethyl)pyrrolidin-1-yl)ethoxy)phenyl)-2,8-dihydro-1H-benzo[2,3]oxepino[4,5-c]chromene-5,11-diol | 504.3 |
| 65 | 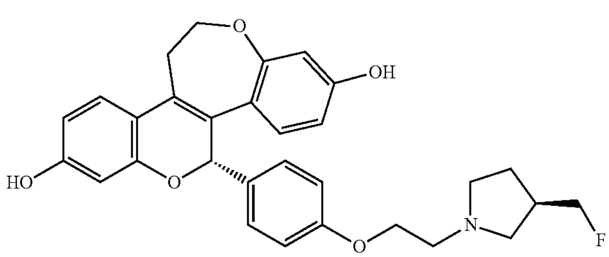 [SMILES: Oc1ccc2c(c1)O[C@@H](c1ccc(OCCN3CC[C@@H](CF)C3)cc1)C1=C2CCOc2cc(O)ccc21] | (S)-8-(4-(2-((R)-3-(fluoromethyl)pyrrolidin-1-yl)ethoxy)phenyl)-1,8-dihydro-2H-benzo[2,3]oxepino[4,5-c]chromene-5,11-diol | 504.2 |

TABLE 1b-continued

| Example | Structure | Name | LCMS [M + H]+ or [M − H]− |
|---|---|---|---|
| 66 | 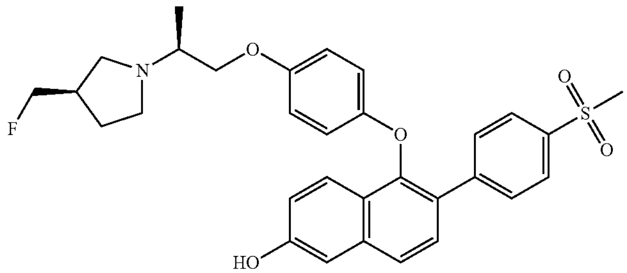 [SMILES: C[C@@H](COc1ccc(Oc2c(-c3ccc(S(C)(=O)=O)cc3)ccc3cc(O)ccc23)cc1)N1CC[C@@H](CF)C1] | 5-[4-[(2S)-2-[(3R)-3-(fluoromethyl)pyrrolidin-1-yl]propoxy]phenoxy]-6-(4-methylsulfonylphenyl)naphthalen-2-ol | 550.3 |
| 67 | 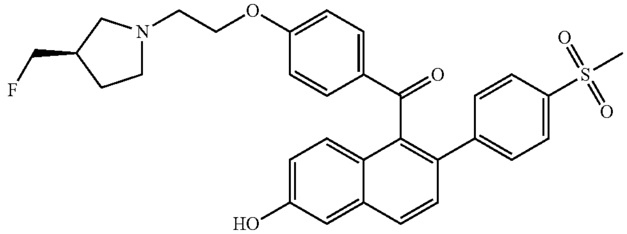 [SMILES: CS(=O)(=O)c1ccc(-c2ccc3cc(O)ccc3c2C(=O)c2ccc(OCCN3CC[C@@H](CF)C3)cc2)cc1] | [4-[2-[(3R)-3-(fluoromethyl)pyrrolidin-1-yl]ethoxy]phenyl]-[6-hydroxy-2-(4-methylsulfonylphenyl)-1-naphthyl]methanone | 548.1 |
| 68 | 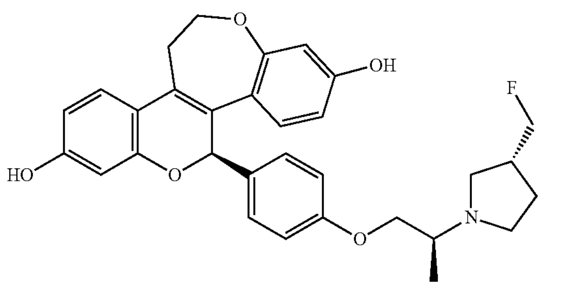 [SMILES: C[C@@H](COc1ccc([C@H]2Oc3cc(O)ccc3C3=C2c2ccc(O)cc2OCC3)cc1)N1CC[C@@H](CF)C1] | (R)-8-(4-((S)-2-((R)-3-(fluoromethyl)pyrrolidin-1-yl)propoxy)phenyl)-2,8-dihydro-1H-benzo[2,3]oxepino[4,5-c]chromene-5,11-diol | 518.3 |
| 69 | 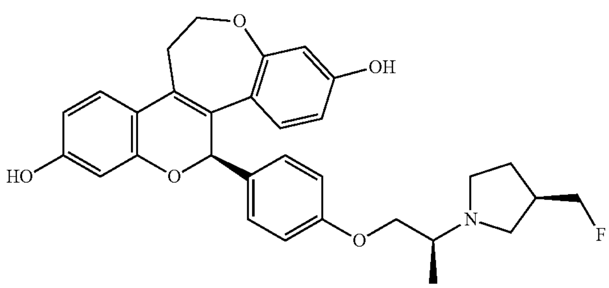 [SMILES: C[C@@H](COc1ccc([C@H]2Oc3cc(O)ccc3C3=C2c2ccc(O)cc2OCC3)cc1)N1CC[C@@H](CF)C1] | (R)-8-(4-((S)-2-((R)-3-(fluoromethyl)pyrrolidin-1-yl)propoxy)phenyl)-1,8-dihydro-2H-benzo[2,3]oxepino[4,5-c]chromene-5,11-diol | 518.2 |
| 70 | 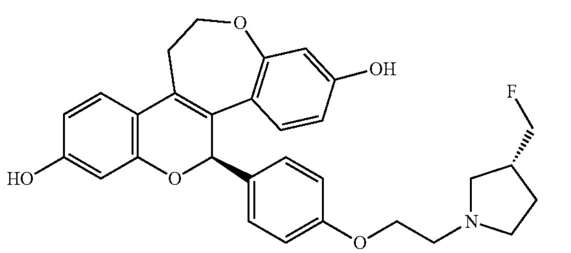 [SMILES: Oc1ccc2c(c1)O[C@H](c1ccc(OCCN3CC[C@@H](CF)C3)cc1)C1=C2CCOc2cc(O)ccc21] | (R)-8-(4-(2-((R)-3-(fluoromethyl)pyrrolidin-1-yl)ethoxy)phenyl)-2,8-dihydro-1H-benzo[2,3]oxepino[4,5-c]chromene-5,11-diol | 504.3 |

TABLE 1b-continued

| Example | Structure | Name | LCMS [M + H]+ or [M − H]− |
|---|---|---|---|
| 71 | 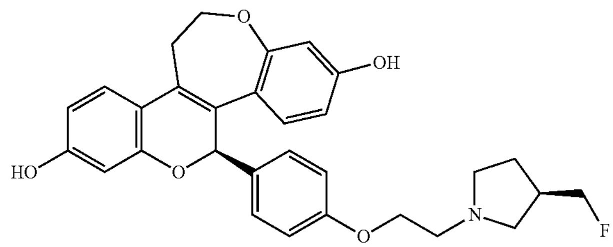 [SMILES: Oc1ccc2c(c1)O[C@H](c1ccc(OCCN3CC[C@@H](CF)C3)cc1)C1=C2CCOc2cc(O)ccc21] | (R)-8-(4-(2-((R)-3-(fluoromethyl)pyrrolidin-1-yl)ethoxy)phenyl)-1,8-dihydro-2H-benzo[2,3]oxepino[4,5-c]chromene-5,11-diol | 504.2 |
| 72 | 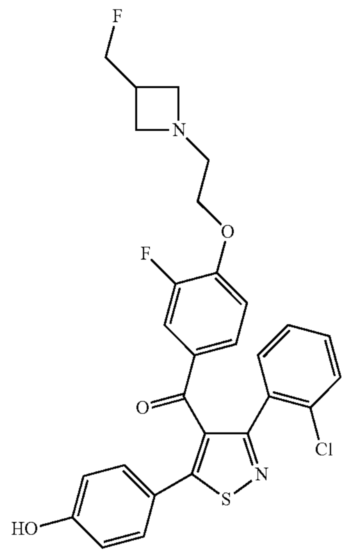 [SMILES: O=C(c1ccc(OCCN2CC(CF)C2)c(F)c1)c1c(-c2ccccc2Cl)nsc1-c1ccc(O)cc1] | [3-(2-Chloro-phenyl)-5-(4-hydroxy-phenyl)-isothiazol-4-yl]-{3-fluoro-4-[2-(3-fluoromethyl-azetidin-1-yl)-ethoxy]-phenyl}-methanone | 541.2 |
| 73 | 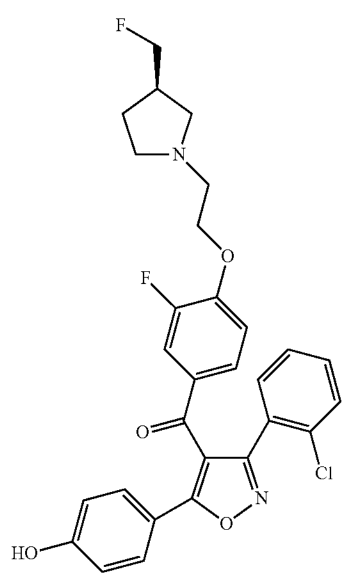 [SMILES: O=C(c1ccc(OCCN2CC[C@@H](CF)C2)c(F)c1)c1c(-c2ccccc2Cl)noc1-c1ccc(O)cc1] | [3-(2-chlorophenyl)-5-(4-hydroxyphenyl)isoxazol-4-yl]-[3-fluoro-4-[2-[(3R)-3-(fluoromethyl)pyrrolidin-1-yl]ethoxy]phenyl]methanone | 540.1 |

TABLE 1b-continued

| Example | Structure | Name | LCMS [M + H]+ or [M − H]− |
|---|---|---|---|
| 74 | 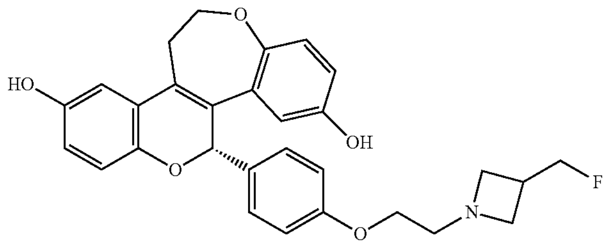 [SMILES: Oc1ccc2c(c1)C1=C(c3cc(O)ccc3OCC1)[C@H](c1ccc(OCCN3CC(CF)C3)cc1)O2] | (S)-8-(4-(2-(3-(fluoromethyl)azetidin-1-yl)ethoxy)phenyl)-1,8-dihydro-2H-benzo[2,3]oxepino[4,5-c]chromene-6,12-diol | 490.2 |
| 75 | 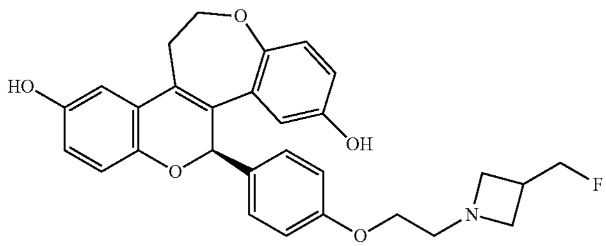 [SMILES: Oc1ccc2c(c1)C1=C(c3cc(O)ccc3OCC1)[C@@H](c1ccc(OCCN3CC(CF)C3)cc1)O2] | (R)-8-(4-(2-(3-(fluoromethyl)azetidin-1-yl)ethoxy)phenyl)-1,8-dihydro-2H-benzo[2,3]oxepino[4,5-c]chromene-6,12-diol | 490.2 |
| 76 | 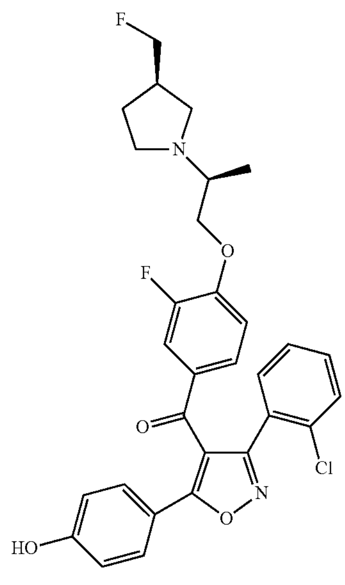 [SMILES: C[C@@H](COc1ccc(C(=O)c2c(-c3ccccc3Cl)noc2-c2ccc(O)cc2)cc1F)N1CC[C@@H](CF)C1] | [3-(2-chlorophenyl)-5-(4-hydroxyphenyl)isoxazol-4-yl]-[3-fluoro-4-[(2S)-2-[(3R)-3-(fluoromethyl)pyrrolidin-1-yl]propoxy]phenyl]methanone | 554.1 |
| 77 | 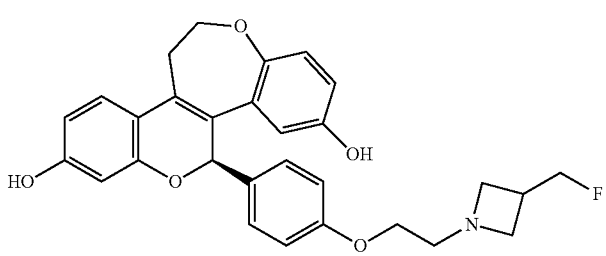 [SMILES: Oc1ccc2c(c1)O[C@H](c1ccc(OCCN3CC(CF)C3)cc1)C1=C2CCOc2ccc(O)cc21] | (R)-8-(4-(2-(3-(fluoromethyl)azetidin-1-yl)ethoxy)phenyl)-2,8-dihydro-1H-benzo[2,3]oxepino[4,5-c]chromene-6,11-diol | 490.2 |
| 78 | 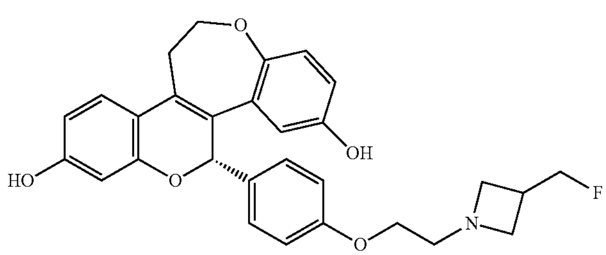 [SMILES: Oc1ccc2c(c1)O[C@@H](c1ccc(OCCN3CC(CF)C3)cc1)C1=C2CCOc2ccc(O)cc21] | (S)-8-(4-(2-(3-(fluoromethyl)azetidin-1-yl)ethoxy)phenyl)-2,8-dihydro-1H-benzo[2,3]oxepino[4,5-c]chromene-6,11-diol | 490.1 |

TABLE 1b-continued

| Example | Structure | Name | LCMS [M + H]+ or [M − H]− |
|---|---|---|---|
| 79 | 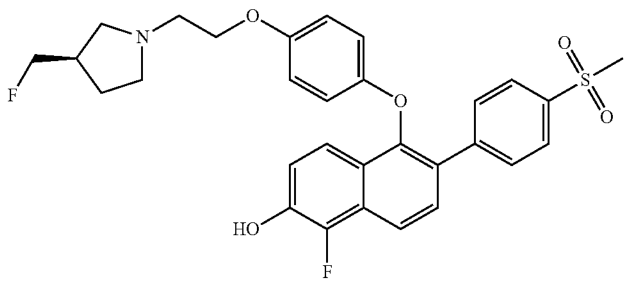 [SMILES: CS(=O)(=O)c1ccc(-c2ccc3c(F)c(O)ccc3c2Oc2ccc(OCCN3CC[C@@H](CF)C3)cc2)cc1] | (R)-1-fluoro-5-(4-(2-(3-(fluoromethyl)pyrrolidin-1-yl)ethoxy)phenoxy)-6-(4-(methylsulfonyl)phenyl)naphthalen-2-ol | 554.1 |
| 80 | 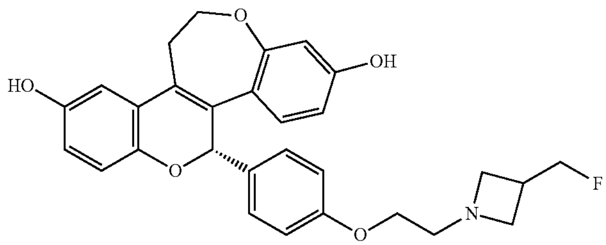 [SMILES: Oc1ccc2c(c1)OCCC1=C2[C@H](c2ccc(OCCN3CC(CF)C3)cc2)Oc2ccc(O)cc21] | (S)-8-(4-(2-(3-(fluoromethyl)azetidin-1-yl)ethoxy)phenyl)-2,8-dihydro-1H-benzo[2,3]oxepino[4,5-c]chromene-5,12-diol | 490.3 |
| 81 | 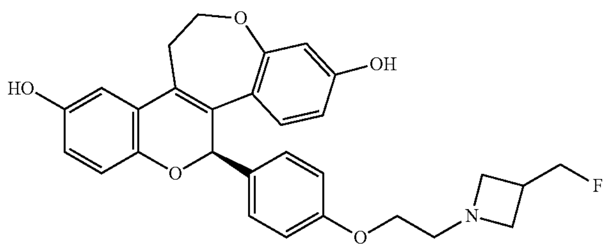 [SMILES: Oc1ccc2c(c1)OCCC1=C2[C@@H](c2ccc(OCCN3CC(CF)C3)cc2)Oc2ccc(O)cc21] | (R)-8-(4-(2-(3-(fluoromethyl)azetidin-1-yl)ethoxy)phenyl)-2,8-dihydro-1H-benzo[2,3]oxepino[4,5-c]chromene-5,12-diol | 490.2 |
| 82 | 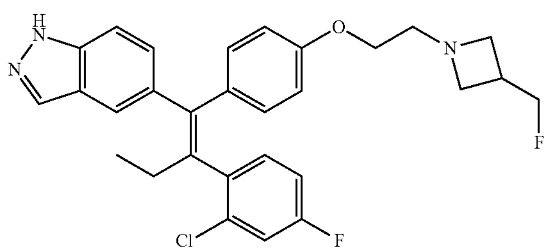 [SMILES: CC/C(=C(/c1ccc(OCCN2CC(CF)C2)cc1)c1ccc2[nH]ncc2c1)c1ccc(F)cc1Cl] | 5-[(E)-2-(2-chloro-4-fluoro-phenyl)-1-[4-[2-[3-(fluoromethyl)azetidin-1-yl]ethoxy]phenyl]but-1-enyl]-1H-indazole | 508.2 |

Synthesis of Compounds

Compounds described herein are synthesized using standard synthetic techniques or using methods known in the art in combination with methods described herein. In additions, solvents, temperatures and other reaction conditions presented herein may vary.

The starting material used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^r$ Ed., (Wiley 1999). General methods for the preparation of compounds can be modified by the use of appropriate reagents and conditions for the introduction of the various moieties found in the formulae as provided herein.

In one aspect, compounds described herein are synthesized as outlined in the Examples.

Throughout the specification, groups and substituents thereof are chosen by one skilled in the field to provide stable moieties and compounds.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In one aspect, compounds described herein exist as a racemic mixture or in enantiomerically enriched or enantiomerically pure form. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In certain embodiments, compounds described herein are prepared as their individual stereoisomers by enzymatic resolution. In some embodiments, resolution of individual stereoisomers is carried out using a lipase or an esterase. In some embodiments, resolution of individual stereoisomers is carried out by lipase or esterase-catalyzed asymmetric deacylation. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

Reference to a use of the (R)-enantiomer, or a pharmaceutically acceptable salt, solvate or prodrug thereof, or a composition that includes the (R)-enantiomer, or a pharmaceutically acceptable salt, solvate or prodrug thereof, refers to any optical purity of the (R)-enantiomer of the compound, or a pharmaceutically acceptable salt, solvate or prodrug thereof, in the composition, including but not limited to optically pure compound, or a pharmaceutically acceptable salt, solvate or prodrug thereof. In some embodiments, the enantiomeric ratio of the (R)-enantiomer of the compound, or a pharmaceutically acceptable salt, solvate or prodrug thereof, is greater than 90:10. In some embodiments, the enantiomeric ratio of the (R)-enantiomer of the compound, or a pharmaceutically acceptable salt, solvate or prodrug thereof, is greater than 95:5. In some embodiments, the enantiomeric ratio of the (R)-enantiomer of the compound, or a pharmaceutically acceptable salt, solvate or prodrug thereof, is greater than 99:1. In some embodiments, the (R)-enantiomer of the compound, or a pharmaceutically acceptable salt, solvate or prodrug thereof, is optically pure. Reference to a use of the (S)-enantiomer, or a pharmaceutically acceptable salt, solvate or prodrug thereof, or a composition that includes the (S)-enantiomer, or a pharmaceutically acceptable salt, solvate or prodrug thereof, refers to any optical purity of the (S)-enantiomer of the compound, or a pharmaceutically acceptable salt, solvate or prodrug thereof, in the composition, including but not limited to optically pure compound, or a pharmaceutically acceptable salt, solvate or prodrug thereof. In some embodiments, the enantiomeric ratio of the (S)-enantiomer of the compound, or a pharmaceutically acceptable salt, solvate or prodrug thereof, is greater than 90:10. In some embodiments, the enantiomeric ratio of the (S)-enantiomer of the compound, or a pharmaceutically acceptable salt, solvate or prodrug thereof, is greater than 95:5. In some embodiments, the enantiomeric ratio of the (S)-enantiomer of the compound, or a pharmaceutically acceptable salt, solvate or prodrug thereof, is greater than 99:1. In some embodiments, the enantiomeric ratio of the (S)-enantiomer of the compound, or a pharmaceutically acceptable salt, solvate or prodrug thereof, is greater than 99:1. In some embodiments, the (S)-enantiomer of the compound, or a pharmaceutically acceptable salt, solvate or prodrug thereof, is optically pure.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In some embodiments, the active entity is a phenolic compound as described herein. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elsevier, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, hydroxyl group(s) in the compounds disclosed herein is/are used to form a prodrug, wherein the hydroxyl group(s) is/are incorporated into an alkyl ester. In some embodiments the alkyl ester is an isopropyl ester or tert-butyl ester. In some embodiments the alkyl ester is an isopropyl ester.

Prodrug forms of the herein described compounds, wherein the prodrug is metabolized in vivo to produce a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX), or (X), as set forth herein are included within the scope of the claims. In some cases, some of the herein-described compounds may be a prodrug for another derivative or active compound.

In some embodiments, sites on the aromatic ring portion of compounds described herein are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms that are present in the compounds described herein is replaced with one or more deuterium atoms.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound described herein with acids. Pharmaceutically acceptable salts are also obtained by reacting a compound described herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, and the like; or with an organic acid to form a salt such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, or a potassium salt), an alkaline earth ion (e.g. a magnesium salt, or a calcium salt), or an aluminum ion (e.g. an aluminum salt). In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, or a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl moiety may be branched or straight chain. The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). Typical alkyl groups include, but are in no way limited to, methyl, ethyl, propyl, isopropyl, butyl, isobutyl, sec-butyl, tertiary butyl, pentyl, neopentyl, hexyl, and the like. In some embodiments, 1 or more hydrogen atoms of an alkyl are replaced with 1 or more deuterium atoms.

As used herein, the term "aryl" refers to an aromatic ring wherein each of the atoms forming the ring is a carbon atom. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In some embodiments, 1 or more hydrogen atoms of an aryl are replaced with 1 or more deuterium atoms.

The term "carbocyclyl" or refers to a monocyclic or polycyclic aliphatic, non-aromatic radical, wherein each of the atoms forming the ring (i.e. skeletal atoms) is a carbon atom. Carbocyclyls may be saturated, or partially unsaturated. Carbocyclyls may be fused with an aromatic ring, and the point of attachment is at a carbon that is not an aromatic ring carbon atom. Carbocyclyl groups include groups having from 3 to 12 ring atoms. In some embodiments, carbocyclyl groups are selected from among cyclopropyl, cyclobutyl, cyclopentyl, cyclopentenyl, cyclohexyl, cyclohexenyl, cycloheptyl, and cyclooctyl. Carbocyclyl groups may be substituted or unsubstituted. Depending on the structure, a carbocyclyl group can be a monoradical or a diradical (i.e., a carbocyclylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a carbocyclyl is a $C_3$-$C_6$carbocyclyl.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is a monofluoroalkyl, wherein one hydrogen atom of the alkyl is replaced by a fluorine atom. In some embodiments, a fluoroalkyl is a difluoroalkyl, wherein two hydrogen atoms of the alkyl are replaced by a fluorine atom. In some embodiments, a fluoroalkyl is a trifluoroalkyl, wherein three hydrogen atom of the alkyl are replaced by a fluorine atom. In some embodiments, a fluoroalkyl is a monofluoroalkyl, difluoroalkyl, or trifluoroalkyl. In some embodiments, a monofluoroalkyl is —CH$_2$F, —CHF$_2$, —CF$_3$, —CHFCH$_3$, —CH$_2$CH$_2$F, —CH$_2$CHF$_2$, —CH$_2$CF$_3$, —CH$_2$CH$_2$CF$_3$, —CH$_2$CH$_2$CH$_2$CF$_3$, —CHCH$_3$CF$_3$, —CH(CF$_3$)$_2$, or —CF(CH$_3$)$_2$.

The term "fluorocarbocyclyl" refers to a carbocyclyl in which one or more hydrogen atoms are replaced by a fluorine atom.

The term "halo" or, alternatively, "halogen" or "halide" means fluoro (F), chloro (Cl), bromo (Br) or iodo (I).

The terms "heteroaryl" or, alternatively, "heteroaromatic" refers to an aryl group that includes one or more ring heteroatoms selected from nitrogen, oxygen and sulfur and one to twenty carbon atoms. Illustrative examples of heteroaryl groups include the following moieties:

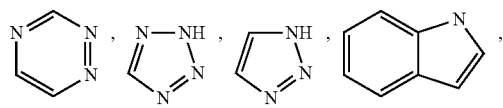

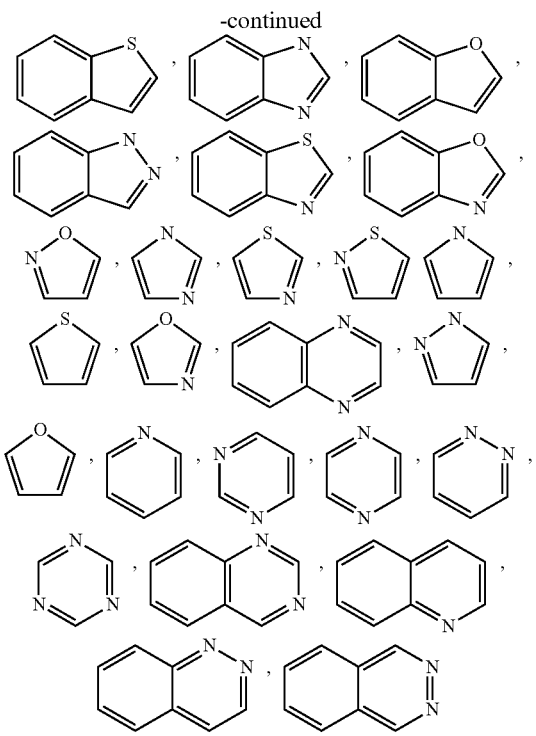

and the like.

Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Depending on the structure, a heteroaryl group can be a monoradical or a diradical (i.e., a heteroarylene group).

A "heterocyclyl" or "heteroalicyclic" group refers to a carbocyclyl group wherein at least one of the carbon atoms of the carbocyclyl is replaced with nitrogen (unsubstituted or substituted, e.g. —NH—, —NR$^{23}$—), oxygen (—O—), or sulfur (e.g. —S—, —S(=O)— or —S(=O)$_2$—). The radicals may be fused with an aryl or heteroaryl. In some embodiments, the heterocyclyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heterocyclyl also includes all ring forms of the carbohydrates, including but not limited to the monosaccharides, the disaccharides and the oligosaccharides. In one aspect, a heterocyclyl is a $C_2$-$C_{10}$ heterocyclyl. In another aspect, a heterocyclyl is a $C_4$-$C_{10}$heterocyclyl. In some embodiments, a heterocyclyl contains 0-2 N atoms in the ring. In some embodiments, a heterocyclyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The methods and formulations described herein include the use of N-oxides (if appropriate), crystalline forms (also known as polymorphs), or pharmaceutically acceptable salts of a compound having the structure of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "enantiomeric ratio" refers to ratio of the percentage of one enantiomer in a mixture to that of the other. In some embodiments, compositions disclosed herein include a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof, with an enantiomeric ratio of at least 80%-(S):20%-(R), at least 85%-(S):15%-(R), at least 90%-(S):10%-(R), at least 95%-(S):5%-(R), at least 99%-(S):1% —(R), or greater than 99%-(S):1%-(R). In some embodiments, compositions described herein include enantiomerically pure compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt, solvate or prodrug thereof.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues.

A "selective estrogen receptor modulator fragment" or "SERMF" is a substructure or structural motif from a selective estrogen receptor modulator molecule. For example, a contemplated SERMF is the substituted benzothiophene of raloxifene, the substituted tetrahydronaphthalene of lasofoxifene, the substituted indole of bazedoxifene, the substituted trans-1,2-diphenylbut-1-ene of tamoxifen, etc. Additional SERMF are described herein in (e.g. see Formula (II), (IIa), (IIb), (IIc), (III), (IIIa), (IIIb), (IIIc), (IV), (IVa), (IVb), (IVc), (IVd), (V), (VI), (VII), (VIII), (IX) or (X)). Additional SERMF are contemplated. For a review on a whole variety of suitable SERM fragments, see J. W. Ullrich and CP. Miller, in Expert Opin. Ther. Patents, 16 (2006) 559-572.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist. The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%. In some embodiments, a degrader as described herein lowers steady state estrogen receptor levels by at least 65%. In some embodiments, a degrader as described herein lowers steady state estrogen receptor levels by at least 85%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that would not occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, and a co-agent, are both administered to a patient simultaneously in the form of a single entity or dosage. The term "non-fixed combination" means that the active ingredients, e.g. a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, and at least one pharmaceutically acceptable inactive ingredient. In some embodiments, the compounds described herein are administered as pharmaceutical compositions in which a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral dosage forms are prepared by mixing a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Buccal formulations that include a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, are prepared as transdermal dosage forms. In one embodiment, the transdermal formulations described herein include at least three components: (1) a formulation of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include a mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Methods of Dosing and Treatment Regimens

In one embodiment, the compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, are used in the preparation of medicaments for the treatment of diseases or conditions in a mammal that would benefit from a reduction of estrogen receptor activity. Methods for treating any of the diseases or conditions described herein in a mammal in need of such treatment, involves administration of pharmaceutical compositions that include at least one compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In some embodiments, daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are from about 1 mg per day to about 1000 mg per day. In some embodiments, daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are from about 10 mg per day to about 1000 mg per day, from about 10 mg per day to about 900 mg per day, from about 10 mg per day to about 800 mg per day, from about 10 mg per day to about 700 mg per day, from about 10 mg per day to about 600 mg per day, from about 10 mg per day to about 500 mg per day, from about 10 mg per day to about 400 mg per day, from about 50 mg per day to about 500 mg per day, or from about 100 mg per day to about 400 mg per day. In some embodiments, daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are from about 50 mg per day to about 300 mg per day. In some embodiments, daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are from about 1 mg per day, 5 mg per day, 10 mg per day, 20 mg per day, 30 mg per day, 40 mg per day, 50 mg per day, 60 mg per day, 70 mg per day, 80 mg per day, 90 mg per day, 100 mg per day, 110 mg per day, 120 mg per day, 130 mg per day, 140 mg per day, 150 mg per day, 160 mg per day, 170 mg per day, 180 mg per day, 190 mg per day, 200 mg per day, 210 mg per day, 220 mg per day, 230 mg per day, 240 mg per day, 250 mg per day, 260 mg per day, 270 mg per day, 280 mg per day, 290 mg per day, 300 mg per day, 310 mg per day, 320 mg per day, 330 mg per day, 340 mg per day, 350 mg per day, 360 mg per day, 370 mg per day, 380 mg per day, 390 mg per day, 400 mg per day, 410 mg per day, 420 mg per day, 430 mg per day, 440 mg per day, 450 mg per day, 460 mg per day, 470 mg per day, 480 mg per day, 490 mg per day, 500 mg per day, 510 mg per day, 520 mg per day, 530 mg per day, 540 mg per day, 550 mg per day, 560 mg per day, 570 mg per day, 580 mg per day, 590 mg per day, 600 mg per day, 610 mg per day, 620 mg per day, 630 mg per day, 640 mg per day, 650 mg per day, 660 mg per day, 670 mg per day, 680 mg per day, 690 mg per day, 700 mg per day, 710 mg per day, 720 mg per day, 730 mg per day, 740 mg per day, 750 mg per day, 760 mg per day, 770 mg per day, 780 mg per day, 790 mg per day, 800 mg per day, 810 mg per day, 820 mg per day, 830 mg per day, 840 mg per day, 850 mg per day, 860 mg per day, 870 mg per day, 880 mg per day, 890 mg per day, 900 mg per day, 910 mg per day, 920 mg per day, 930 mg per day, 940 mg per day, 950 mg per day, 960 mg per day, 970 mg per day, 980 mg per day, 990 mg per day, or 1000 mg per day. In one embodiment, the desired dose is conveniently presented in a single dose or in divided doses administered simultaneously or at appropriate intervals, for example as two, three, four or more sub-doses per day.

In some embodiments, the daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are administered once a day, twice a day, or three times a day. In some embodiments, the daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are administered once a day. In some embodiments, the daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are administered twice a day.

In one embodiment, the daily dosages appropriate for the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, described herein are from about 0.01 to about 10 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In some embodiments, CA-125 blood levels are monitored in humans that are administered (or considered as candidates for treatment with) a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof. CA-125 (also known as mucin-16) is a glycoprotein in humans. In some embodiments, CA-125 levels are elevated in the blood of patients with certain type of cancers. In some embodiments, CA-125 is used as a serum biomarker in patients with certain type of cancers. In some embodiments, the certain types of cancers include, but are not limited to, breast cancer, ovarian cancer, endometrial (uterine) cancer, prostate cancer, and lung cancer. In some embodiments, monitoring CA-125 levels in the blood is used to determine the tumor burden in a human. In some embodiments, monitoring CA-125 levels in the blood is used to determine when to give a human anti-cancer therapy (e.g. a compound of Formula (I), (II), (IIa), (IIb), (IIc), (III), (IIa), (IIIb), (IIIc), (IV), (IVa), (IVb), (IVc), (IVd), (V), (VI), (VII), (VIII), (IX) or (X), or a pharmaceutically acceptable salt thereof). In some embodiments, monitoring CA-125 levels in the blood is used to determine how a human is responding to anti-cancer therapy (e.g. a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof). In some embodiments, CA-125 is used as a biomarker for the diagnosis and management of ovarian cancer. Rising levels of CA-125 after radiation therapy or surgery with no detectable metastases could indicate recurrent ovarian cancer and the need to start anti-cancer treatment.

In certain embodiments, CA-125 levels are used to select patients with cancer for treatment with a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered to a human that is diagnosed with cancer, wherein the CA-125 levels in blood samples from the human are rising. In some embodiments, the cancer is breast cancer or ovarian cancer or endometrial cancer. In some embodiments, the cancer is ovarian cancer. In some embodiments, the human with ovarian cancer has previously undergone a hysterectomy and/or a bilateral salpingo-oophorectomy. In some embodiments, the ovarian cancer patient has previously been treated with chemotherapy. In some embodiments, the ovarian cancer is recurrent ovarian cancer. In some embodiments, the recurrent ovarian cancer is treated with endocrine therapy (e.g. a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof) before metastases develop and treatment with chemotherapy is required. In some embodiments, treatment with a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof delays the development of distant metastases.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered to humans diagnosed with cancer and a CA-125 serum concentration doubling time of less than 10 days, less than 20 days, less than 30 days, less than 40 days, less than 50 days, less than 60 days, less than 70 days, less than 80 days, less than 90 days or less than 100 days. In some embodiments, CA-125 doubling time is less than 40 days. In some embodiments, the cancer is breast cancer, ovarian cancer, endometrial (uterine) cancer, prostate cancer, or lung cancer. In some embodiments, the cancer is ovarian cancer.

Combination Treatments

In certain instances, it is appropriate to administer at least one compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is co-administered with a second therapeutic agent, wherein the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is initiated prior to, during, or after treatment with a second agent described herein, and continues until any time during treatment with the second agent or after termination of treatment with the second agent. It also includes treatments in which a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, as well as combination therapies, is administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agents for Use in Combination Therapy

In some embodiments, methods for treatment of estrogen receptor-dependent or estrogen receptor-mediated conditions or diseases, such as proliferative disorders, including cancer, comprises administration to a mammal a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, in combination with at least one additional therapeutic agent.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, modulators of the immune system, PD-1 inhibitors, poly ADP-ribose polymerase (PARP) inhibitors, and aromatase inhibitors.

In certain instances, it is appropriate to administer at least one compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, in combination with one or more other therapeutic agents. In certain embodiments, the one or more other therapeutic agents is an anti-cancer agent(s).

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy Includes the Use of Anti-Cancer Agents.

Monoclonal antibodies include, but are not limited to, trastuzumab (Herceptin).

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with at least one additional therapeutic agent selected from: abiraterone; abarelix; adriamycin; aactinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; AZD6244; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; bosutinib; brequinar sodium; bropirimine; busulfan; cabozantinib; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dinaciclib; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; ENMD-2076; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; foretinib; fosquidone; fostriecin sodium; fulvestrant; gefitinib; gemcitabine; gemcitabine hydrochloride; gemcitabine-cisplatin; gemtuzumab ozogamicin; goserelin acetate; GSK1120212; histrelin acetate; hydroxyurea; idarubicin hydrochloride; ifosfamide; iimofosine; ibritumomab tiuxetan; idarubicin; ifosfamide; imatinib mesylate; imiquimod; interleukin Il (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; MM-121; mycophenolic acid; nandrolone phenpropionate; nelarabine; nilotinib; nocodazoie; nofetumomab; nogalamycin; ofatumumab; onartuzumab; oprelvekin; ormaplatin; oxaliplatin; oxisuran; paclitaxel; palbociclib (PD-0332991); palifermin; palonosetron hydrochloride; pamidronate; pegfilgrastim;

pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; saracatinib; sargramostim; seliciclib; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; TAK-733; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; U3-1287; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; or zorubicin hydrochloride.

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with the compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Further examples of anti-cancer agents for use in combination with the compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole. In some embodiments, the aromatase inhibitor is anastrozole, letrozole or exemestane.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with a CDK 4/6 inhibitor. In some embodiments, the CDK 4/6 inhibitor is palbociclib (PD-0332991), LEE011 or LY283519. In some embodiments, the CDK 4/6 inhibitor is LEE011. In some embodiments, LEE011 is administered at a dose of about 10 mg per day to about 1000 mg per day. In some embodiments, LEE011 is administered at a dose of about 400 mg per day, about 500 mg per day or about 600 mg per day. In some embodiments, the daily dose of LEE011 is orally administered. In some embodiments, the daily dose of LEE011 is orally administered once a day for three weeks followed by a one week drug holiday where LEE011 is not administered.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with a phosphoinositide 3-kinase (PI3K)/mTOR pathway inhibitor. In some embodiments, the a phosphoinositide 3-kinase (PI3K)/mTOR pathway inhibitor is everolimus, temsirolimus, BEZ235, BYL719, GDC0032, BKM120, BGT226, GDC0068, GDC-0980, GDC0941, INK128 (MLN0128), INK1117, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, CU-906, AZD-2014 or CUDC-907. In some embodiments, the phosphoinositide 3-kinase (PI3K)/mTOR pathway inhibitor is everolimus. In some embodiments, everolimus is administered at a dose of about 1 mg per day to about 20 mg per day. In some embodiments, everolimus is administered at a dose of about 2.5 mg per day, about 5 mg per day, or about 10 mg per day. In some embodiments, the daily dose of everolimus is administered once a day. In some embodiments, the phosphoinositide 3-kinase (PI3K)/mTOR pathway inhibitor is BKM120. In some embodiments, BKM120 is administered at a dose of about 5 mg per day to about 500 mg per day. In some embodiments, BKM120 is administered at a dose of about 50 mg per day to about 100 mg per day. In some embodiments, BKM120 is administered at a dose of about 100 mg per day. In some embodiments, the daily dose of BKM120 is administered once a day. In some embodiments, the phosphoinositide 3-kinase (PI3K)/mTOR pathway inhibitor is BYL719. In some embodiments, BYL719 is administered at a dose of about 25 mg per day to about 1000 mg per day. In some embodiments, BYL719 is administered at a dose of about 250 mg per day or about 350 mg per day. In some embodiments, the daily dose of BYL719 is administered once a day.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with a histone deacetylase inhibitor (HDAC). In some embodiments, the HDAC inhibitor is entinostat, vorinostat (SAHA), panobinostat or mocetinostat. In some embodiments, the HDAC inhibitor is entinostat. In some embodiments, entinostat is administered at a dose of about 0.1 mg per day to about 100 mg per day. In some embodiments, entinostat is administered at a dose of about 4 mg per day to about 15 mg per day. In some embodiments, entinostat is administered orally on days 1 and 15 of a 28 day cycle. In some embodiments, entinostat is administered orally weekly for 3 weeks followed by a 1-week break in a 4-week cycle. In some embodiments, entinostat is administered orally on days 3 and 10 of a 28 day cycle. In some embodiments, entinostat is administered once daily on days 1, 8, 15, 22, and 29. In some embodiments, 10 mg or 15 mg of entinostat is administered every other week or 15 mg on days 1, 8, and 15 every 28 days. In some embodiments, entinostat is orally administered on day 1 and day 8 at a dose of between 4 mg to 8 mg. In some embodiments, 5 mg of entinostat is orally administered once weekly.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with a HER-2 inhibitor. In some embodiments, the HER-2 inhibitor is trastuzumab, pertuzumab or TDM-1.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with an epidermal growth factor receptor (EGFR) inhibitor. In some embodiments, the EGFR inhibitor is lapatinib, gefitinib, erlotinib, cetuximab, canertinib, panitumumab, nimotuzumab, OSI-632, vandetanib, afatinib, MP-412, AEE-788, neratinib, XL-647, dacomitinib, AZD-8931, CUDC-101, AP-26113, MEHD7945A or CO-1686.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with an anti-angiogenesis agent. In some embodiments, the anti-angiogenesis agent is a VEGFR inhibitor. In some embodiments, the anti-angiogenesis agent is a multi-kinase targeting agent. In some embodiments, the anti-angiogenesis agent is bevacizumab, ABR-215050 (tasquinimod), CHIR-258 (dovitinib), EXEL-7647, OSI-930, BIBF-1120, BAY-73-4506, BMS-582664 (brivanib), RO-4929097, JNJ-26483327, AZD-2171 (cediranib), sorafenib, aflibercept, enzastaurin, AG-013736 (axitinib), GSK-786034 (pazopanib), AP-23573, or sunitinib In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with an anti-PD-1 agent. In some embodiments, the anti-PD-1 agent is MK-3475, Nivolumab, MPDL3280A, or MEDI4736.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with an AKT inhibitor. In some embodiments, the AKT inhibitor is GDC0068, MK-2206, AT7867, GSK2110183, GSK2141795, AZD5363 or GSK690693.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with an IGFR inhibitor. In some embodiments, the IGFR inhibitor is cixutumumab, dalotuzumab, BMS-754807, or MEDI-573

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with an FGFR inhibitor. In some embodiments, the FGFR inhibitor is CHIR-258 (dovitinib), E-3810, or AZD4547.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered in combination with doxorubicin, cyclophosphamide, capecitabine, vinorelbine, paclitaxel, doxetaxel, or cisplatin.

Yet other anticancer agents for use in combination with the compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.).

In some embodiments, compounds of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, are used to treat cancer in combination with: a second antiestrogen (e.g., tamoxifen), an antiandrogen (e.g., bicalutamide, flutamide, enzalutamide), a gonadotropin releasing hormone analog (e.g., leuprolide).

Other agents that can be used in the methods and compositions described herein for the treatment or prevention of cancer include platinum coordination complexes (e.g., cisplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with anti-emetic agents to treat nausea or emesis, which may result from the use of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), GABA$_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is adminsiterd with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketolorac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is coadministered with an analgesic.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in combination with radiation therapy (or radiotherapy). Radiation therapy is the treatment of cancer and other diseases with ionizing radiation. Radiation therapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to $\alpha$, $\beta$, and $\gamma$ radiation and ultraviolet light.

In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used in the treatment of breast cancer in combination with at least one additional treatment option for the breast cancer. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used either alone or in combination with other agents used to treat breast cancer, including but not limited to aromatase inhibitors, anthracylines, platins, nitrogen mustard, alkylating agents, taxanes, nucleoside analogs, a phosphoinositide 3-kinase (PI3K)/mTOR pathway inhibitor, CDK 4/6 inhibitors, HER-2 inhibitors, EGFR inhibitors, PD-1 inhibitors, poly ADP-ribose polymerase (PARP) inhibitors, histone deacetylase (HDAC) inhibitors, and HSP90 inhibitors. Illustrative agents used to treat breast cancer, include, but are not limited to, fulvestrant, tamoxifen, anastrozole, letrozole, exemestane, GDC0032, goserelin, leuprolide, raloxifene, toremifene, megestrol acetate, bazedoxifene, cisplatin, carboplatin, capecitabine, cyclophosphamide, docetaxel, doxorubicin, epirubicin, eribulin, filgrastim, fluorouracil, gemcitabine, ixabepilone, LEE011, LY2835219, mitoxantrone, methotrexate, paclitaxel, pamidronate, vinorelbine, pegfilgrastim, pertuzumab, trastuzumab, lapatinib, everolimus, bevacizumab, temsirolimus and combinations thereof, as well as others described herein. Additional non-limiting exemplary agents for the treatment of breast cancer are provided elsewhere herein. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used either alone or in combination with breast cancer surgery. In some embodiments, breast cancer surgery comprises lumpectomy, mastectomy, sentinel node biopsy, or axillary node dissection. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used either alone or in combination with radiation therapy. In some embodiments, radiation comprises external beam radiation or brachytherapy. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used either alone or in combination with hormone therapy (i.e. hormone blocking therapy). In some embodiments, hormone therapy comprises the use of a selective estrogen receptor modulator (e.g. tamoxifen), aromatase inhibitor, or fulvestrant. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used either alone or in combination with surgery to remove the ovaries or medications to stop the ovaries from making estrogen. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used either alone or in combination with trastuzumab, lapatinib, or bevacizumab. In some embodiments, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is used either alone or in combination with bone-building drugs to prevent breast cancer recurrence (e.g. zoledronic acid (Reclast, Zometa)).

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Intermediate 1
2-(3-(Fluoromethyl)azetidin-1-yl)ethanol

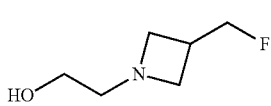

Step 1: tert-Butyl 3-(((methyl sulfonyl)oxy)methyl)azetidine-1-carboxylate

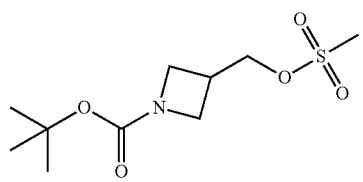 [SMILES: CC(C)(C)OC(=O)N1CC(COS(C)(=O)=O)C1]

Methanesulfonyl chloride (32 mL, 401 mmol) was added over 30 min to a solution of tert-butyl 3-(hydroxymethyl)azetidine-1-carboxylate (50 g, 267 mmol), triethylamine (74 mL, 534 mmol), and DCM (500 mL) at 0° C. The resulting cloudy orange mixture was stirred at 0° C. for 1 h and then diluted with 10% aqueous citric acid (200 mL). The layers were separated, and the organic phase was washed (200 mL 10% aqueous citric acid, 200 mL saturated NaHCO$_3$, and then 100 mL water). The organic phase was dried (Na$_2$SO$_4$) and concentrated to give the title compound as a dark orange oil. $^1$H NMR (400 MHz, DMSO-d$_6$): δ 4.33 (d, J=5.3 Hz, 2H), 3.91 (m, 2H), 3.61 (m, 2H), 3.21 (s, 3H), 2.89 (m, 1H), 1.37 (s, 9H).

Step 2: tert-Butyl 3-(fluoromethyl)azetidine-1-carboxylate

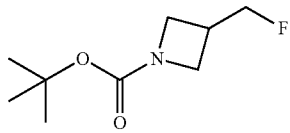

A solution of tert-butyl 3-(((methylsulfonyl)oxy)methyl)azetidine-1-carboxylate (70 g, 267 mmol) and tetrabutylammonium fluoride (1M in THF, 500 mL, 500 mmol) was refluxed for 1 h and then allowed to cool to room temperature. Half of the solvent was removed on a rotary evaporator. The resulting thick oil was diluted with ethyl acetate (300 mL) and then washed (2×200 mL brine). The combined brine layers were extracted with ethyl acetate (200 mL). The organics were combined and washed (200 mL water). This aqueous phase was extracted with ethyl acetate (3×150 mL). The organics were combined, dried (Na$_2$SO$_4$), concentrated, and purified by silica gel chromatography (0-40% ethyl acetate/hexanes) to give the title compound (42 g, 83% over 2 steps) as a yellow oil. $^1$H NMR (400 MHz, DMSO-d$_6$): δ 4.52 (dd, J=47.3, 5.3 Hz, 2H), 3.94-3.83 (m, 2H), 3.66-3.52 (m, 2H), 2.94-2.77 (m, 1H), 1.37 (s, 9H).

Step 3: 3-(Floromethyl)azetidine hydrochloride

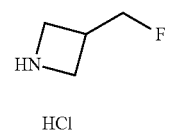

Aqueous HCl (6M, 111 mL, 666 mmol) was added slowly to a solution of tert-butyl 3-(fluoromethyl)azetidine-1-carboxylate (42 g, 222 mmol) and methanol (450 mL) at 0° C. The reaction was stirred overnight (warming to room temperature as the bath expired) and then concentrated. Residual water was azeotropically removed with methanol (3×400 mL) on a rotary evaporator until thick oil was obtained. This oil solidified under high vacuum to give the title compound (27 g, 97%) as a hygroscopic white solid. $^1$H NMR (400 MHz, DMSO-d$_6$): δ 9.18 (br s, 2H), 4.56 (dd, J=47.6, 5.3 Hz, 2H), 4.03-3.92 (m, 2H), 3.78-3.68 (m, 2H), 3.19-3.00 (m, 1H).

Step 4: 2-(3-(Fluoromethyl)azetidin-1-yl)ethanol

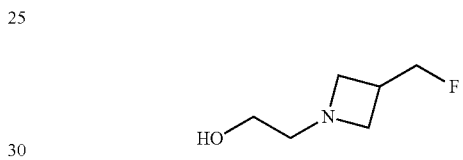

1,8-Diazabicyclo[5.4.0]undec-7-ene (220 mL, 1.47 mol) was added to a vigorously stirred suspension of 3-(fluoromethyl)azetidine hydrochloride (62.0 g, 494 mmol) and anhydrous tetrahydrofuran (1 L). After 15 min, 2-bromoethanol (70 mL, 986 mmol) was added. The reaction was vigorously stirred for 23 h, diluted with ethyl acetate (750 mL), stirred for an additional 15-30 min, and then filtered. The wet filter cake was resuspended in ethyl acetate (550 mL), and filtered with additional ethyl acetate washing. The filtrate was concentrated, placed under high vacuum for 15 min, diluted with ethyl acetate (500 mL), and stirred for 15-30 min. The resulting suspension was filtered with ethyl acetate washing. The filtrate was concentrated, combined with other batches, and distilled (bp ~55° C. at 1 torr) to give approximately 40 g (per batch, 61%) of 2-(3-(fluoromethyl)azetidin-1-yl)ethanol as a clear liquid. $^1$H NMR (400 MHz, DMSO-d$_6$): δ 4.48 (dd, J=47.6, 6.4 Hz, 2H), 4.35 (t, J=5.3 Hz, 1H), 3.31-3.30 (m, 2H), 3.23 (dt, J=7.6, 1.3 Hz 2H), 2.90 (dd, J=7.1, 6.1 Hz, 2H), 2.75-2.62 (m, 1H), 2.40 (t, J=6.2 Hz, 2H); $^{13}$C NMR (100 MHz, DMSO-d$_6$): δ 83.7 (J=163.0 Hz), 61.2, 59.2, 55.9 (J=8.0 Hz), 30.8 (J=19.0 Hz).

2-(3-(Fluoromethyl)azetidin-1-yl)ethanol can also be purified by silica gel chromatography [ethyl acetate/hexanes (10:7)→ethyl acetate/hexanes/methanol/triethylamine (10:7:2:1)].

Intermediate 2 (R)-3-(Fluoromethyl)pyrrolidine hydrochloride

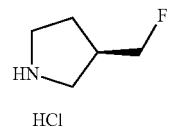

Step 1: (R)-tert-Butyl 3-(((methylsulfonyl)oxy)methyl)pyrrolidine-1-carboxylate

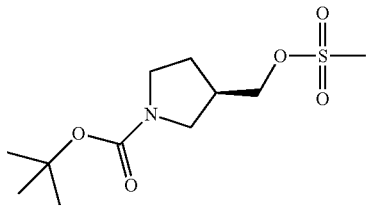 [SMILES: CC(C)(C)OC(=O)N1CC[C@@H](COS(C)(=O)=O)C1]

A mixture of (R)-tert-butyl 3-(hydroxymethyl)pyrrolidine-1-carboxylate (21.5 g, 107 mmol) and triethylamine (30 mL, 214 mmol) in DCM (250 mL) was cooled to 0° C. Methanesulfonyl chloride (12.5 mL, 160.5 mmol) was added dropwise via an addition funnel, and the resulting mixture was stirred at 0° C. then gradually allowed to warm to room temperature over 3 h. A 10% aqueous citric acid solution was added, and the layers were separated. The organic layer was washed (10% aqueous citric acid, saturated aqueous NaHCO$_3$, and then brine), dried (Na$_2$SO$_4$), and concentrated on a rotary evaporator to afford the title compound (30 g, quant) as an orange oil. $^1$H NMR (400 MHz, DMSO-d$_6$): δ 4.26-4.11 (m, 2H), 3.44-3.28 (m, 2H), 3.26-3.14 (m, 1H), 3.18 (s, 3H), 3.05-2.93 (m, 1H), 2.62-2.49 (m, 1H), 2.00-1.87 (m, 1H), 1.72-1.56 (m, 1H), 1.40 (s, 9H).

Step 2: (R)-tert-Butyl 3-(fluoromethyl)pyrrolidine-1-carboxylate

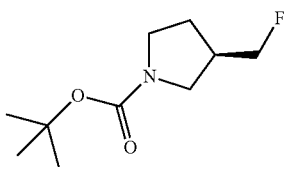

A mixture of tetrabutylammonium fluoride (1M in THF, 530 mL, 530 mmol) and (R)-tert-butyl 3-(((methylsulfonyl)oxy)methyl)pyrrolidine-1-carboxylate (30 g) was refluxed overnight. After cooling, the solvent was removed under reduced pressure, and the residue was partitioned between 10% aqueous citric acid and DCM. The organic layer was washed (water), dried (Na$_2$SO$_4$), and concentrated. The residue was purified by silica gel chromatography (0 to 50% ethyl acetate/hexanes) to afford the title compound (14.3 g, 66% over 2 steps) as a yellow oil. $^1$H NMR (400 MHz, DMSO-d$_6$): δ 4.49-4.41 (m, 1H), 4.37-4.29 (m, 1H), 3.40-3.28 (m, 2H), 3.24-3.18 (m, 1H), 3.02-2.98 (m, 1H), 2.58-2.52 (m, 1H), 1.95-1.88 (m, 1H), 1.67-1.54 (m, 1H), 1.38 (s, 9H).

Step 3: (R)-3-(Fluoromethyl)pyrrolidine hydrochloride

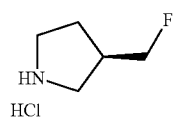

A solution of (R)-tert-butyl 3-(fluoromethyl)pyrrolidine-1-carboxylate (14.3 g, 70.4 mmol) in 1,4-dioxane (60 mL) was cooled in an ice bath. HCl (4M in 1,4-dioxane, 44 mL, 176 mmol) was added, and the resulting pink solution was stirred at room temperature overnight. The solvent was removed under reduced pressure, and diethyl ether was added to the residue. The mixture was concentrated under vacuum to give the title compound (9.5 g, 97%) as a pink solid. $^1$H NMR (400 MHz, DMSO-d$_6$, HCl salt): δ 9.35 (br s, 2H), 4.57-4.47 (m, 1H), 4.44-4.33 (m, 1H), 3.33-3.10 (m, 3H), 2.95-2.87 (m, 1H), 2.69-2.57 (m, 1H), 2.05-1.97 (m, 1H), 1.70-1.61 (m, 1H).

Intermediate 3 (S)-2-((R)-3-(Fluoromethyl)pyrrolidin-1-yl)propan-1-ol

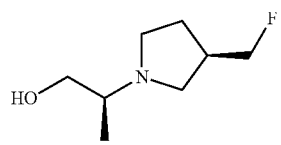

Step 1: (R)-1-(Trityloxy)propan-2-ol

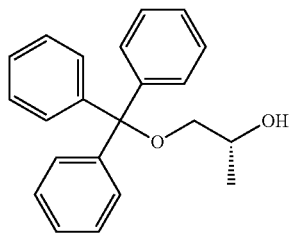 [SMILES: C[C@@H](O)COC(c1ccccc1)(c1ccccc1)c1ccccc1]

Dimethylaminopyridine (165 mg, 1.35 mmol) was added to a solution of (R)-propane-1,2-diol (10.3 g, 135.4 mmol) and trityl chloride (38.1 g 136.7 mmol) in DCM (400 mL) at 0° C. Triethylamine (47.2 mL, 338.4 mmol) was then added dropwise to the reaction mixture. The solution was allowed to warm to room temperature and stirred overnight. The reaction mixture was washed with 1.0 N aq HCl (200 mL), washed with brine, dried (Na$_2$SO$_4$), and concentrated under reduced pressure. The crude material was purified by silica gel chromatography to give the title compound (36.4 g, 84%) as a white solid. $^1$H NMR (300 MHz, DMSO-d$_6$): δ 7.76-7.21 (m, 15H), 4.69 (d, J=5.6 Hz, 1H), 3.82-3.76 (m, 1H), 2.94 (dd, J=8.7, 5.7 Hz, 1H), 2.69 (dd, J=8.7, 5.7 Hz, 1H), 1.06 (d, J=6.4 Hz, 3H).

Step 2: (R)-3-(Fluoromethyl)-1-((S)-1-(trityloxy)propan-2-yl)pyrrolidine

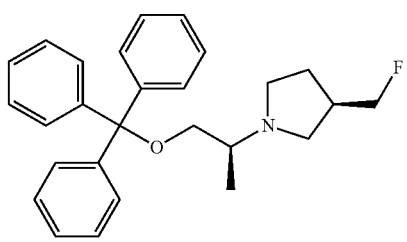 [SMILES: C[C@@H](COC(c1ccccc1)(c1ccccc1)c1ccccc1)N1CC[C@@H](CF)C1]

Triflic anhydride (1.0 M in DCM, 51.8 mL, 51.8 mmol) was added dropwise to a solution of (R)-1-(trityl oxy)propan-2-ol (15.0 g, 47.1 mmol) and diisopropylethylamine (32.8 mL, 188.4 mmol) in DCM (190 mL) at −78° C. The reaction mixture was stirred at −78° C. for 1.5 h, and then a solution of Intermediate 2 (7.9 g, 56.5 mmol) in DCM (20 mL) was added. The mixture was allowed to warm to room temperature and stirred overnight. Water (200 mL) and saturated NaHCO$_3$ (200 mL) were added to the mixture, and the layers were separated. The aqueous layer was extracted with DCM (2×). The combined organic layers were dried (Na$_2$SO$_4$) and concentrated under reduced pressure to afford crude material for the next step.

Step 3: (S)-2-((R)-3-(Fluoromethyl)pyrrolidin-1-yl)propan-1-ol

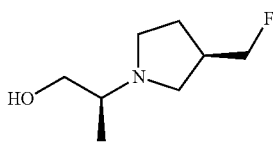

A mixture of (R)-3-(fluoromethyl)-1-((S)-1-(trityloxy)propan-2-yl)pyrrolidine (19.0 g, 47.1 mmol), formic acid (151 mL), and diethyl ether (38 mL) was stirred at room temperature for 8 h and then concentrated under reduced pressure. The residue was dissolved in DCM, and the resulting solution was washed (saturated K$_2$CO$_3$ and then brine), dried (Na$_2$SO$_4$), and concentrated. The residue was purified by silica gel chromatography (10:7 ethyl acetate/hexanes to 10:7:2:1 ethyl acetate/hexane/methanol/triethylamine) to give the title compound (3.9 g, 51% over 2 steps) as a dark orange oil. $^1$H NMR (400 MHz, DMSO-d$_6$): δ 4.38-4.32 (m, 2H), 4.22-4.20 (m, 1H), 3.49-3.44 (m, 1H), 3.21-3.16 (m, 1H), 2.65-2.61 (m, 1H), 2.58-2.53 (m, 1H), 2.52-2.47 (m, 1H), 2.45-2.35 (m, 1H), 2.34-2.30 (m, 1H), 2.29-2.24 (m, 1H), 1.83-1.75 (m, 1H), 1.38-1.30 (m, 1H), 0.98 (d, J=6.5 Hz, 3H).

Intermediate 4 (R)-2-(3-(Fluoromethyl)pyrrolidin-1-yl)ethanol

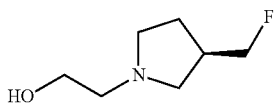

A mixture of 2-bromoethanol (1.0 mL, 14.3 mmol), Intermediate 2 (1.0 g, 7.2 mmol), and K$_2$CO$_3$ (3.0 g, 21.5 mmol) in acetonitrile (24 mL) was heated at 80° C. overnight. The insoluble material was filtered off, and the solvent was removed under reduced pressure. The residue was purified by silica gel chromatography to give the title compound (603 mg, 57%) as a pale yellow oil. $^1$H NMR (400 MHz, DMSO-d$_6$): δ 4.41 (t, J=5.4 Hz, 1H), 4.37-4.18 (m, 2H), 3.48-3.43 (m, 2H), 2.58-2.52 (m, 1H), 2.49-2.37 (m, 5H), 2.30 (dd, J=9.0, 5.2 Hz, 1H), 1.87-1.75 (m, 1H), 1.40-1.30 (m, 1H).

Intermediate 5 (2-(3-(Fluoromethyl)azetidin-1-yl)ethoxy)phenol

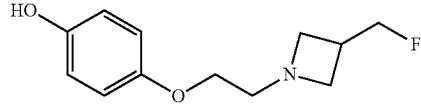 [SMILES: Oc1ccc(OCCN2CC(CF)C2)cc1]

Step 1: 3-(Fluoromethyl)-1-(2-(4-((tetrahydro-2H-pyran-2-yl)oxy)phenoxy)ethyl)azetidine

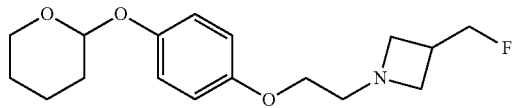 [SMILES: FCC1CN(CCOc2ccc(OC3CCCCO3)cc2)C1]

A mixture of 2-(4-iodophenoxy)tetrahydro-2H-pyran (510 mg, 1.68 mmol), Intermediate 1 (327 mg, 2.46 mmol), K$_2$CO$_3$ (458 mg, 3.31 mmol), CuI (66 mg, 0.34 mmol), and butyronitrile (3.3 mL) was degassed with vacuum/nitrogen cycles (3×). The mixture was heated at 130° C. overnight, allowed to cool to room temperature, and then diluted with ethyl acetate (60 mL). The mixture was washed (30 mL water and then 30 mL brine), dried (MgSO$_4$), and concentrated under reduced pressure. The crude material was purified by silica gel chromatography to give the title compound (356 mg, 69%) as a brown oil. $^1$H NMR (400 MHz, DMSO-d$_6$): δ 6.93 (d, J=8.1 Hz, 2H), 6.82 (d, J=8.1 Hz, 2H), 5.30 (t, J=2.9 Hz, 1H), 4.51 (dd, J=47.7, 5.0 Hz, 2H), 3.84 (br, 2H), 3.81-3.73 (m, 1H), 3.55-3.48 (m, 1H), 3.45-3.18 (br, 2H), 3.18-2.89 (br, 2H), 2.81-2.65 (m, 3H), 1.92-1.65 (m, 3H), 1.64-1.46 (m, 3H).

Step 2: 4-(2-(3-(Fluoromethyl)azetidin-1-yl)ethoxy)phenol

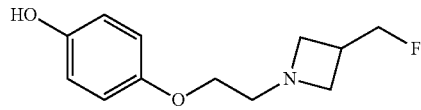 [SMILES: Oc1ccc(OCCN2CC(CF)C2)cc1]

A solution of 3-(fluoromethyl)-1-(2-(4-((tetrahydro-2H-pyran-2-yl)oxy)phenoxy)ethyl)azetidine (674 mg, 2.18 mmol) was stirred in 80% acetic acid/water (21 mL) at room temperature for 7 h. The mixture was concentrated under reduced pressure, and the residue was dissolved in ethyl acetate (60 mL). The organic layer was washed saturated NaHCO$_3$ (3×30 mL) and then brine (30 mL), dried (MgSO$_4$), and concentrated under reduced pressure. The residue was purified by silica gel chromatography to give the desired compound (129 mg, 30%) as an off-white solid. $^1$H NMR (400 MHz, DMSO-d$_6$): δ 8.88 (s, 1H), 6.71 (d, J=9.0 Hz, 2H), 6.64 (d, J=9.0 Hz, 2H), 4.50 (dd, J=47.6, 6.2 Hz, 2H), 3.79 (t, J=5.6 Hz, 2H), 3.30 (td, J=7.6, 1.3 Hz, 2H), 2.98 (t, J=6.6 Hz, 2H), 2.77-2.69 (m, 1H), 2.66 (t, J=5.6 Hz, 2H).

Intermediate 6 4-((S)-2-((R)-3-(Fluoromethyl)pyrrolidin-1-yl)propoxy)phenol

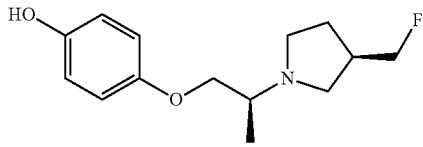 [SMILES: C[C@@H](COc1ccc(O)cc1)N1CC[C@@H](CF)C1]

Step 1: (R)-1-((S)-1-(4-(Benzyloxy)phenoxy)propan-2-yl)-3-(fluoromethyl)pyrrolidine

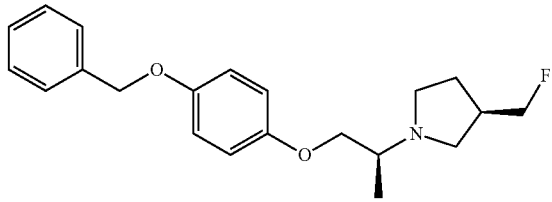 [SMILES: C[C@@H](COc1ccc(OCc2ccccc2)cc1)N1CC[C@@H](CF)C1]

Sodium hydride (60% in mineral oil, 0.20 g, 5.0 mmol) was added to a solution Intermediate 3 (0.40 g, 2.5 mmol) in DMF (10 mL) at 0° C. The mixture was stirred for 5 min, and a solution of 4-(benzyloxy)phenyl trifluoromethanesulfonate (1.0 g, 2.5 mmol) in DMF (5 mL) was added dropwise. The resulting mixture was stirred at 25° C. for 1 h, poured into water (100 mL), and then extracted with ethyl acetate (3×30 mL). The combined organic layers were washed (2×30 mL water), dried (Na$_2$SO$_4$), and concentrated in vacuo. The residue was purified by silica gel chromatography (0~2% methanol in DCM) to afford the title compound (0.50 g, 42%) as a yellow oil. $^1$H NMR (400 MHz, CDCl$_3$): δ 7.44-7.29 (m, 5H), 6.92-6.82 (m, 4H), 5.01 (s, 2H), 4.42-4.37 (m, 1H), 4.29-4.26 (m, 1H), 4.03-3.98 (m, 1H), 3.85-3.80 (m, 1H), 2.95-2.91 (m, 1H), 2.82-2.47 (m, 5H), 1.99-1.95 (m, 1H), 1.57-1.49 (m, 1H), 1.23 (d, J=8.4 Hz, 3H).

Step 2: 4-((S)-2-((R)-3-(Fluoromethyl)pyrrolidin-1-yl)propoxy)phenol

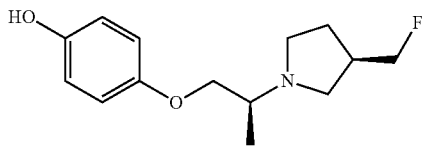 [SMILES: C[C@@H](COc1ccc(O)cc1)N1CC[C@@H](CF)C1]

A mixture of (R)-1-((S)-1-(4-(benzyloxy)phenoxy)propan-2-yl)-3-(fluoromethyl)pyrrolidine (1.4 g, 4.0 mmol), 10% palladium on carbon (0.4 g), and methanol (40 mL) was stirred under hydrogen (50 psi) at 50° C. for 18 h. The mixture was filtered through Celite, and the filtrate was concentrated in vacuo. The residue was re-dissolved in DCM (20 mL), washed (20 mL saturated NaHCO$_3$), dried (Na$_2$SO$_4$), and concentrated in vacuo to afford the title compound (1.0 g, quantitative) as a brown oil. $^1$H NMR (400 MHz, DMSO-d$_6$): δ 8.88 (s, 1H), 6.74 (d, J=8.4 Hz, 2H), 6.65 (d, J=8.4 Hz, 2H), 4.36-4.33 (m, 1H), 4.24-4.21 (m, 1H), 3.96-3.91 (m, 1H), 3.71-3.66 (m, 1H), 2.73-2.54 (m, 4H), 2.45-2.39 (m, 2H), 1.85-1.80 (m, 1H), 1.40-1.34 (m, 1H), 1.10 (d, J=6.4 Hz, 3H).

Intermediate 7 (R)-4-(2-(3-(Fluoromethyl)pyrrolidin-1-yl)ethoxy)phenol

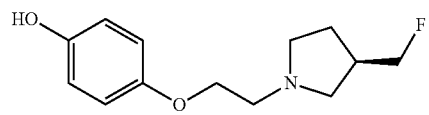 [SMILES: Oc1ccc(OCCN2CC[C@@H](CF)C2)cc1]

The title compound was prepared from 2-(4-iodophenoxy)tetrahydro-2H-pyran and Intermediate 4 following the procedure outlined for Intermediate 6. $^1$H NMR (400 MHz, DMSO-d$_6$): δ 8.89 (s, 1H), 6.74 (d, J=9.0 Hz, 2H), 6.65 (d, J=9.0 Hz, 2H), 4.39-4.18 (m, 2H), 3.94 (t, J=5.9 Hz, 2H), 2.71 (t, J=5.9 Hz, 2H), 2.67-2.60 (m, 1H), 2.59-2.40 (m, 3H), 2.40-2.35 (m, 1H), 1.90-1.78 (m, 1H), 1.44-1.32 (m, 1H).

Intermediate 8 (4-(2-(3-(Fluoromethyl)azetidin-1-yl)ethoxy)benzaldehyde

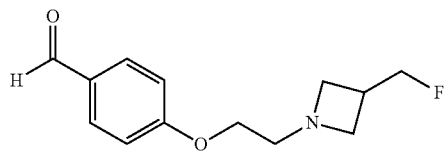 [SMILES: O=Cc1ccc(OCCN2CC(CF)C2)cc1]

A mixture of 4-iodobenzaldehyde (3.18 g, 13.7 mmol), Intermediate 1 (2.75 g, 20.7 mmol), Cs$_2$CO$_3$ (8.95 g, 27.5 mmol), CuI (266 mg, 1.37 mmol), and m-xylene (14 mL) was degassed with vacuum/nitrogen cycles (3×). The mixture was heated at 140° C. overnight, allowed to cool to room temperature, and then concentrated under reduced pressure. The crude material was purified by silica gel chromatography to give the title compound (3.03 g, 93%) as a colorless oil. $^1$H NMR (400 MHz, DMSO-d$_6$): δ 9.86 (s, 1H), 7.85 (d, J=8.8 Hz, 2H), 7.09 (d, J=8.8 Hz, 2H), 4.50 (dd, J=47.6, 6.2 Hz, 2H), 4.04 (t, J=5.5 Hz, 2H), 3.35-3.30 (m, 2H), 3.00 (t, J=6.5 Hz, 2H), 2.76 (t, J=5.5 Hz, 2H), 2.73-2.65 (m, 1H).

Example 1 1-(4-(2-(3-(Fluoromethyl)azetidin-1-yl)ethoxy)benzyl)-2-(4-hydroxyphenyl)-3-methyl-1H-indol-5-ol

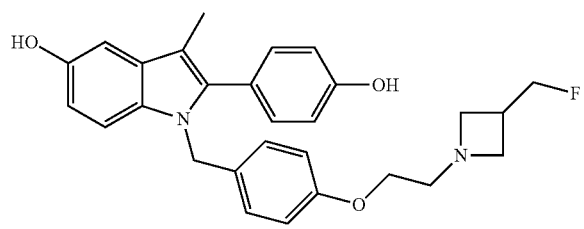 [SMILES: Cc1c(-c2ccc(O)cc2)n(Cc2ccc(OCCN3CC(CF)C3)cc2)c2ccc(O)cc12]

Step 1: 5-(Benzyloxy)-2-(4-(benzyloxy)phenyl)-1-(4-(2-(3-(fluoromethyl)azetidin-1-yl)ethoxy)benzyl)-3-methyl-1H-indole

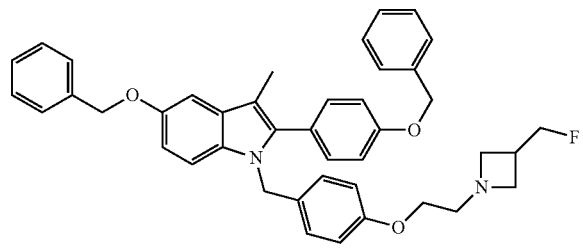 [SMILES: Cc1c(-c2ccc(OCc3ccccc3)cc2)n(Cc2ccc(OCCN3CC(CF)C3)cc2)c2ccc(OCc3ccccc3)cc12]

A mixture of 5-(benzyloxy)-2-(4-(benzyloxy)phenyl)-1-(4-iodobenzyl)-3-methyl-1H-indole (252 mg, 0.40 mmol, see U.S. Pat. No. 5,780,497 for synthesis), Intermediate 1 (81 mg, 0.61 mmol), K$_2$CO$_3$ (113 mg, 0.82 mmol), CuI (19 mg, 0.10 mmol), and butyronitrile (1 mL) was degassed with vacuum/nitrogen cycles (3×). The mixture was heated at 130° C. overnight, allowed to cool to room temperature, and then diluted with ethyl acetate (50 mL). The mixture was washed (30 mL water and then 30 mL brine), dried (MgSO$_4$), and concentrated under reduced pressure. The crude material was purified by silica gel chromatography to give the title compound (166 mg, 65%) as a yellow foam. $^1$H NMR (400 MHz, DMSO-d$_6$): δ 7.50-7.45 (m, 4H), 7.44 (m, 8H), 7.20 (d, J=8.9 Hz, 1H), 7.14-7.10 (m, 3H), 6.81 (dd, J=8.8, 2.4 Hz, 1H), 6.76-6.69 (m, 4H), 5.16 (s, 2H), 5.14 (s, 2H), 5.12 (s, 2H), 4.48 (dd, J=47.6, 6.3 Hz, 2H), 3.80 (t, J=5.5 Hz, 2H), 3.27 (t, J=7.2 Hz, 2H), 2.95 (t, J=6.6 Hz, 2H), 2.76-2.67 (m, 1H), 2.65 (t, J=5.5 Hz, 2H), 2.16 (s, 3H); LCMS: 641.1 [M+H]$^+$.

Step 2: 1-(4-(2-(3-(Fluoromethyl)azetidin-1-yl)ethoxy)benzyl)-2-(4-hydroxyphenyl)-3-methyl-1H-indol-5-ol

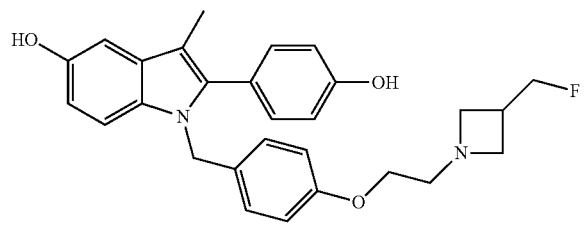 [SMILES: Cc1c(-c2ccc(O)cc2)n(Cc2ccc(OCCN3CC(CF)C3)cc2)c2ccc(O)cc12]

A mixture of 5-(benzyloxy)-2-(4-(benzyloxy)phenyl)-1-(4-(2-(3-(fluoromethyl)azetidin-1-yl)ethoxy)benzyl)-3-methyl-1H-indole (156 mg, 0.24 mmol), 10% Palladium on carbon (74 mg, 0.07 mmol), ethyl acetate (2.6 mL), and ethanol (0.7 mL) was stirred under an atmosphere of hydrogen for 6 h. The reaction mixture was filtered through a pad of Celite, and the Celite was washed with ethyl acetate. The filtrate was concentrated under reduced pressure to give the desired compound (111 mg, 100%). $^1$H NMR (400 MHz, DMSO-d$_6$): δ 9.66 (s, 1H), 8.69 (s, 1H), 7.15 (d, J=8.4 Hz, 2H), 7.06 (d, J=8.7 Hz, 1H), 6.85 (d, J=8.4 Hz, 2H), 6.80 (d, J=2.2 Hz, 1H), 6.77-6.69 (m, 4H), 6.57 (dd, J=8.7, 2.2 Hz, 1H), 5.09 (s, 2H), 4.48 (dd, J=47.6, 6.3 Hz, 2H), 3.80 (t, J=5.5 Hz, 2H), 3.27 (t, J=7.2 Hz, 2H), 2.95 (t, J=6.6 Hz, 2H), 2.77-2.67 (m, 1H), 2.65 (t, J=5.5 Hz, 2H), 2.10 (s, 3H); $^{13}$C NMR (100 MHz, DMSO-d$_6$, HCl salt): δ 157.2, 156.4, 150.9, 138.0, 131.5, 131.3, 130.7, 129.2, 127.3, 122.0, 115.4, 114.4, 111.3, 110.7, 106.5, 102.5, 82.4 (J=164.0 Hz), 63.1, 55.4 (J=7.9 Hz), 52.9, 46.0, 29.7 (J=20.4 Hz), 9.4; HRMS-ESI (m/z): [M+H]$^+$ calcd for C$_{28}$H$_{29}$FN$_2$O$_3$, 461.2240. found, 461.2234.

Example 2 1-(4-((S)-2-((R)-3-(Fluoromethyl)pyrrolidin-1-yl)propoxy)benzyl)-2-(4-hydroxyphenyl)-3-methyl-1H-indol-5-ol

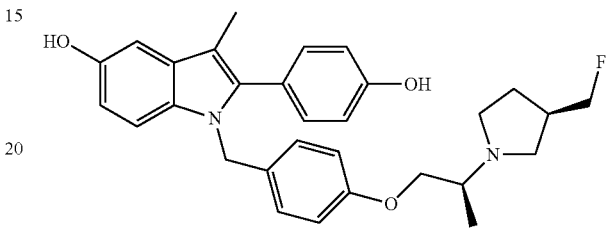

The title compound was prepared from 5-(benzyloxy)-2-(4-(benzyloxy)phenyl)-1-(4-iodobenzyl)-3-methyl-1H-indole and Intermediate 3 following the procedure outlined for Example 1. $^1$H NMR (400 MHz, DMSO-d$_6$): δ 9.67 (s, 1H), 8.70 (s, 1H), 7.16 (d, J=8.4 Hz, 2H), 7.05 (d, J=8.7 Hz, 1H), 6.85 (d, J=8.4 Hz, 2H), 6.80 (d, J=2.2 Hz, 1H), 6.75 (s, 4H), 6.57 (dd, J=8.7, 2.2 Hz, 1H), 5.10 (s, 2H), 4.34-4.14 (m, 2H), 3.94 (dd, J=9.4, 4.7 Hz, 1H), 3.70 (dd, J=9.4, 6.2 Hz, 1H), 2.72-2.51 (m, 4H), 2.45-2.32 (m, 2H), 2.10 (s, 3H), 1.86-1.74 (m, 1H), 1.41-1.27 (m, 1H), 1.07 (d, J=6.4 Hz, 3H); $^{13}$C NMR (100 MHz, DMSO-d$_6$, HCl salt): δ 157.2, 156.4, 150.9, 138.0, 131.6, 131.3, 130.7, 129.2, 127.4, 122.0, 115.4, 114.6, 111.3, 110.7, 106.5, 102.5, 83.9 (J=165.5 Hz), 83.5 (J=165.5 Hz), 67.5, 67.4, 58.5, 58.4, 52.6 (J=6.2 Hz), 52.1 (J=5.7 Hz), 51.5, 50.5, 46.0, 36.8 (J=19.6 Hz), 36.0 (J=19.6 Hz), 25.4 (J=6.9 Hz), 24.1 (J=6.9 Hz), 13.4, 13.2, 9.4 (There are two resonances for each carbon of the side chain due to diastereomers when the nitrogen is protonated); HRMS-ESI (m/z): [M+H]$^+$ calcd for C$_{30}$H$_{33}$FN$_2$O$_3$, 489.2553. found, 489.2550.

Example 3 1-(4-(2-(3-(Fluoromethyl)azetidin-1-yl)ethoxy)benzyl)-2-(4-fluorophenyl)-3-methyl-1H-indol-5-ol

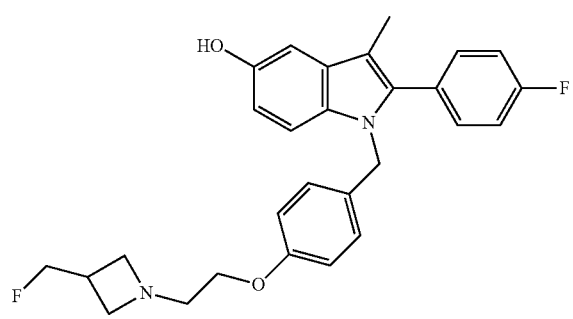 [SMILES: Cc1c(-c2ccc(F)cc2)n(Cc2ccc(OCCN3CC(CF)C3)cc2)c2ccc(O)cc12]

Step 1: 5-(Benzyloxy)-2-(4-fluorophenyl)-3-methyl-1H-indole

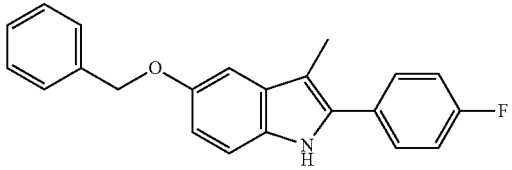 [SMILES: Cc1c(-c2ccc(F)cc2)[nH]c2ccc(OCc3ccccc3)cc12]

To a mixture of (4-(benzyloxy)phenyl)hydrazine hydrochloride (1.0 g, 4.0 mmol) and 1-(4-fluoro phenyl)propan-1-one (638 mg, 4.2 mmol) in EtOH (10 mL) was added concentrated HCl (12 M, 1 mL). The reaction mixture was stirred at reflux for 6 h. The mixture was cooled to room temperature, concentrated. The residue was re-dissolved in ethyl acetate (100 mL), washed with water (30 mL) and saturated brine (50 mL). The organic layer was dried over anhydrous Na$_2$SO$_4$, filtered and concentrated under reduced pressure. The residue was purified by silica gel column chromatography (0-3% ethyl acetate in petroleum ether) to give the title compound (400 mg, 30%) as light yellow solid. $^1$H NMR (400 MHz, CDCl$_3$): δ 7.86 (s, 1H), 7.58-7.48 (m, 4H), 7.45-7.38 (m, 2H), 7.37-7.31 (m, 1H), 7.30-7.24 (m, 1H), 7.22-7.15 (m, 3H), 7.13 (d, J=2.0 Hz, 1H), 6.96 (dd, J=8.8, 2.4 Hz, 1H), 5.16 (s, 2H), 2.40 (s, 3H).

Step 2: 5-(Benzyloxy)-1-(4-bromobenzyl)-2-(4-fluorophenyl)-3-methyl-1H-indole

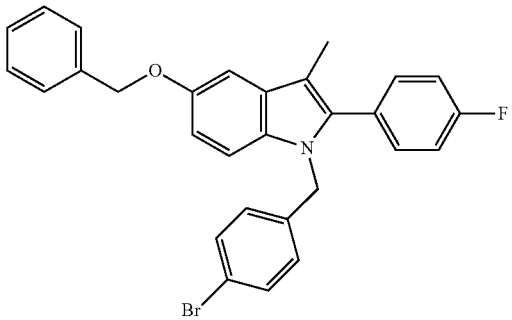 [SMILES: Cc1c(-c2ccc(F)cc2)n(Cc2ccc(Br)cc2)c2ccc(OCc3ccccc3)cc12]

To a solution of 5-benzyloxy-2-(4-fluorophenyl)-3-methyl-1H-indole (0.4 g, 1.21 mmol) in DMF (3 mL) was added sodium hydride (60% dispersion in mineral oil, 72 mg, 1.81 mmol) slowly at 0° C. The mixture was stirred at 0° C. for 30 min before the addition of a solution of 1-bromo-4-(bromomethyl)benzene (0.45 g, 1.81 mmol) in DMF (2 mL). The resulting mixture was stirred at 25° C. for 16 h. The reaction was quenched with water (5 mL) and the mixture was extracted with ethyl acetate (30 mL×3). The combined organic layers were washed with water and brine, dried over anhydrous Na$_2$SO$_4$, filtered and concentrated under reduced pressure. The residue was purified by silica gel column chromatography (0-10% ethyl acetate in hexanes) to give the title compound (580 mg, 81%) as an off-white solid. $^1$H NMR (400 MHz, CDCl$_3$): δ 7.54-7.46 (m, 4H), 7.41 (t, J=7.6 Hz, 2H), 7.35 (d, J=8.0 Hz, 3H), 7.26-7.21 (m, 3H), 7.17 (d, J=2.0 Hz, 1H), 7.14-7.03 (m, 3H), 6.93 (dd, J=8.8, 2.4 Hz, 1H), 6.79 (d, J=8.4 Hz, 2H), 5.15 (s, 2H), 5.11 (s, 2H), 2.24 (s, 3H); LCMS: 500.2 [M+H]$^+$.

Step 3: 4-((5-(Benzyloxy)-2-(4-fluorophenyl)-3-methyl-1H-indol-1-yl)methyl)phenol

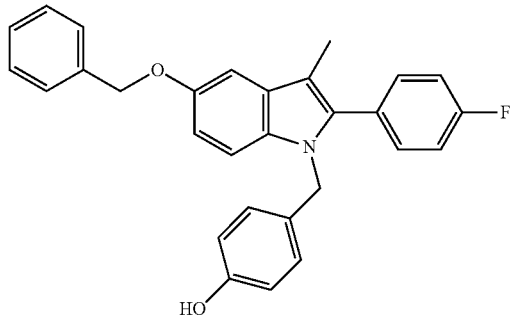 [SMILES: Cc1c(-c2ccc(F)cc2)n(Cc2ccc(O)cc2)c2ccc(OCc3ccccc3)cc12]

A solution of 5-benzyloxy-1-[(4-bromophenyl)methyl]-2-(4-fluorophenyl)-3-methyl-indole (480 mg, 0.81 mmol) in 1,4-dioxane (3 mL) and water (2.5 mL) were added potassium hydroxide (0.14 g, 2.42 mmol), di-tert-butyl-[3-(2,4,6-triiso-propylphenyl)phenyl]phosphane (27 mg, 0.06 mmol) and tris(dibenzylideneacetone)dipalladium (30 mg, 0.03 mmol). The mixture was stirred at 90° C. for 16 h under a nitrogen atmosphere. After cooling to 25° C., the mixture was extracted with ethyl acetate (30 mL×3). The combined organic layers were washed with saturated brine, dried over anhydrous Na$_2$SO$_4$, filtered, and concentrated under reduced pressure. The residue was purified by silica gel column chromatography (0-9% ethyl acetate in petroleum ether) to give the title compound (250 mg, 71%) as a light yellow solid. $^1$H NMR (400 MHz, CDCl$_3$): δ 7.50 (d, J=7.6 Hz, 2H), 7.40 (t, J=7.2 Hz, 2H), 7.36-7.31 (m, 1H), 7.29-7.27 (m, 2H), 7.15 (d, J=2.0 Hz, 1H), 7.14-7.06 (m, 3H), 6.93 (dd, J=8.8, 2.4 Hz, 1H), 6.79 (d, J=8.4 Hz, 2H), 6.68 (d, J=8.4 Hz, 2H), 5.15 (s, 2H), 5.10 (s, 2H), 4.80 (s, 1H), 2.24 (s, 3H).

Step 4: 2-(4-((5-(Benzyloxy)-2-(4-fluorophenyl)-3-methyl-1H-indol-1-yl)methyl)phenoxy)-ethanol

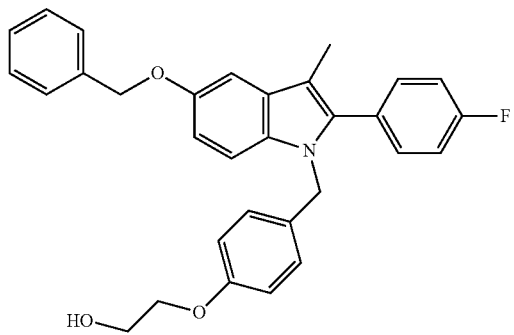 [SMILES: Cc1c(-c2ccc(F)cc2)n(Cc2ccc(OCCO)cc2)c2ccc(OCc3ccccc3)cc12]

To a solution of 4-[[5-benzyloxy-2-(4-fluorophenyl)-3-methyl-indol-1-yl]methyl]phenol (0.3 g, 0.69 mmol) in acetonitrile (5 mL) was added potassium carbonate (0.47 g, 3.4 mmol), followed with 2-bromoethanol (0.43 g, 3.4 mmol). The mixture was stirred at 80° C. for 16 h. After cooling to 25° C., the mixture was diluted with ethyl acetate (50 mL), washed with water and brine, dried over anhydrous Na₂SO₄, filtered, and concentrated under reduced pressure. The residue was purified by silica gel column chromatography (0-20% ethyl acetate in petroleum ether) to give the title compound (0.27 g, 65%) as a light yellow oil. ¹H NMR (400 MHz, CDCl₃): δ 7.50 (d, J=7.2 Hz, 2H), 7.40 (t, J=7.2 Hz, 2H), 7.36-7.31 (m, 1H), 7.29-7.24 (m, 2H), 7.15 (d, J=2.0 Hz, 1H), 7.13-7.06 (m, 3H), 6.92 (dd, J=8.8, 2.4 Hz, 1H), 6.85 (d, J=8.4 Hz, 2H), 6.78 (d, J=8.8 Hz, 2H), 5.14 (s, 2H), 5.11 (s, 2H), 4.03 (t, J=4.4 Hz, 2H), 3.98-3.90 (m, 2H), 2.24 (s, 3H).

Step 5: 2-(4-((5-(Benzyloxy)-2-(4-fluorophenyl)-3-methyl-1H-indol-1-yl)methyl)phenoxy)-ethyl methanesulfonate

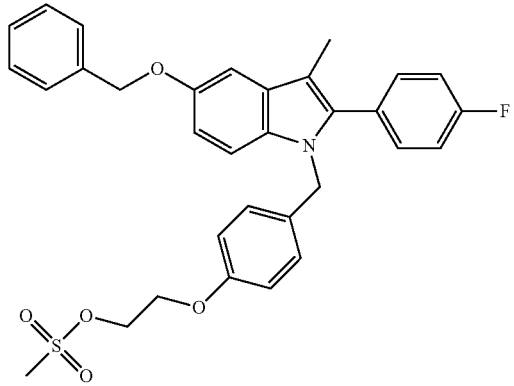 [SMILES: Cc1c(-c2ccc(F)cc2)n(Cc2ccc(OCCOS(C)(=O)=O)cc2)c2ccc(OCc3ccccc3)cc12]

To a solution of 2-[4-[[5-benzyloxy-2-(4-fluorophenyl)-3-methyl-indol-1-yl]methyl]phenoxy]ethanol (0.27 g, 0.45 mmol) in DCM (3 mL) was added triethylamine (125 μL, 0.90 mmol), followed with methanesulfonyl chloride (43 μL, 0.54 mmol) at 0° C. The resulting mixture was stirred at 25° C. for 2 h. The reaction mixture was diluted with ethyl acetate (30 mL). The mixture was washed with water and brine, dried over anhydrous Na₂SO₄, filtered and concentrated under reduced pressure. The residue was purified by silica gel column chromatography (0-18% ethyl acetate in petroleum ether) to give the title compound (0.2 g, 80%) as a light yellow oil.

Step 6: 5-(Benzyloxy)-1-(4-(2-(3-(fluoromethyl)azetidin-1-yl)ethoxy)benzyl)-2-(4-fluoro phenyl)-3-methyl-1H-indole

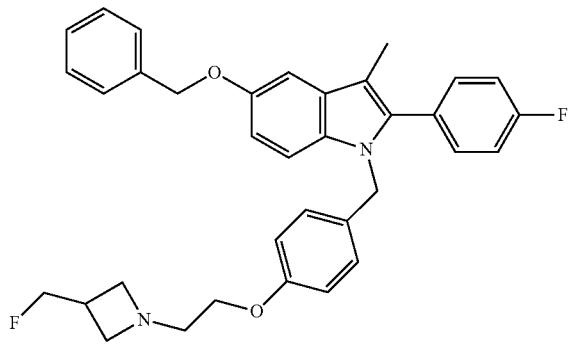 [SMILES: Cc1c(-c2ccc(F)cc2)n(Cc2ccc(OCCN3CC(CF)C3)cc2)c2ccc(OCc3ccccc3)cc12]

To a mixture of 2-[4-[[5-benzyloxy-2-(4-fluorophenyl)-3-methyl-indol-1-yl]methyl]phenoxy]ethyl methanesulfonate (0.1 g, 0.18 mmol) and 3-(fluoromethyl)azetidine hydrochloride (0.11 g, 0.89 mmol) in acetonitrile (1 mL) was added N,N-diiso-propylethylamine (0.24 mL, 1.43 mmol). The mixture was stirred at 80° C. for 16 h. After cooling to 25° C., the mixture was concentrated under reduced pressure to give the title compound as a light yellow oil which was used directly for the next step without further purification. LCMS: 553.3 [M+H]⁺.

Step 7: 1-(4-(2-(3-(Fluoromethyl)azetidin-1-yl)ethoxy)benzyl)-2-(4-fluorophenyl)-3-methyl-1H-indol-5-ol To a solution of crude 2-[4-[[5-benzyloxy-2-(4-fluorophenyl)-3-methyl-indol-1-yl]methyl]phenoxy]-N,N-dimethyl-ethanamine (100 mg) in THF (1 mL) and methanol (1 mL) was added 10% palladium on carbon (30 mg, 0.03 mmol). The mixture was stirred at 25° C. under a hydrogen atmosphere for 6 h, filtered and concentrated under reduced pressure. The residue was purified by reverse-phase HPLC (26-56% acetonitrile with 0.2% formic acid in water) to give the title compound (18 mg, 30%) as an off-white solid. ¹H NMR (400 MHz, DMSO-d₆): δ 8.78 (s, 1H), 8.15 (s, 1H), 7.43-7.35 (m, 2H), 7.35-7.26 (m, 2H), 7.13 (d, J=8.4 Hz, 1H), 6.83 (d, J=2.0 Hz, 1H), 6.75-6.65 (m, 4H), 6.62 (dd, J=8.4, 2.0 Hz, 1H), 5.12 (s, 2H), 4.45 (dd, J=49.6, 6.0 Hz, 2H), 3.80 (t, J=5.6 Hz, 2H), 3.30-3.20 (m, 2H), 3.00 (t, J=6.4 Hz, 2H), 2.73-2.61 (m, 3H), 2.11 (s, 3H). LCMS: 463.2 [M+H]⁺.

Example 4 1-(4-(2-(3-(Fluoromethyl)azetidin-1-yl)ethoxy)benzyl)-3-methyl-2-phenyl-1H-indole

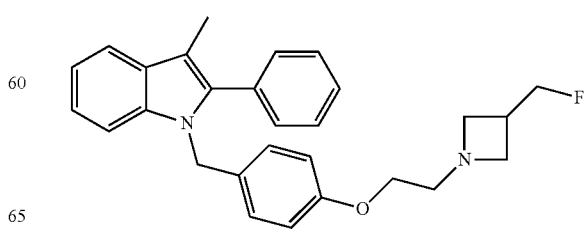

Step 1: 3-Methyl-2-phenyl-1H-indole

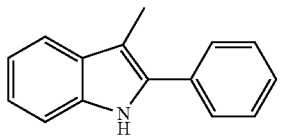 [SMILES: Cc1c(-c2ccccc2)[nH]c2ccccc12]

A solution of phenylhydrazine (5 g, 46.2 mmol), concentrated HCl (5.0 mL, 50.0 mmol) and propiophenone (6.82 g, 50.9 mmol) in ethanol (25.0 mL) was stirred at 80° C. for 16 h. After cooling to 25° C., ethanol was evaporated under reduced pressure and the residue was diluted with ethyl acetate (200 mL), and then washed with water (50 mL) and brine (50 mL). The organic layer was dried over anhydrous $Na_2SO_4$ and concentrated under reduced pressure. The residue was purified by silica gel column chromatography (5% ethyl acetate in petroleum ether) to give the title compound (10 g, quantitative). $^1$H NMR (400 MHz, $CDCl_3$): δ 8.05 (brs, 1H), 7.65-7.56 (m, 3H), 7.51-7.46 (m, 2H), 7.43-7.33 (m, 2H), 7.25-7.19 (m, 1H), 7.19-7.13 (m, 1H), 2.48 (s, 3H).

Step 2: 1-(4-Iodobenzyl)-3-methyl-2-phenyl-1H-indole

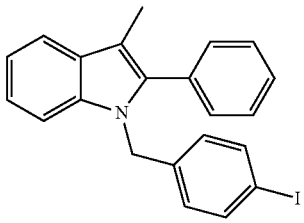 [SMILES: Cc1c(-c2ccccc2)n(Cc2ccc(I)cc2)c2ccccc12]

To a solution of 3-methyl-2-phenyl-1H-indole (10.0 g, 48.25 mmol) in DMF (100 mL) was added sodium hydride (60% dispersion in mineral oil, 2.51 g, 62.72 mmol) at 0° C. The mixture was stirred at 20° C. for 20 min before 1-(bromomethyl)-4-iodo-benzene (18.62 g, 62.72 mmol) was added. The resulting mixture was stirred at 20° C. for additional 4.5 h. The reaction was quenched with water (1000 mL) and the resulting mixture was filtered to give the title compound (13 g, 62%) as a brown solid which was used in the next step without further purification. $^1$H NMR (400 MHz, $CDCl_3$): δ 7.68-7.61 (m, 1H), 7.54 (d, J=8.0 Hz, 2H), 7.46-7.37 (m, 3H), 7.34-7.28 (m, 2H), 7.21-7.11 (m, 3H), 6.69 (d, J=8.0 Hz, 2H), 5.17 (s, 2H), 2.31 (s, 3H).

Step 3: 1-(4-(2-(3-(Fluoromethyl)azetidin-1-yl)ethoxy)benzyl)-3-methyl-2-phenyl-1H-indole

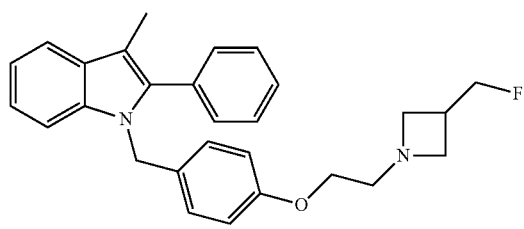 [SMILES: Cc1c(-c2ccccc2)n(Cc2ccc(OCCN3CC(CF)C3)cc2)c2ccccc12]

To a mixture of 1-[(4-iodophenyl)methyl]-3-methyl-2-phenyl-indole (100 mg, 0.24 mmol), t-butyl Xphos (20 mg, 0.047 mmol), Intermediate 1 (47 mg, 0.35 mmol) and $Cs_2CO_3$ (116.2 mg, 0.35 mmol) in toluene (2.0 mL) was added palladium acetate (5.3 mg, 0.024 mmol) at 20° C. The resulting mixture was stirred at 100° C. under nitrogen atmosphere for 18 h. After cooling to 20° C., the reaction solution was diluted with ethyl acetate (50 mL), washed with water (10 mL) and brine (10 mL). The organic layer was dried over anhydrous $Na_2SO_4$ and concentrated under reduced pressure. The residue was purified by reverse-phase HPLC (1-28% acetonitrile/0.2% formic acid in water) to give the title compound (7.2 mg, 7%) as colorless oil. $^1$H NMR (400 MHz, $CD_3OD$): δ 7.57 (d, J=7.6 Hz, 1H), 7.49-7.39 (m, 3H), 7.35 (d, J=6.4 Hz, 2H), 7.25 (d, J=8.0 Hz, 1H), 7.17-7.05 (m, 2H), 6.81-6.71 (m, 4H), 5.22 (s, 2H), 4.54 (d, J=5.6 Hz, 1H), 4.43 (d, J=5.6 Hz, 1H), 3.94 (t, J=5.2 Hz, 2H), 3.57 (t, J=8.0 Hz, 2H), 3.27-3.24 (m, 2H), 2.93-2.80 (m, 3H), 2.27 (s, 3H). LCMS: 429.2 $[M+H]^+$.

Example 5 4-(1-(4-(2-(3-(Fluoromethyl)azetidin-1-yl)ethoxy)benzyl)-3-methyl-1H-indol-2-yl)phenol

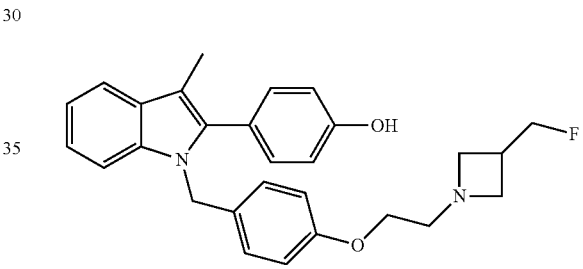

Step 1: 2-(4-(Benzyloxy)phenyl)-3-methyl-1H-indole

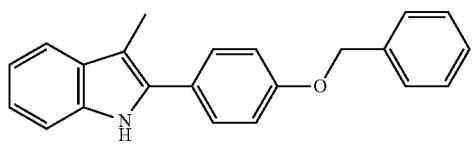 [SMILES: Cc1c(-c2ccc(OCc3ccccc3)cc2)[nH]c2ccccc12]

To a solution of 1-(4-benzyloxyphenyl)propan-1-one (5.0 g, 20.81 mmol) and phenylhydrazine (2.7 g, 24.97 mmol) in ethanol (30 mL) was added concentrated HCl (2.8 mL, 33.30 mmol). The reaction mixture was stirred at 80° C. for 15 h. After cooling to room temperature, the reaction mixture was filtered and the filter cake was washed with water (50 mL), dried in vacuum to give the title compound (6.13 g, 77%) as a brown solid which was used in the next step without further purification. LCMS: 314.2 $[M+H]^+$.

Step 2: 2-(4-(Benzyloxy)phenyl)-1-(4-iodobenzyl)-3-methyl-1H-indole

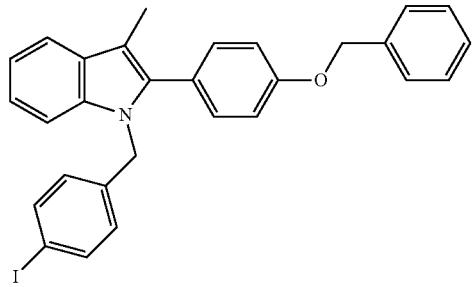 [SMILES: Cc1c(-c2ccc(OCc3ccccc3)cc2)n(Cc2ccc(I)cc2)c2ccccc12]

To a mixture of 2-(4-(benzyloxy)phenyl)-3-methyl-1H-indole (2.4 g, 6.28 mmol) in DMF (15 mL) at 0° C. was added NaH (60% dispersion in mineral oil, 0.38 g, 9.42 mmol) and stirred for 30 min. To the resultant mixture was added 1-(bromomethyl)-4-iodo-benzene (2.24 g, 7.54 mmol) and then the resulting mixture was stirred at 25° C. for 15 h. The reaction was quenched with water (50 mL). The reaction mixture was filtered. The filter cake was washed with water (50 mL), dried in vacuum to give the title compound (1.93 g, 58%) as brown solid which was used in the next step without further purification. $^1$H NMR (400 MHz, CDCl$_3$): δ 7.66-7.59 (m, 1H), 7.55 (d, J=8.4 Hz, 2H), 7.50-7.32 (m, 5H), 7.24-7.11 (m, 5H), 7.02 (d, J=8.4 Hz, 2H), 6.69 (d, J=8.0 Hz, 2H), 5.16 (s, 2H), 5.11 (s, 2H), 2.30 (s, 3H).

Step 3: 2-(4-(Benzyloxy)phenyl)-1-(4-(2-(3-(fluoromethyl)azetidin-1-yl)ethoxy)benzyl)-3-methyl-1H-indole

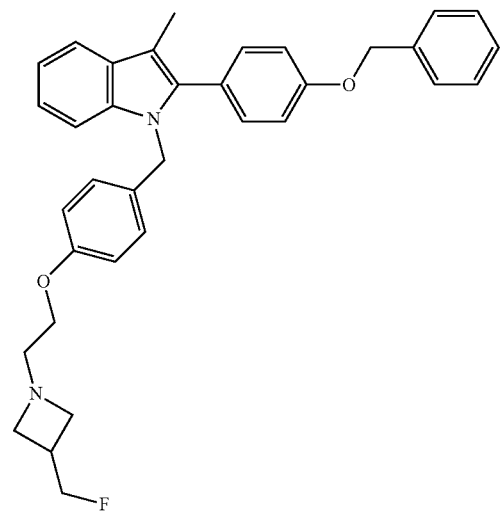 [SMILES: Cc1c(-c2ccc(OCc3ccccc3)cc2)n(Cc2ccc(OCCN3CC(CF)C3)cc2)c2ccccc12]

A mixture of 2-(4-(benzyloxy)phenyl)-1-(4-iodobenzyl)-3-methyl-1H-indole (100 mg, 0.19 mmol), Intermediate 1 (75 mg, 0.57 mmol), potassium carbonate (78 mg, 0.57 mmol) and copper(I) iodide (18 mg, 0.090 mmol) in o-xylene (5 mL) was heated at 130° C. for 15 h. After cooling to room temperature, the reaction mixture was concentrated under reduced pressure. The residue was purified by preparative TLC (70% ethyl acetate in petroleum ether) to give the title compound (55 mg, 53%) as a yellow oil. LCMS: 535.3 [M+H]$^+$.

Step 4: 4-(1-(4-(2-(3-(Fluoromethyl)azetidin-1-yl)ethoxy)benzyl)-3-methyl-1H-indol-2-yl) phenol

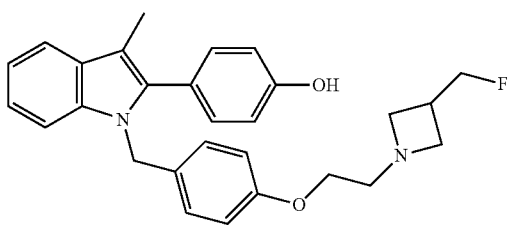 [SMILES: Cc1c(-c2ccc(O)cc2)n(Cc2ccc(OCCN3CC(CF)C3)cc2)c2ccccc12]

To a solution of 2-(4-benzyloxyphenyl)-1-[[4-[2-[3-(fluoromethyl)azetidin-1-yl]ethoxy]phenyl]methyl]-3-methyl-indole (55 mg, 0.10 mmol) in THF (2 mL) and methanol (2 mL) was added 10% Pd on carbon (55 mg, 0.050 mmol). The mixture was stirred under a hydrogen atmosphere (15 psi) at 25° C. for 16 h. The mixture was filtered and concentrated under reduced pressure. The residue was purified by reverse-phase HPLC (35-65% acetonitrile/0.1% NH$_4$HCO$_3$ in water) to give the title compound (18.8 mg, 41%) as a white solid. $^1$H NMR (400 MHz, CD$_3$OD): δ 7.52 (d, J=7.2 Hz, 1H), 7.19 (d, J=7.6 Hz, 1H), 7.13 (d, J=8.4 Hz, 2H), 7.10-7.01 (m, 2H), 6.83 (d, J=8.4 Hz, 2H), 6.79-6.71 (m, 4H), 5.17 (s, 2H), 4.46 (dd, J=47.6, 5.6 Hz, 2H), 3.91 (t, J=5.2 Hz, 2H), 3.52-3.48 (m, 2H), 3.21-3.17 (m, 2H), 2.89-2.77 (m, 3H), 2.22 (s, 3H). LCMS: 445.2 [M+H]$^+$.

Example 6 (4-(2-(3-(Fluoromethyl)azetidin-1-yl)ethoxy)phenyl)(6-hydroxy-2-(4-hydroxyphenyl)-1-methyl-1H-indol-3-yl)methanone

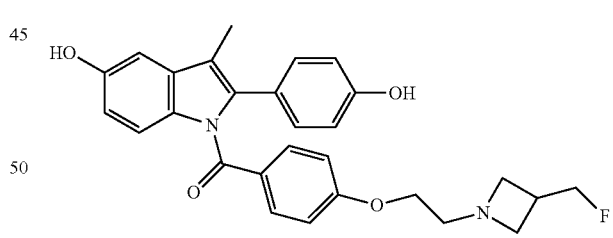

Step 1: 4-Iodo-3-nitrophenol

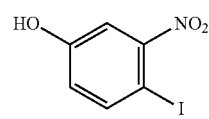

To a solution of 4-amino-3-nitrophenol (10.0 g, 64.88 mmol) dissolved in concentrated HCl (25 mL) was added sodium nitrite (8.95 g, 129.77 mmol) in water (20 mL) dropwise at 0° C. After stirring at 0° C. for 1 h, potassium iodide (21.5 g, 129.77 mmol) in water (40 mL) was added dropwise at 0° C. The resulting mixture was stirred at 26° C. for 16 h. The precipitate was collected by filtration, washed with water and dried in vacuum to give the title compound (15 g, 87%) as red-orange solid which was used in the next step without further purification. ¹H NMR (400 MHz, DMSO-d₆): δ 10.61 (s, 1H), 7.83 (d, J=8.4 Hz, 1H), 7.31 (d, J=2.8 Hz, 1H), 6.87 (dd, J=8.4, 2.8 Hz, 1H).

Step 2: 4-(Benzyloxy)-1-iodo-2-nitrobenzene

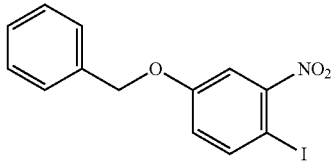

To a mixture of 4-iodo-3-nitrophenol (5.0 g, 18.87 mmol) and potassium carbonate (5.2 g, 37.7 mmol) in acetone (50 mL) was added benzyl bromide (3.6 g, 20.7 mmol). The reaction mixture was stirred at 26° C. for 16 h. The solid was removed by filtration. The resulting residue was concentrated, dissolved in ethyl acetate (100 mL), and washed with water (50 mL×2). The organic layer was dried over anhydrous Na₂SO₄, filtered, and concentrated under reduced pressure to give the title compound (6 g, 89%) as a brown solid which was used in the next step without further purification. ¹H NMR (400 MHz, DMSO-d₆): δ 7.95 (d, J=8.8 Hz, 1H), 7.66 (d, J=2.8 Hz, 1H), 7.50-7.32 (m, 5H), 7.13 (dd, J=2.8, 8.8 Hz, 1H), 5.19 (s, 2H).

Step 3: 5-(Benzyloxy)-2-iodoaniline

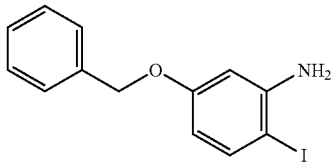 [SMILES: O=[N+]([O-])c1cc(OCc2ccccc2)ccc1I]

A mixture of 4-(benzyloxy)-1-iodo-2-nitrobenzene (2.0 g, 5.63 mmol), activated carbon (270 mg, 22.5 mmol), and FeCl₃ (90 mg, 0.56 mmol) in MeOH (15 mL) was heated to reflux under nitrogen atmosphere for 10 min. To the reaction mixture was added hydrazine monohydrate (1.22 g, 22.5 mmol) dropwise and the mixture was refluxed for additional 8 h. After cooling to room temperature, the mixture was diluted with DCM (50 mL) and water (50 mL), then filtered through Celite, and extracted with DCM (100 mL). The organic layer was separated, dried over anhydrous Na₂SO₄, and concentrated under reduced pressure. The residue was purified by silica gel column chromatography (0-10% ethyl acetate in hexanes) to give the title compound (1.6 g, 87%) as a brown solid. ¹H NMR (400 MHz, DMSO-d₆): δ 7.43-7.27 (m, 6H), 6.43 (d, J=2.8 Hz, 1H), 6.07 (dd, J=8.8, 2.8 Hz, 1H), 5.17 (s, 2H), 4.98 (s, 2H).

Step 4: N-(5-(Benzyloxy)-2-iodophenyl)-2,2,2-trifluoroacetamide

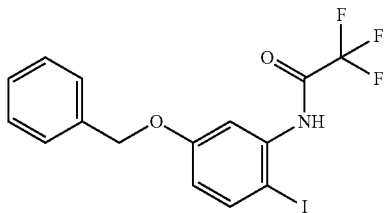 [SMILES: O=C(Nc1cc(OCc2ccccc2)ccc1I)C(F)(F)F]

To a solution of 5-benzyloxy-2-iodo-aniline (5 g, 15.38 mmol) and triethylamine (6.4 mL, 46.13 mmol) in DCM (100 mL) was added 2,2,2-trifluoro acetic anhydride (2.6 mL, 18.45 mmol) at 0° C. The reaction mixture was stirred at 25° C. for 2 h. The solvent was removed in vacuo. The residue was purified by silica gel column chromatography (10% ethyl acetate in petroleum ether) to give the title compound (6.2 g, 95%) as a white solid which was used directly for the next step without further purification. ¹H NMR (400 MHz, DMSO-d₆): δ 11.23 (s, 1H), 7.80 (d, J=8.8 Hz, 1H), 7.45-7.32 (m, 5H), 7.11 (d, J=3.2 Hz, 1H), 6.87 (dd, J=3.2, 8.8 Hz, 1H), 5.12 (s, 2H).

Step 5: N-(5-(Benzyloxy)-2-((4-(benzyloxy)phenyl)ethynyl)phenyl)-2,2,2-trifluoroacetamide

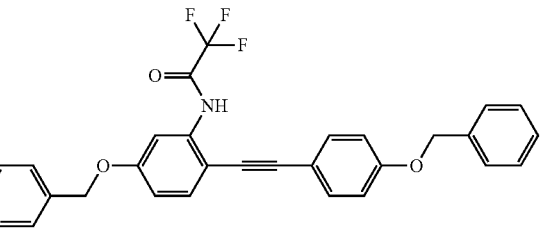

A mixture of N-(5-(benzyloxy)-2-iodophenyl)-2,2,2-trifluoroacetamide (5.0 g, 11.87 mmol), 1-(benzyloxy)-4-ethynylbenzene (3.7 g, 17.81 mmol), triethylamine (4.9 mL, 35.62 mmol), Pd(PPh₃)₂Cl₂ (250 mg, 0.36 mmol) and copper(I) iodide (113 mg, 0.59 mmol) in acetonitrile (50 mL) was stirred at 25° C. for 5 h. The reaction mixture was concentrated under reduced pressure. The residue was purified by silica gel column chromatography (0-30% ethyl acetate in hexanes) to give the title compound (4 g, 61%) as a yellow solid. ¹H NMR (400 MHz, DMSO-d₆): δ 11.17 (s, 1H), 7.51 (d, J=8.8 Hz, 1H), 7.45-7.30 (m, 13H), 7.12 (d, J=2.4 Hz, 1H), 7.07-7.00 (m, 3H), 5.13 (s, 2H), 5.10 (s, 2H).

Step 6: (6-(Benzyloxy)-2-(4-(benzyloxy)phenyl)-1H-indol-3-yl)(4-((tert-butyldimethylsilyl) oxy)phenyl)methanone

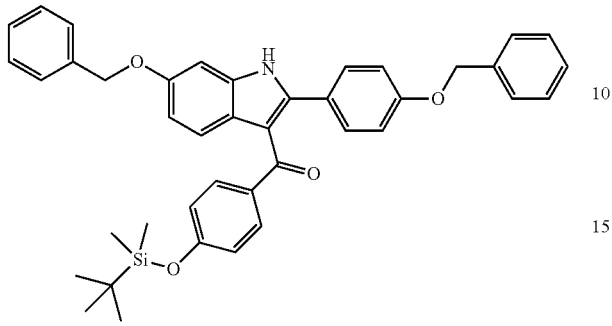

A mixture of N-(5-(benzyloxy)-2-((4-(benzyloxy)phenyl) ethynyl)phenyl)-2,2,2-trifluoro-acetamide (500 mg, 0.997 mmol), tert-butyl(4-iodophenoxy)dimethylsilane (500 mg, 1.50 mmol), potassium carbonate (413 mg, 2.99 mmol) and Pd(PPh$_3$)$_2$Cl$_2$ (70 mg, 0.1 mmol) in acetonitrile (5 mL) was stirred at 25° C. under CO atmosphere (15 psi) for 5 h. The reaction mixture was concentrated under reduced pressure. The residue was purified by silica gel column chromatography (0-30% ethyl acetate in hexanes) to give the title compound (400 mg, 63%) as a brown solid. $^1$H NMR (400 MHz, DMSO-d$_6$): δ 11.71 (s, 1H), 7.49 (d, J=8.8 Hz, 1H), 7.37-7.20 (m, 12H), 7.12 (d, J=8.8 Hz, 2H), 6.90-6.90 (m, 1H), 6.86 (d, J=1.6 Hz, 1H), 6.74 (d, J=8.8 Hz, 3H), 6.52 (d, J=8.8 Hz, 2H), 5.04 (s, 2H), 4.91 (s, 2H), 0.77 (s, 9H), 0.00 (s, 6H).

Step 7: (6-(Benzyloxy)-2-(4-(benzyloxy)phenyl)-1-methyl-1H-indol-3-yl)(4-hydroxyphenyl) methanone

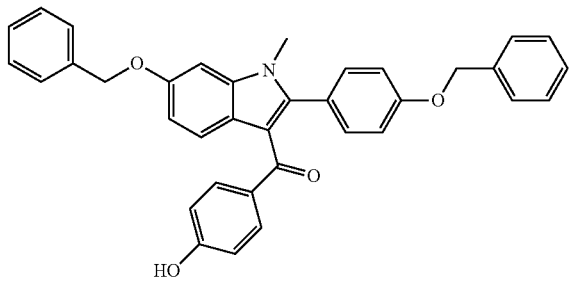 [SMILES: Cn1c(-c2ccc(OCc3ccccc3)cc2)c(C(=O)c2ccc(O)cc2)c2ccc(OCc3ccccc3)cc21]

To a suspension of sodium hydride (60% dispersion in mineral oil, 56 mg, 1.41 mmol) in THF (3 mL) was added [6-benzyloxy-2-(4-benzyloxyphenyl)-1H-indol-3-yl]-[4-[tert-butyl(dimethyl)silyl]oxy-phenyl]methanone (0.6 g, 0.94 mmol) in THF (3 mL) dropwise at 0 □C. After stirring at 0° C. for 30 min, iodomethane (0.07 mL, 1.13 mmol) was added. The resulting mixture was stirred at 25° C. for additional 16 h. The reaction was quenched with saturated NaHCO$_3$ (10 mL), and extracted with ethyl acetate (20 mL×3). The combined organics were dried over anhydrous Na$_2$SO$_4$ and concentrated under reduced pressure. The residue was purified by silica gel column chromatography (0-50% ethyl acetate in petroleum ether) to give the title compound (0.4 g, 79%) as a brown solid. $^1$H NMR (400 MHz, DMSO-d$_6$): δ 10.02 (s, 1H), 7.55-7.46 (m, 3H), 7.44-7.28 (m, 11H), 7.22 (d, J=8.8 Hz, 3H), 6.95-6.84 (m, 3H), 6.54 (d, J=8.6 Hz, 2H), 5.18 (s, 2H), 5.06 (s, 2H), 3.60 (s, 3H).

Step 8: (6-(Benzyloxy)-2-(4-(benzyloxy)phenyl)-1-methyl-1H-indol-3-yl)(4-(2-(3-(fluoro methyl)azetidin-1-yl)ethoxy)phenyl)methanone

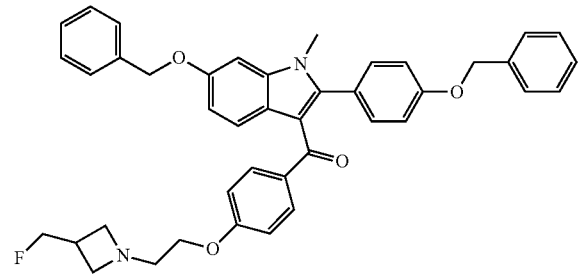 [SMILES: Cn1c(-c2ccc(OCc3ccccc3)cc2)c(C(=O)c2ccc(OCCN3CC(CF)C3)cc2)c2ccc(OCc3ccccc3)cc21]

To a mixture of [6-benzyloxy-2-(4-benzyloxyphenyl)-1-methyl-indol-3-yl]-(4-hydroxyphenyl) methanone (250 mg, 0.460 mmol), triphenylphosphine (0.36 g, 1.39 mmol) and Intermediate 1 (92 mg, 0.69 mmol) in THF (3 mL) was added diiso-propyl azodicarboxylate (0.28 mL, 1.39 mmol) dropwise at 0° C. The resulting mixture was stirred at 25° C. for 16 h and concentrated under reduced pressure. The residue was purified by silica gel column chromatography (50% ethyl acetate in hexanes) to give the title compound (200 mg, 66%) as a brown solid. LCMS: 655.3 [M+H]$^+$.

Step 9: (4-(2-(3-(Fluoromethyl)azetidin-1-yl)ethoxy)phenyl)(6-hydroxy-2-(4-hydroxyphenyl)-1-methyl-1H-indol-3-yl)methanone

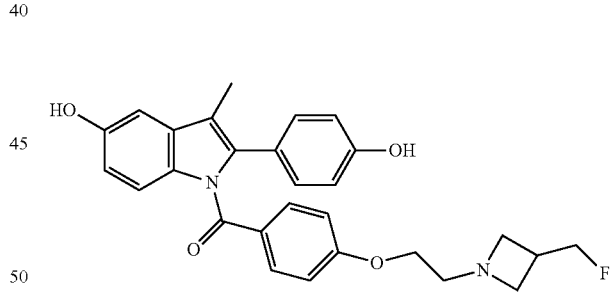

A mixture of (6-(benzyloxy)-2-(4-(benzyloxy)phenyl)-1-methyl-1H-indol-3-yl)(4-(2-(3-(fluoro methyl)azetidin-1-yl) ethoxy)phenyl)methanone (100 mg, 0.153 mmol) and 10% palladium on carbon (20 mg) in MeOH (1 mL) and THF (1 mL) was stirred at 25° C. under hydrogen atmosphere for 16 h. The mixture was filtered through Celite, and the filtrate was concentrated under reduced pressure. The residue was purified by reverse-phase HPLC (acetonitrile 65%/0.1% formic acid in water)) to give the title compound (2.6 mg, 3%) as a black solid. $^1$H NMR (400 MHz, DMSO-d$_6$): δ 8.20 (br. s, 1H), 7.52 (d, J=8.8 Hz, 1H), 7.36 (d, J=8.8 Hz, 2H), 7.04 (d, J=8.8 Hz, 2H), 6.84 (s, 1H), 6.70-6.59 (m, 5H), 4.58-4.38 (m, 2H), 3.86 (t, J=6.4 Hz, 2H), 3.29-3.27 (m, 3H), 2.97 (t, J=6.4 Hz, 2H), 2.67-2.64 (m, 4H), 2.39-2.35 (m, 1H).

Example 7

5-(4-(2-(3-(Fluoromethyl)azetidin-1-yl)ethoxy)phenoxy)-6-(4-(methyl sulfonyl)phenyl)naphthalen-2-ol

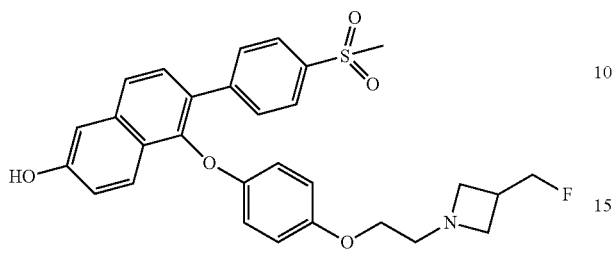

Step 1: 5-Bromo-6-(4-(methylsulfonyl)phenyl)naphthalen-2-ol

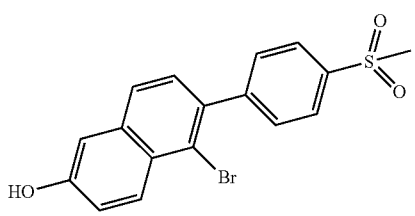 [SMILES: CS(=O)(=O)c1ccc(-c2ccc3cc(O)ccc3c2Br)cc1]

Boron tribromide (0.73 mL, 7.6 mmol) was added dropwise to a solution of 1-bromo-6-methoxy-2-(4-(methylsulfonyl)phenyl)naphthalene (1.48 g, 3.78 mmol, see WO/2004/009086A1 for synthesis) in DCM (16 mL) at −78° C. The reaction mixture was warmed to 0° C., stirred for 2 h, re-cooled to −78° C., and then quenched with methanol (4 mL). The reaction mixture was diluted with water (40 mL) and extracted with ethyl acetate/DCM (1:2). The organic layer was washed (40 mL saturated NaHCO$_3$ and then 40 mL brine), dried (MgSO$_4$), and concentrated under reduced pressure to give the title compound (1.43 g, 100%) as a pink solid. $^1$H NMR (400 MHz, DMSO-d$_6$): δ 10.19 (s, 1H), 8.17 (d, J=9.2 Hz, 1H), 8.03 (d, J=8.5 Hz, 2H), 7.85 (d, J=8.6 Hz, 1H), 7.73 (d, J=8.5 Hz, 2H), 7.38 (d, J=8.6 Hz, 1H), 7.32-7.28 (m, 1H), 7.27-7.25 (m, 1H), 3.31 (s, 3H).

Step 2: 2-((5-Bromo-6-(4-(methylsulfonyl)phenyl)naphthalen-2-yl)oxy)tetrahydro-2H-pyran

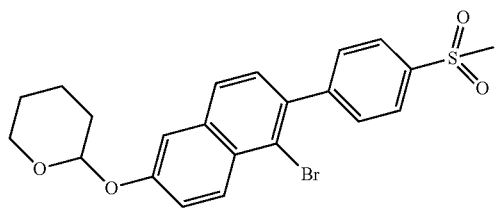 [SMILES: CS(=O)(=O)c1ccc(-c2ccc3cc(OC4CCCCO4)ccc3c2Br)cc1]

Pyridinium p-toluene sulfonate (191 mg, 0.76 mmol) and 3,4-dihydro-2H-pyran (0.7 mL, 7.7 mmol) were added to a suspension of 5-bromo-6-(4-(methylsulfonyl)phenyl)naphthalen-2-ol (1.43 g, 3.78 mmol) in DCM (20 mL). The reaction was stirred at room temperature for 3 h, washed (30 mL water and then 30 mL brine), dried (MgSO$_4$), and concentrated under reduced pressure. The residue was purified by silica gel column chromatography to give the title compound (1.34 g, 77%) as a white solid. $^1$H NMR (400 MHz, DMSO-d$_6$): δ 8.25 (d, J=9.3 Hz, 1H), 8.05 (d, J=8.4 Hz, 2H), 7.96 (d, J=8.6 Hz, 1H), 7.74 (d, J=8.4 Hz, 2H), 7.63-7.60 (m, 1H), 7.52-7.47 (m, 1H), 7.46 (d, J=8.6 Hz, 1H), 5.73-5.71 (m, 1H), 3.84-3.75 (m, 1H), 3.66-3.58 (m, 1H), 3.32 (s, 3H), 2.00-1.78 (m, 3H), 1.73-1.52 (m, 3H).

Step 3: 3-(Fluoromethyl)-1-(2-(4-((2-(4-(methylsulfonyl)phenyl)-6-((tetrahydro-2H-pyran-2-yl)oxy)naphthalen-1-yl)oxy)phenoxy)ethyl)azetidine

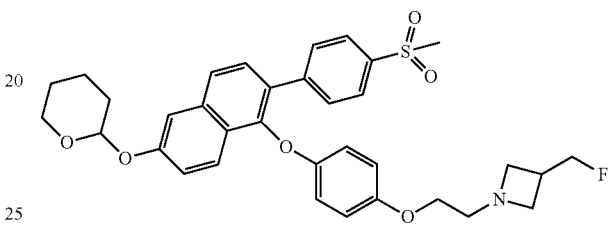

A mixture of 2-((5-Bromo-6-(4-(methylsulfonyl)phenyl)naphthalen-2-yl)oxy)tetrahydro-2H-pyran (139 mg, 0.26 mmol), Intermediate 5 (116 mg, 0.51 mmol), Cs$_2$CO$_3$ (293 mg, 0.90 mmol), CuCl (12 mg, 0.12 mmol), and diglyme (1.6 mL) was degassed with vacuum/nitrogen cycles (3×). The mixture was heated at 140° C. overnight, allowed to cool to room temperature, and diluted with ethyl acetate (60 mL). The mixture was washed (2×20 mL water and then 20 mL brine), dried (MgSO$_4$), and concentrated under reduced pressure. The crude material was purified by silica gel chromatography to give the title compound (103 mg, 66%) as a beige solid. LCMS: 606.1 [M+H]$^+$.

Step 4: 5-(4-(2-(3-(Fluoromethyl)azetidin-1-yl)ethoxy)phenoxy)-6-(4-(methylsulfonyl)phenyl)naphthalen-2-ol

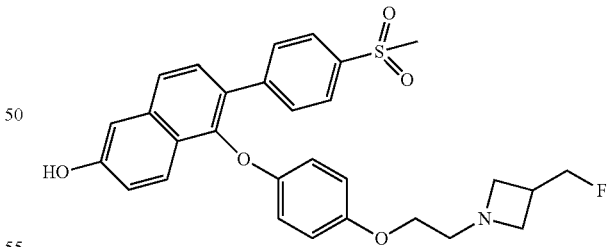

A solution 3-(fluoromethyl)-1-(2-(4-((2-(4-(methylsulfonyl)phenyl)-6-((tetrahydro-2H-pyran-2-yl)oxy)naphthalen-1-yl)oxy)phenoxy)ethyl)azetidine (100 mg, 0.17 mmol) in 80% acetic acid/water (1.7 mL) was stirred at room temperature for 6.5 h. The mixture was concentrated under reduced pressure, and the residue was dissolved in ethyl acetate (30 mL). The organic layer was washed (3×20 mL saturated NaHCO$_3$ and then 20 mL brine), dried (MgSO$_4$), and concentrated under reduced pressure. The residue was purified by silica gel chromatography to give the title compound (65 mg, 73%) as an off-white solid. $^1$H NMR (400 MHz, DMSO-d$_6$): δ 10.05 (s, 1H), 7.90 (d, J=8.4 Hz, 2H), 7.83 (d, J=8.4 Hz, 2H), 7.76 (d, J=8.8 Hz, 1H), 7.71 (d, J=8.8 Hz, 1H), 7.58 (d, J=8.6 Hz, 1H), 7.25 (d, J=2.3 Hz, 1H), 7.09 (dd, J=8.6, 2.3 Hz, 1H), 6.70 (d, J=9.1 Hz, 2H), 6.58 (d, J=9.1 Hz, 2H), 4.47 (dd, J=47.6, 6.3 Hz, 2H), 3.75 (t, J=5.6 Hz, 2H), 3.26 (t, J=7.3 Hz, 2H), 3.21 (s, 3H), 2.95 (t, J=6.5 Hz, 2H), 2.76-2.66 (m, 1H), 2.64 (t, J=5.6 Hz, 2H); $^{13}$C NMR (100 MHz, DMSO-d$_6$, HCl salt): δ 156.5, 152.9, 152.3, 147.0, 142.7, 139.1, 136.6, 129.8, 128.1, 126.8, 125.8, 124.3, 124.3, 124.2, 121.6, 119.7, 115.7, 109.2, 82.4 (J=164.1 Hz), 63.6, 55.4 (J=8.0 Hz), 53.1, 43.4, 29.6 (J=21.3 Hz). HRMS-ESI (m/z): [M+H]$^+$ calcd for C$_{29}$H$_{28}$FNO$_5$S, 522.1750. found, 522.1748.

Example 8

(R)-5-(4-(2-(3-(Fluoromethyl)pyrrolidin-1-yl) ethoxy)phenoxy)-6-(4-(methylsulfonyl)phenyl)naphthalen-2-ol

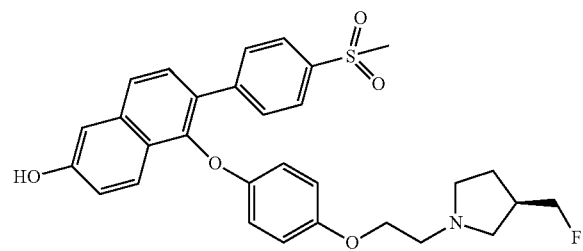 [SMILES: CS(=O)(=O)c1ccc(-c2ccc3cc(O)ccc3c2Oc2ccc(OCCN3CC[C@@H](CF)C3)cc2)cc1]

The title compound was prepared from 2-((5-bromo-6-(4-(methylsulfonyl)phenyl)naphthalen-2-yl)oxy)tetrahydro-2H-pyran and Intermediate 7 following the procedure outlined for Example 7. $^1$H NMR (400 MHz, DMSO-d$_6$): δ 10.06 (s, 1H), 7.90 (d, J=8.4 Hz, 2H), 7.83 (d, J=8.4 Hz, 2H), 7.76 (d, J=8.6 Hz, 1H), 7.71 (d, J=9.2 Hz, 1H), 7.58 (d, J=8.6 Hz, 1H), 7.25 (d, J=2.3 Hz, 1H), 7.09 (dd, J=9.2, 2.3 Hz, 1H), 6.73 (d, J=9.1 Hz, 2H), 6.59 (d, J=9.1 Hz, 2H), 4.36-4.14 (m, 2H), 3.88 (t, J=5.8 Hz, 2H), 3.21 (s, 3H), 2.67 (t, J=5.8 Hz, 2H), 2.62-2.55 (m, 1H), 2.54-2.37 (m, 3H), 2.33 (dd, J=9.1, 5.4 Hz, 1H), 1.88-1.75 (m, 1H), 1.40-1.30 (m, 1H). LCMS: 536.0 [M+H]$^+$.

Example 9

(4-(2-(3-(fluoromethyl)azetidin-1-yl)ethoxy)phenyl) (6-hydroxy-2-(4-hydroxyphenyl)benzo[b]thiophen-3-yl)methanone

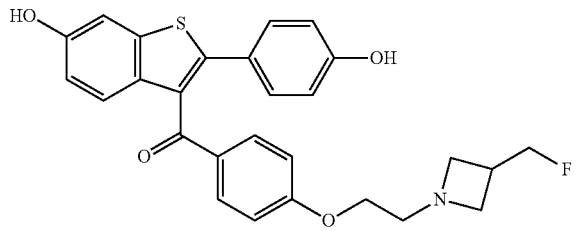 [SMILES: O=C(c1ccc(OCCN2CC(CF)C2)cc1)c1c(-c2ccc(O)cc2)sc2cc(O)ccc12]

A 25-mL RBF with anhydrous DMF (1 mL) was charged with sodium hydride (60% dispersion in mineral oil, 17 mg, 0.43 mmol) at room temperature, followed by Intermediate 1 (52 mg, 0.39 mmol). After being stirred at room temperature for 10 min, a solution of (4-fluorophenyl)-[6-hydroxy-2-(4-hydroxyphenyl)benzothiophen-3-yl]methanone (48 mg, 0.13 mmol, prepared according to procedures in *Tetrahedron Lett.* 1999, 40, 675) in DMF (1 mL) was added. The reaction mixture was heated at 60° C. for 2 h, before being cooled to room temperature. The reaction mixture was diluted with a saturated NH$_4$Cl solution (10 mL), and extracted with ethyl acetate (10 mL×2). The combined organic layers were dried over sodium sulfate and concentrated under reduced pressure. The crude product was purified by reverse-phase HPLC to give the title compound (45 mg, 72%) as a light yellow solid. $^1$H NMR (400 MHz, DMSO-d$_6$) δ 9.76 (s, 2H), 7.67-7.62 (m, 3H), 7.33 (dd, J=2.3, 0.5 Hz, 1H), 7.25 (dd, J=8.8, 0.5 Hz, 1H), 7.19-7.15 (m, 2H), 6.91-6.87 (m, 2H), 6.85 (dd, J=8.7, 2.3 Hz, 1H), 6.69-6.65 (m, 2H), 4.49 (dd, J=47.6, 6.3 Hz, 2H), 3.94 (t, J=5.5 Hz, 2H), 3.29 (dd, J=7.7, 1.5 Hz, 2H), 2.98 (dd, J=7.3, 5.9 Hz, 2H), 2.72-2.67 (m, 3H). LCMS: 478.2 [M+H]$^+$.

Example 10

(4-(2-(3-(fluoromethyl)azetidin-1-yl)ethoxy)phenyl) (2-(4-fluorophenyl)-6-hydroxybenzo[b]thiophen-3-yl)methanone

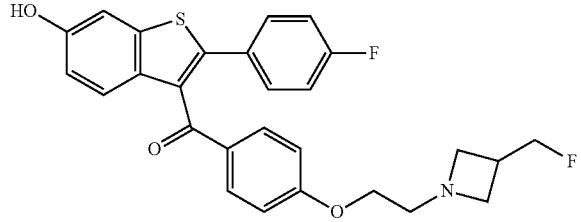 [SMILES: O=C(c1ccc(OCCN2CC(CF)C2)cc1)c1c(-c2ccc(F)cc2)sc2cc(O)ccc12]

Step 1: 2-Hydroxy-2-(4-methoxyphenyl)-N,N-dimethylethanethioamide

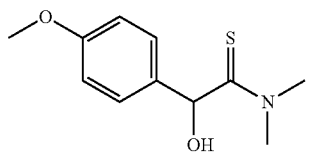

To anhydrous THF (27 mL) cooled to 0° C., was added diisopropylamine (4.04 g, 40 mmol) and n-butyllithium (25 mL, 40 mmol, 1.6 M solution in hexane). After 15 min at 0° C., the reaction mixture was cooled to −78° C. Then a solution of 4-methoxybenzaldehyde (5.0 g, 37 mmol) in THF (10 mL) was added, followed by N,N-dimethylthioformamide (3.56 g., 40 mmol). The reaction mixture was maintained at −78° C. for 3 h and then warmed to 0° C., before being quenched with a saturated solution of ammonium chloride (100 mL). The reaction mixture was extracted with ethyl acetate (2×100 mL). The combined organic layers were dried over sodium sulfate and concentrated under reduced pressure. The crude product was purified by silica gel column chromatography (0-50% ethyl acetate in hexane) to give the desired product (3.03 g, 36%) as an off white solid. ¹H NMR (400 MHz, CDCl₃) δ 7.36-7.30 (m, 2H), 6.89-6.84 (m, 2H), 5.26 (s, 2H), 3.79 (s, 3H), 3.52 (s, 3H), 3.11 (s, 3H).

Step 2:
6-Methoxy-N,N-dimethylbenzo[b]thiophen-2-amine

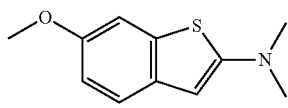

To a solution of 2-hydroxy-2-(4-methoxyphenyl)-N,N-dimethyl-thioacetamide (3.10 g, 13.8 mmol) in DCM (100 mL) was added methanesulfonic acid (4.5 mL, 68.8 mmol). The reaction mixture was stirred for 2 h at room temperature. The resulting red solution was diluted with a saturated sodium bicarbonate solution. The organic layer was separated, dried over sodium sulfate before being concentrated under reduced pressure. The crude residue was purified by silica gel column chromatography, eluting with 0-10% ethyl acetate in heptane to give the title compound (1.45 g, 46%) as an off-white solid. ¹H NMR (400 MHz, CDCl₃) δ 7.32 (d, J=8.6 Hz, 1H), 7.13 (d, J=2.4 Hz, 1H), 6.86 (dd, J=8.6, 2.4 Hz, 1H), 5.93 (s, 1H), 3.82 (s, 3H), 2.96 (s, 6H). LCMS: 208.1 [M+H]⁺.

Step 3: (2-(Dimethylamino)-6-methoxybenzo[b]thiophen-3-yl)(4-fluorophenyl)methanone

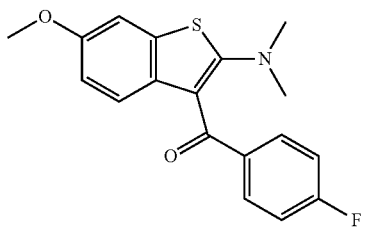 [SMILES: COc1ccc2c(C(=O)c3ccc(F)cc3)c(N(C)C)sc2c1]

Aluminum chloride (986 mg, 7.4 mmol) was suspended in anhydrous DCM (15 mL) at room temperature and 4-fluorobenzoyl chloride (1.08 g, 6.8 mmol) was added slowly via a syringe. The resulting light yellow solution was cooled at 0° C. and a solution of 6-methoxy-N,N-dimethyl-benzothiophen-2-amine (1.4 g, 6.8 mmol) in anhydrous DCM (15 mL) was added. The reaction mixture was warmed up to room temperature after the addition was complete. After being stirred at room temperature for 3 h, the reaction mixture was poured into a mixture of ice water and 1 N HCl and extracted with DCM (2×50 mL). The combined organic layers were washed with saturated sodium bicarbonate solution, brine, and then water. The organics were dried over sodium sulfate, concentrated under reduced pressure and purified by silica gel column chromatography (0-20% ethyl acetate in hexane) to give the title compound (1.19 g, 55%) as a yellow solid. ¹H NMR (400 MHz, CDCl₃) δ 7.91-7.85 (m, 2H), 7.37 (dd, J=8.9, 0.5 Hz, 1H), 7.15-7.06 (m, 3H), 6.83 (dd, J=8.9, 2.5 Hz, 1H), 3.82 (s, 3H), 2.86 (s, 6H). LCMS: 329.8 [M+H]⁺.

Step 4: (2-(Dimethylamino)-6-methoxybenzo[b]thiophen-3-yl)(4-(2-(3-(fluoromethyl)azetidin-1-yl)ethoxy)phenyl)methanone

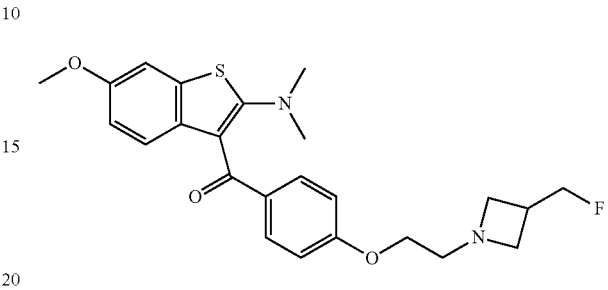

Sodium hydride (60% suspension in mineral oil, 436 mg, 10.9 mmol) was added to anhydrous DMF (10 mL) at room temperature, followed by Intermediate 1 (1.45 g, 10.9 mmol). The reaction mixture was stirred at room temperature for 10 min, before being added to a solution of [2-(dimethylamino)-6-methoxy-benzothiophen-3-yl]-(4-fluorophenyl)methanone (1.09 g, 3.31 mmol) in DMF (10 mL). The reaction mixture was heated at 70° C. for 2 h before being cooled to room temperature. The reaction mixture was diluted with a saturated solution of NH₄Cl (100 mL) and extracted with ethyl acetate (2×100 mL). The combined organics were dried over sodium sulfate and concentrated under reduced pressure. Crude product was purified by silica gel column chromatography (10-100% ethyl acetate/hexanes) to give the title compound (1.20 g, 82%). LCMS: 443.4 [M+H]⁺.

Step 5: (4-(2-(3-(Fluoromethyl)azetidin-1-yl)ethoxy)phenyl)(2-(4-fluorophenyl)-6-methoxbenzo[b]thiophen-3-yl)methanone

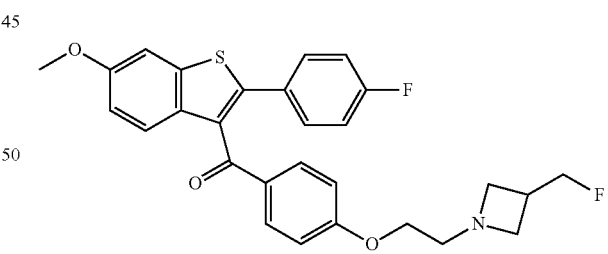

To a cooled solution of [2-(dimethylamino)-6-methoxy-benzothiophen-3-yl]-[4-[2-[3-(fluoromethyl)azetidin-1-yl]ethoxy]phenyl]methanone (110 mg, 0.25 mmol) in THF (2 mL) at 5° C. was added a 1 M bromo-(4-fluorophenyl)magnesium solution in THF (0.37 mL, 0.37 mmol). The reaction mixture was warmed up to room temperature for 2 h before being quenched with an aq. solution of NH₄Cl (50 mL) and then was extracted with ethyl acetate (2×50 mL). The combined organic layers were dried over Na₂SO₄, concentrated to give the crude product (105 mg), which was carried forward to the next step without further purification. LCMS: 494.3 [M+H]⁺.

Step 6: (4-(2-(3-(Fluoromethyl)azetidin-1-yl)ethoxy)
phenyl)(2-(4-fluorophenyl)-6-hydroxybenzo[b]thio-
phen-3-yl)methanone

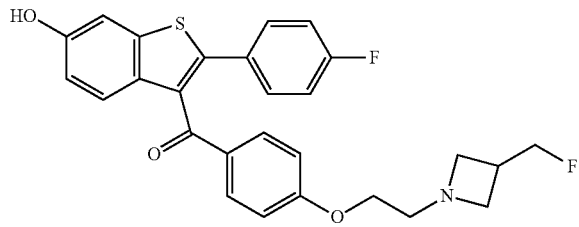 [SMILES: O=C(c1ccc(OCCN2CC(CF)C2)cc1)c1c(-c2ccc(F)cc2)sc2cc(O)ccc12]

[4-[2-[3-(Fluoromethyl)azetidin-1-yl]ethoxy]phenyl]-[2-(4-fluorophenyl)-6-methoxy-benzothiophen-3-yl]methanone (105 mg, 0.21 mmol) in dichloromethane (2 mL) was cooled to −5° C., and a 1 M solution of boron tribromide in dichloromethane (0.42 mL, 0.42 mmol) was added. The reaction mixture was stirred at 0° C. for 1 h before being poured into ice water. The mixture was extracted with ethyl acetate (50 mL) and separated. The organic layer was dried over sodium sulfate before being concentrated under reduced pressure. Purification of the crude product by reverse-phase HPLC gave the title compound (36 mg, 36%) as a yellow solid. $^1$H NMR (400 MHz, DMSO-d6) δ 9.86 (s, 1H), 7.68-7.63 (m, 2H), 7.42-7.37 (m, 3H), 7.30 (dd, J=8.8, 0.5 Hz, 1H), 7.19-7.14 (m, 2H), 6.92-6.87 (m, 3H), 4.48 (dd, J=47.6, 6.3 Hz, 2H), 3.95 (t, J=5.5 Hz, 2H), 3.29-3.25 (m, 2H), 2.99-2.94 (m, 2H), 2.76-2.64 (m, 3H). LCMS: 480.2 [M+H]$^+$.

Example 11

3-(4-(2-(3-(Fluoromethyl)azetidin-1-yl)ethoxy)phe-
noxy)-2-(4-hydroxyphenyl)benzo[b]thiophen-6-ol

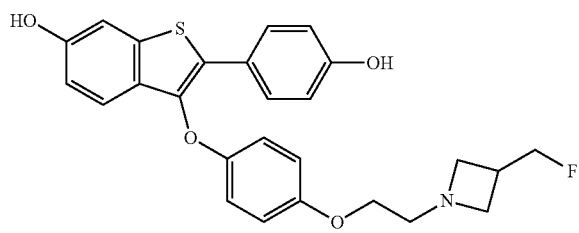 [SMILES: Oc1ccc(-c2sc3cc(O)ccc3c2Oc2ccc(OCCN3CC(CF)C3)cc2)cc1]

Step 1: 3-Bromo-6-methoxy-2-(4-methoxyphenyl)
benzo[b]thiophene 1-oxide

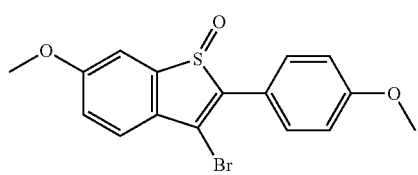

To a solution of 3-bromo-6-methoxy-2-(4-methoxyphenyl)benzothiophene (4.0 g, 11 mmol) in DCM (20 mL) was added trifluoroacetic acid (20 mL, 264.5 mmol). After 5 min, hydrogen peroxide (11 mmol) was added. The reaction mixture was stirred at room temperature for 2 h before a saturated aq. solution of sodium bisulfite was added, and vigorous stirring continued for 15 min. The reaction mixture was concentrated under reduced pressure, and the residue was partitioned between DCM (100 mL) and a saturated sodium bicarbonate solution (100 mL). The organic layer was separated, dried over Na$_2$SO$_4$ and then concentrated to give the crude title compound (3.87 g) as a brown solid. $^1$H NMR (400 MHz, CDCl$_3$) δ 7.80-7.75 (m, 2H), 7.55 (d, J=8.5 Hz, 1H), 7.50 (d, J=2.3 Hz, 1H), 7.13 (dd, J=8.5, 2.4 Hz, 1H), 7.06-7.01 (m, 2H), 3.92 (s, 3H), 3.87 (s, 3H).

Step 2: 3-(4-Iodophenoxy)-6-methoxy-2-(4-
methoxyphenyl)benzo[b]thiophene 1-oxide

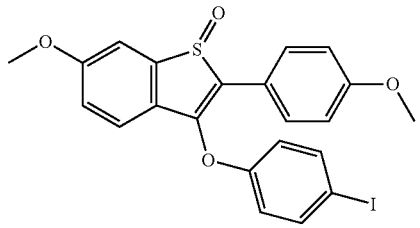

Sodium hydride (60% dispersion in mineral oil, 120 mg, 3.0 mmol) was suspended in DMF (7 mL) before 4-iodophenol (660 mg, 3.0 mmol) was added. The reaction mixture was stirred at room temperature for 10 min and then 3-bromo-6-methoxy-2-(4-methoxyphenyl)benzothiophene 1-oxide (1.0 g, 2.7 mmol) was added. The resulting mixture was then heated to 70° C. for 2 h, before being cooled to room temperature. The reaction mixture was quenched with an aq. saturated solution of NH$_4$Cl (100 mL), and then extracted with ethyl acetate (2×100 mL). The combined organic layers were dried, and then concentrated under reduced pressure. The crude product was purified by flash column chromatography (0-40% ethyl acetate in Heptane) to give the title compound (0.8 g, 59%) as a light yellow solid. LCMS: 505.1 [M+H]$^+$.

Step 3: 3-(4-(2-(3-(Fluoromethyl)azetidin-1-yl)
ethoxy)phenoxy)-6-methoxy-2-(4-methoxyphenyl)
benzo[b]thiophene 1-oxide

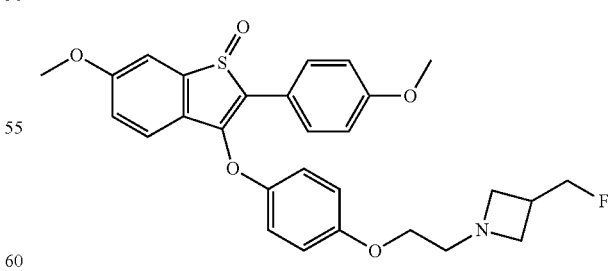

A mixture of 3-(4-iodophenoxy)-6-methoxy-2-(4-methoxyphenyl)benzothiophene 1-oxide (100 mg, 0.198 mmol), Intermediate 1 (52.8 mg, 0.397 mmol), cuprous iodide (15.1 mg, 0.0793 mmol) and potassium carbonate (82.2 mg, 0.595 mmol) in butyronitrile (2 mL) was heated under N$_2$ at 115° C. for 24 h when monitoring the reaction by LCMS showed completion conversion. The reaction mixture was cooled to room temperature, diluted with ethyl acetate (25 mL), and filtered. The green filtrate was concentrated and the resulting residue was purified by silica gel column chromatography (10-100% ethyl acetate in heptane) to give the title compound (60 mg, 59%). LCMS: 510.3 [M+H]+.

Step 4: 3-(Fluoromethyl)-1-(2-(4-((6-methoxy-2-(4-methoxyphenyl)benzo[b]thiophen-3-yl)oxy)phenoxy)ethyl)azetidine

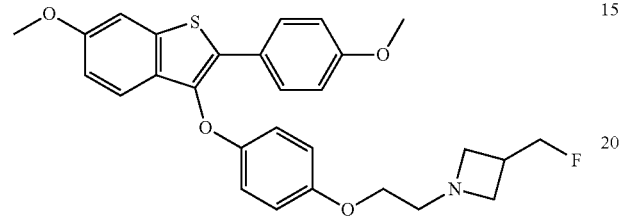

To a solution of 3-[4-[2-[3-(fluoromethyl)azetidin-1-yl] ethoxy]phenoxy]-6-methoxy-2-(4-methoxyphenyl)benzothiophene 1-oxide (60 mg, 0.12 mmol) in THF (3 mL) cooled to 0° C. was added a 4 M solution of lithium aluminum hydride in THF (0.045 mL, 0.18 mmol). After being stirred at 0° C. for 1 h, the reaction was quenched with 1 N NaOH solution (10 mL). The reaction mixture was extracted with ethyl acetate (2×10 mL). The combined organics were concentrated under reduced pressure to give the crude title compound (41 mg), which was used in the next step without further purification. LCMS: 494.4 [M+H]+.

Step 5: 3-(4-(2-(3-(Fluoromethyl)azetidin-1-yl) ethoxy)phenoxy)-2-(4-hydroxyphenyl)benzo[b]thiophen-6-ol

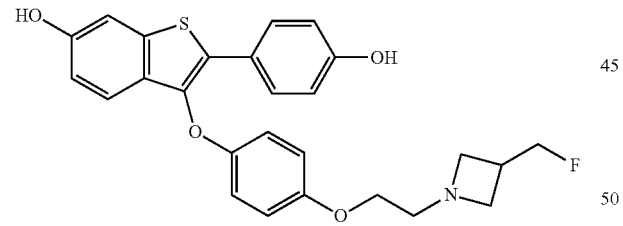

To a solution of 3-(fluoromethyl)-1-[2-[4-[6-methoxy-2-(4-methoxyphenyl)benzothiophen-3-yl]oxyphenoxy]ethyl] azetidine (41 mg, 0.083 mmol) in DCM (2 mL) cooled at −5° C. was added a 1 M solution of boron tribromide in dichloromethane (0.16 mL, 0.16 mmol). The reaction mixture was stirred at −5° C. for 4 h before being poured into ice water. The reaction mixture was extracted with ethyl acetate (2×10 mL). The combined organics were dried over sodium sulfate, before being concentrated under reduced pressure. The crude product was purified by reverse-phase HPLC to give the title compound (20 mg, 52%) as an off white solid. 1H NMR (400 MHz, DMSO-d6) δ 8.27 (s, 1H), 7.51-7.47 (m, 2H), 7.25 (dd, J=2.1, 0.5 Hz, 1H), 7.08 (dd, J=8.6, 0.5 Hz, 1H), 6.83 (s, 4H), 6.81-6.76 (m, 3H), 4.55 (d, J=6.3 Hz, 1H), 4.43 (d, J=6.3 Hz, 1H), 3.82 (t, J=5.6 Hz, 2H), 2.98 (dd, J=7.3, 5.9 Hz, 2H), 2.89 (d, J=0.5 Hz, 2H), 2.73 (d, J=0.7 Hz, 1H), 2.70-2.66 (m, 3H). LCMS: 466.1 [M+H]+.

Example 12

3-(4-((S)-2-((R)-3-(Fluoromethyl)pyrrolidin-1-yl) propoxy)phenoxy)-2-(4-methoxyphenyl)benzo[b] thiophen-6-ol

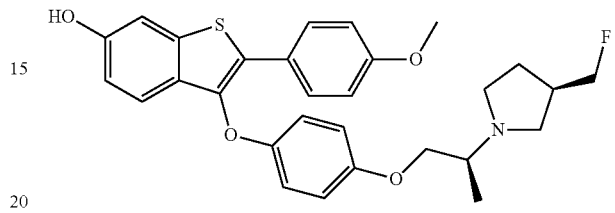

Step 1:
6-Benzyloxy-2-(4-bromo-phenyl)-benzo[b]thiophene

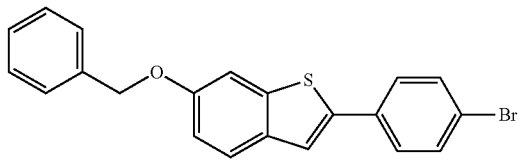 [SMILES: Brc1ccc(-c2cc3ccc(OCc4ccccc4)cc3s2)cc1]

Benzylbromide (4.49 g, 26.4 mmol) and K2CO3 (6.0 g, 44 mmol) were added to a solution of 2-(4-bromo-phenyl)-benzo[b]thiophen-6-ol (6.75 g, 22 mmol, see WO/2010/132601A1 for synthesis) in acetonitrile (150 mL). The mixture was heated at 80° C. for 2 h, filtered, and the filtrate was concentrated in vacuo. The residue was washed with hexane to afford the desired compound (7.3 g, 84%). 1H NMR (400 MHz, DMSO-d6): δ 7.78-7.76 (m, 2H), 7.74-7.34 (m, 8H), 7.27-7.22 (m, 1H), 7.11-7.09 (m, 1H), 6.83-6.81 (m, 1H), 5.15 (s, 2H).

Step 2: 6-(Benzyloxy)-3-bromo-2-(4-bromophenyl) benzo[b]thiophene

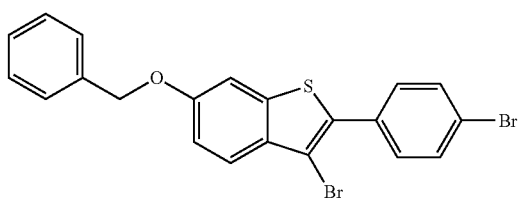 [SMILES: Brc1ccc(-c2sc3cc(OCc4ccccc4)ccc3c2Br)cc1]

N-Bromoacetamide (2.72 g, 19.7 mmol) was added to a suspension of 6-benzyloxy-2-(4-bromo-phenyl)-benzo[b] thiophene (7.3 g, 18.5 mmol) in DCM (150 mL). The reaction mixture was stirred at room temperature for 2 h, diluted with DCM (100 mL), washed (water and then brine), and then concentrated. Recrystallization from ethyl acetate gave the title compound (4.4 g, 45%) as a light brown solid.

¹H NMR (400 MHz, DMSO-d₆): δ 7.62-7.30 (m, 11H), 7.25-7.00 (m, 1H), 5.12 (s, 2H).

Step 3: 6-(Benzyloxy)-3-bromo-2-(4-bromophenyl)benzo[b]thiophene 1-oxide

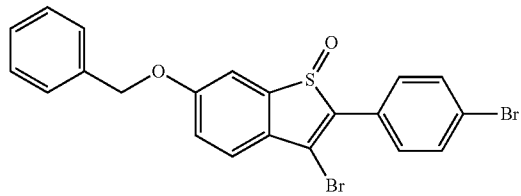 [SMILES: O=S1C(c2ccc(Br)cc2)=C(Br)c2ccc(OCc3ccccc3)cc21]

Trifluoroacetic acid (25 mL) was added dropwise to a solution of 6-(benzyloxy)-3-bromo-2-(4-bromophenyl)benzo[b]thiophene (4.4 g, 8.6 mmol) in DCM (30 mL). Hydrogen peroxide (30%, 2.3 mL) was added to the reaction, and the mixture was stirred at room temperature for 2 h. The reaction mixture was quenched by addition of sodium bisulfite (500 mg in 5 mL water) and stirred vigorously for 15 min. The solvent was removed under reduced pressure, and the residue was diluted with DCM. The mixture was carefully washed (saturated NaHCO₃), concentrated, and purified by silica gel chromatography (1:1 DCM/petroleum ether) to give the title compound (2.6 g, 57%) as a pale yellow solid. ¹H NMR (400 MHz, DMSO-d₆): δ 7.85-7.79 (m, 3H), 7.51-7.34 (m, 8H), 7.20 (m, 1H), 5.24 (s, 2H).

Step 4: 6-(Benzyloxy)-2-(4-bromophenyl)-3-(4-((S)-2-((R)-3-(fluoromethyl)pyrrolidin-1-yl)propoxy)phenoxy)benzo[b]thiophene 1-oxide

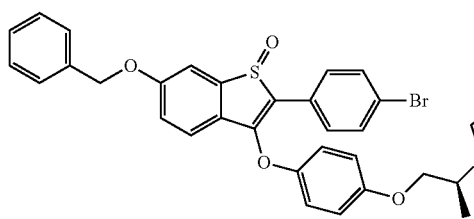

Sodium hydride (170 mg, 60%, dispersed in oil) was added in three portions within 20 min to a solution of Intermediate 6 (0.9 g, 3.55 mmol) in DMF (20 mL). 6-(Benzyloxy)-3-bromo-2-(4-bromophenyl)benzo[b]thiophene 1-oxide (1.9 g, 3.55 mmol) was added to the mixture, and the reaction mixture was stirred at room temperature for 1 h. The reaction mixture was diluted with ethyl acetate (200 mL) and washed (water). The aqueous phase was back extracted with DCM (50 mL), and the combined organic extracts were dried (MgSO₄) and concentrated to give the title compound (0.95 g, 24%) as a yellow solid. ¹H NMR (400 MHz, CDCl₃): δ 7.58 (d, J=8.4 Hz, 2H), 7.48 (d, J=2.0 Hz, 1H), 7.43-7.35 (m, 7H), 7.27-7.25 (m, 1H), 7.11-7.05 (m, 3H), 6.82 (d, J=8.8 Hz, 2H), 5.14 (s, 2H), 4.56-3.61 (m, 4H), 3.32-3.04 (m, 5H), 2.91-2.82 (m, 1H), 2.37-2.31 (m, 1H), 2.05-2.01 (m, 1H), 1.27 (d, J=8.4 Hz, 3H).

Step 5: (R)-1-((S)-1-(4-((6-(Benzyloxy)-2-(4-bromophenyl)benzo[b]thiophen-3-yl)oxy)phenoxy)propan-2-yl)-3-(fluoromethyl)pyrrolidine

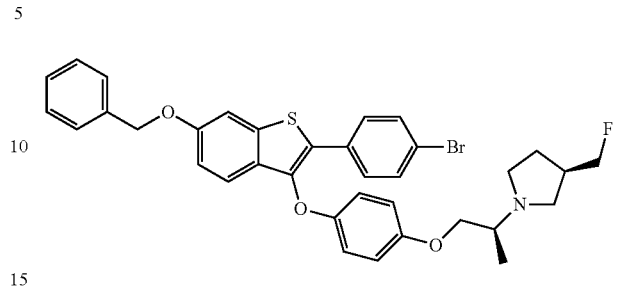

A solution of 6-(benzyloxy)-2-(4-bromophenyl)-3-(4-((S)-2-((R)-3-(fluoromethyl)pyrrolidin-1-yl)propoxy)phenoxy)benzo[b]thiophene 1-oxide (0.9 g, 1.36 mmol), HCl (1M in ether, 15.0 mL, 15.0 mmol), and DCM (5 mL) was stirred for 1 h, concentrated under reduced pressure, and then re-dissolved in THF (15 mL). Chlorotrimethylsilane (1.47 g, 13.6 mmol) and triphenylphosphine (1.3 g, 5.0 mmol) were added to the reaction mixture, and the mixture was heated to reflux for 8 h. The reaction mixture was concentrated, diluted with ethyl acetate (200 mL), washed (saturated NaHCO₃), and reconcentrated. The crude product was purified by silica gel chromatography (30:1 DCM/methanol) to afford the desired compound (0.45 g, 51%). ¹H NMR (400 MHz, CDCl₃): δ 7.56-7.31 (m, 11H), 7.06-7.00 (m, 3H), 6.83 (d, J=8.8 Hz, 2H), 5.11 (s, 2H), 4.28-4.14 (m, 2H), 4.04-3.83 (m, 2H), 2.96-2.51 (m, 6H), 2.02-1.99 (m, 1H), 1.55-1.53 (m, 1H), 1.25 (d, J=7.0 Hz, 3H).

Step 6: (R)-1-((S)-1-(4-((6-(Benzyloxy)-2-(4-methoxyphenyl)benzo[b]thiophen-3-yl)oxy)phenoxy)propan-2-yl)-3-(fluoromethyl)pyrrolidine

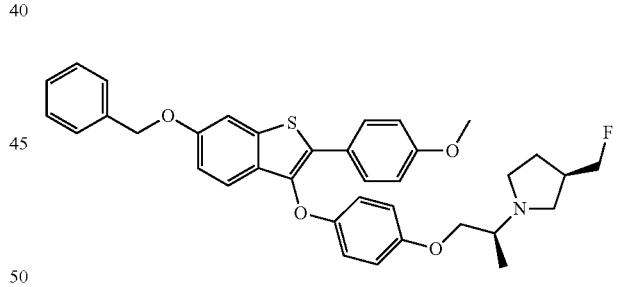

Sodium methoxide (3.12 g, 57.9 mmol) was added to a mixture of (R)-1-((S)-1-(4-((6-(benzyloxy)-2-(4-bromophenyl)benzo[b]thiophen-3-yl)oxy)phenoxy)propan-2-yl)-3-(fluoromethyl)pyrrolidine (450 mg, 0.69 mmol), CuI (131 mg, 0.69 mmol), DMF (4.8 mL), MeOH (10.5 mL), and ethyl acetate (0.28 mL). The reaction mixture was heated at 110° C. for 12 h, diluted with ethyl acetate (60 mL), washed (brine), and concentrated. The residue was purified by silica gel chromatography (12:1 DCM/MeOH) to obtain the title compound (320 mg, 77%) as a light yellow solid. ¹H NMR (400 MHz, CDCl₃): δ 7.58-7.25 (m, 11H), 7.05-6.95 (m, 3H), 6.84-6.81 (m, 2H), 5.11 (s, 2H), 4.41-4.28 (m, 2H), 4.05-3.84 (m, 2H), 3.82 (s, 3H), 2.97-2.57 (m, 6H), 2.04-1.98 (m, 1H), 1.58-1.46 (m, 1H), 1.25 (d, J=7.0 Hz, 3H).

Step 7: 3-(4-((S)-2-((R)-3-(Fluoromethyl)pyrrolidin-1-yl)propoxy)phenoxy)-2-(4-methoxyphenyl)benzo[b]thiophen-6-ol

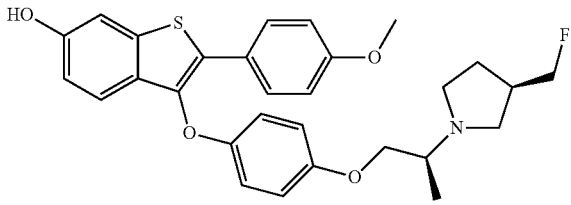 [SMILES: COc1ccc(-c2sc3cc(O)ccc3c2Oc2ccc(OC[C@H](C)N3CC[C@@H](CF)C3)cc2)cc1]

A mixture of (R)-1-((S)-1-(4-((6-(benzyloxy)-2-(4-methoxyphenyl)benzo[b]thiophen-3-yl)oxy)phenoxy)propan-2-yl)-3-(fluoromethyl)pyrrolidine (0.35 g, 0.58 mmol), Pd(OH)$_2$ (0.1 g), and ammonium formate (0.4 g, 5.8 mmol) in methanol (10 mL) was heated at reflux for 12 h. The reaction mixture was filtered, and the filtrate was concentrated under reduced pressure. The crude material was purified by reverse-phase HPLC to give the desired compound (48 mg, 16%) as a white solid. $^1$H NMR (400 MHz, DMSO-d$_6$): δ 9.60 (br s, 1H), 7.43 (d, J=8.7 Hz, 2H), 7.39 (d, J=8.6 Hz, 1H), 7.20 (d, J=2.3 Hz, 1H), 7.05-7.02 (m, 4H), 6.92 (d, J=9.1 Hz, 2H), 6.87 (dd, J=8.6, 2.3 Hz, 1H), 4.38-4.30 (m, 1H), 4.26-4.18 (m, 1H), 4.02-3.97 (m, 1H), 3.80-3.74 (m, 1H), 3.78 (s, 3H), 2.75-2.64 (m, 2H), 2.64-2.53 (m, 2H), 2.45-2.37 (m, 2H), 1.88-1.75 (m, 1H), 1.43-1.31 (m, 1H), 1.11 (d, J=7.0 Hz, 3H); HRMS-ESI (m/z): [M+H]$^+$ calcd for C$_{29}$H$_{30}$FNO$_4$S, 508.1958. found, 508.1955.

Example 13

6-(2-(Ethyl(4-(2-(3-(fluoromethyl)azetidin-1-yl)ethoxy)benzyl)amino)-4-methoxyphenyl)-5,6,7,8-tetrahydronaphthalen-2-ol

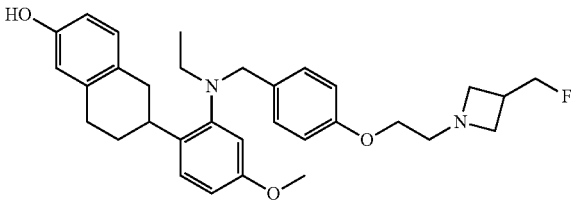 [SMILES: CCN(Cc1ccc(OCCN2CC(CF)C2)cc1)c1cc(OC)ccc1C1CCc2cc(O)ccc2C1]

Step 1: 6-(2-(Ethyl(4-(-(3-(fluoromethyl)azetidin-1-yl)ethoxy)benzyl)amino)-4-methoxyphenyl)-5,6,7,8-tetrahydronaphthalen-2-yl pivalate

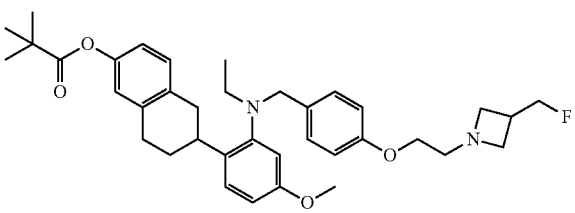 [SMILES: CCN(Cc1ccc(OCCN2CC(CF)C2)cc1)c1cc(OC)ccc1C1CCc2cc(OC(=O)C(C)(C)C)ccc2C1]

Sodium triacetoxyborohydride (399 mg, 1.88 mmol) was added to a solution of 6-(2-(ethyl amino)-4-methoxyphenyl)-5,6,7,8-tetrahydronaphthalen-2-yl pivalate (215 mg, 0.564 mmol, see U.S. Pat. No. 7,612,114 for synthesis), Intermediate 8 (405 mg, 1.71 mmol), and acetic acid (0.24 mL, 4.19 mmol) in DCE (5 mL). The reaction was stirred at room temperature overnight and then quenched with saturated NaHCO$_3$ (5 mL). The mixture was diluted with DCM (50 mL), washed (25 mL saturated NaHCO$_3$ and then 25 mL brine), dried (Na$_2$SO$_4$), and concentrated under reduced pressure. The residue was purified by silica gel chromatography to yield the title compound (227 mg, 67%). $^1$H NMR (400 MHz, DMSO-d$_6$): δ 7.17 (d, J=8.6 Hz, 1H), 7.08 (d, J=8.6 Hz, 2H), 7.05 (d, J=8.3 Hz, 1H), 6.84-6.78 (m, 3H), 6.75 (d, J=8.6 Hz, 2H), 6.68 (dd, J=8.6, 2.8 Hz, 1H), 4.50 (dd, J=47.7, 6.3 Hz, 2H), 3.93 (d, J=2.1 Hz, 2H), 3.85 (t, J=5.6 Hz, 2H), 3.71 (s, 3H), 3.61-3.50 (m, 1H), 3.30 (td, J=7.6, 1.2 Hz, 2H), 2.98 (t, J=6.8 Hz, 2H), 2.87 (q, J=6.8 Hz, 2H), 2.85-2.78 (m, 2H), 2.76-2.54 (m, 5H), 1.80-1.66 (m, 1H), 1.63-1.55 (m, 1H), 1.30 (s, 9H), 0.90 (t, J=6.8 Hz, 3H). LCMS: 603.3 [M+H]$^+$.

Step 2: 6-(2-(Ethyl(4-(2-(3-(fluoromethyl)azetidin-1-yl)ethoxy)benzyl)amino)-4-methoxyphenyl)-5,6,7,8-tetrahydronaphthalen-2-ol

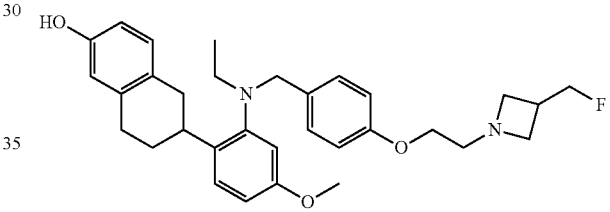

A suspension of 6-(2-(ethyl(4-(2-(3-(fluoromethyl)azetidin-1-yl)ethoxy)benzyl)amino)-4-methoxyphenyl)-5,6,7,8-tetrahydronaphthalen-2-yl pivalate (220 mg, 0.367 mmol) and K$_2$CO$_3$ (255 mg, 1.85 mmol) in methanol (3.7 mL) was stirred at room temperature for 1 h. The reaction was concentrated under reduced pressure and then diluted with ethyl acetate (20 mL). The mixture was washed (20 mL saturated NaHCO$_3$ and then 20 mL brine), dried (Na$_2$SO$_4$), and concentrated under reduced pressure. The crude residue was purified by reverse-phase HPLC (acetonitrile, water, TFA). The resulting material was freebased with ethyl acetate and saturated NaHCO$_3$ to give the title compound (95 mg, 50%) as a white foam. $^1$H NMR (400 MHz, DMSO-d$_6$): δ 9.01 (s, 1H), 7.14 (d, J=8.7 Hz, 1H), 7.09 (d, J=8.4 Hz, 2H), 6.80 (d, J=8.7 Hz, 1H), 6.77 (d, J=2.7 Hz, 1H), 6.75 (d, J=8.7 Hz, 2H), 6.66 (dd, J=8.4, 2.7 Hz, 1H), 6.52-6.47 (m, 2H), 4.49 (dd, J=47.7, 6.3 Hz, 2H), 3.97-3.88 (m, 2H), 3.85 (t, J=5.6 Hz, 2H), 3.71 (s, 3H), 3.55-3.45 (m, 1H), 3.31 (t, J=7.5 Hz, 2H), 2.99 (t, J=6.6 Hz, 2H), 2.86 (q, J=6.6 Hz, 2H), 2.79-2.64 (m, 5H), 2.63-2.51 (m, 2H), 1.77-1.61 (m, 1H), 1.60-1.52 (m, 1H), 0.87 (t, J=6.8 Hz, 3H); $^{13}$C NMR (100 MHz, DMSO-d$_6$): δ 157.6, 157.3, 155.0, 149.5, 136.7, 136.4, 130.9, 129.7, 129.4, 127.2, 127.2, 114.8, 113.9, 112.9, 110.1, 109.1, 84.6 (J=164.0 Hz), 66.2, 58.2, 57.2, 56.0 (J=7.6 Hz), 54.9, 48.5, 38.9, 32.8, 30.7 (J=20.0 Hz), 30.4, 30.0, 12.3. HRMS-ESI (m/z): [M+H]$^+$ calcd for C$_{32}$H$_{39}$FN$_2$O$_3$, 519.3023. found, 519.3015.

Example 14

4-(3-(2-Chlorophenyl)-4-(4-(2-(3-(fluoromethyl)azetidin-1-yl)ethoxy)phenyl)isoxazol-5-yl)phenol

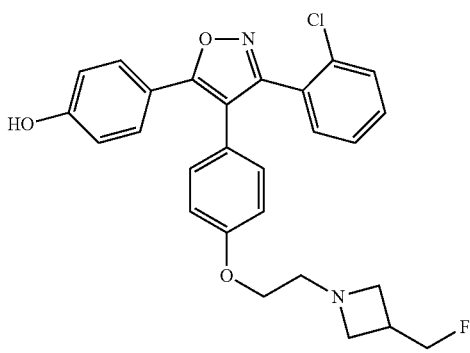 [SMILES: Oc1ccc(-c2onc(-c3ccccc3Cl)c2-c2ccc(OCCN3CC(CF)C3)cc2)cc1]

Step 1: 4-Bromo-3-(2-chlorophenyl)-5-(4-((tetrahydro-2H-pyran-2-yl)oxy)phenyl)isoxazole

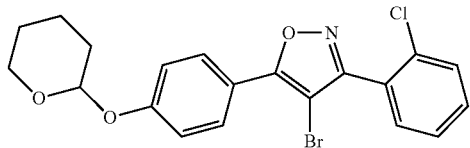 [SMILES: Clc1ccccc1-c1noc(-c2ccc(OC3CCCCO3)cc2)c1Br]

Pyridinium p-toluene sulfonate (507 mg, 2.02 mmol) and 3,4-dihydro-2H-pyran (1.3 mL, 14.3 mmol) were added to a suspension of 4-(4-bromo-3-(2-chlorophenyl)isoxazol-5-yl)phenol (3.79 g, 10.08 mmol, see WO/2012/052395A1 for synthesis) in DCM (100 mL). The reaction mixture was stirred at room temperature for 5 h, diluted with DCM, washed (200 mL saturated NaHCO$_3$), dried (MgSO$_4$), and then concentrated under reduced pressure. The residue was purified by silica gel chromatography to give the title compound (3.90 g, 83%) as a white solid. $^1$H NMR (400 MHz, DMSO-d$_6$): δ 8.01 (d, J=8.9 Hz, 2H), 7.71 (dd, J=8.0, 0.9 Hz, 1H), 7.67-7.54 (m, 3H), 6.99 (d, J=8.9 Hz, 2H), 5.65-5.61 (m, 1H), 3.80-3.71 (m, 1H), 3.64-3.56 (m, 1H), 1.97-1.73 (m, 3H), 1.70-1.50 (m, 3H). LCMS: 349.5 [(M-THP)+H]$^+$.

Step 2: 4-(3-(2-Chlorophenyl)-5-(4-((tetrahydro-2H-pyran-2-yl)oxy)phenyl)isoxazol-4-yl)phenol

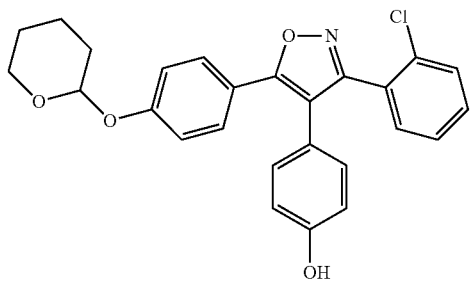 [SMILES: Oc1ccc(-c2c(-c3ccccc3Cl)noc2-c2ccc(OC3CCCCO3)cc2)cc1]

A mixture of 4-bromo-3-(2-chlorophenyl)-5-(4-((tetrahydro-2H-pyran-2-yl)oxy)phenyl)isoxazole (909 mg, 2.09 mmol), (4-hydroxyphenyl)boronic acid (921 mg, 4.18 mmol), K$_3$PO$_4$ monohydrate (1.44 g, 6.27 mmol), bis(triphenylphosphine)palladium(II) dichloride (76 mg, 0.11 mmol), and dioxane (21 mL) was degassed with vacuum/nitrogen cycles (3×). The reaction mixture was heated at 90° C. for 25 h, allowed to cool to room temperature, diluted with ethyl acetate (60 mL), washed (30 mL water and then 30 mL brine), dried (MgSO$_4$), and then concentrated under reduced pressure. The residue was purified by silica gel chromatography to give the title compound (366 mg, 39%) as a yellow solid. $^1$H NMR (400 MHz, DMSO-d$_6$): δ 9.59 (s, 1H), 7.55-7.48 (m, 4H), 7.48-7.39 (m, 2H), 7.08 (d, J=8.8 Hz, 2H), 6.96 (d, J=8.5 Hz, 2H), 6.69 (d, J=8.5 Hz, 2H), 5.55-5.51 (m, 1H), 3.78-3.69 (m, 1H), 3.61-3.53 (m, 1H), 1.92-1.67 (m, 3H), 1.67-1.46 (m, 3H).

Step 3: 3-(2-Chlorophenyl)-4-(4-(2-(3-(fluoromethyl)azetidin-1-yl)ethoxy)phenyl)-5-(4-((tetrahydro-2H-pyran-2-yl)oxy)phenyl)isoxazole

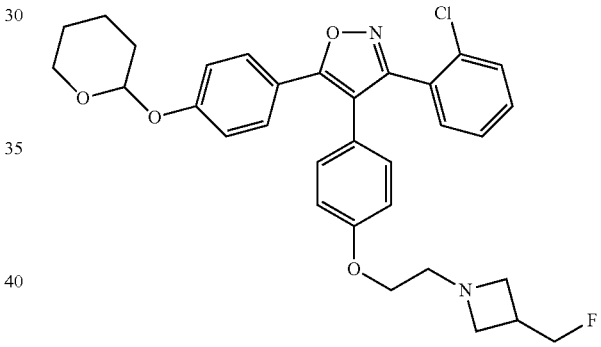

Diisopropyl azodicarboxylate (0.32 mL, 1.63 mmol) was added to a mixture of 4-(3-(2-Chlorophenyl)-5-(4-((tetrahydro-2H-pyran-2-yl)oxy)phenyl)isoxazol-4-yl)phenol (360 mg, 0.80 mmol), Intermediate 1 (192 mg, 1.44 mmol), and triphenylphosphine (427 mg, 1.63 mmol) in THF (8 mL) at room temperature. The mixture was stirred for 4 h, and then concentrated under reduced pressure. The residue was purified by silica gel chromatography to yield the title compound (276 mg, 61%) as a white foam. $^1$H NMR (400 MHz, DMSO-d$_6$): δ 7.54-7.45 (m, 5H), 7.44-7.39 (m, 1H), 7.08 (d, J=9.0 Hz, 2H), 7.06 (d, J=9.0 Hz, 2H), 6.85 (d, J=8.5 Hz, 2H), 5.53-5.50 (m, 1H), 4.50 (dd, J=47.6, 6.2 Hz, 2H), 3.86 (t, J=5.6 Hz, 2H), 3.77-3.69 (m, 1H), 3.60-3.53 (m, 1H), 3.30 (t, J=7.2 Hz, 2H), 2.98 (t, J=6.3 Hz, 2H), 2.77-2.64 (m, 3H), 1.93-1.68 (m, 3H), 1.66-1.46 (m, 3H). LCMS: 563.1 [M+H]$^+$.

Step 4: 4-(3-(2-Chlorophenyl)-4-(4-(2-(3-(fluoromethyl)azetidin-1-yl)ethoxy)phenyl)isoxazol-5-yl)phenol

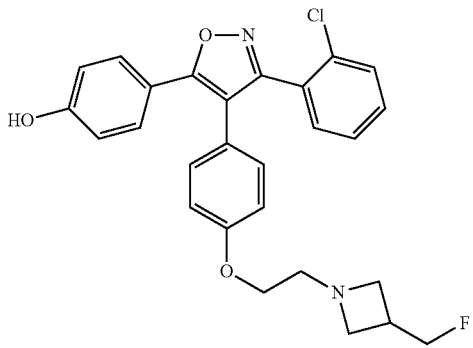 [SMILES: Oc1ccc(-c2onc(-c3ccccc3Cl)c2-c2ccc(OCCN3CC(CF)C3)cc2)cc1]

A mixture of 3-(2-chlorophenyl)-4-(4-(2-(3-(fluoromethyl)azetidin-1-yl)ethoxy)phenyl)-5-(4-((tetrahydro-2H-pyran-2-yl)oxy)phenyl)isoxazole (264 mg, 0.47 mmol) in 80% acetic acid/water (1.7 mL) was stirred at room temperature for 7 h. The mixture was concentrated under reduced pressure, and the residue was dissolved in ethyl acetate (40 mL). The organic layer was washed (3×20 mL saturated NaHCO$_3$ and then 20 mL brine), dried (MgSO$_4$), and concentrated under reduced pressure. The residue was purified by silica gel chromatography to give the title compound (169 mg, 75%) as a white solid. $^1$H NMR (400 MHz, DMSO-d$_6$): δ 10.07 (s, 1H), 7.53-7.44 (m, 3H), 7.42 (dd, J=7.3, 1.7 Hz, 1H), 7.40 (d, J=8.7 Hz, 2H), 7.04 (d, J=8.7 Hz, 2H), 6.84 (d, J=8.7 Hz, 2H), 6.81 (d, J=8.7 Hz, 2H), 4.49 (dd, J=47.6, 6.2 Hz, 2H), 3.86 (t, J=5.6 Hz, 2H), 3.30 (t, J=7.1 Hz, 2H), 2.98 (t, J=6.4 Hz, 2H), 2.78-2.63 (m, 3H). LCMS: 479.0 [M+H]$^+$.

Example 15

(R)-4-(3-(2-Chlorophenyl)-4-(4-(2-(3-(fluoromethyl)pyrrolidin-1-yl)ethoxy)phenyl)isoxazol-5-yl)phenol

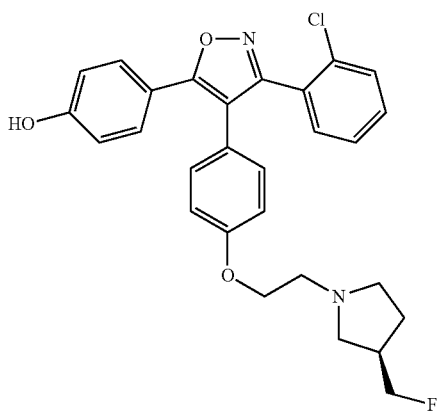 [SMILES: Oc1ccc(-c2onc(-c3ccccc3Cl)c2-c2ccc(OCCN3CC[C@@H](CF)C3)cc2)cc1]

The title compound was prepared from 4-(3-(2-Chlorophenyl)-5-(4-((tetrahydro-2H-pyran-2-yl)oxy)phenyl)isoxazol-4-yl)phenol and Intermediate 4 following the procedure outlined for Example 14. $^1$H NMR (400 MHz, DMSO-d$_6$): δ 10.07 (s, 1H), 7.54-7.45 (m, 3H), 7.42 (dd, J=7.3, 1.8 Hz, 1H), 7.40 (d, J=8.8 Hz, 2H), 7.09 (d, J=8.8 Hz, 2H), 6.87 (d, J=8.8 Hz, 2H), 6.81 (d, J=8.8 Hz, 2H), 4.39-4.17 (m, 2H), 4.00 (t, J=5.9 Hz, 2H), 2.74 (t, J=5.9 Hz, 2H), 2.67-2.60 (m, 1H), 2.60-2.40 (m, 3H), 2.37 (dd, J=8.9, 5.3 Hz, 1H), 1.90-1.76 (m, 1H), 1.42-1.33 (m, 1H). LCMS: 493.0 [M+H]$^+$.

Example 16

4-(3-(2-Chloro-phenyl)-4-{3-fluoro-4-[2-(3-fluoromethyl-azetidin-1-yl)-ethoxy]-phenyl}-isothiazol-5-yl)-phenol

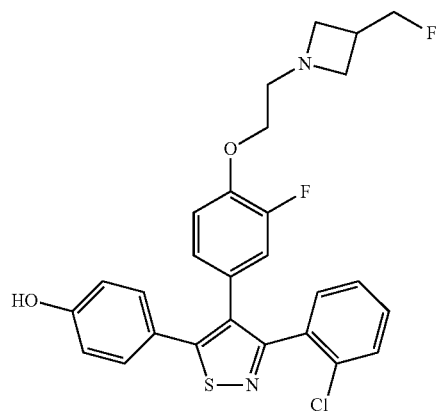 [SMILES: Oc1ccc(-c2snc(-c3ccccc3Cl)c2-c2ccc(OCCN3CC(CF)C3)c(F)c2)cc1]

Step 1: 3-(2-Chloro-phenyl)-5-(4-methoxy-phenyl)-isothiazole

A suspension of platinum oxide (57 mg, 0.25 mmol) in denatured ethanol (2 mL) was stirred for 5 min under an atmosphere of hydrogen. The vessel was evacuated and refilled with nitrogen (×3) before the addition of a suspension of 3-(2-chloro-phenyl)-5-(4-methoxy-phenyl)-isoxazole (prepared according to the procedure in WO2012084711) (300 mg) in denatured ethanol (8 mL). The vessel was evacuated and refilled with hydrogen (×3) and the resultant mixture was stirred at ambient temperature for 4 h. The solid was removed by filtration through a pad of celite, washed with ethyl acetate and the filtrate concentrated under reduced pressure. The resultant residue was suspended in toluene (10 mL), p-chloranil (258 mg, 1.05 mmol) and P$_2$S$_5$ (350 mg, 1.58 mmol) were added and the mixture heated under reflux for 1.5 h. The reaction was allowed to cool to room temperature and quenched with H$_2$O. The mixture was extracted with ethyl acetate (×3) and DCM (×3). The combined organic layer was dried (Na$_2$SO$_4$) and concentrated under reduced pressure. The crude material was purified by silica gel column chromatography, eluting with 0%-20% ethyl acetate in cyclohexane giving the title compound (95 mg, 30%) as an orange gum. LCMS: 302.1 [M+H]$^+$.

Step 2: 4-Bromo-3-(2-chloro-phenyl)-5-(4-methoxy-phenyl)-isothiazole

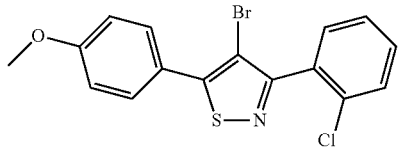 [SMILES: COc1ccc(-c2snc(-c3ccccc3Cl)c2Br)cc1]

A mixture of 3-(2-chloro-phenyl)-5-(4-methoxy-phenyl)-isothiazole (180 mg, 0.60 mmol), N-bromosuccinimide (139 mg, 0.78 mmol) and p-toluenesulfonic acid monohydrate (8 mg, 0.04 mmol) in DCM (5 mL) was stirred at room temperature for 4 h. A further portion of N-bromosuccinimide (139 mg, 0.78 mmol) and p-toluenesulfonic acid monohydrate (8 mg, 0.04 mmol) was added and the mixture was stirred for 65 h. The reaction was quenched with sodium metabisulfite solution and the mixture was extracted with ethyl acetate (×3). The combined organic layer was washed with brine, dried (Na$_2$SO$_4$) and concentrated under reduced pressure. The crude material was purified by silica gel column chromatography, eluting with 0%-15% ethyl acetate in cyclohexane giving the title compound as an amber gum (68 mg, 30%). LCMS: 379.9 [M+H]$^+$.

Step 3: 4-[4-Bromo-3-(2-chloro-phenyl)-isothiazol-5-yl]-phenol

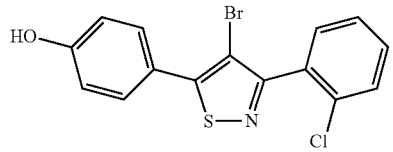 [SMILES: Oc1ccc(-c2snc(-c3ccccc3Cl)c2Br)cc1]

To a solution of 4-bromo-3-(2-chloro-phenyl)-5-(4-methoxy-phenyl)-isothiazole (68 mg, 0.18 mmol) in DCM (5 mL) at −78° C. was added BBr$_3$ (1M in DCM, 0.89 mL, 0.89 mmol) dropwise. The resultant solution was warmed to room temperature and stirred for 20 h. The reaction mixture was cooled to 0° C., quenched with H$_2$O and diluted with DCM. The phases was separated with a phase separator and the organic dried (Na$_2$SO$_4$) then concentrated under reduced pressure. The crude material was purified by silica gel column chromatography, eluting with DCM giving the title compound (43 mg, 65%) as a white solid. LCMS: 366.1 [M+H]$^+$.

Step 4: 4-Bromo-3-(2-chloro-phenyl)-5-[4-(tetrahydro-pyran-2-yloxy)-phenyl]-isothiazole

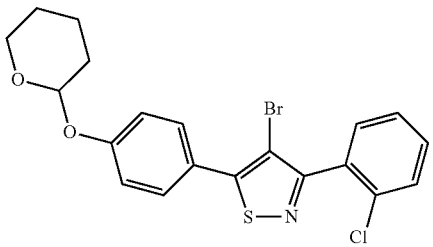 [SMILES: Clc1ccccc1-c1nsc(-c2ccc(OC3CCCCO3)cc2)c1Br]

A mixture of 4-[4-bromo-3-(2-chloro-phenyl)-isothiazol-5-yl]-phenol (43 mg, 0.12 mmol), 3,4-dihydro-2H-pyran (43 µL, 0.47 mmol) and pyridinium p-toluenesulfonate (3 mg, 0.01 mmol) in DCM (2 mL) was stirred for 1.2 h. The reaction was quenched with saturated aqueous sodium bicarbonate solution and extracted with DCM (×3). The combined organic layer was concentrated under reduced pressure and the resultant residue was purified by silica gel column chromatography, eluting with 0%-10% ethyl acetate in cyclohexane. This gave the title compound (33 mg, 61%) as a colorless glass. LCMS: 450.1 [M+H]$^+$.

Step 5: 4-{3-(2-Chloro-phenyl)-5-[4-(tetrahydro-pyran-2-yloxy)-phenyl]-isothiazol-4-yl}-2-fluoro-phenol

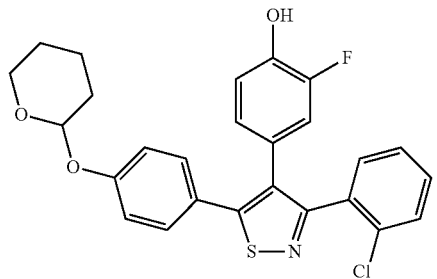 [SMILES: Oc1ccc(-c2c(-c3ccccc3Cl)nsc2-c2ccc(OC3CCCCO3)cc2)cc1F]

A vial was charged with 4-bromo-3-(2-chloro-phenyl)-5-[4-(tetrahydro-pyran-2-yloxy)-phenyl]-isothiazole (33 mg, 0.07 mmol), 3-fluoro-4-hydroxyphenylboronic acid (34 mg 0.22 mmol), palladium (II) acetate (1 mg, 0.004 mmol), potassium carbonate (15 mg, 0.11 mmol) and DMF (1.5 mL). The vessel was evacuated and refilled with argon (×3) then stirred at 110° C. for 18 h. To the mixture was added 3-fluoro-4-hydroxyphenylboronic acid (10 mg 0.06 mmol), palladium (II) acetate (2 mg, 0.01 mmol) and potassium carbonate (15 mg, 0.11 mmol). The black reaction mixture was stirred for a further 4 h at 110° C. before being cooled, diluted with ethyl acetate and filtered. The organic was washed with brine (×3) and the aqueous extracted with ethyl acetate (×2). The combined organic was washed with brine, dried (Na$_2$SO$_4$) and concentrated under reduced pressure. The crude material was purified by silica gel column chromatography, eluting with 0%-20% ethyl acetate in cyclohexane. This gave the title compound (16 mg, 47%) as a colorless glass. LCMS: 482.2 [M+H]$^+$.

Step 6: 4-(3-(2-Chloro-phenyl)-4-{3-fluoro-4-[2-(3-fluoromethyl-azetidin-1-yl)-ethoxy]-phenyl}-isothiazol-5-yl)-phenol

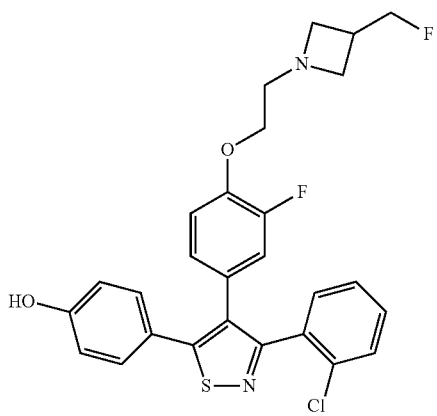

To a mixture of 4-{3-(2-chloro-phenyl)-5-[4-(tetrahydro-pyran-2-yloxy)-phenyl]-isothiazol-4-yl}-2-fluoro-phenol (16 mg, 0.03 mmol), Intermediate 1 (8 mg, 0.06 mmol), triphenylphosphine (17 mg, 0.07 mmol) in THF (1 mL) was added DIAD (13 µL, 0.07 mmol). The resultant solution was stirred at room temperature for 6 h then concentrated under reduced pressure. The crude material was purified by silica gel column chromatography, eluting with 0%-5% MeOH in DCM. The resultant gum was dissolved in a mixture of acetonitrile (1 mL), H$_2$O (0.25 mL) and acetic acid (2 mL) and stirred at room temperature for 18 h. A further portion of acetic acid (1 mL) and H$_2$O (0.25 mL) were added and stirring was continued for 4 h. The solvent was evaporated under reduced pressure and the resultant residue was taken up into ethyl acetate and washed with saturated sodium bicarbonate solution (×2). The combined organic phase was washed with brine, dried (Na$_2$SO$_4$) and concentrated under reduced pressure. The crude material was purified by silica gel column chromatography, eluting with 0%-8% MeOH in DCM giving the title compound (5 mg, 32%) as a white solid. $^1$H NMR (400 MHz, CDCl$_3$): δ 7.37-7.20 (m, 4H), 7.17-7.11 (m, 2H), 6.81-6.75 (m, 2H), 6.74-6.62 (m, 3H), 4.56 (d, J=5.7 Hz, 1H), 4.44 (d, J=5.7 Hz, 1H), 3.96 (t, J=5.4 Hz, 2H), 3.51 (t, J=7.4 Hz, 2H), 3.18 (t, J=6.9 Hz, 2H), 2.93-2.77 (m, 3H). LCMS: 513.2 [M+H]$^+$.

Example 17

[3-(2-Chloro-phenyl)-5-(4-hydroxy-phenyl)-isoxazol-4-yl]-{3-fluoro-4-[2-(3-fluoromethyl-azetidin-1-yl)-ethoxy]-phenyl}-methanone

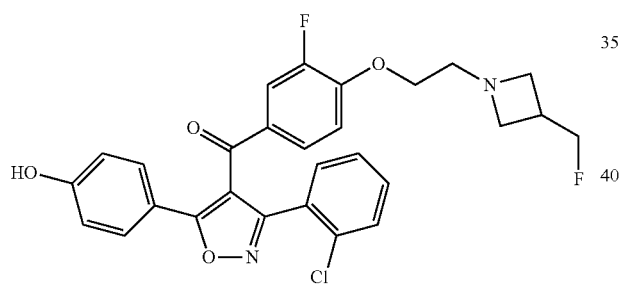

Step 1: 1-(3,4-Difluoro-phenyl)-3-(4-methoxy-phenyl)-propynone

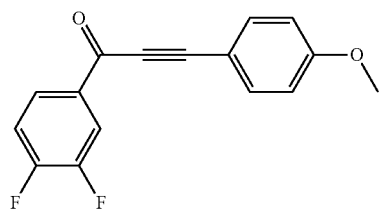 [SMILES: COc1ccc(C#CC(=O)c2ccc(F)c(F)c2)cc1]

To a mixture of 3,4-difluorobenzoyl chloride (4.3 g, 24.36 mmol), 1-ethynyl-4-methoxy-benzene (3.22 g, 24.36 mmol), bis(triphenylphosphine)palladium(II) dichloride (171 mg, 0.24 mmol) and copper(I) iodide (93 mg, 0.49 mmol) in THF (75 mL) under an atmosphere of nitrogen was added triethylamine (10.2 mL, 73.08 mmol). The resultant mixture was sonicated to break up the resultant precipitate and the reaction mixture was stirred at room temperature for 4 h. The solid was removed by filtration and the filter cake washed with EtOAc and the filtrate concentrated under reduced pressure. The crude material was purified by silica gel column chromatography eluting with 0-100% EtOAc in cyclohexane to give the title compound as a beige solid (5.9 g, 89%). LCMS: 273.0 [M+H]$^+$.

Step 2: [3-(2-chloro-phenyl)-5-(4-methoxy-phenyl)-isoxazol-4-yl]-(3,4-difluoro-phenyl)-methanone

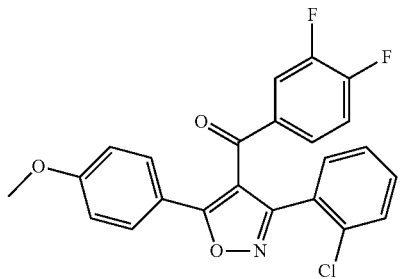 [SMILES: COc1ccc(-c2onc(-c3ccccc3Cl)c2C(=O)c2ccc(F)c(F)c2)cc1]

A suspension of 1-(3,4-difluoro-phenyl)-3-(4-methoxy-phenyl)-propynone (423 mg, 1.55 mmol) in Et$_2$O (8 mL) was added to a solution of 2-chloro-N-hydroxybenzenecarboximidoyl chloride (196 mg, 1.03 mmol) in Et$_2$O (8 mL). The reaction mixture was cooled to 0° C. and a solution of triethylamine (0.173 ml, 1.24 mmol) in Et$_2$O (2 mL) was added dropwise over 1 h. On complete addition, the mixture was warmed to room temperature and stirred for 65 h. The reaction was quenched by the addition of water, brine was added and the mixture extracted with EtOAc. The organic layer was dried over anhydrous Na$_2$SO$_4$, filtered and evaporated in vacuo. The crude product was purified by flash chromatography on silica eluting with 0-20% EtOAc in cyclohexane to give the title compound (353 mg, 44%) as a white solid. LCMS: 426.0 [M+H]$^+$.

Step 3: [3-(2-Chloro-phenyl)-5-(4-hydroxy-phenyl)-isoxazol-4-yl]-(3,4-difluoro-phenyl)-methanone

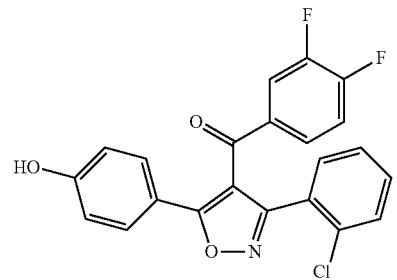 [SMILES: O=C(c1ccc(F)c(F)c1)c1c(-c2ccccc2Cl)noc1-c1ccc(O)cc1]

Boron tribromide (4.14 mL, 4.14 mmol, 1M in DCM) was added dropwise to a solution of [3-(2-chloro-phenyl)-5-(4-methoxy-phenyl)-isoxazol-4-yl]-(3,4-difluoro-phenyl)-methanone (353 mg, 0.83 mmol) in DCM (20 mL) at −78° C. The mixture was stirred at −78° C. for 10 min before being warmed to ambient temperature and stirred for 18 h. The reaction was cooled to 0° C. then quenched with water before being extracted with DCM (×3). The combined organic layer was washed with brine, dried (Na$_2$SO$_4$) and concentrated under reduced pressure. The crude product was dissolved in DCM (10 mL) then cooled to −78° C. before being treated with boron tribromide (4.14 mL, 4.14 mmol, 1M in DCM) dropwise. The reaction mixture was warmed to ambient temperature and stirred for 65 h. The reaction was cooled to 0° C. then quenched with water and extracted with DCM (×3). The combined organic was washed with brine, dried (Na₂SO₄) and concentrated under reduced pressure. The crude material was purified by silica gel column chromatography, eluting with 0%-4% MeOH in DCM. This gave the title compound as an off white foam (238 mg, 70%). LCMS: 412.2 [M+H]⁺.

Step 4: {3-(2-Chloro-phenyl)-5-[4-(tetrahydro-pyran-2-yloxy)-phenyl]-isoxazol-4-yl}-(3,4-difluoro-phenyl)-methanone

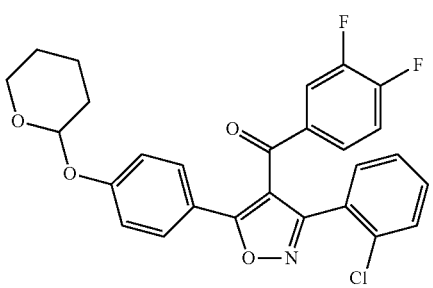 [SMILES: O=C(c1ccc(F)c(F)c1)c1c(-c2ccccc2Cl)noc1-c1ccc(OC2CCCCO2)cc1]

To a solution of [3-(2-chloro-phenyl)-5-(4-hydroxy-phenyl)-isoxazol-4-yl]-(3,4-difluoro-phenyl)-methanone (238 mg, 0.58 mmol) in DCM (6 mL) was added 3,4-dihydro-2H-pyran (79 µL, 0.87 mmol) and pyridinium p-toluenesulfonate (29 mg, 0.12 mmol). The reaction mixture was stirred for 4 h before the further addition of 3,4-dihydro-2H-pyran (158 µL, 1.74 mmol), pyridinium p-toluenesulfonate (58 mg, 0.23 mmol) and 4A molecular sieves. The reaction was stirred for 18 h before the reaction was filtered and purified by silica gel column chromatography, eluting with 0%-4% MeOH in DCM. This gave the title compound as a colorless glass (180 mg, 63%). LCMS: 496.3 [M+H]⁺.

Step 5: {3-(2-Chloro-phenyl)-5-[4-(tetrahydro-pyran-2-yloxy)-phenyl]-isoxazol-4-yl}-{3-fluoro-4-[2-(3-fluoromethyl-azetidin-1-yl)-ethoxy]-phenyl}-methanone

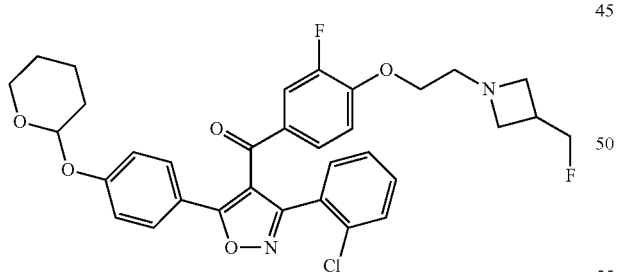

A mixture of {3-(2-chloro-phenyl)-5-[4-(tetrahydro-pyran-2-yloxy)-phenyl]-isoxazol-4-yl}-(3,4-difluoro-phenyl)-methanone (110 mg, 0.22 mmol), Intermediate 1 (35 mg, 0.27 mmol) and cesium carbonate (502 mg, 1.54 mmol) in MeCN (5 mL) was heated under reflux for 2 h. The mixture was allowed to cool to ambient temperature and a further portion of 2-(3-fluoromethyl-azetidin-1-yl)-ethanol (50 mg, 0.38 mmol) was added. The reaction was heated under reflux for 3 h then allowed to cool to ambient temperature and diluted with water. The mixture was extracted with ethyl acetate (×3), the combined organic layer was washed with brine, dried (Na₂SO₄) and concentrated under reduced pressure. The crude material was purified by silica gel column chromatography, eluting with 0%-10% MeOH in DCM. This gave the title compound as a colourless glass (51 mg, 38%). LCMS: 609.2 [M+H]⁺.

Step 6: [3-(2-Chloro-phenyl)-5-(4-hydroxy-phenyl)-isoxazol-4-yl]-{3-fluoro-4-[2-(3-fluoromethyl-azetidin-1-yl)-ethoxy]-phenyl}-methanone

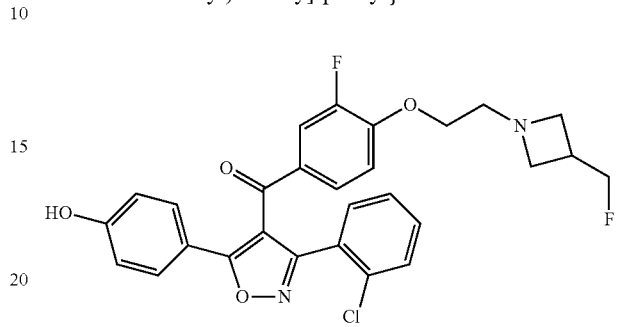

A mixture of {3-(2-chloro-phenyl)-5-[4-(tetrahydro-pyran-2-yloxy)-phenyl]-isoxazol-4-yl}-{3-fluoro-4-[2-(3-fluoromethyl-azetidin-1-yl)-ethoxy]-phenyl}-methanone (60 mg, 0.10 mmol), acetic acid (1 mL), water (0.25 mL) and acetonitrile (1 mL) was stirred for 18 h. Acetic acid (1 mL) was added to the reaction and the mixture stirred for a further 4 h. The reaction was diluted with ethyl acetate then basified with saturated aqueous NaHCO₃ solution. The phases were separated and the aqueous phase extracted with ethyl acetate. The combined organic layer was washed with saturated NaHCO₃ solution, dried (Na₂SO₄) and concentrated under reduced pressure. The crude material was purified by silica gel column chromatography, eluting with 0%-8%2M methanolic ammonia in DCM. This gave the title compound as a pale yellow solid (6 mg, 10%). ¹H NMR (400 MHz, CDCl₃): δ 7.58-7.52 (m, 1H), 7.48-7.41 (m, 3H), 7.38-7.31 (m, 4H), 6.78-6.71 (m, 2H), 6.64 (t, J=8.3 Hz, 1H), 4.56 (d, J=5.3 Hz, 1H), 4.44 (d, J=5.3 Hz, 1H), 4.02 (t, J=5.3 Hz, 2H), 3.56 (t, J=7.8 Hz, 2H), 3.25 (t, J=7.4 Hz, 2H), 2.97-2.79 (m, 3H). LCMS: 525.1 [M+H]⁺.

Example 18

4-(Cyclohexylidene-{4-[2-(3-fluoromethyl-azetidin-1-yl)-ethoxy]-phenyl}-methyl)-phenol

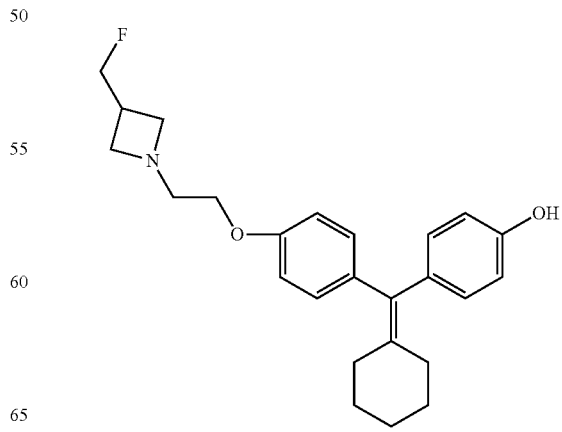

193

Step 1:
4-[Cyclohexylidene-(4-iodo-phenyl)methyl]-phenol

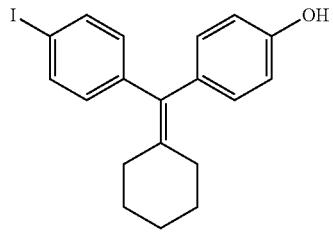 [SMILES: Oc1ccc(C(=C2CCCCC2)c2ccc(I)cc2)cc1]

Titanium tetrachloride (10.8 g, 56.6 mmol) was added dropwise to a stirred, cooled (0° C.) suspension of zinc (7.5 g, 115.4 mmol) in tetrahydrofuran (100 mL). On complete addition, the mixture was heated at 70° C. for 30 min then allowed to cool to ambient temperature. A solution of (4-hydroxy-phenyl)-(4-iodo-phenyl)-methanone (prepared according to the procedure in J. Med. Chem. 52, (15), 4694-2009) (5 g, 15.4 mmol) and cyclohexanone (0.15 g, 15.4 mmol) in tetrahydrofuran (100 mL) was added dropwise over 15 min. The mixture was heated at 70° C. for 15 min then allowed to cool to ambient temperature. The reaction was quenched by the addition of water (200 mL) and the resultant aqueous phase extracted into ethyl acetate (2×50 mL). The combined extract was washed with water (50 mL), dried (Na$_2$SO$_4$) and evaporated to dryness. The resultant oil was purified by flash column chromatography on silica eluting with 10-40% ethyl acetate in cyclohexane to give the title compound as a cream solid (4.7 g, 78%). LCMS: 391 [M+H]$^+$.

Step 2: (4-Iodo-phenyl)-[4-(tetrahydro-pyran-2-yloxy)-phenyl]-methanone

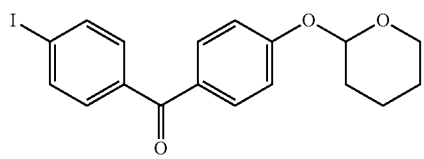 [SMILES: O=C(c1ccc(I)cc1)c1ccc(OC2CCCCO2)cc1]

A solution of p-toluenesulphonic acid (150 mg, 0.79 mmol), (4-iodo-phenyl)-[4-(tetrahydro-pyran-2-yloxy)-phenyl]-methanone (2.4 g, 6.15 mmol) and 3,4-dihydropyran (1.4 mL, 61.5 mmol) in DCM (50 mL) was stirred at room temperature for 15 min. The mixture was washed with aqueous sodium carbonate solution (30 mL) and water (30 mL), dried (Na$_2$SO$_4$) and evaporated under reduced pressure. The residual oil was purified by flash column chromatography on silica eluting with cyclohexane to give a solid which was triturated with diethylether to give the title compound as a cream solid (1.2 g, 41%).

194

Step 3: (Cyclohexylidene-{4-[2-(3-fluoromethyl-azetidin-1-yl)-ethoxy]-phenyl})-methyl)-phenol

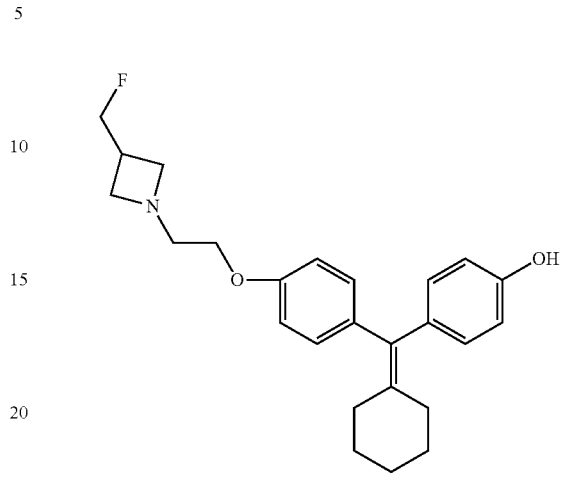

A degassed mixture of (4-iodo-phenyl)-[4-(tetrahydro-pyran-2-yloxy)-phenyl]-methanone (500 mg, 1.05 mmol), Intermediate 1 (168 mg, 1.26 mmol), potassium carbonate (290 mg, 2.0 mmol), copper iodide (20 mg, 0.105 mmol) and 1,10 phenanthroline (0.40 mg, 0.21 mmol) in butyronitrile (10 mL) was heated under microwave irradiation at 140° C. for 1 h then at 160° C. for 2 h. The reaction mixture was allowed to cool to ambient temperature, diluted with methanol and ethyl acetate and applied to an SCX cartridge. The cartridge was eluted with methanol followed by 2M ammonia in methanol. Appropriate basic fractions were combined and evaporated to give the free base of the title compound as a clear oil. The free base was dissolved in methanol (5 mL) was treated with fumaric acid (0.5 eq.) and then evaporated to give a solid which was triturated with diethyl ether to give a cream solid (2.6 mg, 5%). $^1$H NMR (400 MHz, CD$_3$OD): δ 6.98 (d, J=8.8 Hz, 2H), 6.87-6.82 (m, 4H), 6.68-6.64 (m, 3H), 4.58 (d, J=4.5 Hz, 1H), 4.46 (d, J=4.5 Hz, 1H), 4.11 (t, J=5.0 Hz, 2H), 4.03 (t, J=13.7 Hz, 2H), 3.83-3.77 (m, 2H), 3.15-2.99 (m, 1H), 2.25-2.16 (m, 4H), 1.64-1.51 (m, 6H). LCMS: 396.2 [M+H]$^+$.

Example 19

(R,Z)-1-(2-(4-(1,2-Diphenylbut-1-en-1-yl)phenoxy)ethyl)-3-(fluoromethyl)pyrrolidine

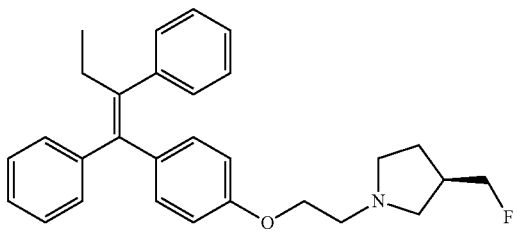 [SMILES: CC/C(=C(\c1ccccc1)c1ccc(OCCN2CC[C@@H](CF)C2)cc1)c1ccccc1]

Step 1: 4-(1,2-Diphenylbut-1-en-1-yl)phenol

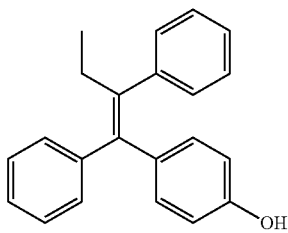 [SMILES: CC/C(=C(\c1ccccc1)c1ccc(O)cc1)c1ccccc1]

To a stirred mixture of propiophenone (8.12 g, 60.54 mmol) in THF (100 mL) was added TiCl$_4$ (11 mL, 100.9 mmol) dropwise at −5° C. and the mixture was heated at 70° C. for 2 h. After cooling to room temperature, a solution of 4-hydroxybenzophenone (10.0 g, 50.45 mmol) in THF (50 mL) and zinc powder (16.49 g, 252.24 mmol) were added. The reaction mixture was stirred at 70° C. for additional 4 h. After cooling to room temperature, the reaction mixture was diluted with water (100 mL) and extracted with ethyl acetate (100 mL×2). The combined organic layers were dried over anhydrous Na$_2$SO$_4$, filtered and concentrated under reduced pressure. The residue was purified by silica gel column chromatography (10% ethyl acetate in hexanes) to give the title compound (14.2 g, 66%, a mixture of Z/E=1/1) as light yellow solid.

Step 2: (R,Z)-1-(2-(4-(1,2-Diphenylbut-1-en-1-yl)phenoxy)ethyl)-3-(fluoromethyl)pyrrolidine

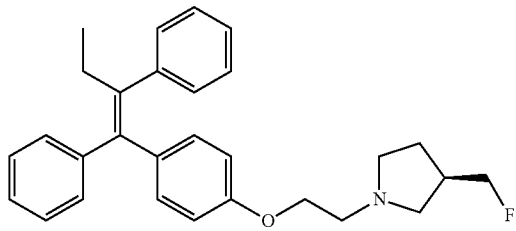 [SMILES: CC/C(=C(\c1ccccc1)c1ccc(OCCN2CC[C@@H](CF)C2)cc1)c1ccccc1]

To a solution of Intermediate 4 (0.29 g, 2 mmol), 4-[1,2-diphenylbut-1-enyl]phenol (1:1 mixture of Z/E isomers, 0.3 g, 1 mmol) and triphenylphosphine (0.79 g, 3 mmol) in THF (6 mL) was added diisopropyl azodicarboxylate (0.61 g, 3 mmol) dropwise at 0° C. The reaction mixture was stirred at 25° C. for 12 h. The reaction mixture was quenched with water (20 mL) and extracted with ethyl acetate (20 mL×2). The combined organic layers were dried over anhydrous Na$_2$SO$_4$, filtered and concentrated under reduced pressure. The residue was purified by silica gel column chromatography (40% ethyl acetate in petroleum ether) and then further purified by reverse-phase HPLC (acetonitrile 74-100%/0.2% NH$_4$OH in water) to give the title compound (15 mg, 4%) as white solid. $^1$H NMR (400 MHz, CD$_3$OD): δ 7.36-7.33 (m, 2H), 7.28-7.09 (m, 6H), 6.77 (d, J=8.8 Hz, 2H), 6.57 (d, J=8.8 Hz, 2H), 4.38-4.36 (m, 1H), 4.26-4.24 (m, 1H), 3.98 (t, J=5.6 Hz, 2H), 2.86-2.79 (m, 3H), 2.72-2.42 (m, 6H), 1.99-1.93 (m, 1H), 1.56-1.51 (m, 1H), 0.90 (t, J=7.2 Hz, 3H). LCMS: 430.2 [M+H]$^+$.

Example 20

(R)-1-((S)-1-(4-((Z)-1,2-Diphenylbut-1-en-1-yl)phenoxy)propan-2-yl)-3-(fluoromethyl)pyrrolidine

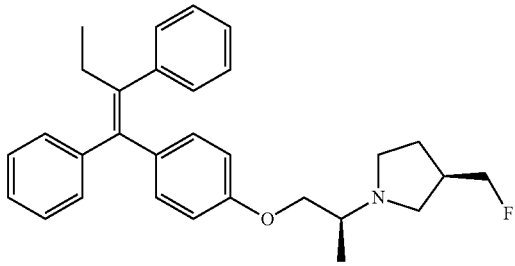 [SMILES: CC/C(=C(\c1ccccc1)c1ccc(OC[C@H](C)N2CC[C@@H](CF)C2)cc1)c1ccccc1]

The title compound was prepared from Intermediate 3 in 3% yield as a white solid, following the same procedure as shown in Step 2, Example 19. $^1$H NMR (400 MHz, CD$_3$OD): δ 7.35-7.33 (m, 2H), 7.26-7.11 (m, 6H), 6.79 (d, J=8.8 Hz, 2H), 6.61 (d, J=8.8 Hz, 2H), 4.44-4.29 (m, 2H), 3.96-3.95 (m, 2H), 3.14-2.62 (m, 6H), 2.48-2.42 (m, 2H), 2.04-1.98 (m, 1H), 1.68-1.62 (m, 1H), 1.31-1.18 (m, 3H), 0.91 (t, J=7.6 Hz, 3H). LCMS: 444.2 [M+H]$^+$.

Example 21

(Z)-1-(2-(4-(1,2-Diphenylbut-1-en-1-yl)phenoxy)ethyl)-3-(fluoromethyl)azetidine

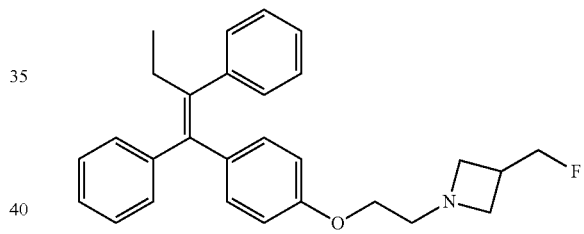

The title compound was prepared from Intermediate 1 in 10% yield as a white solid, following the same procedure as shown in Step 2, Example 19. $^1$H NMR (400 MHz, CD$_3$OD): δ 7.35-7.33 (m, 2H), 7.28-7.09 (m, 6H), 6.76 (d, J=8.8 Hz, 2H), 6.54 (d, J=8.8 Hz, 2H), 4.52-4.39 (m, 2H), 3.86 (t, J=5.6 Hz, 2H), 3.48 (t, J=7.6 Hz, 2H), 3.16 (t, J=7.6 Hz, 2H), 2.84-2.78 (m, 3H), 248-2.42 (m, 2H), 0.90 (t, J=7.2 Hz, 3H); LCMS: 416.2 [M+H]$^+$.

Example 22

(R,Z)-4-(1-(4-(2-(3-(Fluoromethyl)pyrrolidin-1-yl)ethoxy)phenyl)-2-phenylbut-1-en-1-yl)phenol

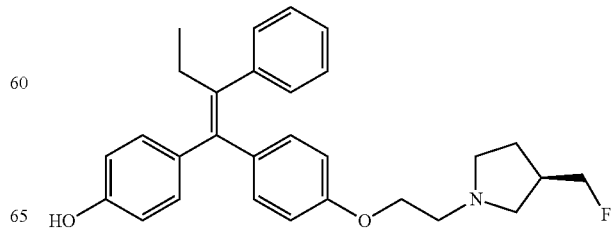

Step 1: (R,E)-4-(1-(4-(2-(3-(Fluoromethyl)pyrroli-din-1-yl)ethoxy)phenyl)-2-phenylbut-1-en-1-yl)phenyl pivalate

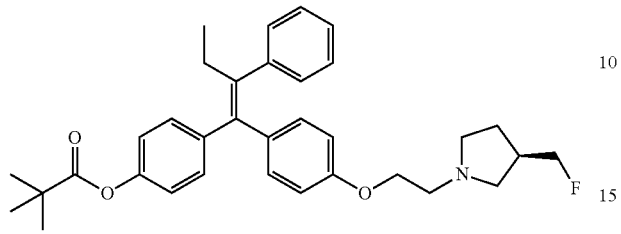

To a solution of (E)-4-(1-(4-hydroxyphenyl)-2-phenylbut-1-en-1-yl)phenyl pivalate (0.2 g, 0.50 mmol), Intermediate 4 (147 mg, 1.0 mmol) and triphenyl phosphine (0.39 g, 1.5 mmol) in anhydrous THF (3 mL) was added diiso-propyl azodicarboxylate (0.3 mL, 1.5 mmol) at 0° C. under nitrogen atmosphere. The resulting mixture was warmed up to room temperature and stirred for 16 h. The mixture was concentrated under reduced pressure. The residue was purified by preparative TLC (ethyl acetate) to give the title compound (0.1 g, 38%) as a colorless oil. LCMS: 530.3 [M+H]$^+$.

Step 2: (R,Z)-4-(1-(4-(2-(3-(Fluoromethyl)pyrroli-din-1-yl)ethoxy)phenyl)-2-phenylbut-1-en-1-yl)phenol

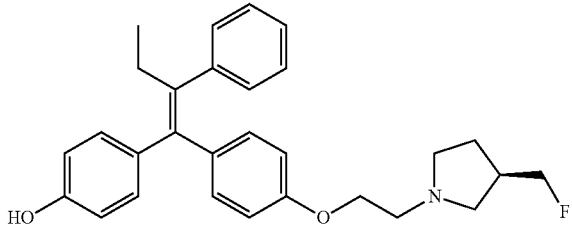 [SMILES: CC/C(=C(\c1ccc(O)cc1)c1ccc(OCCN2CC[C@@H](CF)C2)cc1)c1ccccc1]

To a solution of (R,E)-4-(1-(4-(2-(3-(fluoromethyl)pyrrolidin-1-yl)ethoxy)phenyl)-2-phenylbut-1-en-1-yl)phenyl pivalate (100 mg, 0.19 mmol) in methanol (2 mL) was added potassium carbonate (52 mg, 0.38 mmol). The mixture was stirred at room temperature for 2 h. The mixture was filtered and concentrated under reduced pressure. The residue was purified by reverse-phase HPLC (16-46% acetonitrile in water) to give the title compound (27 mg, 32%) as a white solid. $^1$H NMR (400 MHz, DMSO-d$_6$): δ 9.48 (s, 1H), 7.17-7.15 (m, 2H), 7.09-7.08 (m, 3H), 6.97 (d, J=8.4 Hz, 2H), 6.74 (d, J=8.4 Hz, 2H), 6.68 (d, J=8.4 Hz, 2H), 6.57 (d, J=8.8 Hz, 2H), 4.33-4.32 (m, 1H), 4.21-4.20 (m, 1H), 3.89 (t, J=6.0 Hz, 2H), 2.68 (t, J=6.0 Hz, 2H), 2.59-2.55 (m, 1H), 2.45-2.33 (m, 4H), 1.83-1.79 (m, 1H), 1.38-1.34 (m, 1H), 0.84 (t, J=7.2 Hz, 3H). LCMS: 446.2 [M+H]$^+$.

Example 23

((Z)-4-(1-(4-(2-(3-(Fluoromethyl)azetidin-1-yl) ethoxy)phenyl)-2-phenylbut-1-en-1-yl)phenol

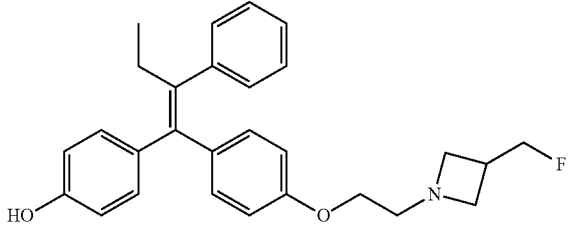 [SMILES: CC/C(=C(\c1ccc(O)cc1)c1ccc(OCCN2CC(CF)C2)cc1)c1ccccc1]

The title compound was prepared from Intermediate 1 in 9% yield following the same procedure as shown in Step 2, Example 22. $^1$H NMR (400 MHz, DMSO-d$_6$): δ 7.17-7.12 (m, 2H), 7.09-7.05 (m, 3H), 6.97 (d, J=8.4 Hz, 2H), 6.74 (d, J=8.8 Hz, 2H), 6.69 (d, J=8.4 Hz, 2H), 6.54 (d, J=8.4 Hz, 2H), 4.48 (dd, J=47.6, 6.0 Hz, 2H), 3.75 (t, J=5.6 Hz, 2H), 3.28-3.24 (m, 2H), 2.94 (t, J=6.0 Hz, 2H), 2.70-2.63 (m, 2H), 2.45-2.40 (m, 3H), 0.84 (t, J=7.2 Hz, 3H). LCMS: 432.2 [M+H]$^+$.

Example 24

4-((Z)-1-(4-((S)-2-((R)-3-(Fluoromethyl)pyrrolidin-1-yl)propoxy)phenyl)-2-phenylbut-1-en-1-yl)phenol

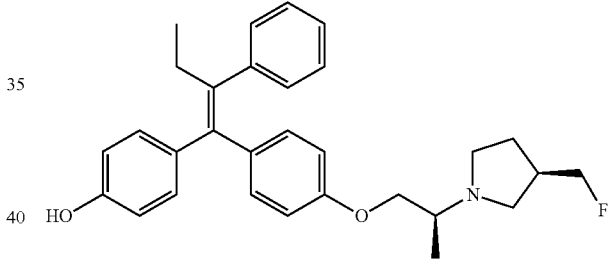

The title compound was prepared from Intermediate 3 in 3% yield following the same procedure as shown in Step 2, Example 22. $^1$H NMR (400 MHz, DMSO-d$_6$): δ 7.19-7.17 (m, 2H), 7.10-7.06 (m, 3H), 6.97 (d, J=8.0 Hz, 2H), 6.74 (d, J=8.0 Hz, 2H), 3.67 (t, J=6.4 Hz, 1H), 2.66-2.53 (m, 4H), 2.41-2.35 (m, 4H), 1.80-1.77 (m, 1H), 1.36-1.33 (m, 1H), 1.06 (d, J=6.0 Hz, 3H); LCMS: 460.3 [M+H]$^+$.

Example 25

(E)-5-(1-(4-(2-(3-(Fluoromethyl)azetidin-1-yl) ethoxy)phenyl)-2-phenylbut-1-en-1-yl)-1H-indazole

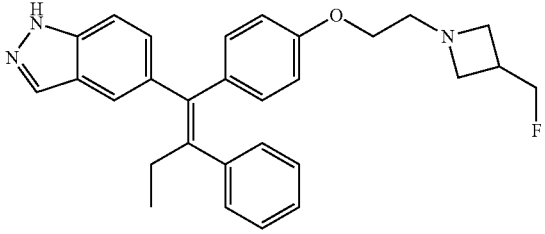 [SMILES: CC/C(=C(/c1ccc(OCCN2CC(CF)C2)cc1)c1ccc2[nH]ncc2c1)c1ccccc1]

Step 1: 5-Bromo-1-((2-(trimethylsilyl)ethoxy)methyl)-1H-indazole

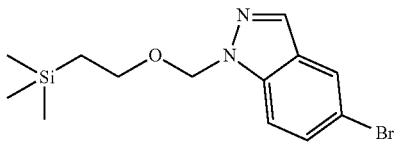 [SMILES: C[Si](C)(C)CCOCn1ncc2cc(Br)ccc21]

A mixture of 5-bromo-1H-indazole (20 g, 101.5 mmol) in THF (300 mL) was cooled to 0° C., and NaH (60% dispersion in mineral oil, 6.1 g, 152.3 mmol) was added in portions. After stirring for 30 min, (2-(chloromethoxy)ethyl)trimethylsilane (27 mL, 152.3 mmol) was added. The reaction mixture was warmed to 25° C. and stirred for 15 h. The reaction was quenched with saturated aq. NH$_4$Cl (10 mL) and a clear yellow solution was obtained which was poured into cold water and then extracted with ethyl acetate (300 mL×2). The combined organic layers were washed with brine (300 mL), dried over Na$_2$SO$_4$, filtered and concentrated under reduced pressure. The residue was purified by column chromatography (eluting with 0-10% ethyl acetate in petroleum ether) to give the title compound (35.3 g, 85%) as yellow oil. $^1$H NMR (400 MHz, CDCl$_3$): δ 7.96 (s, 1H), 7.90 (s, 1H), 7.53-7.45 (m, 2H), 5.73 (s, 2H), 3.53 (t, J=8.0 Hz, 2H), 0.88 (t, J=8.0 Hz, 2H), −0.07 (s, 9H).

Step 2: (4-Iodophenyl)(1-((2-(trimethylsilyl)ethoxy)methyl)-1H-indazol-5-yl)methanol

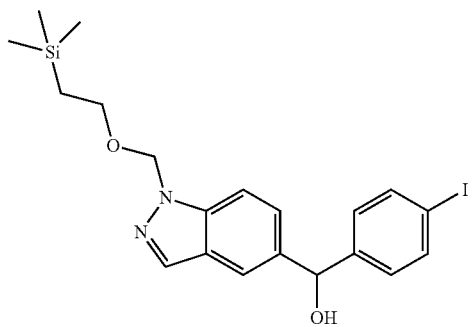 [SMILES: C[Si](C)(C)CCOCn1ncc2cc(C(O)c3ccc(I)cc3)ccc21]

To a solution of 2-[(5-bromoindazol-1-yl)methoxy]ethyl-trimethyl-silane (35.3 g, 86.3 mmol) in THF (300 mL) was added n-BuLi (2.5 M in hexanes, 38 mL, 94.9 mmol) dropwise at −78° C. under nitrogen atmosphere and the mixture solution was stirred for 30 min. Then the reaction mixture was added a solution of 4-iodobenzaldehyde (22 g, 94.9 mmol) in THF (50 mL) and stirred at −78° C. for additional 2 h. The mixture was quenched with saturated aq. NH$_4$Cl solution (50 mL). The mixture was diluted with water (100 mL) and extracted with ethyl acetate (300 mL×2). The combined organic layers were washed with brine (300 mL), dried over anhydrous Na$_2$SO$_4$ and concentrated under reduced pressure. The residue was purified by silica gel column chromatography (eluting with 0-17% ethyl acetate in petroleum ether) to give the title compound (21 g, 51%) as yellow oil. $^1$H NMR (400 MHz, CDCl$_3$): δ 7.99 (s, 1H), 7.74 (s, 1H), 7.68 (d, J=8.4 Hz, 2H), 7.54 (d, J=8.8 Hz, 1H), 7.38 (dd, J=8.4, 1.2 Hz, 1H), 7.17 (d, J=8.4 Hz, 2H), 5.93 (s, 1H), 5.72 (s, 2H), 3.53 (t, J=8.0 Hz, 2H), 0.88 (t, J=8.0 Hz, 2H), −0.07 (s, 9H).

Step 3: (4-Iodophenyl)(1-((2-(trimethylsilyl)ethoxy)methyl)-1H-indazol-5-yl)methanone

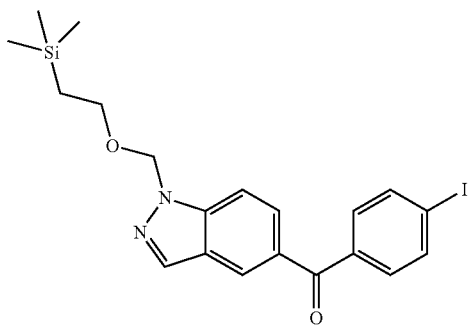 [SMILES: C[Si](C)(C)CCOCn1ncc2cc(C(=O)c3ccc(I)cc3)ccc21]

To a solution of (4-iodophenyl)-[1-(2-trimethylsilylethoxymethyl)indazol-5-yl]methanol (21 g, 43.7 mmol) in dichloromethane (300 mL) was added manganese dioxide (38 g, 437 mmol). The mixture was stirred at 25° C. for 15 h. The mixture was filtered and the filtrate was concentrated to give the title compound (20 g, 96%) as a yellow solid. $^1$H NMR (400 MHz, CDCl$_3$): δ 8.20 (s, 1H), 8.13 (s, 1H), 7.98 (dd, J=8.4, 1.2 Hz, 1H), 7.88 (d, J=8.4 Hz, 2H), 7.68 (d, J=8.8 Hz, 1H), 7.54 (d, J=8.0 Hz, 2H), 5.79 (s, 2H), 3.58 (t, J=8.4 Hz, 2H), 0.91 (t, J=8.4 Hz, 2H), −0.05 (s, 9H).

Step 4: 5-(1-(4-Iodophenyl)-2-phenylbut-1-en-1-yl)-1H-indazole

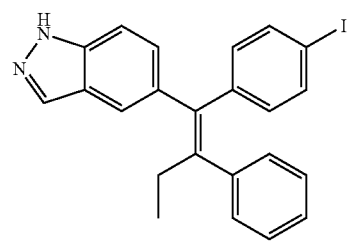 [SMILES: CC/C(=C(/c1ccc(I)cc1)c1ccc2[nH]ncc2c1)c1ccccc1]

Zn powder (547 mg, 8.4 mmol) was suspended in dry THF (10 mL) and cooled to 0° C. To the resultant suspension was added TiCl$_4$ (0.5 mL, 4.5 mmol) dropwise under nitrogen atmosphere. The mixture was warmed to 15° C. and then heated to 70° C. for 2 h. After cooling to room temperature, a solution of (4-iodophenyl)-[1-(2-trimethylsilylethoxymethyl)indazol-5-yl]methanone (500 mg, 1.05 mmol) and propiophenone (0.44 mL, 3.34 mmol) in dried THF (10 mL) was added. The mixture was heated to 70° C. in the dark for 2 h under a nitrogen atmosphere. After cooling to room temperature, the reaction mixture was concentrated under reduced pressure. The residue was purified by silica gel column chromatography (eluted with 0-30% ethyl acetate in petroleum ether) and followed by preparative TLC (eluted with 30% ethyl acetate in petroleum ether) to give the title compound (a mixture of E and Z isomers, 300 mg, 64%) as a white solid.

Step 5: 5-(1-(4-Iodophenyl)-2-phenylbut-1-en-1-yl)-1-((2-(trimethyl silyl)ethoxy)methyl)-1H-indazole

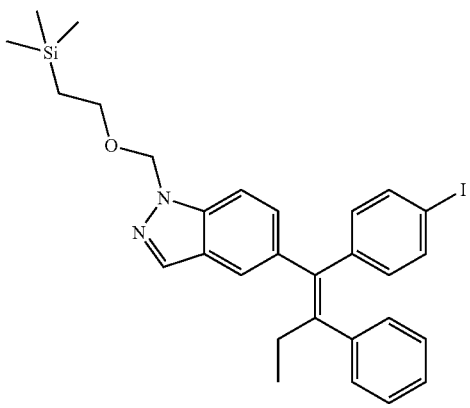 [SMILES: CC/C(=C(/c1ccc(I)cc1)c1ccc2c(cnn2COCC[Si](C)(C)C)c1)c1ccccc1]

To a mixture of 5-[1-(4-iodophenyl)-2-phenyl-but-1-enyl]-1H-indazole (300 mg, 0.67 mmol) in THF (6 mL) was added NaH (60% dispersion in mineral oil, 40 mg, 1 mmol) in portions at 0° C. The reaction mixture was stirred for 30 min and then (2-(chloromethoxy)ethyl)trimethylsilane (0.18 mL, 1 mmol) was added. The reaction mixture was warmed to 15° C. and stirred for an additional 15 h. The reaction was quenched with saturated aqueous NH$_4$Cl solution (2 mL) which was poured into cold water and then extracted by ethyl acetate (50 mL×2). The combined organic layers were washed with brine (50 mL), dried over anhydrous Na$_2$SO$_4$ and concentrated under reduced pressure. The residue was purified by preparative TLC (eluted with 19% ethyl acetate in petroleum ether) to give the title compound (180 mg, 44%) as a yellow oil. LCMS: 581.2 [M+H]$^+$.

Step 6: 5-(1-(4-(2-(3-(Fluoromethyl)azetidin-1-yl)ethoxy)phenyl)-2-phenylbut-1-en-1-yl)-1-((2-(trimethyl silyl)ethoxy)methyl)-1H-indazole

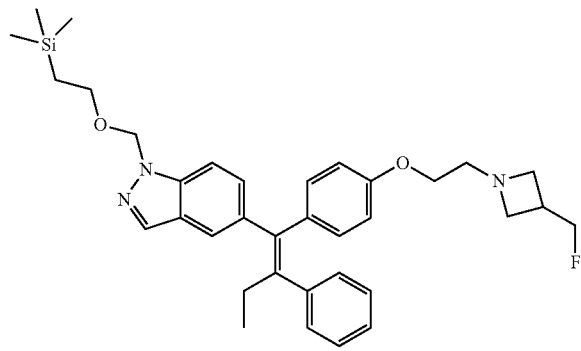 [SMILES: CC/C(=C(/c1ccc(OCCN2CC(CF)C2)cc1)c1ccc2c(cnn2COCC[Si](C)(C)C)c1)c1ccccc1]

A mixture of 2-[[5-[1-(4-iodophenyl)-2-phenyl-but-1-enyl]indazol-1-yl]methoxy]ethyl-tri-methyl-silane (180 mg, 0.31 mmol), Intermediate 1 (124 mg, 0.93 mmol), potassium carbonate (129 mg, 0.93 mmol) and copper(I) iodide (59 mg, 0.31 mmol) in o-xylene (5 mL) was heated to 130° C. for 15 h. After cooling to room temperature, the reaction mixture was concentrated under reduced pressure. The residue was purified by preparative TLC (eluted with 75% ethyl acetate in petroleum ether) to give the title compound (a mixture of E and Z isomers, 100 mg, 47%) as yellow oil. LCMS: 586.4 [M+H]$^+$.

Step 7: (E)-5-(1-(4-(2-(3-(Fluoromethyl)azetidin-1-yl)ethoxy)phenyl)-2-phenylbut-1-en-1-yl)-1H-indazole

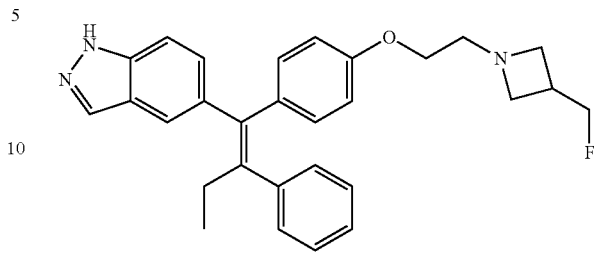

To a solution of 5-(1-(4-(2-(3-(fluoromethyl)azetidin-1-yl)ethoxy)phenyl)-2-phenylbut-1-en-1-yl)-1-((2-(trimethylsilyl)ethoxy)methyl)-1H-indazole (100 mg, 0.15 mmol) in THF (2 mL) was added TBAF (1 M solution in THF, 1 mL, 1 mmol). The mixture was heated to 80° C. for 15 h. After cooling to room temperature, the mixture was concentrated under reduced pressure. The residue was dissolved in ethyl acetate (100 mL), washed 10% citric acid (50 mL×2) and brine (50 mL). The organic layer was dried over anhydrous Na$_2$SO$_4$, filtered and concentrated under reduced pressure. The residue was purified by reverse-phase HPLC (acetonitrile 55-85%/0.05% NH$_4$OH in water) to give the title compound (5.2 mg, 8%) as a white solid. $^1$H NMR (400 MHz, CD$_3$OD): δ 8.04 (s, 1H), 7.66 (s, 1H), 7.50 (d, J=8.8 Hz, 1H), 7.21-7.10 (m, 6H), 6.79 (d, J=8.8 Hz, 2H), 6.55 (d, J=8.4 Hz, 2H), 4.45 (dd, J=47.6, 5.6 Hz, 2H), 3.86 (t, J=5.2 Hz, 2H), 3.50-3.46 (m, 2H), 3.19-3.15 (m, 2H), 2.87-2.78 (m, 3H), 2.49 (q, J=7.2 Hz, 2H), 0.94 (t, J=7.2 Hz, 3H). LCMS: 456.2 [M+H]$^+$.

Example 26

(R,E)-5-(2-(2-Chloro-4-methoxyphenyl)-2-cyclobutyl-(4-(2-(3-(fluoromethyl)pyrrolidin-1-yl)ethoxy)phenyl)vinyl)-3-fluoro-1H-indazole

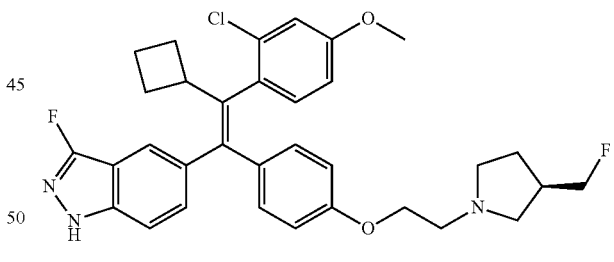

Step 1 (R)-3-(Fluoromethyl)-1-(2-(4-iodophenoxy)ethyl)pyrrolidine

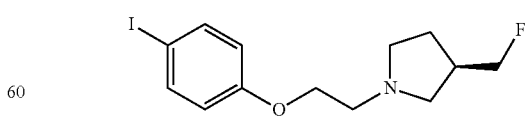

A mixture of 1,4-diiodobenzene (4.5 g, 13.6 mmol), Intermediate 4 (1 g, 6.80 mmol), CuI (258 mg, 1.36 mmol), Cs$_2$CO$_3$ (4.4 g, 13.6 mmol) and butyronitrile (27 mL) was degassed with vacuum/nitrogen cycles (3×) and then heated at 125° C. for 2 days. The mixture was cooled to room temperature, diluted with ethyl acetate, washed (water and then brine), dried (Na₂SO₄), and concentrated. The residue was purified by silica gel chromatography (10% MeOH in DCM) to afford the title compound (1.18 g, 50%) as brown oil. ¹H NMR (400 MHz, DMSO-d₆): δ 7.57 (d, J=8.9 Hz, 2H), 6.88 (d, J=8.9 Hz, 2H), 4.38-4.17 (m, 2H), 4.02 (t, J=5.8 Hz, 2H), 2.74 (t, J=5.8 Hz, 2H), 2.65-2.60 (m, 1H), 2.56-2.40 (m, 3H), 2.38-2.35 (m, 1H), 1.87-1.78 (m, 1H), 1.41-1.33 (m, 1H). LCMS: 350.0 [M+H]⁺.

Step 2: 5-((Z)-2-Cyclobutyl-2-(5,5-dimethyl-1,3,2-dioxaborinan-2-yl)-1-(4-(2-((R)-3-(fluoromethyl)pyrrolidin-1-yl)ethoxy)phenyl)vinyl)-3-fluoro-1-(tetrahydro-2H-pyran-2-yl)-1H-indazole

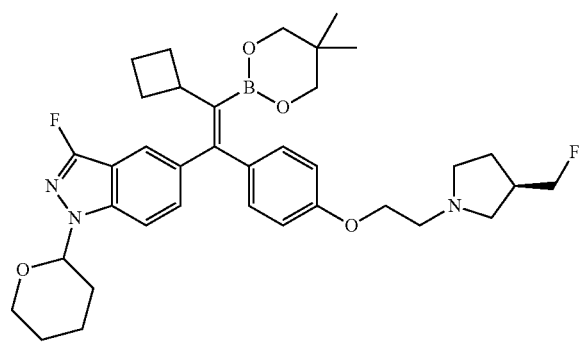 [SMILES: CC1(C)COB(/C(=C(\c2ccc(OCCN3CC[C@@H](CF)C3)cc2)c2ccc3c(c2)c(F)nn3C2CCCCO2)C2CCC2)OC1]

A mixture of 5-(cyclobutylethynyl)-3-fluoro-1-(tetrahydro-2H-pyran-2-yl)-1H-indazole (0.5 g, 1.68 mmol, see WO/2013/142266A1 for synthesis), 5,5,5',5'-tetramethyl-2,2'-bi(1,3,2-dioxaborinane) (397.5 mg, 1.76 mmol), and ethylenebis(triphenylphosphine)platinum(0) (25 mg, 0.03 mmol) in 1,4-dioxane (3.4 mL) was degassed with vacuum/nitrogen cycles (3×). The mixture was heated at 100° C. for 2 h, cooled to room temperature, and then diluted with 1,4-dioxane (3.4 mL). Cesium carbonate (1.09 g, 3.35 mmol), water (0.067 mL), (R)-3-(fluoromethyl)-1-(2-(4-iodophenoxy)ethyl)pyrrolidine (585.2 mg, 1.68 mmol) and bis(triphenylphosphine)palladium(II) dichloride (58.8 mg, 0.08 mmol) were added to the reaction mixture. The mixture was degassed with vacuum/nitrogen cycles (3×), stirred at room temperature for 2 h, diluted with water, and then extracted with diethyl ether. The organic extracts were washed (water and then brine), dried (Na₂SO₄), and concentrated to afford the title compound (1.2 g, quant) as a brown foam. LCMS: 634.1 [M+H]⁺.

Step 3: 5-((E)-2-(2-Chloro-4-methoxyphenyl)-2-cyclobutyl-1-(4-(2-((R)-3-(fluoromethyl)pyrrolidin-1-yl)ethoxy)phenyl)vinyl)-3-fluoro-1-(tetrahydro-2H-pyran-2-yl)-1H-indazole

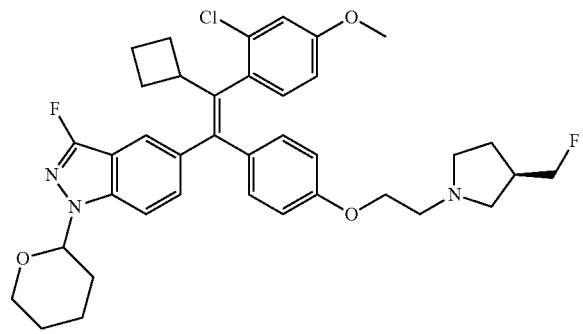 [SMILES: COc1ccc(/C(=C(\c2ccc(OCCN3CC[C@@H](CF)C3)cc2)c2ccc3c(c2)c(F)nn3C2CCCCO2)C2CCC2)c(Cl)c1]

A mixture of 5-((Z)-2-Cyclobutyl-2-(5,5-dimethyl-1,3,2-dioxaborinan-2-yl)-1-(4-(2-((R)-3-(fluoromethyl)pyrrolidin-1-yl)ethoxy)phenyl)vinyl)-3-fluoro-1-(tetrahydro-2H-pyran-2-yl)-1H-indazole (600 mg, 0.95 mmol), 1-bromo-2-chloro-4-methoxybenzene (315 mg, 1.42 mmol), PdCl₂(PPh₃)₂ (66 mg, 0.09 mmol), 1,4-dioxane (3.8 mL), and 4M aq. KOH (1.4 mL, 5.6 mmol) was degassed with vacuum/nitrogen cycles (3×) and then heated at 90° C. for 2 h. The reaction mixture was allowed to cool to room temperature, diluted with water, and then extracted with diethyl ether. Combined extracts were washed (water and then brine), dried (Na₂SO₄), and concentrated. The residue was purified by silica gel chromatography (0-100% ethyl acetate in hexanes) to give the title compound (401 mg, 64%) as an off-white foam. LCMS: 662.0 [M+H]⁺.

Step 4: (R,E)-5-(2-(2-Chloro-4-methoxyphenyl)-2-cyclobutyl-1-(4-(2-(3-(fluoromethyl)pyrrolidin-1-yl)ethoxy)phenyl)vinyl)-3-fluoro-1H-indazole

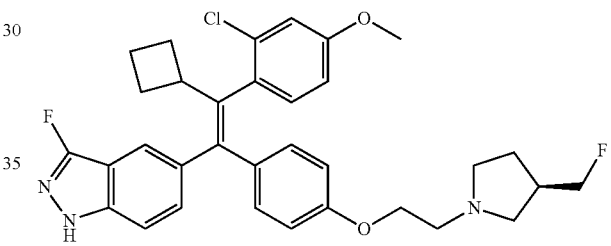

A solution of 5-((E)-2-(2-chloro-4-methoxyphenyl)-2-cyclobutyl-1-(4-(2-((R)-3-(fluoromethyl) pyrrolidin-1-yl)ethoxy)phenyl)vinyl)-3-fluoro-1-(tetrahydro-2H-pyran-2-yl)-1H-indazole (401 mg, 0.64 mmol) in 80% acetic acid/water (2 mL) was heated at 80° C. overnight. The reaction mixture was concentrated, diluted with ethyl acetate, washed (saturated NaHCO₃, water and then brine), dried (Na₂SO₄), and concentrated. The residue was purified by reverse-phase HPLC (55-65% acetonitrile/water with 0.1% TFA). Acetonitrile was removed under reduced pressure, and the remaining aqueous phase was neutralized with saturated NaHCO₃. The aqueous phase was extracted with ethyl acetate, and the organic phase was then washed (water and then brine), dried (Na₂SO₄), and concentrated to afford the title compound (38 mg). ¹H NMR (400 MHz, DMSO-d₆): δ 12.60 (s, 1H), 7.49-7.46 (m, 2H), 7.20 (dd, J=8.7, 1.6 Hz, 1H), 7.16 (d, J=8.4 Hz, 1H), 6.94 (d, J=2.6 Hz, 1H), 6.86-6.83 (m, 3H), 6.59 (d, J=8.8 Hz, 2H), 4.32-4.30 (m, 1H), 4.20-4.18 (m, 1H), 3.88 (t, J=5.5 Hz, 2H), 3.73 (s, 3H), 3.35-3.31 (m, 1H), 3.10-2.85 (br, 1H), 2.71-2.62 (m, 2H), 2.59 (m, 1H), 2.41 (br, 2H), 2.33-2.32 (m, 1H), 1.86-1.76 (m, 4H), 1.69-1.55 (m, 2H), 1.38-1.34 (m, 2H). LCMS: 578.0 (M+H)⁺.

Example 27

(R,E)-5-(2-(3-Chloro-5-(trifluoromethyl)1 97yridine-2-yl)-2-cyclobutyl-1-(4-(2-(3-(fluoromethyl)pyrrolidin-1-yl)ethoxy)phenyl)vinyl)-3-fluoro-1H-indazole

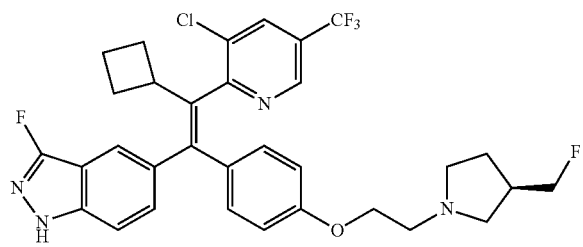

The title compound was prepared from 5-((Z)-2-cyclobutyl-2-(5,5-dimethyl-1,3,2-dioxaborinan-2-yl)-1-(4-(2-((R)-3-(fluoromethyl)pyrrolidin-1-yl)ethoxy)phenyl)vinyl)-3-fluoro-1-(tetrahydro-2H-pyran-2-yl)-1H-indazole and 2-bromo-3-chloro-5-(trifluoromethyl)pyridine following the procedure outlined for Example 26. $^1$H NMR (400 MHz, DMSO-d$_6$): δ 12.66 (s, 1H), 9.05-9.04 (m, 1H), 8.34 (d, J=1.9 Hz, 1H), 7.52 (dd, J=8.9, 1.8 Hz, 1H), 7.49 (s, 1H), 7.21 (dd, J=8.7, 1.6 Hz, 1H), 6.75 (d, J=8.8 Hz, 2H), 6.60 (d, J=8.8 Hz, 2H), 4.32-4.29 (m, 1H), 4.20-4.17 (m, 1H), 3.88 (m, 2H), 3.51-3.42 (m, 1H), 3.10-2.90 (br, 1H), 2.66-2.55 (m, 3H), 2.40-2.32 (m, 3H), 2.04-1.97 (m, 1H), 1.90-1.86 (m, 1H), 1.79-1.70 (m, 3H), 1.66-1.57 (m, 1H), 1.40-1.34 (m, 2H). LCMS: 616.9 [M+H]$^+$.

Example 28

2-(4-(2-((R)-3-(Fluoromethyl)pyrrolidin-1-yl)ethoxy)phenyl)-3-(4-hydroxyphenyl)-2,3-dihydrobenzo[b][1,4]oxathiin-6-ol

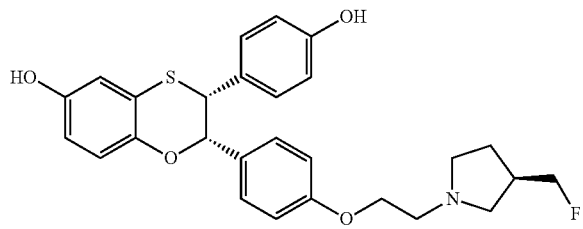 [SMILES: Oc1ccc([C@H]2Sc3cc(O)ccc3O[C@H]2c2ccc(OCCN3CC[C@@H](CF)C3)cc2)cc1]

Step 1: 5-Hydroxybenzo[d][1,3]oxathiol-2-one

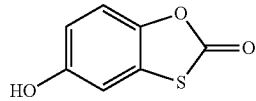

To a solution of thiourea (10.56 g, 138 mmol) in 2N HCl (140 mL) was added a solution of benzoquinone (10 g, 193 mmol) in acetic acid (140 mL) dropwise. The resulting solution was stirred at room temperature for 30 min and then heated to 110° C. for 3 h under nitrogen atmosphere. The reaction was cooled in an ice bath and stored at 0° C. for 16 h. The resultant precipitate was filtered and the filtered cake was re-dissolved in ethyl acetate (200 mL). The organic solution was washed with water (100 mL×3), dried over anhydrous Na$_2$SO$_4$, and concentrated under reduced pressure to give the title compound (15.6 g, 84%) as a white solid which was used in the next step without further purification. $^1$H NMR (400 MHz, CDCl$_3$): δ 7.15 (d, J=9.2 Hz, 1H), 6.91 (d, J=2.4 Hz, 1H), 6.78 (dd, J=9.2, 2.4 Hz, 1H), 5.22 (s, 1H).

Step 2: 5-(Benzyloxy)benzo[d][1,3]oxathiol-2-one

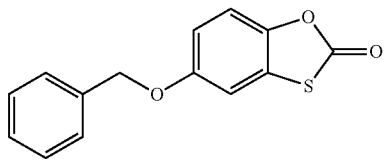 [SMILES: O=c1oc2ccc(OCc3ccccc3)cc2s1]

To a solution of 5-hydroxybenzo[d][1,3]oxathiol-2-one (11 g, 65.41 mmol) in acetone (200 mL) at 0° C. was added potassium iodide (10.68 g, 65.41 mmol), potassium carbonate (18.08 g, 130.82 mmol), and benzyl bromide (13.98 mmol, 87.76 mmol) slowly. The mixture was stirred at 0° C. for 1 h and then warmed up to room temperature and stirred for 16 h. The reaction was quenched with water (100 mL) and extracted with ethyl acetate (100 mL×3). The combined organic layers were washed with water (100 mL×3), dried over anhydrous Na$_2$SO$_4$, and concentrated under reduced pressure. The residue was purified by silica gel column chromatography (0-10% ethyl acetate in petroleum ether) to give the title compound (11 g, 65%) as white solid. $^1$H NMR (400 MHz, CDCl$_3$): δ 7.42-7.39 (m, 5H), 7.19 (d, J=9.2 Hz, 1H), 7.00 (d, J=2.4 Hz, 1H), 6.94 (d, J=9.2, 2.4 Hz, 1H), 5.07 (s, 2H).

Step 3: 4-(Benzyloxy)-2-mercaptophenol

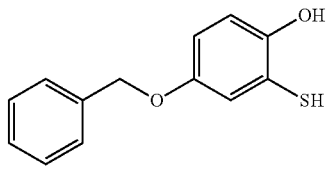 [SMILES: Oc1ccc(OCc2ccccc2)cc1S]

A solution of 5-(benzyloxy)benzo[d][1,3]oxathiol-2-one (1 g, 3.87 mmol) in THF (20 mL) and EtOH (10 mL) was purged with nitrogen for 20 min before adding 5 N NaOH (3.1 mL). The reaction was stirred at room temperature with continuous bubbling of nitrogen. Then the mixture was cooled to 0° C. and 2N HCl was added to bring pH to neutral. The mixture was extracted with ethyl acetate (10 mL×3). The combined organic layers were dried over anhydrous Na$_2$SO$_4$, concentrated under reduced pressure to give the title compound (800 mg, 89%) as a green solid which was used directly for the next step without further purification. $^1$H NMR (400 MHz, acetone-d$_6$): δ 7.40-7.35 (m, 5H), 7.19 (d, J=9.2 Hz, 1H), 6.8 (d, J=2.4 Hz, 1H), 6.79 (d, J=9.2, 2.4 Hz, 1H), 4.97 (s, 2H), 2.96 (brs, 1H).

Step 4: 1,2-Bis(4-hydroxyphenyl)ethanone

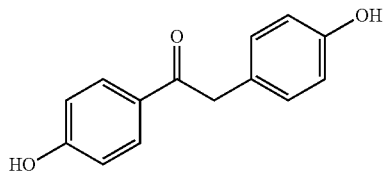 [SMILES: O=C(Cc1ccc(O)cc1)c1ccc(O)cc1]

A solution of 1,2-bis(4-methoxyphenyl)ethanone (20 g, 78.03 mmol) and pyridine hydrochloride (63 g, 546.2 mmol) was heated to 200° C. for 5 h. After cooling to room temperature, the mixture was poured into ice water and extracted with ethyl acetate (200 mL×3). The combined organic layers were dried over anhydrous Na$_2$SO$_4$ and concentrated under reduced pressure to give title compound (17 g, 95%) as a yellow solid which was used directly for the next step without further purification. $^1$H NMR (400 MHz, CD$_3$OD): δ 7.93 (d, J=9.2 Hz, 2H), 7.06 (d, J=8.8 Hz, 2H), 6.83 (d, J=8.4 Hz, 2H), 6.71 (d, J=8.4 Hz, 2H), 4.13 (s, 1H).

Step 5: 2-(4-Hydroxyphenyl)-1-(4-(methoxymethoxy)phenyl)ethanone

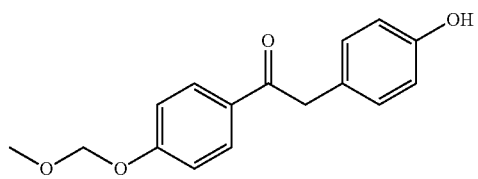 [SMILES: COCOc1ccc(C(=O)Cc2ccc(O)cc2)cc1]

To a solution of compound 1,2-bis(4-hydroxyphenyl)ethanone (10 g, 43.81 mmol) in DMF (100 mL) at 0° C. was added chloromethyl methyl ether (4.99 mL, 65.72 mmol) and N,N-diiso-propylethylamine (9.2 mL, 52.58 mmol). The mixture was stirred at 0° C. for 30 min and then stirred at 26° C. for 18 h. The reaction was quenched with water (100 mL) and extracted with ethyl acetate (200 mL×3). The combined organic layers were washed with water (20 mL×3), dried over anhydrous Na$_2$SO$_4$, and concentrated under reduced pressure. The residue was purified by silica gel column chromatography (0-20% ethyl acetate in petroleum ether) to give the title compound (11 g, 92%) as a yellow solid. $^1$H NMR (400 MHz, DMSO-d$_6$): δ 9.26 (s, 1H), 7.99 (d, J=9.2 Hz, 2H), 7.10 (d, J=8.8 Hz, 2H), 7.04 (d, J=8.8 Hz, 2H), 6.98 (d, J=8.0 Hz, 2H), 5.28 (s, 2H), 4.15 (s, 2H).

Step 6: 1-(4-(Methoxymethoxy)phenyl)-2-(4-((triiso-propylsilyl)oxy)phenyl)ethanone

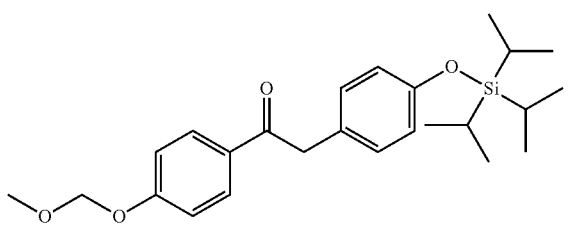 [SMILES: COCOc1ccc(C(=O)Cc2ccc(O[Si](C(C)C)(C(C)C)C(C)C)cc2)cc1]

To a solution of 2-(4-hydroxyphenyl)-1-[4-(methoxymethoxy)phenyl]ethanone (11 g, 40.4 mmol) in DMF (100 mL) was added chlorotriiso-propylsilane (15.58 g, 80.79 mmol) and imidazole (5.5 g, 80.79 mmol) at 0° C. The reaction mixture was stirred at 26° C. for 16 h. The reaction was quenched with water (100 mL) and extracted by ethyl acetate (100 mL×3). The combined organic layers were washed with water (150 mL×6), dried over anhydrous Na$_2$SO$_4$, concentrated under reduced pressure. The residue was purified by silica gel column chromatography (0-10% ethyl acetate in petroleum ether) to give the title compound (15 g, 87%) as a yellow oil. $^1$H NMR (400 MHz, DMSO-d$_6$): δ 7.97 (d, J=9.2 Hz, 2H), 7.27-7.04 (m, 4H), 6.82 (d, J=8.4 Hz, 2H), 5.23 (s, 2H), 4.16 (s, 2H), 3.48 (s, 3H). 1.28-1.21 (m, 3H), 1.08-1.06 (m, 18H).

Step 7: 2-Bromo-1-(4-hydroxyphenyl)-2-(4-((triiso-propyl silyl)oxy)phenyl)ethanone

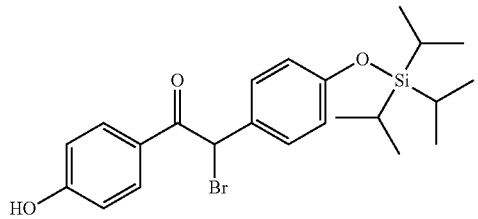 [SMILES: CC(C)[Si](Oc1ccc(C(Br)C(=O)c2ccc(O)cc2)cc1)(C(C)C)C(C)C]

A solution of 1-[4-(methoxymethoxy)phenyl]-2-(4-triiso-propylsilyloxyphenyl)ethanone (5.7 g, 13.3 mmol) in THF (120 mL) was added trimethylphenylammonium tribromide (5.5 g, 14.63 mmol) at 0° C. The mixture was stirred at ° C. for 10 min and then stirred at 26° C. for 4 h. The mixture was filtered and the filtrate was concentrated under reduced pressure to give the title compound (6 g, 97%) as yellow oil which was used in the next step without further purification.

Step 8: 2-((5-(Benzyloxy)-2-hydroxyphenyl)thio)-1-(4-hydroxyphenyl)-2-(4-((triiso-propylsilyl) oxy) phenyl)ethanone

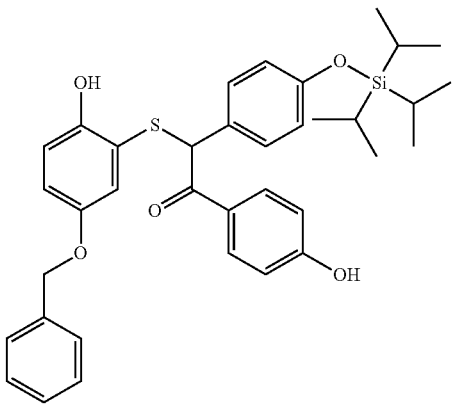 [SMILES: CC(C)[Si](Oc1ccc(C(Sc2cc(OCc3ccccc3)ccc2O)C(=O)c2ccc(O)cc2)cc1)(C(C)C)C(C)C]

To a solution of 4-benzyloxy-2-mercapto-phenol (3 g, 12.91 mmol) was added 2-bromo-1-(4-hydroxyl phenyl)-2-(4-triiso-propylsilyloxyphenyl) ethanone (6 g, 12.91 mmol) in DMF (10 mL) dropwise. The mixture was cooled to 0° C., N,N-diiso-propylethylamine (3.3 mL, 19.37 mmol) was added dropwise, and then stirred at 26° C. for 3 h. The reaction was quenched with HCl (1 N) to adjust pH to neutral and then water (20 mL) was added. The resultant mixture was extracted with ethyl acetate (30 mL×3). The combined organic layers were washed with water (2×30 mL), dried over anhydrous Na$_2$SO$_4$ and concentrated under reduced pressure. The residue was purified by silica gel column chromatography (10% ethyl acetate in petroleum ether) to give the title compound (5.2 g, 66%) as yellow oil. $^1$H NMR (400 MHz, DMSO-d$_6$): δ 7.94 (d, J=8.4 Hz, 2H), 7.40-7.20 (m, 9H), 6.86-6.18 (m, 7H), 6.17 (s, 1H), 5.92 (s, 1H), 4.97 (s, 1H), 4.86 (s, 2H), 1.25-1.19 (m, 3H), 1.08-1.01 (m, 18H).

Step 9: 4-((2S,3R)-6-(Benzyloxy)-3-(4-((triiso-propylsilyl)oxy)phenyl)-2,3-dihydrobenzo[b][1,4]oxathiin-2-yl)phenol

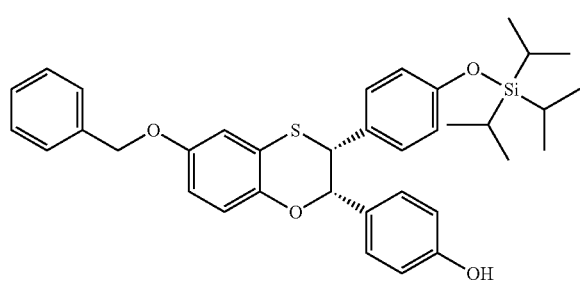 [SMILES: CC(C)[Si](Oc1ccc([C@H]2Sc3cc(OCc4ccccc4)ccc3O[C@H]2c2ccc(O)cc2)cc1)(C(C)C)C(C)C]

To a solution of 2-((5-(benzyloxy)-2-hydroxyphenyl)thio)-1-(4-hydroxyphenyl)-2-(4-((triiso-propylsilyl) oxy)phenyl)ethanone (5.0 g, 8.13 mmol) in dichloromethane (100 mL) was added trifluoroacetic acid (6.1 mL, 81.32 mmol) and triethylsilane (5.2 mL, 32.53 mmol) slowly at 0° C. The reaction was stirred at 0° C. for 3 h. The reaction was quenched with saturated NaHCO$_3$ aqueous solution (30 mL) and extracted with DCM (50 mL×3). The combined organic layers were dried over anhydrous Na$_2$SO$_4$, and concentrated under reduced pressure. The residue was purified by silica gel column chromatography (0-20% ethyl acetate in petroleum ether) to give the title compound (mixture of cis-enantiomers, 3 g, 62%) as a yellow oil. $^1$H NMR (400 MHz, CDCl$_3$): δ 7.46-7.40 (m, 5H), 6.91 (d, J=8.4 Hz, 1H), 6.86-6.80 (m, 3H), 6.77 (d, J=8.0 Hz, 2H), 6.71 (dd, J=8.4, 2.0 Hz, 1H), 6.66-6.63 (m, 4H), 5.41 (d, J=2.0 Hz, 1H), 5.04 (s, 2H), 4.84 (s, 1H), 4.28 (d, J=2.0 Hz, 1H), 1.27-1.19 (m, 3H), 1.09-1.07 (m, 18H).

Step 10: 2-(4-(2-((R)-3-(Fluoromethyl)pyrrolidin-1-yl)ethoxy)phenyl)-3-(4-hydroxyphenyl)-2,3-dihydrobenzo[b][1,4]oxathiin-6-ol

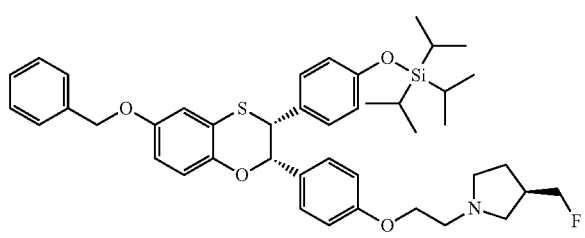 [SMILES: CC(C)[Si](Oc1ccc([C@H]2Sc3cc(OCc4ccccc4)ccc3O[C@H]2c2ccc(OCCN3CC[C@@H](CF)C3)cc2)cc1)(C(C)C)C(C)C]

To a solution of triphenylphosphine (0.66 g, 2.5 mmol) in toluene (2 mL) was added diiso-propyl azodicarboxylate (0.5 mL, 2.5 mmol) slowly at 0° C. under nitrogen atmosphere. Then a solution of 4-[6-benzyloxy-3-(4-triiso-propylsilyloxyphenyl)-2,3-dihydro-1,4-benzoxathiin-2-yl]phenol (mixture of cis isomers, 0.5 g, 0.83 mmol) and Intermediate 4 (0.38 g, 2.5 mmol) in toluene (3 mL) was added to the mixture dropwise. The mixture was stirred at 0° C. for 10 min and then stirred at 100° C. for 16 h. After cooling to room temperature, the mixture was concentrated under reduced pressure. The residue was purified by silica gel column chromatography (0-50% ethyl acetate in petroleum ether) and then further purified by preparative TLC (ethyl acetate) to give the title compound (mixture of cis-enantiomers, 0.8 g, 79%) as white solid. LCMS: 728.3 [M+H]$^+$.

Step 11: 2-(4-(2-((R)-3-(Fluoromethyl)pyrrolidin-1-yl)ethoxy)phenyl)-3-(4-hydroxyphenyl)-2,3-dihydrobenzo[b][1,4]oxathiin-6-ol

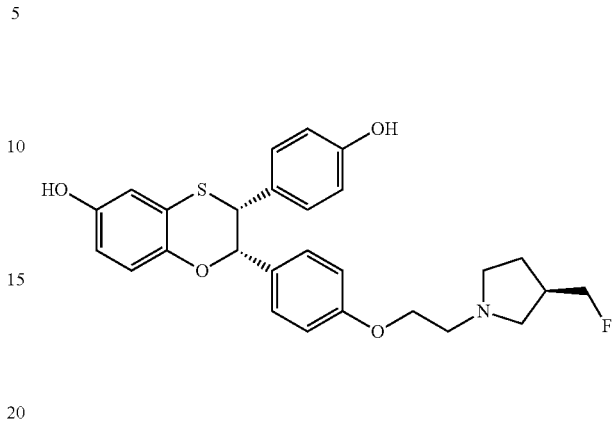

To a solution of [4-[6-benzyloxy-2-[4-[2-[(3R)-3-(fluoromethyl)pyrrolidin-1-yl]ethoxy]phenyl]-2,3-dihydro-1,4-benzoxathiin-3-yl]phenoxy]-triiso-propylsilane (0.25 g, 0.34 mmol) in dichloromethane (5 mL) at −78° C. was added tribromoborane (0.52 mL, 0.52 mmol). The reaction mixture was stirred at −78° C. for 3 h. The reaction was quenched with MeOH (10 mL) and concentrated under reduced pressure. The residue was purified by reverse-phase HPLC (acetonitrile 30-60%/0.1% formic acid in water) to give the title compound (a mixture of cis-enantiomers, 6.9 mg, 2.8%) as white solid. $^1$H NMR (400 MHz, DMSO-d$_6$): δ 8.12 (s, 1H), 6.99-6.80 (m, 2H), 6.78-6.72 (m, 5H), 6.54-6.49 (m, 4H), 5.38 (s, 1H), 4.60 (s, 1H), 4.36-4.23 (m, 2H), 4.01-3.98 (m, 2H), 2.76-2.74 (m, 2H), 2.65-2.64 (m, 1H), 2.58-2.56 (m, 2H), 2.41-2.38 (m, 2H), 1.86-1.83 (m, 1H), 1.41-1.36 (m, 1H); LCMS: 482.2 [M+H]$^+$.

Example 29

2-(4-(2-(3-(Fluoromethyl)azetidin-1-yl)ethoxy)phenyl)-3-(4-hydroxyphenyl)-2, 3-dihydrobenzo[b][1,4]oxathiin-6-ol

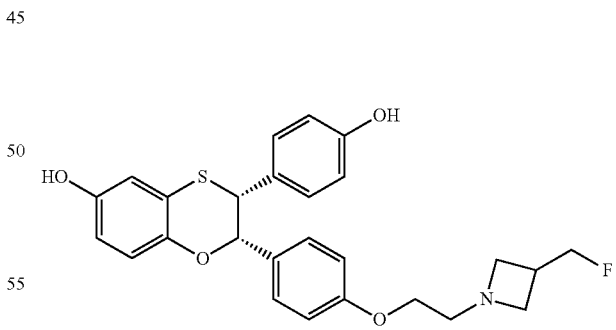

The title compound was prepared from Intermediate 1 in 14% yield following the same procedures as described in Steps 10 and 11 in Example 28. $^1$H NMR (400 MHz, DMSO-d$_6$): δ 9.29 (s, 1H), 9.19 (s, 1H), 7.01-6.98 (m, 2H), 6.80-6.72 (m, 5H), 6.53-6.48 (m, 4H), 5.39 (s, 1H), 4.59 (s, 1H), 4.58 (d, J=5.6 Hz, 1H), 4.46 (d, J=5.6 Hz, 1H), 3.94 (t, J=4.2 Hz, 2H), 3.62-3.59 (m, 2H), 2.99-2.96 (m, 3H), 2.87-2.82 (m, 2H). LCMS: 468.1 [M+H]$^+$.

Example 30

2-(4-((S)-2-((R)-3-(Fluoromethyl)pyrrolidin-1-yl)propoxy)phenyl)-3-(4-hydroxyphenyl)-2,3-dihydrobenzo[b][1,4]oxathiin-6-ol

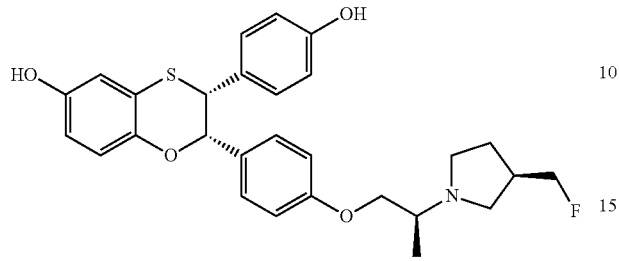

The title compound was prepared from Intermediate 3 following the same procedures as described in Steps 10 and 11 in Example 28. $^1$H NMR (400 MHz, CD$_3$OD): δ 7.00 (d, J=8.4 Hz, 2H), 6.83 (d, J=8.4 Hz, 2H), 6.76-6.71 (m, 3H), 6.55 (s, 1H), 6.48-6.46 (m, 3H), 5.38 (s, 1H), 4.52-4.50 (m, 2H), 4.42 (s, 1H), 4.40-4.38 (m, 2H), 4.09 (s, 1H), 4.08-4.02 (m, 2H), 2.20-2.13 (m, 2H); LCMS: 496.2 [M+H]$^+$.

Example 31

2-(4-(2-(3-(Fluoromethyl)azetidin-1-yl)ethoxy)phenyl)-3-(3-hydroxyphenyl)-2,3-dihydrobenzo[b][1,4]oxathiin-6-ol

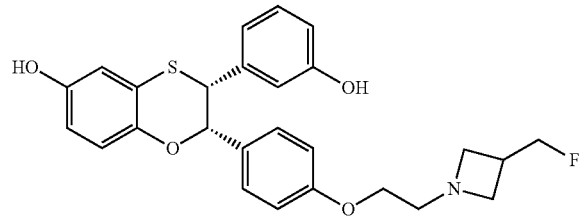

Step 1: 1-(2-(4-(6-(Benzyloxy)-3-(3-(benzyloxy)phenyl)-2,3-dihydrobenzo[b][1,4]oxathiin-2-yl)phenoxy)ethyl)-3-(fluoromethyl)azetidine

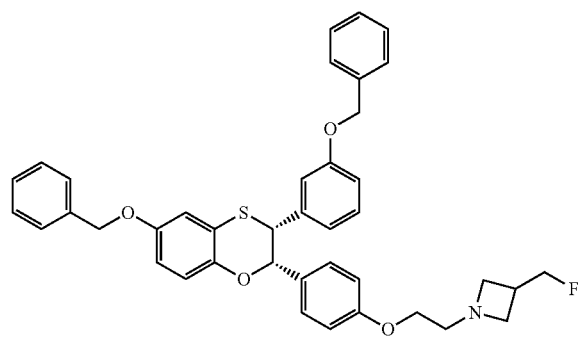 [SMILES: FCC1CN(CCOc2ccc([C@@H]3Oc4ccc(OCc5ccccc5)cc4S[C@@H]3c3cccc(OCc4ccccc4)c3)cc2)C1]

To a solution of 6-benzyloxy-3-(3-benzyloxyphenyl)-2-(4-iodophenyl)-2,3-dihydro-1,4-benzoxathiine (50 mg, 0.08 mmol, prepared according to schemes in *Proc. Natl. Acad. Sci. USA* 2004, 101, 5776) and Intermediate 1 (52 mg, 0.39 mmol) in toluene (2 mL) was added cesium carbonate (51 mg, 0.16 mmol) and 2-di-tert-butylphosphino-2',4',6'-triisopropylbiphenyl (3.3 mg, 0.01 mmol). The reaction mixture was degassed with nitrogen for 5 min and methanesulfonato (2-di-t-butylphosphino-2',4',6'-tri-i-propyl-1,1'-biphenyl) (2'-amino-1,1'-biphenyl-2-yl)palladium(II) (6.1 mg, 0.01 mmol) was added. The reaction mixture was heated to 100° C. for 16 h. After cooling to room temperature, the reaction mixture was filtered and the filtrate was concentrated under reduced pressure. The residue was purified by preparative TLC (eluted with 2% MeOH in DCM) to give the title compound (mixture of cis isomers, 100 mg, 72% purity) as brown solid. LCMS: 648.3 [M+H]$^+$.

Step 2: 2-(4-(2-(3-(Fluoromethyl)azetidin-1-yl)ethoxy)phenyl)-3-(3-hydroxyphenyl)-2,3-dihydrobenzo[b][1,4]oxathiin-6-ol

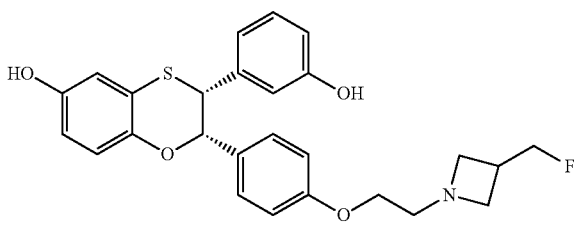

To a solution of 1-[2-[4-[(2S,3R)-6-benzyloxy-3-(3-benzyloxyphenyl)-2,3-dihydro-1,4-benzoxathiin-2-yl]phenoxy]ethyl]-3-(fluoromethyl)azetidine (100 mg, 0.11 mmol) in DCM (5 mL) was added tribromoborane (0.1 mL, 1.1 mmol) at −78° C. under nitrogen atmosphere. The mixture was stirred at −78° C. for 1 h. The reaction was quenched with saturated NaHCO$_3$ aqueous solution (0.5 mL) and concentrated under reduced pressure. The residue was purified by preparative HPLC (acetonitrile 10-40%/0.2% formic acid in water) to give the title compound (mixture of cis-enantiomers, 15 mg, 27%) as a brown solid. $^1$H NMR (400 MHz, CD$_3$OD): δ 8.47 (s, 1H), 7.06 (d, J=8.8 Hz, 1H), 6.87-6.82 (m, 4H), 6.60-6.52 (m, 4H), 6.36 (d, J=8.0 Hz, 1H), 5.43 (s, 1H), 4.64 (d, J=4.0 Hz, 1H), 4.52 (d, J=4.0 Hz, 1H), 4.51 (s, 1H), 4.21-4.02 (m, 5H), 3.48 (d, J=4.4 Hz, 2H), 3.20-3.14 (m, 1H). LCMS: 468.1 [M+H]$^+$.

Example 32

(4-(2-(3-(Fluoromethyl)azetidin-1-yl)ethoxy)phenyl)(6-hydroxy-2-(4-hydroxyphenyl)-3,4-dihydronaphthalen-1-yl)methanone

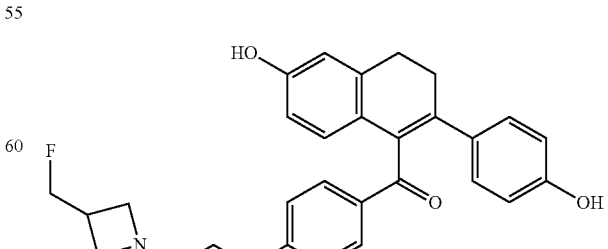

Step 1: (4-(2-(3-(Fluoromethyl)azetidin-1-yl)ethoxy) phenyl)(6-methoxy-2-(4-methoxy phenyl)-3,4-dihydronaphthalen-1-yl)methanone

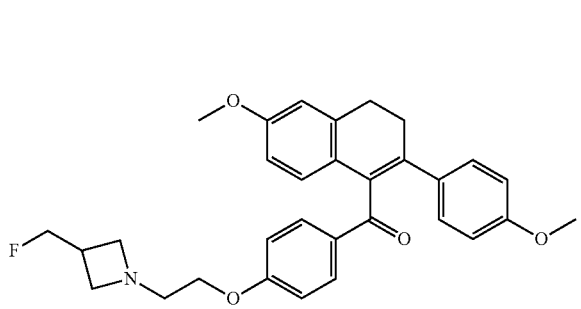 [SMILES: COc1ccc(C2=C(C(=O)c3ccc(OCCN4CC(CF)C4)cc3)c3ccc(OC)cc3CC2)cc1]

To a solution of (4-hydroxyphenyl)-[6-methoxy-2-(4-methoxyphenyl)-3,4-dihydronaphthalen-1-yl]methanone (0.2 g, 0.52 mmol, prepared according to procedures in *J. Med. Chem.* 1992, 35, 931) in THF (5 mL) was added Intermediate 1 (0.14 g, 1.04 mmol) and triphenylphosphine (0.41 g, 1.55 mmol). The reaction solution was purged with nitrogen atmosphere for 2 min and then diiso-propyl azodicarboxylate (0.31 g, 1.55 mmol) was added dropwise at 0° C. The reaction was stirred at 25° C. for 16 h. The reaction was concentrated under reduced pressure. The residue was purified by preparative TLC (eluted with ethyl acetate) to give the title compound (200 mg, 77%) as a colorless oil.

Step 2: (4-(2-(3-(Fluoromethyl)azetidin-1-yl)ethoxy) phenyl)(6-hydroxy-2-(4-hydroxy phenyl)-3,4-dihydronaphthalen-1-yl)methanone and 11-[4-[2-[3-(fluoromethyl)azetidin-1-yl]ethoxy]phenyl]-11H-benzo[a]fluorene-3,9-diol

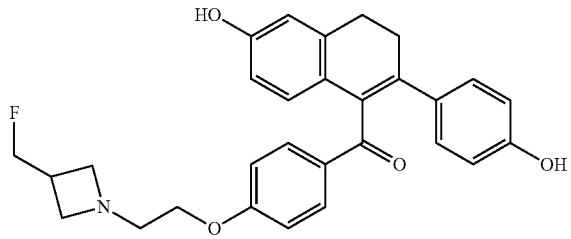 [SMILES: O=C(C1=C(c2ccc(O)cc2)CCc2cc(O)ccc21)c1ccc(OCCN2CC(CF)C2)cc1]

To a solution of [4-[2-[3-(fluoromethyl)azetidin-1-yl]ethoxy]phenyl]-[6-methoxy-2-(4-methoxy phenyl)-3,4-dihydronaphthalen-1-yl]methanone (100 mg, 0.2 mmol) in anhydrous DCM (5 mL) was added tribromoborane (1 M in DCM, 0.6 mL, 0.6 mmol) at −40° C. The resultant mixture was stirred at −40° C. for 5 h. The reaction was quenched with MeOH (2 mL) at −40° C., and concentrated. The residue was purified by reverse-phase HPLC (20-50% acetonitrile/0.2% formic acid in water) to give the crude product which was further purified by silica gel column chromatography (0-10% MeOH in DCM) to provide pure product as a light yellow solid (5.5 mg, 6%), $^1$H NMR (400 MHz, CDCl$_3$): δ 7.78 (d, J=9.2 Hz, 2H), 7.05 (d, J=8.4 Hz, 2H), 6.84 (d, J=8.4 Hz, 2H), 6.70-6.68 (m, 2H), 6.55-6.48 (m, 3H), 4.88 (s, 1H), 4.53 (d, J=5.2 Hz, 1H), 4.42 (d, J=5.6 Hz, 1H), 4.03 (t, J=5.2 Hz, 2H), 3.66-3.56 (m, 4H), 2.96-2.92 (m, 4H), 2.76-2.72 (m, 1H). LCMS: 474.2 [M+H]$^+$.

Example 33 8-(4-(2-(3-(Fluoromethyl)azetidin-1-yl) ethoxy)phenyl)-2,8-dihydro-1H-benzo[2,3]oxepino[4,5-c]chromene-5,11-diol

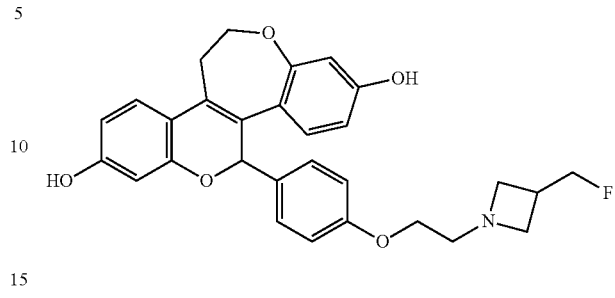

Step 1: 5,11-Bis((tert-butyldimethylsilyl)oxy)-2,8-dihydro-1H-benzo[2,3]oxepino[4,5-c]chromen-8-ol

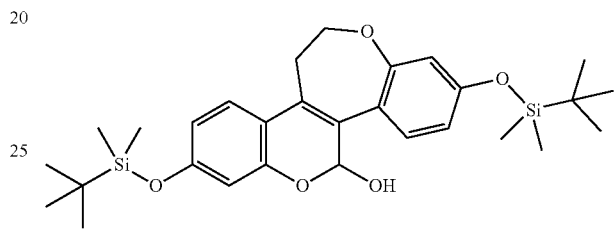

To a solution of 5,11-bis((tert-butyldimethylsilyl)oxy)-1H-benzo[2,3]oxepino[4,5-c]chromen-8(2H)-one (500 mg, 0.95 mmol, prepared according to procedures in *J. Med. Chem.* 2009, 52, 7544) in DCM (5 mL) was added di-isobutylaluminum hydride (1 M in THF, 1.2 mL, 1.2 mmol) dropwise at −20° C. under nitrogen atmosphere. The mixture was stirred at −20° C. for 1.5 h. The reaction was quenched with 40% potassium sodium tartrate aqueous solution (5 mL) and extracted with DCM (20 mL×3). The combined organic layers were washed with 40% potassium sodium tartrate aqueous solution (10 mL) and brine (10 mL), dried over anhydrous Na$_2$SO$_4$, filtered and concentrated under reduced pressure. The residue was purified by silica gel column chromatography (0-3% ethyl acetate in petroleum ether) to give the title compound (90 mg, 18%) as light yellow solid. $^1$H NMR (400 MHz, CDCl$_3$): δ 7.43 (d, J=8.4 Hz, 1H), 7.27 (d, J=8.4 Hz, 1H), 6.67 (d, J=8.4 Hz, 1H), 6.63-6.58 (m, 2H), 6.56 (d, J=8.4 Hz, 1H), 6.07 (d, J=7.6 Hz, 1H), 4.64-4.47 (m, 2H), 3.05 (d, J=7.6 Hz, 1H), 2.98-2.78 (m, 2H), 1.00 (s, 18H), 0.24 (s, 12H).

Step 2: 1-(2-(4-(5,11-Bis((tert-butyldimethylsilyl) oxy)-2,8-dihydro-1H-benzo[2,3]oxepino[4, 5-c] chromen-8-yl)phenoxy)ethyl)-3-(fluoromethyl)azetidine

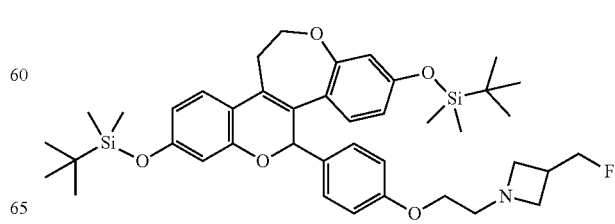

To a solution of 1-[2-(4-bromophenoxy)ethyl]-3-(fluoromethyl)azetidine (263 mg, 0.91 mmol) in tetrahydrofuran (3 mL) was added n-butyllithium in hexane (2.5 M, 0.45 mL, 1.13 mmol) slowly at −78° C. under N$_2$ atmosphere. The mixture was stirred at −78° C. for 30 min. Then a solution of 5,11-bis((tert-butyldimethylsilyl)oxy)-2,8-dihydro-1H-benzo[2,3]oxepino[4,5-c]chromen-8-ol (160 mg, 0.30 mmol) in THF (1 mL) was added slowly. Then the resulting mixture was stirred at −78° C. for 30 min. The reaction mixture was quenched with saturated NH$_4$Cl aqueous solution at −78° C., and then extracted with ethyl acetate (20 mL×2). The combined organic layers were washed with water (5 mL) and brine (5 mL), dried (Na$_2$SO$_4$), and concentrated under reduced pressure to give the title compound (380 mg, 48% purity) as a light yellow oil.

To a solution of the light yellow oil in DCM (3 mL) was added concentrated HCl (0.1 mL, 1.2 mmol) at 16° C., and then the mixture was stirred at 16° C. for 30 minutes. Diluted with DCM (30 mL), the reaction mixture was washed with water (3 mL), NaHCO$_3$ (3 mL) and brine (5 mL), dried (Na$_2$SO$_4$), filtered and concentrated under reduced pressure. The residue was purified by column chromatography on silica gel (0-3% MeOH in DCM) to give the title compound (150 mg, 76%) as light yellow solid. LCMS: 718.4 [M+H]$^+$.

Step 3: 8-(4-(2-(3-(Fluoromethyl)azetidin-1-yl)ethoxy)phenyl)-2,8-dihydro-1H-benzo[2,3]oxepino[4,5-c]chromene-5,11-diol

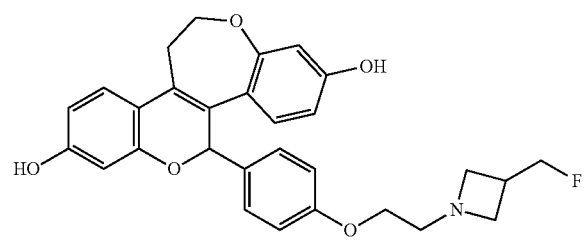 [SMILES: Oc1ccc2c(c1)OC(c1ccc(OCCN3CC(CF)C3)cc1)C1=C2CCOc2cc(O)ccc21]

A solution of 1-(2-(4-(5,11-bis((tert-butyldimethylsilyl)oxy)-2,8-dihydro-1H-benzo[2,3]oxepino [4,5-c]chromen-8-yl)phenoxy)ethyl)-3-(fluoromethyl)azetidine (150 mg, 0.19 mmol) in THF (2 mL) was added tetrabutylammonium fluoride (1 M in THF, 0.6 mL, 0.60 mmol), and the mixture was stirred at 18° C. for 16 h. The reaction mixture was diluted with ethyl acetate (50 mL), the mixture was washed with brine (3 mL×5), dried over anhydrous Na$_2$SO$_4$, and concentrated under reduced pressure. The residue was purified by silica gel column chromatography (eluted with 0-5% MeOH in DCM) followed by reverse phase chromatography (27-57% acetonitrile/0.05% NH$_4$OH in water) to give the title compound (19 mg, 18%) as a light pink solid. $^1$H NMR (400 MHz, CD$_3$OD): δ 7.36 (d, J=8.8 Hz, 2H), 7.15 (d, J=8.4 Hz, 1H), 7.01 (d, J=9.2 Hz, 1H), 6.80 (d, J=8.4 Hz, 2H), 6.49 (s, 1H), 6.48-6.45 (m, 1H), 6.34 (dd, J=8.4, 2.0 Hz, 1H), 6.14 (d, J=2.0 Hz, 1H), 6.03 (s, 1H), 4.65-4.58 (m, 2H), 4.50 (dd, J=47.2, 4.4 Hz, 1H), 4.04 (t, J=4.4 Hz, 2H), 3.93 (t, J=8.4 Hz, 2H), 3.69 (t, J=8.0 Hz, 2H), 3.25-3.17 (m, 2H), 3.09-2.94 (m, 1H), 2.89-2.75 (m, 2H). LCMS: 490.2 [M+H]$^+$.

Example 34 cis-5-(4-(2-(3-(Fluoromethyl)azetidin-1-yl)ethoxy)phenyl)-6-phenyl-5,6,7,8-tetrahydronaphthalen-2-ol

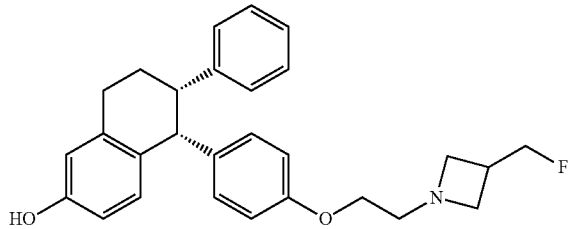 [SMILES: Oc1ccc2c(c1)CC[C@H](c1ccccc1)[C@@H]2c1ccc(OCCN2CC(CF)C2)cc1]

Step 1: 3-(Fluoromethyl)-1-(2-(4-(cis-6-methoxy-2-phenyl-1,2,3,4-tetrahydro naphthalen-1-yl)phenoxy)ethyl)azetidine

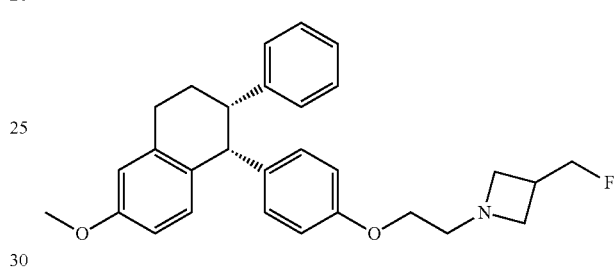

To a solution of 4-(cis-6-methoxy-2-phenyl-tetralin-1-yl)phenol (75.0 mg, 0.23 mmol, prepared according to procedures in *J. Med Chem.* 1969, 12, 881) in toluene (5 mL) was added Intermediate 1 (60 mg, 0.45 mmol) and triphenylphosphine (179 mg, 0.68 mmol). The reaction mixture was purged with nitrogen atmosphere for 2 min and then diisopropyl azodicarboxylate (138 mg, 0.68 mmol) was added dropwise at 0° C. The reaction was stirred at 100° C. for 16 h. After cooling to room temperature, the mixture was concentrated under reduced pressure. The residue was purified by silica gel column chromatography (eluted with 0-10% MeOH in DCM) to give the title compound (a mixture of cis-enantiomers, 64 mg, 63%) as a yellow oil. LCMS: 446.1 [M+H]$^+$.

Step 2: cis-5-(4-(2-(3-(Fluoromethyl)azetidin-1-yl)ethoxy)phenyl)-6-phenyl-5,6,7,8-tetrahydronaphthalen-2-ol

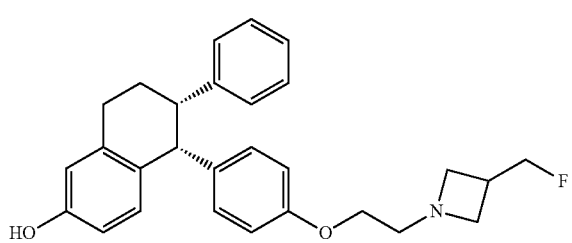 [SMILES: Oc1ccc2c(c1)CC[C@H](c1ccccc1)[C@@H]2c1ccc(OCCN2CC(CF)C2)cc1]

To a solution of 3-(fluoromethyl)-1-[2-[4-[(1R,2S)-6-methoxy-2-phenyl-tetralin-1-yl]phenoxy]ethyl]azetidine (a mixture of cis-enantiomers, 40.0 mg, 0.090 mmol) in DCM (3 mL) was added boron tribromide (1M in DCM, 0.18 mL, 0.18 mmol) dropwise at −40° C. The reaction was stirred at −40° C. for 5 h. The reaction was quenched with saturated aqueous sodium bicarbonate (5 mL) and extracted with dichloromethane (5 mL×2). The organic layers were dried over anhydrous Na₂SO₄, filtered and concentrated under reduced pressure. The residue was purified by reverse-phase HPLC (acetonitrile 50-80%/0.1% NH₄HCO₃ in water) to give the title compound (a mixture of cis-enantiomers, 2.7 mg, 4%) as a white solid. $^1$H NMR (400 MHz, DMSO-d₆): δ 7.19-7.10 (m, 3H), 6.80 (d, J=7.6 Hz, 2H), 6.70-6.65 (m, 2H), 6.52 (d, J=8.4 Hz, 3H), 6.31 (d, J=8.4 Hz, 2H), 4.53 (d, J=5.2 Hz, 1H), 4.42 (d, J=5.6 Hz, 1H), 4.20 (d, J=5.2 Hz, 1H), 3.89 (t, J=5.2 Hz, 2H), 3.58 (t, J=8.0 Hz, 2H), 3.28-3.25 (m, 3H), 3.03-2.87 (m, 5H), 2.26-2.18 (m, 1H), 1.77-1.75 (m, 1H). LCMS: 431.9 [M+H]⁺.

Example 72 [3-(2-Chloro-phenyl)-5-(4-hydroxy-phenyl)-isothiazol-4-yl]-{3-fluoro-4-[2-(3-fluoromethyl-azetidin-1-yl)-ethoxy]-phenyl}-methanone Step 1: 3-(2-Chloro-phenyl)-5-(4-methoxy-phenyl)-isoxazole-4-carboxylic acid methyl ester

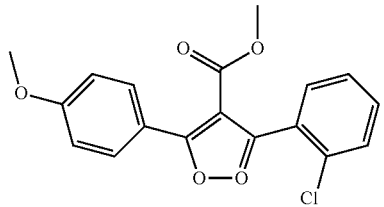

To a mixture of (4-methoxy-phenyl)-propynoic acid methyl ester (1.00 g, 5.26 mmol) and 2-chlorobenzohydroximinoyl chloride (666 mg, 3.51 mmol) in diethyl ether (18 mL) at 0° C. was added a solution of triethylamine (586 μL, 4.21 mmol) in diethyl ether (3 mL) portionwise over 1 h. The resultant mixture was allowed to warm to RT and stirred for 18 h then quenched by the addition of H₂O. The reaction mixture was extracted with diethyl ether (×3). The combined organic layer was washed with brine, dried (Na₂SO₄) and concentrated under reduced pressure. The crude material was purified by silica gel column chromatography, eluting with 0%-20% EtOAc in cyclohexane to afford the title compound as an off white solid (663 mg, 55%). LCMS [M+H]⁺=344.2, RT=4.05 min.

Step 2: 3-(2-Chloro-phenyl)-5-(4-methoxy-phenyl)-isothiazole-4-carboxylic acid methyl ester

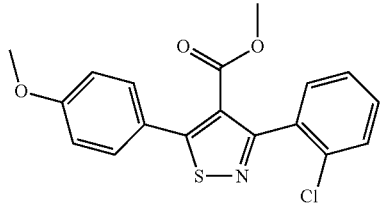

A suspension of platinum oxide (101 mg, 0.46 mmol) in IMS (4 mL) was stirred for 5 min under an atmosphere of hydrogen. The vessel was evacuated and refilled with nitrogen (×3) before the addition of a suspension of 3-(2-chloro-phenyl)-5-(4-methoxy-phenyl)-isoxazole-4-carboxylic acid methyl ester (766 mg, 2.22 mmol) in IMS (16 mL). The vessel was evacuated and refilled with hydrogen (×3) and the resultant mixture was stirred at RT for 4 h. The black reaction mixture was filtered through a pad of celite and the filtrate concentrated under reduced pressure. The resultant residue was taken up into THF (20 mL) then treated with P₂S₅ (1.48 g, 6.66 mmol), sodium bircarbonate (410 mg, 4.88 mmol) and p-chloranil (1.20 g, 4.88 mmol). The reaction mixture was stirred for 65 h then quenched with H₂O and extracted with EtOAc (×3). The combined organic layer was dried (Na₂SO₄) and concentrated under reduced pressure. The crude material was purified by silica gel column chromatography, eluting with 0%-80% EtOAc in cyclohexane to afford the title compound as an oily white solid (298 mg, 37%). LCMS [M+H]-=360.1, RT=4.11 min.

Step 3: 3-(2-Chloro-phenyl)-5-(4-methoxy-phenyl)-isothiazole-4-carboxylic acid

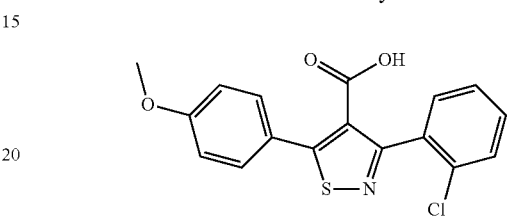

A mixture of 3-(2-chloro-phenyl)-5-(4-methoxy-phenyl)-isothiazole-4-carboxylic acid methyl ester (298 mg, 0.83 mmol), 2N aqueous LiOH solution (2.07 mL, 4.14 mmol), MeOH (5 mL), THF (5 mL) and H₂O (2 mL) was heated at 50° C. for 18 h. Further 2N LiOH (2.07 mL, 4.14 mmol) and MeOH (2 mL) were added to the reaction and the mixture heated at 50° C. for 20 h. The reaction was allowed to cool to RT, acidified with 1M HCl and extracted with EtOAc (×3). The combined organic layer was washed with brine, dried (Na₂SO₄) and concentrated under reduced pressure. The crude material was purified by silica gel column chromatography, eluting with 0%-8% MeOH in DCM to afford the title compound as an off white solid (173 mg, 60%). LCMS [M+H]⁺=345.9, RT=3.45 min.

Step 4: [3-(2-Chloro-phenyl)-5-(4-methoxy-phenyl)-isothiazol-4-yl]-(3,4-difluoro-phenyl)-methanone

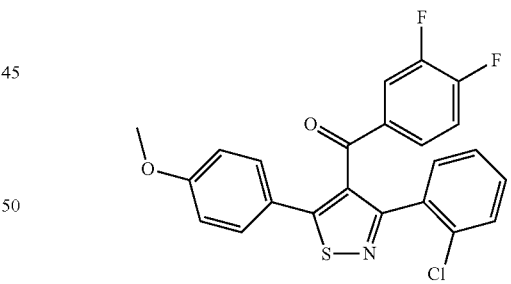

To a solution of 3-(2-chloro-phenyl)-5-(4-methoxy-phenyl)-isothiazole-4-carboxylic acid (860 mg, 2.49 mmol) in DCM (50 mL) was added oxalyl chloride (842 μL, 9.96 mmol). The mixture was placed in a water bath before the addition of DMF (1 drop). The reaction was stirred at RT for 4.5 h then concentrated in vacuo. The resultant residue was dissolved in THF (20 mL) and cooled to −78° C. To the solution was added 3,4-difluorophenylmagnesium bromide (24.9 mL, 12.45 mmol, 0.5M solution in THF) dropwise. On complete addition the reaction mixture was allowed to slowly warm to RT and stirred for 6 h. The reaction was cooled on an ice bath and quenched with H₂O, warmed to RT and acidified with 2M HCl. The mixture was extracted with EtOAc (×3). The combined organic layer was washed with brine, dried (Na₂SO₄) and concentrated in vacuo. The resultant residue was purified by silica gel column chromatography eluting with 0%-20% EtOAc in cyclohexane. This gave the title compound as a yellow glass (589 mg, 54%). LCMS [M+H]⁺=441.8, RT=4.27 min.

Step 5: [3-(2-Chloro-phenyl)-5-(4-hydroxy-phenyl)-isothiazol-4-yl]-(3,4-difluoro-phenyl)-methanone

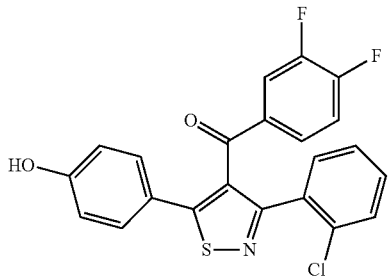

To a solution of [3-(2-chloro-phenyl)-5-(4-methoxy-phenyl)-isothiazol-4-yl]-(3,4-difluoro-phenyl)-methanone (589 mg, 1.33 mmol) in DCM at −78° C. was added BBr₃ (1M solution in DCM, 13.33 mL, 13.33 mmol). The reaction was stirred at −78° C. for 15 min, allowed to warm to RT and stirred for 20 h. The reaction was cooled on an ice bath before and quenched with H₂O then warmed to RT. The mixture was diluted with DCM/H₂O and the phases separated. The aqueous phase was extracted with DCM (×2) and the combined organic layer washed with H₂O and passed through a phase separator. The organic layer was dried (Na₂SO₄) and concentrated in vacuo. The resultant residue was purified by silica gel column chromatography eluting with 0%-40% EtOAc in cyclohexane. This gave the title compound as a pale yellow solid (371 mg, 65%). LCMS [M+H]⁺=427.8, RT=3.88 min.

Step 6: {3-(2-Chloro-phenyl)-5-[4-(tetrahydro-pyran-2-yloxy)-phenyl]-isothiazol-4-yl}-(3,4-difluoro-phenyl)-methanone

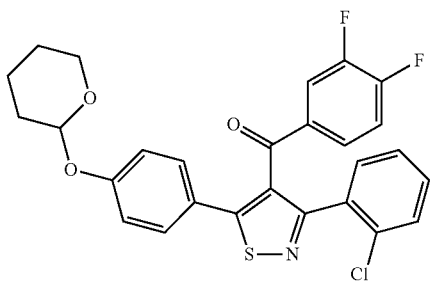

A mixture of [3-(2-chloro-phenyl)-5-(4-hydroxy-phenyl)-isothiazol-4-yl]-(3,4-difluoro-phenyl)-methanone (371 mg, 0.87 mmol), 3,4-dihydro-2H-pyran (318 μL, 3.48 mmol), pyridinium p-toluenesulfonate (22 mg, 0.09 mmol) in DCM (10 mL) was stirred at RT for 4 h. The reaction was diluted with H₂O then extracted with DCM (×3), the combined organic layer was dried (Na₂SO₄) and concentrated in vacuo. The resultant residue was purified by silica gel column chromatography eluting with 0%-20% EtOAc in cyclohexane. This gave the title compound as a colourless glass (364 mg, 82%). LCMS [M+H]⁺=511.9, RT=4.63 min.

Step 7: {3-(2-Chloro-phenyl)-5-[4-(tetrahydro-pyran-2-yloxy)-phenyl]-isothiazol-4-yl}-{3-fluoro-4-[2-(3-fluoromethyl-azetidin-1-yl)-ethoxy]-phenyl}-methanone

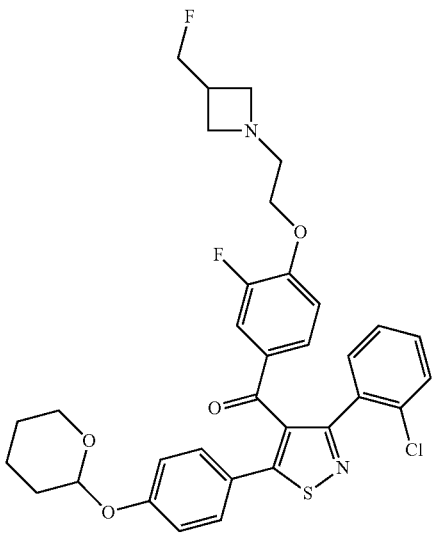 [SMILES: O=C(c1ccc(OCCN2CC(CF)C2)c(F)c1)c1c(-c2ccccc2Cl)nsc1-c1ccc(OC2CCCCO2)cc1]

A mixture of {3-(2-chloro-phenyl)-5-[4-(tetrahydro-pyran-2-yloxy)-phenyl]-isothiazol-4-yl}-(3,4-difluoro-phenyl)-methanone (364 mg, 0.71 mmol), 2-(3-fluoromethyl-azetidin-1-yl)-ethanol (142 mg, 1.07 mmol) and cesium carbonate (1.62 g, 4.98 mmol) in acetonitrile (15 mL) was heated under reflux for 20 h. The reaction was cooled to RT, diluted with H₂O and extracted with EtOAc (×2). The combined organic layer was washed with brine, dried (Na₂SO₄) and concentrated in vacuo. The resultant residue was purified by silica gel column chromatography eluting with 0%-10% MeOH in DCM. This gave the title compound as an amber gum (327 mg, 74%). LCMS [M+H]⁺=628.0, RT=2.76 min.

Step 8: [3-(2-Chloro-phenyl)-5-(4-hydroxy-phenyl)-isothiazol-4-yl]-{3-fluoro-4-[2-(3-fluoromethyl-azetidin-1-yl)-ethoxy]-phenyl}-methanone A solution of {3-(2-chloro-phenyl)-5-[4-(tetrahydro-pyran-2-yloxy)-phenyl]-isothiazol-4-yl}-{3-fluoro-4-[2-(3-fluoromethyl-azetidin-1-yl)-ethoxy]-phenyl}-methanone (327 mg, 0.52 mmol), acetic acid (20 mL), acetonitrile (12 mL) and H₂O (7 mL) were stirred at RT for 18 h. The mixture was diluted with brine then extracted with EtOAc (×2). The combined organic layer was washed with saturated NaHCO₃ solution, dried (Na₂SO₄) and concentrated in vacuo. The resultant residue was purified by silica gel column chromatography eluting with 0%-8% MeOH in DCM. The resultant residue was triturated with Et₂O then recrystallized from EtOAc. This gave the title compound as a white solid (48 mg, 17%). LCMS [M+H]⁺=541.2, RT=3.54 min. ¹H NMR (400 MHz, CDCl₃): δ 7.51-7.43 (m, 1H), 7.39 (dd, 1H, J=2.1, 11.5 Hz), 7.35-7.27 (m, 4H), 7.17-7.11 (m, 2H), 6.69-6.59 (m, 3H), 4.55 (d, 1H, J=5.4 Hz), 4.43 (d, 1H, J=5.4 Hz), 4.02 (t, 2H, J=5.4 Hz), 3.57 (t, 2H, J=7.6 Hz), 3.26 (t, 2H, J=7.3 Hz), 2.97-2.80 (m, 3H).

Example 82: 5-[(E)-2-(2-chloro-4-fluoro-phenyl)-1-[4-[2-[3-(fluoromethyl)azetidin-1-yl]ethoxy]phenyl]but-1-enyl]-1H-indazole Step 1: (Z)-5-(1-(4-(2-(3-(Fluoromethyl)azetidin-1-yl)ethoxy)phenyl)-2-(4,4,5,5-tetramethyl-1,3,2-dioxaborolan-2-yl)but-1-en-1-yl)-1-(tetrahydro-2H-pyran-2-yl)-1H-indazole and (E)-5-(2-(4-(2-(3-(fluoromethyl)azetidin-1-yl)ethoxy)phenyl)-1-(4,4,5,5-tetramethyl-1,3,2-dioxaborolan-2-yl)but-1-en-1-yl)-1-(tetrahydro-2H-pyran-2-yl)-1H-indazole

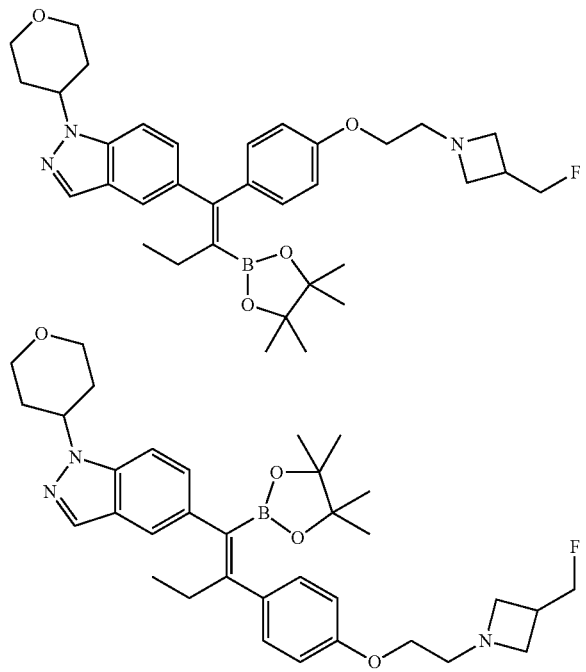

A mixture of 5-[(Z)-1,2-bis(4,4,5,5-tetramethyl-1,3,2-dioxaborolan-2-yl)but-1-enyl]-1-tetrahydropyran-2-yl-indazole (Intermediate 28 in *J. Med. Chem.* 2015, 58, 4888-4904, 2.0 g, 3.93 mmol), $K_3PO_4$ (2.5 g, 11.8 mmol), 1-[2-(4-bromophenoxy)ethyl]-3-(fluoromethyl)azetidine (1134 mg, 3.93 mmol), $Pd(PPh_3)_2Cl_2$ (276 mg, 0.39 mmol) in dioxane (20 mL) and water (1 mL) was stirred vigorously at 50° C. under $N_2$ for 16 hours. The reaction mixture was directly carried over to the next step without purification.

Step 2: (E)-5-(2-(2-Chloro-4-fluorophenyl)-1-(4-(2-(3-(fluoromethyl)azetidin-1-yl)ethoxy)phenyl)but-1-en-1-yl)-1-(tetrahydro-2H-pyran-2-yl)-1H-indazole and (Z)-5-(1-(2-chloro-4-fluorophenyl)-2-(4-(2-(3-(fluoromethyl)azetidin-1-yl)ethoxy)phenyl)but-1-en-1-yl)-1-(tetrahydro-2H-pyran-2-yl)-1H-indazole

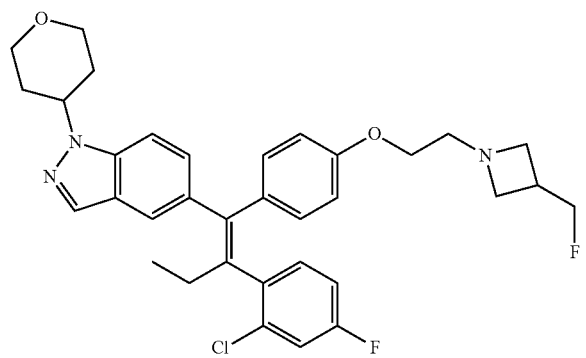

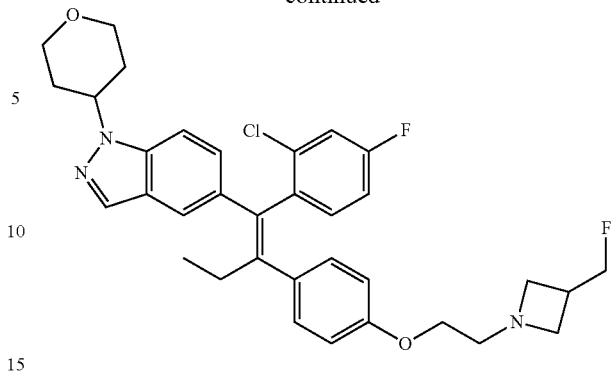

To a mixture of (Z)-5-(1-(4-(2-(3-(fluoromethyl)azetidin-1-yl)ethoxy)phenyl)-2-(4,4,5,5-tetramethyl-1,3,2-dioxaborolan-2-yl)but-1-en-1-yl)-1-(tetrahydro-2H-pyran-2-yl)-1H-indazole and (E)-5-(2-(4-(2-(3-(fluoromethyl)azetidin-1-yl)ethoxy)phenyl)-1-(4,4,5,5-tetramethyl-1,3,2-dioxaborolan-2-yl)but-1-en-1-yl)-1-(tetrahydro-2H-pyran-2-yl)-1H-indazole in dioxane (From step 1) was added KOH (656 mg, 11.7 mmol), $Pd(PPh_3)_2Cl_2$ (274 mg, 0.39 mmol) and 2-chloro-4-fluoroiodobenzene (1.1 g, 4.29 mmol). The resulting mixture was stirred at 80° C. under $N_2$ atmosphere for 16 hours. The reaction mixture was concentrated and purified with silica gel column (0-10% MeOH in DCM) to afford a mixture of (E)-5-(2-(2-chloro-4-fluorophenyl)-1-(4-(2-(3-(fluoromethyl)azetidin-1-yl)ethoxy)phenyl)but-1-en-1-yl)-1-(tetrahydro-2H-pyran-2-yl)-1H-indazole and (Z)-5-(1-(2-chloro-4-fluorophenyl)-2-(4-(2-(3-(fluoromethyl)azetidin-1-yl)ethoxy)phenyl)but-1-en-1-yl)-1-(tetrahydro-2H-pyran-2-yl)-1H-indazole (1.6 g, 70% isolated yield, 2 isomers 1:1) as light yellow oil.

Step 3: (E)-5-(2-(2-Chloro-4-fluorophenyl)-1-(4-(2-(3-(fluoromethyl)azetidin-1-yl)ethoxy)phenyl)but-1-en-1-yl)-1H-indazole

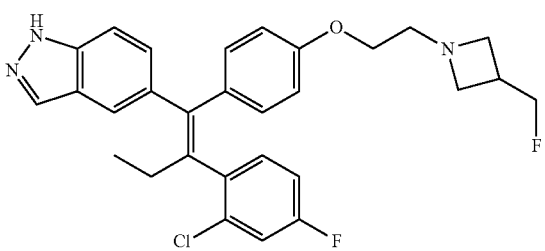 [SMILES: CC/C(=C(/c1ccc(OCCN2CC(CF)C2)cc1)c1ccc2[nH]ncc2c1)c1ccc(F)cc1Cl]

To a mixture of (E)-5-(2-(2-chloro-4-fluorophenyl)-1-(4-(2-(3-(fluoromethyl)azetidin-1-yl)ethoxy)phenyl)but-1-en-1-yl)-1-(tetrahydro-2H-pyran-2-yl)-1H-indazole and (Z)-5-(1-(2-chloro-4-fluorophenyl)-2-(4-(2-(3-(fluoromethyl)azetidin-1-yl)ethoxy)phenyl)but-1-en-1-yl)-1-(tetrahydro-2H-pyran-2-yl)-1H-indazole (From step 2) in methanol (10 mL) was added 4 M HCl in dioxane (10 mL, 40 mmol). The mixture was stirred at 10° C. for 3 hours. The reaction mixture was concentrated and was purified with reverse phase chromatography (acetonitrile 25-55%/0.25% formic acid in water) and followed by further reverse phase chromatography (acetonitrile 65-95%/0.1% $NH_4OH$ in water) to afford (E)-5-(2-(2-chloro-4-fluorophenyl)-1-(4-(2-(3-(fluoromethyl)azetidin-1-yl)ethoxy)phenyl)but-1-en-1-yl)-1H-indazole (270 mg, 39%) as off-white solid. LCMS: 508.2 $[M+H]^+$. $^1H$ NMR (400 MHz, DMSO-$d_6$) δ 13.10 (s, 1H), 8.09 (s, 1H), 7.65 (s, 1H), 7.53 (d, J=8.4 Hz, 1H), 7.38-7.27

(m, 2H), 7.20-7.08 (m, 2H), 6.81 (d, J=8.4 Hz, 2H), 6.59 (d, J=8.4 Hz, 2H), 4.56-4.38 (m, 2H), 3.75 (t, J=5.6 Hz, 2H), 3.25 (t, J=7.2 Hz, 2H), 2.93 (t, J=6.4 Hz, 2H), 2.75-2.59 (m, 3H), 2.35 (q, J=7.2 Hz, 2H), 0.89 (t, J=7.2 Hz, 3H).

Example 901: Breast Cancer Cell ERa High Content Fluorescence Imaging Assay (F10)

MCF7 breast cancer cells were seeded on day 1 at a density of 10,000 cells per well in 384 well poly-lysine coated tissue culture plate (Greiner #T-3101-4), in 50 ul/well RPMI (phenol red free), 10% FBS (Charcoal stripped), containing L-glutamine. On day-2, compounds were prepared at 2 compound source concentrations: 100 uM and 1 uM (ultimately to give 2 overlapping titration curves), in a Labcyte low dead volume plate, 10 ul/well, and 10 ul of DMSO in designated wells for backfill, and 5 uM Fulvestrant (control compound) in designated wells. Compounds and controls were dispensed using a Labcyte Echo acoustic dispenser to dispense compounds with a pre-defined serial dilution (1.8×, 10 point, in duplicate) and appropriate backfill and control compounds (final total volume transferred was 417.5 nl and compound dispense volume ranges from 2.5 nl to 417.5 nl; 0.84% DMSO (v/v) final), ultimately producing a concentration range from 0.05 nM to 835 nM. Cell plates were incubated at 37° C., for 4 hours. Fixation and permeabilization were carried out using a Biotek EL406 plate washer and dispenser as follows. Cells were fixed by addition of 15 ul of 16% paraformaldehyde (Electron Microscopy Sciences #15710-S) directly to the 50 ul cell culture medium in each well using the peristaltic pump 5 ul cassette on a Biotek EL406 (final concentration of formaldehyde was 3.7% w/v). Samples were incubated 30 minutes. Well contents was aspirated and 50 ul/well of Phosphate Buffered Saline (PBS) containing 0.5% w/v bovine serum albumen, 0.5% v/v Triton X-100 (Antibody Dilution Buffer) was added to each well. Samples were incubated for 30 minutes. Well contents were aspirated and washed 3 times with 100 ul/well of PBS. Immunofluorescence staining of estrogen receptor alpha (ESR1) was carried out using a Biotek EL406 plate washer and dispenser as follows. The well supernatant was aspirated from the wells and 25 ul/well of anti-ESR1 mAb (F10) (Santa Cruz sc-8002) diluted 1:1000 in Antibody Dilution Buffer was dispensed. Samples were incubated for 2 hours at room temperature. Samples were washed 4 times with 100 ul/well of PBS. 25 ul/well of secondary antibody solution (Alexafluor 488 conjugate anti-mouse IgG (LifeTechnologies #A21202) diluted 1:1000 and Hoechst 33342 1 ug/ml diluted in Antibody Dilution Buffer) were dispensed into each well. Samples were incubated for 2 hours at room temperature. Samples were washed 3 times with 100 ul/well of PBS using a Biotek EL406. Quantitative fluorescence imaging of ESR1 was carried out using a Cellomics Arrayscan V (Thermo). Fluorescence images of the samples (Channel 1: XF53 Hoechst (DNA stain); Channel 2: XF53 FITC (ESR1 stain)) were acquired using a Cellomics VTI Arrayscan using the Bioapplication "Compartmental Analysis" using the auto-exposure (based on DMSO control wells) setting "peak target percentile" set to 25% target saturation for both channels. Channel 1 (DNA stain) was used to define the nuclear region (Circ). Measurements of "Mean_CircAvgIntCh2", which is the Alexafluor 488 fluorescence intensity (ESR1) within the nuclear region, was measured on a per cell basis and averaged over all the measured cells. Data analysis was carried out using Genedata Screener Software, with DMSO and 5 nM Fulvestrant treated samples being used to define the 0% and 100% changes in ESR1. The "Robust Fit" method was used to define the inflexion point of curve (EC50) and the plateau of the maximal effect (Sin f).

Illustrative biological data for representative compounds from Tables 1a and 1b are presented in Tables 2a and 2b, respectively:

TABLE 2a

| Example | ER-alpha MCF7 HCS $EC_{50}$ (µM) | ER-alpha MCF7 HCS $S_{inf}$ (%) |
|---|---|---|
| 1 | 0.00046 | −95 |
| 2 | 0.0016 | −93 |
| 3 | 0.0055 | −92 |
| 4 | 0.2 | −81 |
| 5 | 0.065 | −93 |
| 6 | 0.55 | −50 |
| 7 | 0.0016 | −95 |
| 8 | 0.00027 | −95 |
| 9 | 0.0011 | −97 |
| 10 | 0.00045 | −96 |
| 11 | 0.00013 | −94 |
| 12 | 0.31 | −50 |
| 13 | 0.0075 | −55 |
| 14 | 0.00021 | −99 |
| 15 | 0.0023 | −84 |
| 16 | <0.0000004 | −99.2 |
| 17 | 0.0003 | −102 |
| 18 | 0.012 | −89 |
| 19 | 0.015 | −75 |
| 20 | 0.024 | −73 |
| 21 | 0.011 | −97 |
| 22 | 0.00058 | −83 |
| 23 | 0.00059 | −95 |
| 24 | 0.00018 | −58 |
| 25 | 0.0015 | −92 |
| 26 | 0.0006 | −75 |
| 27 | 0.00085 | −73 |
| 28 | 0.001 | −97 |
| 29 | 0.00055 | −101 |
| 30 | 0.0011 | −99 |
| 31 | 0.0011 | −97 |
| 32 | 0.00019 | −101 |
| 33 | 0.000073 | −98 |
| 34 | 0.000016 | −99.3 |
| 35 | 0.00055 | −98 |
| 36 | 0.0025 | −97 |
| 37 | 0.0044 | −97 |
| 38 | 0.00088 | −96 |
| 39 | 0.0016 | −96 |
| 40 | 0.00062 | −93 |

TABLE 2b

| Example | ER-alpha MCF7 HCS $EC_{50}$ (uM) | ER-alpha MCF7 HCS $S_{inf}$ (%) |
|---|---|---|
| 41 | 0.0000518 | −97.8 |
| 42 | 0.000025 | −97.5 |
| 43 | 0.0000179 | −96.0 |
| 44 | 0.0000278 | −98.1 |
| 45 | 0.00000632 | −97.5 |
| 46 | 0.000030 | −97.8 |
| 47 | 0.000115 | −94.1 |
| 48 | 0.000662 | −92.8 |
| 49 | 0.000187 | −95.6 |
| 50 | 0.0000581 | −97.9 |
| 51 | 0.0000405 | −97.1 |
| 52 | 0.0000583 | −95.8 |
| 53 | 0.0000666 | −92.6 |
| 54 | 0.0000666 | −92.6 |
| 55 | 0.0000199 | −98.7 |
| 56 | 0.0000285 | −95.6 |
| 57 | 0.0000469 | −93.4 |
| 58 | 0.000026 | −99.8 |
| 59 | 0.000026 | −99.8 |
| 60 | 0.0158 | −91.9 |

TABLE 2b-continued

| Example | ER-alpha MCF7 HCS EC$_{50}$ (uM) | ER-alpha MCF7 HCS S$_{inf}$ (%) |
|---|---|---|
| 61 | 0.0158 | −91.9 |
| 62 | 0.000005 | −96.7 |
| 63 | 0.0000050 | −96.7 |
| 64 | 0.000045 | −101 |
| 65 | 0.000045 | −101 |
| 66 | 0.0000060 | −93.4 |
| 67 | 0.000414 | −97.6 |
| 68 | 0.000006 | −92.8 |
| 69 | 0.0000060 | −92.8 |
| 70 | 0.000079 | −96.2 |
| 71 | 0.000079 | −96.2 |
| 72 | 0.0000159 | −99.0 |
| 73 | 0.000123 | −97.6 |
| 74 | 0.00019 | −93.3 |
| 75 | 0.0032 | −99.7 |
| 76 | 0.000091 | −101 |
| 77 | 0.00959 | −84.5 |
| 78 | 0.000611 | −90.0 |
| 79 | 0.000072 | −89.6 |
| 80 | 0.0000196 | −98.3 |
| 81 | 0.0000219 | −99.5 |
| 82 | 0.0000225 | −96.9 |

Example 902: ERα Co-Activator Assay (PGC1a)

ERα Co-activator Peptide Antagonist Assay: Test compounds were prepared at 1 mM in dimethylsulfoxide and serially diluted in a 12 point, 1 to 3-fold titration using a Biomek FX in 384 well clear V-bottom polypropylene plates (Greiner cat #781280). A 3× compound intermediate dilution was prepared by mixing 1 μl of each concentration of the compound serial dilution with 32.3 μl of TR-FRET Coregulator Buffer E (Life Technologies PV4540). 2 μl of the 3× compound intermediate dilution was transferred to a 1536-well (Aurora Biotechnologies MaKO 1536 Black Plate, #00028905) using a Biomek FX. A Beckman Coulter Bioraptr Dispenser was used to dispense: 2 μl per well of "3×ERα solution": 22 nM ERα (human estrogen receptor alpha, GST-tagged ESR1 ligand binding domain, spanning residues S282-V595, either wildtype sequence or containing the mutations: Y537S or D538G) in TR-FRET Coregulator Buffer E containing 7.5 mM dithiothreitol (DTT); and 2 μl of 3× Assay mix (750 nM Fluorescein-PGC1a peptide (sequence: EAEEPSLLKKLLLAPANTQ; Life Technologies PV4421), 12 nM Estradiol, 15 nM Anti-GST Tb-labeled antibody in TR-FRET Coregulator Buffer E (with 7.5 mM DTT). "No receptor" control wells received buffer without GST-ERα protein. Plates were centrifuged at 1800 rpm for 20 seconds in V-spin centrifuge and incubated for 2 hours at room temperature with the plates covered. Measurements were made using a Perkin Elmer EnVision Fluorescence Reader using TR-FRET setting (Top mirror: Perkin Elmer Lance/DELFIA Dual emission (PE #2100-4160); Excitation filter: Perkin Elmer UV (TFR) 340 nm (PE #2100-5010); Emission filtes: Chroma 495 nm/10 nm and 520 nm/25 nm (Chroma#PV003 filters for LanthaScreen, 25 mm diameter for EnVision;) Excitation light: 100%; Delay: 100 us; Window time: 200; Numer of sequential windows: 1; Time between flashes:2000 us; Number of flashes: 100; Number of flashes (2$^{nd}$ detector): 100). Percentage inhibition values were calculated relative to no compound (dimethylsulfoxide only) controls and a "no ERα controls". Curve fitting and IC50 calculations were carried out using Genedata Screener software.

Example 903: Ishikawa Uterine Cell Alkaline Phosphatase Assay

Subconfluent Ishikawa cells in a T225 are incubated 24 hours in an estrogen free basal medium (EFBM) consisting of DMEM:Ham's F-12 50:50 phenol red free basal medium containing 5% Charcoal Dextran treated FBS and 20 mM HEPES. Cells are plated the following day in EFBM in clear 384 well plates at a concentration of 2.5×105 cells per mL, 16 μL per well (4000 cells per well). A 12 point semilog dilution of each compound is carried out in DMSO and subsequently diluted in EFBM. An equal volume of compound in EFBM is added immediately after plating cells, and the cells are incubated for 3 days. The cells are fixed with 5% formalin, and rinsed with PBS. Alkaline Phosphatase substrate 4-Nitrophenyl phosphate disodium salt hexahydrate is added (1 mg/mL final concentration) to a solution containing 2 mM MgCl$_2$, 1 M diethanolamine, and adjusted to pH 9.0. The substrate solution is added to the cell cultures (16 μL per well), and OD405 is measured in a multiwall plate spectrophotometer when the optical density at 405 nm wavelength of cells treated with 17β-estradiol in the concentration range of 1-30 nM reaches 1.0-1.2 absorbance units. Cells treated with DMSO alone serve as a background control. Percent activity in background subtracted samples is measured as follows: % activity=OD405 sample/OD405 max of 17β-estradiol treated cells×100.

Example 904: Ovarian Cancer Cell Viability Assays

BG-1 cells are diluted in RPMI containing 10% FBS and 20 mM HEPES. 16 microliters of the cell suspension is added to each well of a 384 well plate, and the cells are incubated overnight. The following day an eleven point, serial semilog dilution of each compound is added to the cells in 16 μL at a final concentration ranging from 0.3-0.000003 μM. After 5 to 7 days' compound exposure, 16 μL of CellTiter-GLo (Promega, Madison Wis.) is added to the cells, and the relative luminescence units (RLUs) of each well is determined. CellTiter-Glo added to 32 μL of medium without cells is used to obtain a background value. The Percent viability of each sample is determined as follows: (RLU sample-RLU background/RLU untreated cells-RLU background)×100=% viability.

Viability effects in additional ER+ ovarian cancer cell lines, including A1847, SKOV3, SW626, A2780, can be profiled in assays similar to Example 38.

Example 905: Ovarian Cancer Cell ER-α in Cell Western Assay

BG-1 cells are diluted in RPMI containing 10% charcoal-stripped FBS and 20 mM HEPES. 16 microliters of the cell suspension is added to each well of a poly-D-lysine 384 well plate, and the cells are incubated overnight. The following day an eleven point, serial semilog dilution of each compound is added to the cells in 16 μL at a final concentration ranging from 0.3-0.000003 M. At 4 or 24 hr post compound addition, the cells are fixed (10% formalin in PBS) for 20 minutes. Following fixation the cells are permeablized in PBS 0.1% Triton and blocked with LICOR blocking buffer (50 μl/well, 90'). The wells are then incubated overnight at 4° C. with SP1 rabbit monoclonal Ab (Thermo Scientific) diluted 1:1000 in LICOR blocking buffer/0.1% Tween-20. Wells treated with blocking buffer with Tween but no antibody are used as a background control. All wells are washed with 0.1% Tween-20/PBS and then incubated in goat anti-mouse IRDye™ 800 CW (LICOR Inc.; 1:10000) and DRAQ5 DNA dye (1:2000 for 2 mM stock) diluted in LICOR blocking buffer containing 0.1% Tween-20 and 0.01% SDS for 60 minutes. Cells are then washed (50 µL/well, 5' each) in 0.1% Tween-20/PBS. Plates are scanned on a LICOR Odyssey infrared imaging system. Integrated intensities in the 800 nm channel and 700 nm channel are measured to determine levels of ER and DNA respectively. Percent ER levels are determined as follows:

(Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ ovarian cancer cell lines, including A1847, SKOV3, SW626, A2780, can be profiled in assays similar to Example 39.

Other cancer cell lines contemplated for testing compounds described herein include: ER-positive endometrial cell lines (Ishikawa, ECC1, HEC-1, EnCa-101) and ER-positive cervical cell lines (Caski, HeLa, SiHa).

Example 906: PEO Cell Viability Assays

PEO-1, PEO-4 and PEO-6 ovarian cancer cell lines were adjusted to a concentration of 20,000 cells per mL in RPMI containing 10% FBS. 16 microliters of the cell suspension (320 cells) was added to each well of a 384 well plate, and the cells were incubated overnight to allow the cells to adhere. The following day a 10 point, serial 1:5 dilution of each compound was added to the cells in 16 µL at a final concentration ranging from 1-0.0000005 M. After 7 days' compound exposure, 16 µL of CellTiter-GLo (Promega, Madison Wis.) was added to the cells, and the relative luminescence units (RLUs) of each well was determined. CellTiter-Glo added to 32 µL of medium without cells was used to obtain a background value. The Percent viability of each sample was determined as follows: (RLU sample-RLU background/RLU untreated cells-RLU background)×100=% viability.

Example 907: PEO ER Western Analysis

Cells were plated in RPMI 5% CSS for 48 hours, then treated with compound for 4 or 24 hours. Cells were lysed in modified radioimmunoprecipitation buffer (mRIPA; 10 mM Tris, 150 mM NaCl, 1% (v/v) NP-40, 0.5% deoxycholate, 0.1% SDS, 5 mM EDTA, pH 7.4) containing Halt Protease & Phosphatase Single-Use Inhibitor Cocktail (Thermo Scientific, Cat. No. 78442). Total protein of the clarified lysates was quantitated by Lowry Assay (Biorad DC protein assay). NuPAGE® LDS Sample Buffer and Sample Reducing Agent were added to the lysates and heated to 70° C. for 10 mins. 15 ug of total cell protein was separated electrophoretically in a NuPAGE 4-12% Bis Tris Gel in MOPS SDS running buffer, then transferred to a nitrocellulose membrane in transfer buffer using an XCell II blot module. Membranes were incubated in Blocking Buffer (LI-COR, Lincoln, Nebr.) for 30 minutes at room temperature, followed by 60 minute incubations with a rabbit antibody against ER alpha (SP-1, Thermo Fisher Scientific, Cat. No. RM-9101), ER beta (Cell Signaling Technology, Cat. No. 5513), or mouse antibody against alpha tubulin (Sigma, Cat. No. T6199). Following incubation with an IRDye® Conjugated Goat Anti Mouse or Anti Rabbit IgG (LI-COR), protein bands were quantified using an Odyssey® Infrared Imaging System. Graphing of data to determine ER levels was performed using Graphpad PRISM® software. % ER levels were calculated as follows:

% ER=(fluorescence ER band of sample-bkgrd/fluorescence Tubulin band of sample-bkgrd)/(fluorescence ER band of untreated cells-bkgrd/fluorescence Tubulin of untreated cells-bkgrd)

Example 908: Breast Cancer Model; Xenograft Assay (MCF-7)

Time release pellets containing 0.72 mg 17-β Estradiol were subcutaneously implanted into nu/nu mice. MCF-7 cells were grown in RPMI containing 10% FBS at 5% $CO_2$, 37° C. Cells were spun down and re-suspended in 50% RPMI (serum free) and 50% Matrigel at $1 \times 10^7$ cells/mL. MCF-7 cells were subcutaneously injected (100 µL/animal) on the right flank 2-3 days post pellet implantation. Tumor volume (length×width$^2$/2) was monitored bi-weekly. When tumors reached an average volume of ~200 mm$^3$ animals were randomized and treatment was started. Animals were treated with Vehicle or Compound daily for 4 weeks. Tumor volume and body weight were monitored bi-weekly throughout the study. At the conclusion of the treatment period, plasma and tumor samples were taken for pharmacokinetic and pharmacodynamic analyses, respectively.

Example 909: Breast Cancer Model; Xenograft Assay (MCF-7 Derivative)

Female nu/nu mice (with supplemental 17-β Estradiol pellets; 0.72 mg; 60 day slow release) bearing MCF-7 tumors (mean tumor volume 200 mm$^3$) were treated with Tamoxifen (citrate) by oral gavage. Tumor volume (length× width$^2$/2) and body weight were monitored twice weekly. Following a significant anti-tumor response in which tumor volume remained static, evident tumor growth was first observed at approximately 100 days of treatment. At 120 days of treatment, tamoxifen dose was increased. Rapidly growing tumors were deemed tamoxifen resistant and selected for in vivo passage into new host animals. Tumor Fragments (~100 mm$^3$/animal) from the tamoxifen resistant tumors were subcutaneously implanted into the right flank of female nu/nu mice (with 17-β Estradiol pellets (0.72 mg; 60 day slow release)). Passaged tumors were maintained under constant Tamoxifen selection, and Tumor volume (length× width$^2$/2) was monitored weekly. When tumor volume reached ~150-250 mm$^3$, animals were randomized into treatment groups (mean tumor volume 200 mm$^3$) and tamoxifen treatment was terminated (except for a tamoxifen control arm). Animals were treated with Vehicle or Compound daily for 4 weeks. Tumor volume and body weight were monitored twice weekly for the duration of the study. At the conclusion of the treatment period; plasma and tumor samples were taken for pharmacokinetic and pharmacodynamic analyses, respectively.

Example 910: Ovarian Cancer Model; Xenograft Assay (BG-1)

Time release pellets (0.72 mg 17-0 Estradiol/60 days) are subcutaneously implanted into female nu/nu mice. BG-1 cells are grown in DMEM Ham's F-12 50/50 containing 10% FBS, 10 mM Sodium Pyruvate, 10 mM Non-Essential Amino Acids at 5% $CO_2$, 37° C. Prior to injection, cells are trypsinized and suspended in 50% DMEM Ham's F-12 (serum free) and 50% Matrigel at $5 \times 10^7$ cells/mL. BG-1 cells are subcutaneously injected (100 µL/animal) on the right flank 2-3 days post pellet implantation. Tumor volume (length×width²/2) is monitored bi-weekly. When tumors reach an average volume of ~250 mm³ animals are randomized and treatment started. Animals are treated with Vehicle or Compound daily. Tumor volume and body weight are monitored bi-weekly throughout the study. At the conclusion of the treatment period; plasma and tumor samples are taken for pharmacokinetic and pharmacodynamic analyses, respectively.

Example 911: Endometrial Cancer Model; Xenograft Assay (ECC-1)

ECC-1 cells were grown in DMEM (phenol red, 4.5 g/L glucose and L-glutamine) containing 10% FBS, 1% Non-Essential Amino Acids and 100units Penicillin/Streptomycin at 10% $CO_2$, 37° C. Cells were spun down and re-suspended in 50% DMEM (serum free) and 50% Matrigel (BD, high concentration) at $5 \times 10^7$ cells/mL. Time release pellets (0.72 mg 17-β Estradiol/60 days) were subcutaneously implanted into female nu/nu mice. ECC-1 cells were subcutaneously injected (100 µL/animal) on the right flank 2-3 days post pellet implantation. Tumor volume was monitored and when tumors reached a suitable size for transplant they were excised. Excised tumors were cut into small pieces (~100 mm³) and serially transplanted (10G trocar, right flank) into female nu/nu containing estradiol pellets (0.72 mg 17-β Estradiol/60 days) for 2-3 days. Tumor volume (length×width×width/2) was monitored and when palpable tumors were observed, animals were randomized and treatment was started. Animals were treated with Vehicle or Compound daily for 4 weeks or until tumor volume reached 2000 mm³ (whichever came first). Tumor volume and body weight were monitored bi-weekly throughout the study. At the conclusion of the treatment period; plasma and tumor samples were taken for pharmacokinetic and pharmacodynamic analyses, respectively.

Example 912: Immature Uterine Wet Weight-Antagonist Mode

Female immature CD-IGS rats (21 days old upon arrival) were treated for three days. Animals were dosed daily for three days. Vehicle or test compound was administered orally by gavage followed 15 minutes later by an oral dose of 0.1 mg/kg Ethynyl Estradiol. On the fourth day 24 hours after dose, plasma was collected for pharmacokinetic analysis. Immediately following plasma collection, the animals were euthanized and the uterus was removed and weighed.

Example 913: Immature Uterine Wet Weight-Agonist Mode

Female immature CD-IGS rats (21 days old upon arrival) were treated for three days. Animals were dosed daily for three days. Vehicle or test compound was administered orally by gavage. On the fourth day 24 hours after dose, plasma was collected for pharmacokinetic analysis. Immediately following plasma collection, the animals were euthanized and the uterus was removed and weighed.

Example 914: Adult Uterine Wet Weight-10 Day

Female CD-IGS rats (69 days old, Charles River Laboratories) were purchased and split into groups. Group 1 was ovariectomized at the vendor (Charles River Laboratories) at 60 days of age and the study was started 2 weeks after surgery, while groups 2-8 were intact. Vehicle or test compound was administered orally for 10 days. Two hours after the $10^{th}$ and final dose, cardiac punctures were performed and serum was collected for pharmacokinetic and estradiol analyses. Immediately following serum collection, the animals were euthanized and the uterus and ovaries were removed and weighed. Uteri and ovaries from 2 animals per group were fixed in 10% neutral buffered formalin and sent out to be paraffin embedded, sectioned and stained for H&E (SDPath). Stained tissues were analyzed in house and then sent out to be read by a board certified pathologist. Uteri and ovaries from 4 animals per group were flash frozen in liquid $N_2$ for transcriptional analysis, examining a select set of genes modulated by the estrogen receptor.

Example 915: Breast Cancer Clinical Trial

Purpose: The purposes of this study are to assess the efficacy of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, as first- or second-line treatment of estrogen receptor (ER) positive metastatic breast cancer, collect information on any side effects the compound may cause, and evaluate the pharmacokinetic properties of the compound.

Intervention: Patients are administered 1-50 mg/kg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, per day or twice a day.

Outcome Measures: Primary Outcome Measures: Tumor Response and/or Disease Control.

Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, orally once or twice a day. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Female subjects that are 18 years and older.

Inclusion Criteria: Histologically or cytologically confirmed diagnosis of invasive breast cancer, stage IV disease; at least one measurable target lesion as defined by RECIST that has not been previously treated with local therapy; post-menopausal status; ER positive breast cancer; HER2-negative breast cancer; up to one prior hormonal therapy for advanced or metastatic disease; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from treatment-related toxicity.

Exclusion Criteria: HER2-positive breast cancer; prior chemotherapy regimen for metastatic disease; history of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 916: Endometrial Carcinoma Clinical Trial

Purpose: The purposes of this study are to assess the efficacy of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, in the treatment of advanced or metastatic endometrial carcinoma, collect information on any side effects the compound may cause, and evaluate the pharmacokinetic properties of the compound.

Intervention: Patients are administered 1-50 mg/kg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, per day or twice a day.

Outcome Measures: Primary Outcome Measures: tumor response and/or disease control.

Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, orally once or twice a day. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Female subjects that are 18 years and older.

Inclusion Criteria: Histologically or cytologically confirmed diagnosis of advanced or metastatic endometrial carcinoma; at least one measurable target lesion as defined by RECIST that has not been previously treated with local therapy; hormone receptor positive endometrial carcinoma; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria: History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 917: Ovarian Cancer Clinical Trial

Purpose: The purposes of this study are to assess the efficacy of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, in the treatment of advanced ovarian cancer, collect information on any side effects the compound may cause, and evaluate the pharmacokinetic properties of the compound.

Intervention: Patients are administered 1-50 mg/kg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, per day or twice a day.

Outcome Measures: Primary Outcome Measures: tumor response and/or disease control Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, orally once or twice a day. Prior to each dosing cycle, a physical exam, blood work (including tumor markers, e.g., CA-125) and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Female subjects that are 18 years and older.

Inclusion Criteria: Histologically or cytologically confirmed diagnosis of advanced ovarian cancer; at least one measurable target lesion as defined by RECIST that has not been previously treated with local therapy; ER positive ovarian cancer; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria: History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 918: ER-Positive NSCLC Clinical Trial

Purpose: The purposes of this study are to assess the efficacy of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, as single agent or in combination in the treatment of advanced or metastatic estrogen receptor (ER) positive non-small cell lung cancer (NSCLC), collect information on any side effects the compound may cause as single agent or in combination, and evaluate the pharmacokinetic properties of the compound as single agent or in combination.

Intervention: Patients are administered 1-50 mg/kg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, per day or twice a day as single agent or in combination.

Outcome Measures: Primary Outcome Measures: tumor response and/or disease control. Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, orally once or twice a day as single agent or in combination. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Male and female subjects that are 18 years and older.

Inclusion Criteria: Histologically or cytologically confirmed diagnosis of advanced or metastatic ER-positive NSCLC; at least one measurable target lesion as defined by RECIST that has not been previously treated with local therapy; ECOG performance status 0-1; life expectancy>12 weeks; adequate liver and bone marrow function: AST<2.5× ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria: History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 919: Endometriosis Clinical Trial

Purpose: The purposes of this study are to assess the efficacy of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, as single agent or in combination in the treatment of patients with symptomatic/severe endometriosis, collect information on any side effects the compound may cause as single agent or in combination, and evaluate the pharmacokinetic properties of the compound as single agent or in combination.

Intervention: Patients are administered 1-50 mg/kg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, per day or twice a day as single agent or in combination.

Outcome Measures: The outcome measures of this study are symptoms improvement and/or pain relief and shrinkage of endometrial tissue.

Detailed Description: Patients will be given a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, orally once or twice a day as single agent or in combination. Prior to each dosing cycle, a physical exam, blood work and assessment of any side effects will be performed.

Eligibility: Female subjects that are 18 years and older.

Inclusion Criteria: Diagnosis of symptomatic endometriosis; pre- or peri-menopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.

Exclusion Criteria: Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; various medical or psychiatric illness.

Example 920: Uterine Leiomyoma Clinical Trial

Purpose: The purposes of this study are to assess the efficacy of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, as single agent or in combination in the treatment of patients with symptomatic uterine leiomyoma, collect information on any side effects the compound may cause as single agent or in combination, and evaluate the pharmacokinetic properties of the compound as single agent or in combination.

Intervention: Patients are administered 1-50 mg/kg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, per day or twice a day as single agent or in combination.

Outcome Measures: The outcome measures of this study are symptoms improvement and/or pain relief and shrinkage of leiomyomas.

Detailed Description: Patients will be given a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, orally once or twice a day as single agent or in combination. Prior to each dosing cycle, a physical exam, blood work and assessment of any side effects will be performed.

Eligibility: Female subjects that are 18 years and older.

Inclusion Criteria: Diagnosis of symptomatic uterine leiomyoma; pre- or peri-menopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.

Exclusion Criteria: Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; serious medical or psychiatric illness.

Example 921: Parenteral Pharmaceutical Composition

To prepare a parenteral pharmaceutical composition suitable for administration by injection (subcutaneous, intravenous), 100 mg of a water-soluble compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or pharmaceutically acceptable salt thereof, is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 922: Oral Solution

To prepare a pharmaceutical composition for oral delivery, an aqueous 20% propylene glycol solution is prepared. To this is added a sufficient amount of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, to provide a 20 mg/mL solution.

Example 923: Oral Capsule

To prepare a pharmaceutical composition for oral delivery, 10-1500 mg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is mixed with starch. The mixture is incorporated into an oral dosage unit such as a hard gelatin capsule, which is suitable for oral administration.

In another embodiment, 10-1500 mg of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is placed into Size 4 capsule, or size 1 capsule (hypromellose or hard gelatin) and the capsule is closed.

Example 924: Oral Tablet

A tablet is prepared by mixing 48% by weigh of a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 925: Topical Gel Composition

To prepare a pharmaceutical topical gel composition, a compound of Formula (I), (II), (IIa), (IIb), (IIc), (III), (IIIa), (IIIb), (IIIc), (IV), (IVa), (IVb), (IVc), (IVd), (V), (VI), (VII), (VIII), (IX) or (X), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A compound that has the following structure of Formula (IIa):

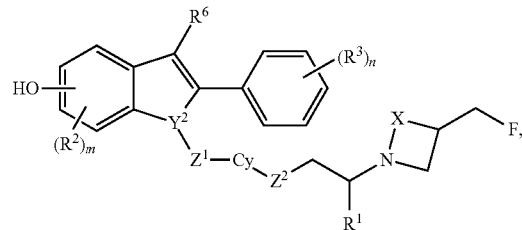

Formula (IIa)

stereoisomers, tautomers, or pharmaceutically acceptable salts thereof, wherein:

$Z^1$ and $Z^2$ are independently —O—, —(CH$_2$)—, —C(O)—, or a bond;

Cy is $C_6$-$C_{20}$ aryl, $C_3$-$C_{12}$ carbocyclyl, $C_2$-$C_{20}$ heterocyclyl, or $C_1$-$C_{20}$ heteroaryl;

X is —(CH$_2$)—;

$R^1$ is H, F, Cl, —CN, —CH$_2$OH, —CH(CH$_3$)OH, —C(CH$_3$)$_2$OH, —CH(CF$_3$)OH, —CH$_2$F, —CHF$_2$, —CH$_2$CHF$_2$, —CF$_3$, —CH$_3$, —C(O)NH$_2$, —C(O)NHCH$_3$, or —C(O)N(CH$_3$)$_2$;

each $R^2$ and each $R^3$ are independently halogen, —CN, —OR$^{10}$, —NR$^{13}$R$^{14}$, C$_1$-C$_4$ alkyl, —C$_1$-C$_4$ alkyl-OH, —OC$_2$-C$_4$ alkyl-OH, C$_1$-C$_4$ fluoroalkyl, —C(=O)OR$^{12}$, —NHC(=O)R$^{11}$, —C(=O)NHR$^{12}$, —SO$_2$R$^{11}$, —NHSO$_2$R$^{11}$, or —SO$_2$NHR$^{12}$;

$R^6$ is H, halogen, C$_1$-C$_6$ alkyl, or C$_1$-C$_6$ fluoroalkyl;

each $R^{10}$ is independently H, C$_1$-C$_4$ alkyl, or C$_1$-C$_4$ fluoroalkyl;

each $R^{11}$ is independently C$_1$-C$_4$ alkyl or C$_1$-C$_4$ fluoroalkyl;

each $R^{12}$ is independently H, C$_1$-C$_4$ alkyl, or C$_1$-C$_4$ fluoroalkyl;

each $R^{13}$ and each $R^{14}$ are independently H or C$_1$-C$_4$ alkyl;

m is 0, 1, 2 or 3; and n is 0, 1, 2 or 3;

where carbocyclyl, heterocyclyl, aryl, and heteroaryl are optionally substituted with one or more groups independently comprising F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OCF$_3$, —OCHF$_2$, —OP(O)(OH)$_2$, —S(O)$_2$N(CH$_3$)$_2$, —SCH$_3$, —S(O)$_2$CH$_3$, —S(O)$_3$H, cyclopropyl, oxetanyl, azetidinyl, 1-methylazetidin-3-yl)oxy, N-methyl-N-oxetan-3-ylamino, azetidin-1-ylmethyl, pyrrolidin-1-yl, and morpholino.

2. The compound of claim 1, wherein $R^6$ is $C_1$-$C_6$ alkyl.

3. The compound of claim 2, wherein $R^6$ is —$CH_3$.

4. The compound of claim 1, wherein Cy is phenyl or $C_2$-$C_9$ heteroaryl.

5. The compound of claim 1, wherein $Z^1$ is —($CH_2$)—.

6. The compound of claim 1, wherein $Z^2$ is —O—.

7. The compound of claim 1, wherein $R^1$ is H or —$CH_3$.

8. A pharmaceutical composition comprised of a compound of claim 1 and a pharmaceutically acceptable carrier, glidant, diluent, or excipient.

9. A process for making a pharmaceutical composition which comprises combining a compound of claim 1, with a pharmaceutically acceptable carrier, glidant, diluent, or excipient.

10. A method of treating an ER mediated disease or disorder in a patient having the ER-mediated disease or disorder, the method comprising administering a therapeutically effective amount of the pharmaceutical composition of claim 8 to the patient, wherein the ER-mediated disease or disorder comprises breast cancer, lung cancer, ovarian cancer, endometrial cancer, prostate cancer, or uterine cancer.

11. The method of claim 10 wherein the cancer is breast cancer.

12. The method of claim 10 further comprising administering an additional therapeutic agent comprising an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, or an agent for treating immunodeficiency disorders.

13. A kit for treating a condition mediated by an estrogen receptor, wherein the condition comprises breast cancer, lung cancer, ovarian cancer, endometrial cancer, prostate cancer, or uterine cancer, the kit comprising:
a) a pharmaceutical composition of claim 8; and
b) instructions for use.

14. The compound of claim 1 selected from:
1-(4-(2-(3-(Fluoromethyl)azetidin-1-yl)ethoxy)benzyl)-2-(4-hydroxyphenyl)-3-methyl-1H-indol-5-ol;
1-(4-(2-(3-(Fluoromethyl)azetidin-1-yl)ethoxy)benzyl)-2-(4-fluorophenyl)-3-methyl-1H-indol-5-ol;
1-(4-(2-(3-(Fluoromethyl)azetidin-1-yl)ethoxy)benzyl)-3-methyl-2-phenyl-1H-indole;
4-(1-(4-(2-(3-(Fluoromethyl)azetidin-1-yl)ethoxy)benzyl)-3-methyl-1H-indol-2-yl)phenol;
1-[[4-[2-[3-(fluoromethyl)azetidin-1-yl]ethoxy]phenyl]methyl]-2-(4-hydroxy-3-methyl-phenyl)-3-methyl-indol-5-ol;
2-(3-chloro-4-hydroxy-phenyl)-1-[[4-[2-[3-(fluoromethyl)azetidin-1-yl]ethoxy]phenyl]methyl]-3-methyl-indol-5-ol;
2-(2-chloro-4-hydroxy-phenyl)-1-[[4-[2-[3-(fluoromethyl)azetidin-1-yl]ethoxy]phenyl]methyl]-3-methyl-indol-5-ol;
4-fluoro-1-[[4-[2-[3-(fluoromethyl)azetidin-1-yl]ethoxy]phenyl]methyl]-2-(4-hydroxyphenyl)-3-methyl-indol-5-ol;
6-fluoro-1-(4-(2-(3-(fluoromethyl)azetidin-1-yl)ethoxy)benzyl)-2-(4-hydroxyphenyl)-3-methyl-1H-indol-5-ol; and
1-[[4-[2-[3-(fluoromethyl)azetidin-1-yl]ethoxy]phenyl]methyl]-2-(4-hydroxy-2-methyl-phenyl)-3-methyl-indol-5-ol; or a pharmaceutically acceptable salt thereof.

* * * * *